United States Patent
Cigan et al.

(10) Patent No.: US 12,371,692 B2
(45) Date of Patent: *Jul. 29, 2025

(54) METHODS FOR IMPROVING THE HEALTH OF PORCINE SPECIES BY TARGETED INACTIVATION OF CD163

(71) Applicant: Genus PLC, DeForest, WI (US)

(72) Inventors: Andrew Mark Cigan, Madison, WI (US); Jonathan Edward Lightner, Jefferson, WI (US); Matthew Scott Culbertson, Wilmington, NC (US); William Thomas Christianson, Hendersonville, TN (US); Benjamin Beaton, DeForest, WI (US); Brian Burger, Madison, WI (US); Dylan Barnes, Madison, WI (US); Matthew Campbell, Madison, WI (US)

(73) Assignee: Genus plc, DeForest, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/192,492

(22) Filed: Mar. 29, 2023

(65) Prior Publication Data
US 2023/0272397 A1   Aug. 31, 2023

Related U.S. Application Data

(63) Continuation of application No. 17/581,239, filed on Jan. 21, 2022, now Pat. No. 11,535,850, which is a continuation of application No. 17/515,139, filed on Oct. 29, 2021, which is a continuation of application No. 17/307,369, filed on May 4, 2021, now Pat. No. 11,208,659.

(60) Provisional application No. 63/021,370, filed on May 7, 2020, provisional application No. 63/020,128, filed on May 5, 2020.

(51) Int. Cl.
| | |
|---|---|
| A01K 67/027 | (2024.01) |
| A01K 67/0275 | (2024.01) |
| C12N 9/22 | (2006.01) |
| C12N 15/113 | (2010.01) |
| C12N 15/877 | (2010.01) |

(52) U.S. Cl.
CPC ........ C12N 15/113 (2013.01); A01K 67/0275 (2013.01); C12N 9/22 (2013.01); C12N 15/8778 (2013.01); A01K 2217/052 (2013.01); A01K 2227/108 (2013.01); C12N 2310/20 (2017.05); C12N 2320/34 (2013.01)

(58) Field of Classification Search
None
See application file for complete search history.

(56) References Cited

U.S. PATENT DOCUMENTS

| | | | |
|---|---|---|---|
| 4,873,191 A | 10/1989 | Wagner et al. | |
| 9,820,475 B2 | 11/2017 | Prather et al. | |
| 9,854,790 B2 * | 1/2018 | Ait-Ali | A01K 67/0275 |
| 10,091,975 B2 * | 10/2018 | Prather | C12N 15/8509 |
| 10,827,730 B2 * | 11/2020 | Prather | C07K 14/70596 |
| 11,208,659 B2 * | 12/2021 | Cigan | A01K 67/0275 |
| 11,535,850 B2 * | 12/2022 | Cigan | C12N 15/113 |
| 2014/0068727 A1 | 3/2014 | Doudna et al. | |

FOREIGN PATENT DOCUMENTS

| | | |
|---|---|---|
| WO | WO2017023337 | 2/2017 |
| WO | WO2018073237 | 4/2018 |
| WO | WO2019203807 | 10/2019 |

OTHER PUBLICATIONS

Shanmukhappa, Kumar, et al., Role of CD151, A tetraspanin, in porcine reproductive and respiratory syndrome virus infection, Virology Journal, 2007, 4:62.
Shimozawa, Nobubiro et al., Abnormalities in Cloned Mice Are Not Transmitted to the Progeny, Genesis, 2002, 35:203-207.
Snuder, Eric J., and Meulenberg, Janneke J.M., The molecular biology of arteriviruses, J Gen Virology, 1998, 79·961-979.
Soares, Miguel, P., Bach, Fritz H., Heme oxygenase-1: from biology to therapeutic potential, Trends in Molecular Medicine, 2009, 15(2):50-58.
Stein, Michael, et al., Interleukin 4 Potently Enhances Murine Macrophage Mannose Receptor Activity: A Marker of Alternative Immunologic Macrophage Activation, J Exp Med, 1992, 176:287-292.
Stephen, Sam L., et al., Scavenger Receptors and Their Potential as Therapeutic Targets in the Treatment of Cardiovascular Disease, International Journal of Hypertension, 2010, pp. 1-21.
Stephenson, Rachel J., et al., Multiplex Serology for Common Viral Infections in Feral Pigs (*Sus scrofa*) in Hawaii between 2007 and 2010, J. Wildlife Diseases, 2015, 51(1):239-243.
Suarez, Paloma, et al., Open Reading Frame 5 of Porcine Reproductive and Respiratory Syndrome Virus as a Cause of Virus-Induced Apoptosis, J Virology, 1996, 70(5):2876-2882.
Sulahian, Timothy H., et al., Human Monocytes Express CD163, Which is Unregulated by IL-10 and Identical to p. 155, Cytokine, 2000, 12(9):1312-1321.

(Continued)

*Primary Examiner* — Michael C Wilson
(74) *Attorney, Agent, or Firm* — Tony N. Woolard; Daniel M. Lorentzen

(57) ABSTRACT

The present disclosure relates to methods and compositions useful for prevention of porcine reproductive and respiratory syndrome virus (PRRSv) in animals, including animals of the species *Sus scrofa*. The present teachings relate to swine wherein at least one allele of a CD163 gene has been inactivated, and to specific methods and nucleic acid sequences used in gene editing to inactivate the CD163 gene. Swine wherein both alleles of the CD163 gene are inactivated are resistant to porcine reproductive and respiratory syndrome virus (PRRSv). Elite lines comprising homozygous CD163-edited genes retain their superior properties.

19 Claims, No Drawings

Specification includes a Sequence Listing.

(56) References Cited

OTHER PUBLICATIONS

Sur, Jung-Hyang, et al., In Vivo Detection of Porcine Reproductive and Respiratory Syndrome Virus RNA by In Situ Hybridization at Different Times Postinfection, J Clinical Microbiology, 1996, 34(9):2280-2286.
Sur, Jung-Hyang, et al., Porcine Reproductive and Respiratory Syndrome Virus Replicates in Testicular Germ Cells, Alters Spermatogenesis, and Induces Germ Cell Death by Apoptosis, J Virology, 1997, 71(12):9170-9179.
Tait-Burkard, Christine, et al., Livestock 2.0—genome editing for fitter, healthier, and more productive farmed animals, Genome Biology, 2018, 19(204):1-11.
Terns, Michael P. and Terns, Rebecca M., CRISPR-Based Adaptive Immune Systems, Curr Opin Microbiol, 2011, 14(3):321-327.
Trible, Benjamin R., et al., Recognition of the Different Structural Forms of the Capsid Protein Determines the Outcome following Infection with Porcine Circovirus Type 2, J Virology, 2012, 86(24):13508-13514.
Vadori, M. and Cozzi, B., The immunological barriers to xenotransplantation, Tissue Antigens, 2015, 86:239-225.
Van Breedam, Wander, et al., Porcine reproductive and respiratory syndrome virus entry into the porcine macrophage, J General Virology, 2010, 91:1659-1667.
Van Breedam, Wander, et al., The M/GP5 Glycoprotein Complex of Porcine Reproductive and Respiratory Syndrome Virus Binds the Sialoadhesin Receptor in a Sialic Acid-Dependent Manner, PLoS Pathogens, 2010, 6(1):1-11.
Van Den Heuvel, Michel M., et al., Regulation of CD163 on human macrophages: cross-linking of CD163 induces signaling and activation, J Lenkocyte Biology, 1999, 66(5):858-866.
Van Den Hoff, Maurice J.B., et al., Electroporation in 'intracellular' buffer increases cell survival, Nucleic Acids Research, 1992, 20(11):2902.
Vanderheiden, Nathalie, et al., Involvement of Si loadhesin in Entry of Porcine Reproductive and Respiratory Syndrome Virus into Porcine Alveolar Macrophages, 2003, J Virolog 77(15):8207-8215.
Van Gorp, Hanne, et al., Scavenger receptor CD163, a Jack-of-all-trades and potential target for cell-directed therapy, 2010, 47:1650-1660.
Van Gorp, Hanne, et al., Identification of the CD163 Protein Domains Involved in Infection of the Porcine Reproductive and Respiratory Syndrome Virus, 2010, J Virology, 84(6):3101-3105.
Van Gorp, Hanne, et al., Sialoadhesin and CD163 join forces during entry of the porcine reproductive and respiratory syndrome virus, J General Virology, 2008, 89:2943-2953.
Vinson, Mary, et al., Characterization of the Sialic Acid-binding Site in Sialoadhesin by Site-directed Mutagenesis, J Biological Chemistry, 1996, 271(16):9267-9272.
Walters, Eric M. and Prather, Randall S., Advancing Swine Models for Human Health and Diseases, Missouri Medicine, 2013, 110(3):212-215.
Wang, Haoyi, et al., One-Step Generation of Mice Carrying Mutations in Multiple Genes by CRISPR/Cas-Mediated Genome Engineering, Cell, 2013, 153(4):910-918.
Watanabe, Masahito, et al., Knockout of exogenous EGFP gene in porcine somatic cells using zinc-finger nucleases, Biochem and Biophysical Research Communications, 2010, 402:14-18.
Welch, Sino-Kun and Calvert, Jay G., A brief review of CD163 and its role in PRRSV infection, Virus Research, 2010, 154:98-103.
Wells, Kevin D., et al., Replacement of Porcine CD163 Scavenger Receptor Cysteine-Rich Domain 5 with a CD163-Like Homolog Confers Resistance of Pigs to Genotype I but Not Genotype 2 Porcine Reproductive and Respiration Syndrome Virus, J Virology, 2017, 91(2):1-11.
Wensvoort, G., et al., Mystery swine disease in the Netherlands: The isolation of Lelystad virus, Veterinary Quarterly, 1991, 13(3):121-130.

Whitworth, Kristin M., et al., Gene-edited pigs are protected from porcine reproductive and respiratory syndrome virus, Nature Biotechnology, 2016, 34(1):20-22.
Whitworth, K. M., et al., "Disruption the Sialoadhesin and CD163 Genes to Create Pigs Resistant to PRRSV Infectivity," Abstract, Swine in Biomedical Research in Chicago, Illinois, Jul. 17-19, 2011, S1-25, pp. 39-40.
Whitworth, Kristin M., et al., Method of Oocyte Activation Affects Cloning Efficiency in Pigs, Mol Reprod Dev, 2002, 76:1.11.
Whitworth, Kristin M., et al., Activation Method Does Not Alter Abnormal Placental Gene Expression and Development in Cloned Pigs, Mol Reprod Dev, 2010, 77:1016-1030.
Whitworth, K. M., et al., "Pigs Resistant to PRRSV Infectivity," Poster Presented at Swine in Biomedical Research in Chicago, Ilinois, Jul. 18, 2011, 1 page.
Whitworth, Kristin M., et al., Scriptaid Corrects Gene Expression of a Few Aberrantly Reprogrammed Transcripts in Nuclear Transfer Pig Blastocyst Stage Embryos, Cellular Reprogramming, 2011, 13(3):191-204.
Whitworth, Kristin M. and Prather, Randall S., Gene editing as applied to prevention of reproductive porcine reproductive and respiratory syndrome, Mol Reprod Dev, 2017, 84:926-933.
Whitworth, Kristin M., et al., Use of the CRISPR/Cas9 System to Produce Genetically Engineered Pigs from In Vitro-Derived Oocytes and Embryos, Biol of Reproduction, 2014, 91(3):78, 1-13.
Whitworth, K. M., et al., "Use of the CRISPR/Cas9 System to Produce Pigs With a Genetically Modified CD163 Gene by Using Somatic Cell Nuclear Transfer of In Vitro Derived Oocytes," Abstract, Swine in Biomedical Research Conference, Raleigh, North Carolina, Jul. 20-22, 2014, p. 103.
Whitworth, Kristin M., et al., Use of the CRISPR/Cas9 system to produce pigs with a genetically modified CD163 gene by somatic cell unclear transfer of in vitro derived oocytes, Division of Animal Science, University of Missouri, Columbia, Poster, p. 1.
Whitworth, K.M., et al., Gene editing of CD163 protects pigs from PRRSV infectivity, Abstracts from the UC Davis Transgenic Animal Research Conference XI, Aug. 13-17, 2017, Transgenic Res, 2018, 27:473-474.
Whyte, Jeffrey J., et al., Gene Targeting With Zinc Finger Nucleases to Produce Cloned eGFP Kouckout Pigs, Mol Reprod Dev, 2011, 78(1):1-3.
Whyte, Jeffrey and Prather, Randall S., Genetic modifications of pigs for medicine and agriculture, Mol Reprod Dev, 2011, 78(10-11):879-891.
Wiedenheft, Blake, et al., RNA-guided genetic silencing systems in bacteria and archaea, Nature, 2012, 482:331-338.
Wills, R. W., et al., Porcine reproductive and respiratory syndrome virus: Persistent infection, Veterinary Microbiok 1997, 55:231-240.
Winckler, C. and Willen, S., The Reliability and Repeatability of a Lameness Scoring System for Use as an Indicator of Welfare in Dairy Cattle, Acta Agric Scand Sect A, Animal Sci Suppl, 2001, 30:103-107.
Wissink, E.H.J., et al., Identification of porcine alveolar macrophage glycoproteins involved in infection of porcine respiratory and reproductive syndrome virus, Arch Virol, 2003, 148:177-187.
Merck Sharp and Dohme Corp., Normal Rectal Temperature Ranges, 2009, pp. 1.
Miao, Yi-hang, et al., Centrosome Abnormalities During Porcine Oocyte Aging, Environmental and Molecular Mutagenesis, 2009, 50:666-671.
Misinzo, Getakl, M., et al., Involvement of proteases in porcine reproductive and respiratory syndrome virus uncoating upon internalization in primary macrophages, Vet. Res., 2008, 39:55-69.
Molitor, T.W., et al., Immunity to PRRSV: Double-edged sword, Veterinary Microbiology, 1997, 55:265-276.
Morgan, S.B., et al., Pathology and Virus Distribution in the Lung and Lymphoid Tissues of Pigs Experimentally Inoculated with Three Distinct Type I PRRS Virus Isolates of Varying Pathogenicity, Transboundary and Emerging Diseases, 2014, 63(2016):285-295.
Murtaugh, M.P., et al., Comparison of the structural protein coding sequences of the VR-2332 and Lelystad virus strains of the PRRS virus, Arch Virol, 1995, 140:1451-1460.

(56) References Cited

OTHER PUBLICATIONS

Nath, Deepa, et al., The Amino-terminal Immunoglobulin-like Domain of Sialoadhesin Contains the Sialic Acid Binding Site, J Biol Chem, 1995, 270(44):26184-26191.
Nauwynck, H.J., et al., Entry of porcine reproductive and respiratory syndrome virus into porcine alveolar macrophages via receptor-medicated endocytosis, J General Virology, 1999, 80:297-305.
Nelson, Chris J., et al., Porcine Reproductive and Respiratory Syndrome Virus Comparison: Divergent Evolution on Two Continents, J Virology, 1999, 73(1):270-280.
Neumann, Eric J., et al., Assessment of the economic impact of porcine reproductive and respiratory syndrome on swine production in the United States, JAVMA, 2005, 227(3):385-392.
Nielsen, H.S., et al., Generation of an Infectious Clone of VR-2332, a Highly Virulent North American-Type Isolate of Porcine Reproductive and Respiratory Syndrome Virus, J Virology, 2003, 77(6):3702-3711.
Nielsen, Marianne Jensby, et al., The macrophage scavenger receptor CD163: endocytic properties of cytoplasmic tail variants, J Leukocyte Biology, 2006, 79:837-845.
Niu, Yaya, et al., Generation of Gene-Modified Cynomolgus Monkey via Cas9/RNA-Mediated Gene Targeting in One-Cell Embryos, Cell, 2014, 156:836-843.
Nussbaum, Diana J. and Prather, Randall S., Differential Effects of Protein Synthesis Inhibitors on Porcine Oocyte Activation, Mol Reprod and Develop, 1995, 41:70-75.
Oetke, Cornelia, et al., Sialoadhesin-Deficient Mice Exhibit Subtle Changes in B- and T-Cell Populations and Reduced Immunoglobulin M Levels, Mol and Cell Biol, 2006, 26(4):1549-1557.
Park, Kwang-Wook, et al., Developmental Potential of Porcine Nuclear Transfer Embryos Derived from Transgenic Fetal Fibroblasts Infected with the Gene for the Green Fluorescent Protein: Comparison of Different Fusion/Activation Conditions, Biol of Reprod, 2001, 65:1681-1685.
Park, Kwang-Wook, et al., Production fo Nuclear Transfer-Derived Swine That Express the Enhanced Green Fluorescent Protein, Animal Biotech, 2001, 12(2):173-181.
Patience, John F. and Thacker, Phil A., Nutrition of the Breeding Herd, Prairie Swine Centre, 1989, pp. 149-171.
Patton, John B., et al., Modulation of CD163 receptor expression and replication of porcine reproductive and respiratory syndrome virus in porcine macrophages, Virus Research, 2009, 140:161-171.
Plagemann, Peter G.W., Lactage Dehydrogenase-Elevating Virus and Related Viruses, Fields Virology, 3$^{rd}$ Ed., 1996, Ch. 36, pp. 1105-1120.
Popescu, Luca, et al., Genetically edited pigs lacking CD163 show no resistance following infection with the African swine fever virus isolate, Georgia 2007/1 Virology, 2017, 501:102-106.
Prather, Randall S., et al., Genetic engineering alveolar macropbages for host resistance to PRRSV, Veterinary Microbiology, 2017, 209:124-129.
Prather, Randall S., et al., Knockout of maternal CD163 protects fetuses from infection with porcine reproductive and respiratory syndrome virus (PRRSV), Nature Scientific Reports, 2017, 7(13371):1-5.
Prather, R.S., et al., Genetic Engineering of Pigs for PRRSV Resistance, Animal Sciences, Univ Missouri-Columbia, College of Ag Food and Natural Resources, Animal Reproductive Biology Group, Slides, pp. 1-43.
Prather, Randall S., et al., An Intact Sialoadhesin (Sn/SIGLECI/CD169) Is Not Required for Attachment/Internalization of the Porcine Reproductive and Respiratory Syndrome Virus, J Virology, 2013, 87(17):9538-9546.
Prather. R.S., Genetic Engineering of Pigs for PRRSV Resistance, Animal Sciences, Univ Missouri-Columbia, College of Ag Food and Natural Resources, Animal Reproductive Biology Group, Slides, pp. 1-55.
Prather, R.S., et al., Genetic engineering the pig to better understand PRRSv infection, 2014 North American PRRS Symposium, 2014, p. 33.
Prather, R.S., Genetic Engineering for Profitable Port Production: is Resistance to PRRSv Possible?, Animal Sciences, Univ Missouri-Columbia, College of Ag Food and Natural Resources, Animal Reproductive Biology Group, Slides, pp. 1-70.
Prather, Randall S., et al., CRISPR/Cas9-Mediated Genetic Engineering: Is CD163 an Entry Mediator for PRRSv Infection?, International Plant and Animal Genome Conference XXIII, Abstract, Jan. 9-15, 2015, 1 page.
Provost, Chantale, et al., Identification of a new cell line permissive to porcine reproductive and respiratory syndrome virs infection and replication which is phenotypically distinct from MARC-145 cell line, Virology Journal, 2012, 9(267):1-14.
Reed, L.J. and Muench, H., A Simple Method of Estimating Fifty Per Cent Endpoints, American Journal of Hygiene, 1938, 27(3):493-497.
Rezaee, Ramin and Abdollahi, Mohammad, The Importance of Translatability in Drug Discovery, Expert Opinion on Drug Discovery, 2017, 12(3):237-239.
Ritter, M., et al., The Scavenger Receptor CD163: Regulation, Promoter Structure and Genomic Organization, Pathobiology, 1999, 67:257-261.
Ritter, Mirko, et al., Genomic Organization and Chromosomal Localization of the Human CD163 (M130) Gene: A Member of the Scavenger Receptor Cysteine-Rich Superfamily, Biochem and Biophysical Research Communications, 1999, 260(2):466-474.
Robl, J.M., et al., Nuclear Transplantation in Bovine Embryos, J Anim Sci, 1987, 64:642-647.
Ropp, Susan L., et al., Characterization of Emerging European-Like Porcine Reproductive and Respiratory Syndrome Virus Isolates in the United States, J Virology, 2004, 78(7):3684-3703.
Ross, Jason W., et al., Optimization of square-wave electroporation for transfection of porcine fetal fibroblasts, Transgenic Res, 2010, 19(4):611-620.
Rowland, Raymond R.R., et al., Control of porcine reproductive and respiratory syndrome (PRRS) through genetic improvements in disease resistance and tolerance, Frontiers in Genetics, 2012, 3(260):1-6.
Rowland, Raymond R.R., et al., The Evolution of Porcine Reproductive and Respiratory Syndrome Virus: Quasispecies and Emergence of a Virus Subpopulation during Infection of Pigs with VR-2332, Virology, 1999, 259:262-266.
Saeidnia, Soodabeh, et al., From in vitro Experiments to in vivo and Clinical Studies; Pros and Cons, Current Drug Discovery Technologies, 2015, 12(4):218-224.
Sanchez, Carmen, et al., The Porcine 2A10 Antigen Is Homologous to Human CD163 and Related to Macrophage Differentiation, J Immunology, 1999, 162:5230-5237.
Sanchez-Torres, C., et al., Expression of porcine CD163 on monocytes/macrophages correlates with permissiveness to African swine fever infection, Arch Virol, 2003, 148:2307-2323.
Sangamo BioSciences, Efficient Generation of Transgenic Pigs Using Zinc Finger Nuclease (ZFN) Technology, Demonstration of ZFN Technology for Efficient Creation of Animals as a Source of Organs for Transplantation into Humans, Press Release, 2011, p. 1.
Schaer, Christian A., et al., Constitutive Endocytosis of CD163 Mediates Hemoglobin-Heme Uptake and Determines the Noninflammatory and Protective Transcriptional Response of Macrophages to Hemoglobin, Circ Res, 2006, 99:943-950.
Schaer, Dominik J., et al., CD163 is the macrophage scavenger receptor for native and chemically modified hemoglobins in the absence of haptoglobin, Blood, 2006, 107(1):373-380.
Schaer, DJ, et al., Hemophagocytic macrophages constitute a major compartment of heme oxygenase expression in sepsis, Eur J Haematol, 2006, 77:432-436.
Schurgers, Evebien, et al., Discrepancy between the in vitro and in vivo effects of marine mesenchymal stem cells on T-cell proliferation and collagen-induced arthritis, Arthritis Research & Therapy, 2010, 12(R31):3-11.
Aigner, Bernhard, et al., Transgenic pigs as models for translational biomedical research, J Mol Med, 2010, 88:653-664.
Albina, E., et al., Immune response and persistence of the porcine reproductive and respiratory syndrome virus in infected pigs and far units, The Veterinary Record, May 28, 1994, 134:567-573.

(56) References Cited

OTHER PUBLICATIONS

Allende, R., et al., North American and European porcine reproductive and respiratory syndrome viruses differ in non-structural protein coding regions, J General Virology 99, 80:307-315.

Allende, R., et al., Porcine Reproductive and Respiratory Syndrome Virus: Description of Persistence in Individual Pigs upon Experimental Infection, J Virology, Nov. 2000, 74(22):10834-10837.

American Society for Cell Biology. "Small details between 'in vivo' and 'in vitro' studies make for big differences." ScienceDaily. ScienceDaily, Dec. 13, 2010.

Andreyev, V.G., et al., Genetic variation and phylogenetic relationships of 22 porcine reproductive and respiratory syndrome virus (PRRSV) field strains based on sequence analysis of open reading frame 5, Arch Virol 1997, 142:993-1001.

ATCC CRL-3216, 293T, Organism: *Homo sapiens*, human, Tissue: embryonic kidney.

Bauer, B.K., et al., 1 Arginine Supplementation in vitro Increases Porcine Embryo Development and Affects mRNA Transcript Expression, Reproduction, Fertility and Development, Dec. 7, 2010, 23(1):107.

Beaton, Benjamin P. and Wells, Kevin D., Compound Transgenics: Recominase-Mediated Gene Stacking, Transgenic Animal Technology, pp. 565-678.

Benfield, David A., et al., Characterization of swine infertility and respiratory syndrome (SIRS) virus (isolate ATCC VR-2332), J Vet Diagn Invest, 1992 4:127-133.

Benfield, David A., et al., Pathogenesis and persistence of PRRS, Allen D. Leman Swine Conference, 1998, pp. 169-171.

Berg, H., 200-Biological Implications of Electric Field Effects Part V. Fusion of Blastomeres and Blastocysts of Monns Embryos, Bioelectrochemistry and Bioenergetics, 1982, 9:223-228.

Boddicker, Nicholas J., et al., Genomne-wide association and genomic prediction for host response to porcine reproductive and respiratory syndrome virus infection, Genetics Selection Evolution, 2014, 46(18):1-14.

Bookstein, Robert, et al., Promoter deletion and loss of retinoblastoma gene expression in human prostate carcinoma, Proc. Natl. Acad. Sci. USA, 1990, 87:7762-7766.

Borg, Natalie A., et al., CD1d-lipid-antigen recognition by the semi-invariant NKT T-cell receptor, Nature, Jul. 5, 2007, 448:44-49.

Brinster, Ralph L., et al., Factors affecting the efficiency of introducing foreign DNA into mice by microinjecting eggs, Proc. Natl. Acad. Sci., Jul. 1985, 82:4438-4442.

Burkard, Christine, et al., Pigs Lacking the Scavenger Receptor Cysteme-Rich Domain 5 of CD163 Are Resistant to Procine Reproductive and Respiratory Syndrome Virus I Infection, J. Virology, 2018, 92(16):1-17.

Burkard, Christine, et al., Precision engineering for PRRSV resistance in pigs: Macrophages from genome edited pigs lacking CD163 SRCR5 domain are fully resistant to both PRRSV genotypes while maintaining biological function, PLOS Pathogens, Feb. 23, 2017, 13(2):1-28.

Burlac, C., et al., Identification of human preformed antibody targets in GTKO pigs, Xenotransplantation 2012, 19:92-101.

Calvert, Jay G., et al., CD163 Expression Confers Susceptibility to Porcine Reproductive and Respiratory Syndrome Viruses, J of Virology, Jul. 2007, 81(14):7371-7379.

Carter, D. Bart, et al., Phenotyping of Transgenic Cloned Piglets, Cloning and Stem Cells, 2002, 4(2):131-145.

Chin, Kun-Kuet and Shwu-Pen Chang, The-104G nucleotide of the human CYP21 gene is important for CYP21 transcription activity and protein interaction, Nucleic Acids Research, 1998, 26(8):1959-1964.

Christopher-Hennings, Jane, et al., Persistence of porcine reproductive and respiratory syndrome virus in serum and semen of adult boars, J Vet Diagn Invest, 1995, 7:456-464.

Christopher-Hennings, J, et al., Effects of a modified-live virus vaccine against porcine reproductive and respiratory syndrome in boars, AJVR, 1997, 58(1):40-45.

Ciotti, M., et al., Coding defect and a TATA box mutation at the bilirubin UDP-glucuronosyltransferase gene cause Crigler-Najjar type I disease, Biochimica et Biophysica Acta, 1998, 1407:40-50.

Cong, Le, et al., Multiplex Genome Engineering Using CRISPR/Cas Systems, Science, Feb. 15, 2013, 339(6121):819-823.

Cooper, David K C, Modifying the sugar icing on the transplantation cake, Glycobiology, 2016, 26(6):571-581.

Crocker, Paul R. and Gordon, Siamon, Properties and Distribution of a Lectin-Like Hemagglutinin Differentially Expressed by Murine Stromal Tissue Macrophages, J Exp Med, The Rockefeller Univ. Press, Dec. 1986, 164:1862-1875.

Crocker, Paul R., et al., Molecular analysis of sialoside binding to sialoadhesin by NMR and site-directed mutagenesis. Biochem J. 1999, 341:355-361.

Dai, Yifan, et al., Targeted disruption of the $\alpha$1, 3-galactosyltransferase gene in cloned pigs, Nature, Mar. 2002, 20:251-255.

Das, Phani B., et al., The Minor Envelope Glycoproteins GP2a and GP4 of Porcine Reproductive and Respiratory Syndrome Virus Interact with the Receptor CD163, J Virology, Feb. 2010, 84(4):1731-1740.

Dee, S. A. and Molitor, T. W., Elimination of porcine reproductive and respiratory syndrome virus using a test and removal process, Veterinary Record, 1998, 143:474-476.

Delputte, P.L., et al., Effect of virus-specific antibodies on attachment, internalization and infection of porcine reproductive and respiratory syndrome virus in primary macrophages, Vet Immunology and Immunopathology, 2004, 102:179-188.

Delputte, P.L., et al., Involvement of the Matrix Protein in Attachment of Porcine Reproductive and Respiratory Syndrome Virus to a Heparinlike Receptor on Porcine Alveolar Macrophages, J Virology, May 2002, 76(9):4312-4320.

Delputte, P.L., et al., Porcine Arterivirus Infection of Alveolar Macrophages Is Mediated by Sialic Acid on the Virus, J Virology, Aug. 2004, 78(15):8094-8101.

Delputte, P.L., et al., Porcine Arterivirus Attachment to the Macrophage-Specific Receptor Sialoadhesin Is Dependent on the Sialic Acid-Binding Activity of the N-Terminal Immunoglobulin Domain of Sialoadhesin, J Virology, Sep. 2007, 81(17):9546-9550.

Delputte, P.L., et al., Porcine Sialoadhesin (CD169/Siglec-1) Is an Endocytic Receptor that Allows Targeted Delivery of Toxins and Antigens to Macrophages, PLoS ONE, Feb. 2011, 6(2):1-12.

Etzerodt, Anders, et al., Plasma Clearance of Hemoglobin and Haptoglobin in Mice and Effect of CD163 Gene Targeting Disruption, Antioxidants & Redox Signaling, 2013, 18(17):2254-2263.

Etzerodt, Andres and Moestrup, Soren K., CD163 and Inflammation: Biological, Diagnostic, and Therapeutic Aspects, Antioxidants & Redox Signaling, 2013, 18(17):2352-2363.

Fabriek, Babs O., et al., The macrophage scavenger receptor CD163, Immunobiology, 2005, 210:153-160.

Fabriek, Babs O., et al., The macrophage scavenger receptor CD163 functions as an innate immune sensor for bacteria, Blood Journal, Jan. 22, 2009, 113(4):887-892.

Fisher, D. and Goodall, A.H., Membrane fusion by viruses and chemical agents, Techniques in Cellular Physiology, 1981. P115:1-36.

Fridman, Al and Tainsky, Ma, Critical pathways in cellular senescence and immortalization revealed by gene expression profiling, Oncogene, 2008, 27:5975-5987.

Gaj, Thomas, et al., ZFN, TALEN and CRISPR/Cas-based methods for genome engineering, Trends Biotechnol, 2013, 31(7):397-405.

Galili, Uri, Xenotransplantation and ABO incompatible transplantation: The similarities they share, Transfusion and Apheresis Science, 2006, 35:45-58.

Gaudreault, N., et al., Factors affecting the permissiveness of porcine alveolar macrophages for porcine reproductive and respiratory syndrome virus, Arch Virol, 2009, 154:133-136.

Gerrits, Roger J., et al., Perspectives for artificial insemination and genomics to improve global swine populations, Theriogenology, 2005, 63:283-299.

Goryenin, Igor, et al., Applications of Whole Cell and Large Pathway Mathematical Models in the Pharmaceutical Industr Chapter 12, Metabolic Engineering in the Post Genomic Era, Horizon Bioscience, 2004, p. 344.

(56) References Cited

OTHER PUBLICATIONS

Graham, Christopher F., The Fusion of Cells with One- and Two-Cell Mouse Embryos, Wistar Inst Symp Monogt., 1969, 9:19-35.
Graversen, Jonas H., et al., Targeting the Hemoglobin Scavenger receptor CD163 in Macrophages Highly Increases the Anti-Inflammatory Potency of Dexamethasone, Molecular Therapy, Aug. 2012, 20(8):1550-1558.
Groenen, Martien A. M., et al., Analyses of pig genomes provide insight into porcine demography and evolution, Nature, Nov. 15, 2012, 491(7424):393-398.
Hai, Tang et al., One-step generation of knockout pigs by zygote injection of CRISPR/Cas System, Cell Research, 2014, 34:372-375.
Halbur, P.G., et al., Comparison of the Pathogenicity of Two US Porcine Reproductive and Respiratory Syndrome Virus Isolates with that of the Lelystad Virus, Vet Pathol, 1995, 32:648-660.
Hammer, Robert E., et al., Production of transgenic rabbits, sheep and pigs by microinjection, Nature, Jun. 1985, 315:680-683.
Hao, Y.H., et al., Production of endothelial nitric oxide synthase (eNOS) over-expressing piglets, Transgenic Res, 2006, 15:739-750.
Hauschild, Janet, et al., Efficient generation of a biallehc knockout in pigs using zinc-finger nucleases, PNAS, 2011, 108(36):1-6.
Holtkamp, Derald J., et al., Assessment of the economic impact of porcine reproductive and respiratory syndrome virus on United States port producers, J Swine Health and Production, 2013, 21(2):72-84.
Huang, Y.W., et al., Porcine DC-SIGN: Molecular cloning, gene structure, tissue distribution and binding characteristics, Dev and Comparative Immunology, 2009, 33:464-480.
Hwang, Woong Y, et al., Efficient genome editing in zebrafish using a CRISPR-Cas system, Nature Biotechnology, 2013, 31(3):227-229.
Hyder, Salman M., et al., Identification of an Estrogen Response Element in the 3'-Flanking Region of the Murine c-fos Protooncogene, J Biological Chemistry, 1992, 267(25):18047-18054.
Im, Gi-Sun, et al., In vitro development of preimplantation porcine nuclear transfer embryos cultured in different media and gas atmospheres, Theriogenology, 2004, 61:1125-1135.
Jeney, Viktona, et al., Pro-oxidant and cytotoxic effects of circulating heme, 2002, 100(3):879-887.
Kefpaber, Kerry K., Reproductive Failure of Unknown Etiology, 1989, 1(2):1-10.
Kim, Hyongbum and Kim, Jin-Soo, A guide to genome engineering with programmable nucleases, Nature Reviews Genetic, 2014, 15:321-334.
Kim, H.S., et al., Enhanced replication of porcine reproductive and respiratory syndrome (PRRS) virus in a homogeneous subpopulation of MA-104 cell line, Arch Virol, 1993, 133:477-483.
Kim, Jeong-Ki, et al., Defining the Cellular Target(s) of Porcine Reproductive and Respiratory Syndrome Virus Blocking Monoclonal Antibody 7G10, J Virology, 2006, 80(2):689-696.
Kleinjan, Dirk-Jan and Coutinho, Pedro, Cis-ruption mechanisms: disruption of cis-regulatory control as a cause of human genetic disease, Briefings Functional Genomics and Proteomics, 2009, 8(4):317-332.
Kolston, Paul J., Comparing in vitro, in situ, and in vivo experimental data in a three-dimensional model of mammalian cochlear mechanics, Proc Natl Acad Sci, 1999, 96:3676-3681.
Kristiansen, Mette, et al., Identification of the haemoglobin scavenger receptor, Nature, 2001, 409: 198-201.
Kwon, Deug-Nam, et al., Production of biallelic CMP-Neu5Ac hydroxylase knock-out pigs, Scientific Reports, 2013, 3(1981)1-10.
Ladinig, Andrea, et al., Pathogenicity of three type 2 porcine reproductive and respiratory virus strains in experimentally inoculated pregnant gilts, Virus Research, 2015, 203:34-35.
Lager, Kelly M., et al., Evaluation of protective immunity in gilts inoculated with the NADC-8 isolate of porcine reproductive and respiratory syndrome virus (PRRSV) and challenge-exposed with an antigenically distinct PRRSV isolate, AJVR, 1998, 60(8):1022-1027.

Lai, Liangxue, et al., Generation of cloned transgenic pigs rich in omega-3 fatty acids, Nature Biotechnology, 2006, 24(4):435-436.
Lai, Liangxue, et al., Production of α-1,3-Galactosyltransferase Knockout Pigs by Nuclear Transfer Cloning, Science, 2002, 295:1089-1092.
Lai, Liangxue, and Prather, Randall S., Creating genetically modified pigs by using nuclear transfer, Reprod Biol and Endocrinology, 2003, 1(82):1-6.
Lai, Liangxue and Prather, Randall S., Production of Cloned Pigs by Using Somnatic Dells as Donors, Cloning and Stem Cells, 2003, 5(4):233-241.
Lai, Liangxue and Prather, Randall S., A method for Producing Cloned Pigs by Using Somatic Cells as Donors, Methods in Molecular Biology, Germ Cell Protocols, 2004, vol. 2, Ch. 9, pp. 149-163.
Lawson, Stevewn R., et al., Porcine reproductive and respiratory syndrome virus infection of gnotobiotic pigs: sites of virus replication and co-localization with MAC-387 staining at 21 days post-infection, Virus Research, 1997, 51:105-113.
Lee, Kiho, et al., Engraftment of human iPS cells and allogeneic porcine cells into pigs with inactivated RAG2 and accompanying severe combined immunodeficiency, PNAS, 2014, 111(20):7260-7265.
Lee, Kiho, et al., Piglets Produced From Cloned Blastocysts Cultured In Vitro With GM-CSP, Mol Reprod, Dev, 2013, 80(2):145-154.
Li, Dali, et al., Heritable gene targeting in the mouse and rat using CRISPR-Cas system, Nature Biotechnology, 2013, 31(8):681-683.
Li, Rongfeng, et al., Cloned Transgenic Swine Via In Vitro Production and Cryopreservation, Biology of Reprod, 2006, 75:226-230.
Li, Ying and Jaiswal, Anil K., Regulation of Human NAD(P)H:Quinone Oxidereductase Gene, J Biol Chern, 1992, 267(21):15097-15104.
Lillico, Simon G., et al., Live pigs produced from genome edited zygotes, Scientific Reports, 2013, 3:2847-2850.
Loudianos, G., et al., Molecular characterization of disease in the Sardinian population—evidence of a founder effect, Hum Matat, 1999, 14(4):294-303.
Lunney, Joan K. and Chen, Hongbo, Genetic control of host resistance to porcine reproductive and respiratory syndrome virus (PRRSV) infection, Virus Research, 2010, 154:161-169.
Machaty, Zoltan, et al., Complete Activation of Porcine Oocytes Induced by the Sulfhydryl Reagent, Thimerosal, Biol of Reprod, 1997, 57:1123-1127.
Machaty, Zoltan, et al., Development of Early Porcine Embryos In Vitro and In Vivo, Biol of Reprod, 1998, 59:451-455.
Madsen, Mette, et al., Molecular Characterization of the Haptoglobin Hemoglobin Receptor CD163, J Biol Chem, 2004, 279(49):51561-51567.
Mansour, Suzanne L., et al., Disruption of the proto-oncogene int-2 in mouse embryo-derived stem cells: a general strategy for targeting mutations to non-selectable genes, Nature, 1988, 336:348-352.
Mayes, M.A., et al., Parthenogenic Activation of Pig Oocytes by Protein Kinase Inhibition, Biol of Reprod, 1995, 53:270-275.
McGrath, James and Solter, Davor, Nuclear Transplantation in the Mouse Embryo by Microsurgery and Cell Fusion, Science, 1983, 220(4603)1300-1302.
Meng, X.J., Heterogeneity of porcine reproductive and respiratory syndrome virus: implications for current vaccine efficacy and future vaccine development, Veterinary Microbiology, 2000, 74:309-329.
Meng, Xiang-Jin, et al., Sequence comparison of open reading frames 2 to 5 of low and high virulence United States isolates of porcine reproductive and respiratory syndrome virus, J Gen Virology, 1995, 76:3181-3188.
Mengeling, William L., et al., Identification and clinical assessment of suspected vaccine-related field strains of porcine reproductive and respiratory syndrome virus, AJVR, 1999, 60(3):334-340.
Yang, Dongshan, et al., Generation of PPARy mono-allelic knock-out pigs via zinc-finger nucleases and nuclear transfer cloning, Cell Research, 2011, 23:979-982.

(56) References Cited

OTHER PUBLICATIONS

Yoon, In J., et al., Persistent and contact infection in nursery pigs experimentally infected with porcine reproductive and respiratory syndrome (PRRS) virus, Swine Health and Production, 1993, 1(4):5-8.
Yoshioka, Koji, et al., Birth of Piglets Derived from Porcine Zygotes Cultured in a Chemically Defined Medium, Biol of Reprod, 2002, 66:112-119.
Zhang, Qingzhan and Yoo, Dongwan, PRRS virus receptors and their role for pathogenesis, Veterinary Microbiology, 2015, 177:229-241.
Zhao, Jianguo, et al., Histone Deacetylase Inhibitors Improve In Vitro and In Vivo Development Competence of Somatic Cell Nuclear Transfer Porcine Embryos, Cellular Reprogramming, 2010, 12(1):75-83.
Zhao, Jianguo, et al., Significant Improvement in Cloning Efficiency of an Inbred Miniature Pig by Histone Deacetylase Inhibitor Treatment after Somatic Cell Nuclear Transfer, Biology of Reproduction, 2009, 81:525-530.
Abeydeera, L.R. and Day, B.N., Fertilization and subsequent development in vitro of pig oocytes inseminated in a modified tris-buffered medium with frozen-thawed ejaculated spermatozoa, Biol. Reprod., 1997, 57:729-734.
Agung et al., In vitro fertilization and development of porcine oocytes matured in follicular fluid, J Reprod Dev., 2013, 59:103-106.
Alkan, F., et al., CRISPR-Cas9 off-targeting assessment with nucleic acid duplex energy parameters, Genome Biol, 2018, 19:177.
Altschul, S.P., et al., Basic local alignment search tool, J. Mol. Biol., 1990, 215:403-410.
Appeltant et al., Porcine oocyte maturation in vitro: role of cAMP and oocyte-secreted factors—A practical approach, J Reprod Dev., 2016, 62:439-449.
Bae, S., et al., Cas-OFFinder: a fast and versatile algorithm that searches for potential off-target sites of Cas9 RNA-guided endonucleases, Bioinformatics, 2014, 30:1473-1475.
Cameron, P., et al., Mapping the genomic landscape of CRISPR-Cas9 cleavage, Nat Methods 2017, 14:600-606.
Chenna, R., et al., Multiple sequence alignment with the Clustal series of programs, Nucleic Acids Research, 2003, 31:3497-3500.
Fowler et al., The production of pig preimplantation embryos in vitro: Current progress and future prospects, Reprod Biol., 2018, 18:203-211.
Fonfara et al., Phylogeny of Cas9 determines functional exchangeability of dual-RNA and Cas9 among orthologous type II CRISPR-Cas systems, Nucleic Acids Research, 2014, 42:2577-2590.
Gnirke, A., et al., Solution hybrid selection with ultra-long oligonucleotides for massively parallel targeted sequencing, Nat. Biotechnol., 2009, 27:182-189.
Guo, Chunhe, et al., Highly Efficient Generation of Pigs Harboring a Partial Deletion of the CD163 SRCR5 Domain, Which are Fully Resistant to Porcine Reproductive and Respiratory Syndrome Virus 2 Infection, Frontiers in immunology, 2019, 10(1846):1-14.
Haft, Daniel H., et al., A guild of 45 CRISPR-associated (Cas) protein families and multiple CRISPR/Cas subtypes exist in prokaryotic genomes, PLoS Comput. Bio., 2005, 1(6):474-483.
Jinek, M., et al., A programmable dual RNA-guided DNA endonuclease in adaptive bacterial immunity, Science, 2012, 337:816-821.
Joung et al., TALENs: a widely applicable technology for targeted genome editing, Nat. Rev. Mol. Cell. Biol., 2013, 14:49-55.
Kang, Soo Ji, et al., Comparision of Seven Commercial TaqMan Master Mixes and Two Real-Time PCR Platforms Regarding the Rapid Detection of Porcine DNA, Food Sci Anim Resour, 2021, 41(1):85-94.
Karvelis et al., Rapid characterization of CRISPR-Cas9 protospacer adjacent motif sequence elements, Genome Biology, 2015, 16:253.
Larkin Ma et al., Clustal W and Clustal X version 2.0, Bioinformatics, 2007, 23:2947-2948.
Lavitrano et al., Efficient production by sperm-mechiated gene transfer of human decay accelerating factor (hDAF) transgenic pigs for xenotransplantation, Proc. Natl. Acad. Sci. USA, 2002, 99:14230-14236.
Lavitrano et al., Sperm-mediated gene transfer, Reprod. Fert. Develop., 2006, 18:19-23.
Lo, Transformation by iontophoretic microinjection of DNA: multiple integrations without tandem insertions, Mol. Cell Biol., 1983, 3:1803-1814.
Onofre, Gabriela et al., Scavenger receptor CD163 and its biological functions, ACTA MEDICA, 2009, 52:57-61.
Ran, F. A., et al., In vivo genome editing using Staphylococcus aureus Cas9, Nature, 2015, 520:186-191.
Sapranauskas et al., The Streptococcus thermophilus CRISPR/Cas system provides immunity in Escherichia coli, Nucleic Acids Research, 2011, 39:9275-9282.
Shah et al., Protospacer recognition motifs: mixed identities and functional diversity, RNA Biol., 2013, 10:891-899.
Suzuki, C., et al., Effects of amino acid supplements and replacement of polyvinyl alcohol with bovine serum albumin in porcine zygote medium, Reprod. Fertil. Dev., 2006 18:789-795.
Svitashev et al., Genome editing in maize directed by CRISPR-Cas9 ribonucleoprotein complexes, Nature Communications, 2016, 7:113274.
Thompson et al., Germ line transmission and expression of a corrected HPRT gene produced by gene targeting in embryonic stem cells, Cell, 1989, 56:313-321.
Thompson, J.D. and Clustal, W: improving the sensitivity of progressive multiple sequence alignment through sequence weighting, position-specific gap penalties and weight matrix choice et al., Nucleic Acids Research, 1994, 22:4673-4680.
Tsai, S.Q., et al., GUIDE-seq enables genome-wide profiling of off-target cleavage by CRISPR-Cas nucleases, Nat Biotechnol. 2015, 33;187-197.
Tsai, S.Q., et al., CIRCLE-seq: a highly sensitive in vitro screen for genome-wide CRISPR-Cas9 nuclease off-targets, Nat. Methods, 2017, 14;607-614.
Van Der Putten et al., Efficient insertion of genes into the mouse germ line via retroviral vectors, Proc. Natl. Acad. Sci. USA, 1985, 82:6148-1652.
Wakayama et al., Full-term development of mice from emicleated oocytes injected with cumulus cell nuclei, Nature, 1998, 394:369-374.
Wilmut et al., Viable offspring derived from fetal and adult mammalian cells, Nature, 1997, 385:810-813.
Yoshioka, K., et al., Birth of piglets derived from porcine zygotes cultured in a chemically defined medium, Biol. Reprod., 2002, 60:112-119.
Yoshioka, K., Defined System for In Vitro Production of Porcine Embryos Using a Single Basic Medium, J. Reprod. Dev. 2008, 54:208-213.
Yoshioka, K., J., Development and application of a chemically defined medium for the in vitro production of porcine embryos, Reprod Dev., 2011, 57:9-16.
Zetsche et al., Cpf1 is a single RNA-guided endonuclease of a class 2 CRISPR-Cas system, Cell, 2015, 163:759-771.
Zhang et al., Off-target Effects in CRISPR/Cas9-mediated Genome Engineering, Mol Ther Nucleic Acids, 2015, 4:e264.
Zhao, C., et al., CRISPR-offinder: a CRISPR guide RNA design and off-target searching tool for user-defined protospacer adjacent motif, Int. J. Biol. Sci., 2017, 13:1470-1478.

\* cited by examiner

```
                      SEQUENCE LISTING

Sequence total quantity: 564
SEQ ID NO: 1           moltype = DNA  length = 150
FEATURE                Location/Qualifiers
source                 1..150
                       mol_type = other DNA
                       organism = Sus scrofa
SEQUENCE: 1
tttcgcagac tttagaagat gttctgccca tttaagttcc ttcactttttg ctgtagtcgc   60
tgttctcagt gcctgactag ttctcttggt gagtactttg acaaatttac ttgtaaccta  120
gcccactgtg acaagaaaca ctgaaaagca                                    150

SEQ ID NO: 2           moltype = DNA  length = 150
FEATURE                Location/Qualifiers
source                 1..150
                       mol_type = other DNA
                       organism = Sus scrofa
SEQUENCE: 2
tttcgcagac tttagaagat gttctgccca tttaagttcc ttcactttttg ctgtagtcgc   60
tgttctcagt gcctgactag ttctcttggt gagtactttg acaaatttac ttgtaaccta  120
gcccactgtg acaagaaaca ctgaaaagca                                    150

SEQ ID NO: 3           moltype = DNA  length = 150
FEATURE                Location/Qualifiers
source                 1..150
                       mol_type = other DNA
                       organism = Sus scrofa
SEQUENCE: 3
gtggtgaaaa caagtgctct ggaagagtgg aggtgaaagt gcaggaggag tggggaactg   60
tgtgtaataa tggctgacat ggatgtggtc tctgttgttt gtaggcagct gggatgtcca  120
actgctatca aagccactgg atgggctaat                                    150

SEQ ID NO: 4           moltype = DNA  length = 150
FEATURE                Location/Qualifiers
source                 1..150
                       mol_type = other DNA
                       organism = Sus scrofa
SEQUENCE: 4
tggctgggac atggatgtgg tctctgttgt ttgtaggcag ctgggatgtc caactgctat   60
caaagccact ggatgaattt tagtgcaggt tctgacgca tttggatgga tcatgtttct  120
tgtcgaggga atgagtcagc tctctgggac                                    150

SEQ ID NO: 5           moltype = DNA  length = 150
FEATURE                Location/Qualifiers
source                 1..150
                       mol_type = other DNA
                       organism = Sus scrofa
SEQUENCE: 5
gtaggcagct gggatgtcca actgctatca aagccactgg atgggctaat tttagtgcag   60
gttctggacg catttgatgg atcatgtttc ttgtcgaggg aatgagtcag ctctctggga  120
ctgcaaacat gatggatggg gaaagcataa                                    150

SEQ ID NO: 6           moltype = DNA  length = 150
FEATURE                Location/Qualifiers
source                 1..150
                       mol_type = other DNA
                       organism = Sus scrofa
SEQUENCE: 6
taggcagctg ggatgtccaa ctgctatcaa agccactgga tgggctaatt ttagtgcagg   60
ttctggacgc atttgatgga tcatgtttct tgtcgaggga atgagtcagc tctctgggac  120
tgcaaacatg atggatgggg aaagcataac                                    150

SEQ ID NO: 7           moltype = DNA  length = 150
FEATURE                Location/Qualifiers
source                 1..150
```

```
                              mol_type = other DNA
                              organism = Sus scrofa
SEQUENCE: 7
gtccaactgc tatcaaagcc actggatggg ctaattttag tgcaggttct ggacgcattt      60
ggatggatca tgtttgaggg aatgagtcag ctctctggga ctgcaaacat gatggatggg    120
gaaagcataa ctgtactcac caacaggatg                                      150

SEQ ID NO: 8                  moltype = DNA   length = 150
FEATURE                       Location/Qualifiers
source                        1..150
                              mol_type = other DNA
                              organism = Sus scrofa
SEQUENCE: 8
ctggacgcat ttggatggat catgtttctt gtcgagggaa tgagtcagct ctctgggact      60
gcaaacatga tggatgaaag cataactgta ctcaccaaca ggatgctgga gtaacctgct    120
caggtaagac atacacaaat aagtcaagcc                                      150

SEQ ID NO: 9                  moltype = DNA   length = 150
FEATURE                       Location/Qualifiers
source                        1..150
                              mol_type = other DNA
                              organism = Sus scrofa
SEQUENCE: 9
tggacgcatt tggatggatc atgtttcttg tcgagggaat gagtcagctc tctgggactg      60
caaacatgat ggatgaaagc ataactgtac tcaccaacag gatgctggag taacctgctc    120
aggtaagaca tacacaaata agtcaagcct                                      150

SEQ ID NO: 10                 moltype = DNA   length = 150
FEATURE                       Location/Qualifiers
source                        1..150
                              mol_type = other DNA
                              organism = Sus scrofa
SEQUENCE: 10
ctctagatgg atctgattta gagatgaggc tggtgaatgg aggaaaccgg tgcttaggaa      60
gaatagaagt caaataagga cggtggggaa cagtgtgtga tgataacttc aacataaatc    120
atgcttctgt ggtttgtaaa caacttgaat                                      150

SEQ ID NO: 11                 moltype = DNA   length = 150
FEATURE                       Location/Qualifiers
source                        1..150
                              mol_type = other DNA
                              organism = Sus scrofa
SEQUENCE: 11
cttctgtggt ttgtaaacaa cttgaatgtg gaagtgctgt cagtttctct ggttcagcta      60
attttggaga aggttgacca atctggtttg atgatcttgt atgcaatgga aatgagtcag    120
ctctctggaa ctgcaaacat gaaggatggg                                      150

SEQ ID NO: 12                 moltype = DNA   length = 150
FEATURE                       Location/Qualifiers
source                        1..150
                              mol_type = other DNA
                              organism = Sus scrofa
SEQUENCE: 12
tgatgatctt gtatgcaatg gaaatgagtc agctctctgg aactgcaaac atgaaggatg      60
gggaaagcac aattgatgct gaggatgctg gagtgatttc ttaagtaagg actgacctg    120
ggtttgttct gttctccatg agagggcaaa                                      150

SEQ ID NO: 13                 moltype = DNA   length = 150
FEATURE                       Location/Qualifiers
source                        1..150
                              mol_type = other DNA
                              organism = Sus scrofa
SEQUENCE: 13
agacacgtgg ggcaccgtct gtgattctga cttctctctg gaggcggcca gcgtgctgtg      60
cagggaacta cagtgactgt ggtttccctc ctggggggag ctcactttgg agaaggaagt    120
ggacagatct gggctgaaga attccagtgt                                      150

SEQ ID NO: 14                 moltype = DNA   length = 150
FEATURE                       Location/Qualifiers
source                        1..150
                              mol_type = genomic DNA
                              organism = Sus scrofa
SEQUENCE: 14
agaagatgtt ctgccccattt aagttccttc acttttgctg tagtcgctgt tctcagtgcc      60
tgcttggtca ctagttcttg gtgagtactt tgacaaattt acttgtaacc tagcccactg    120
tgacaagaaa cactgaaaag caaataattc                                      150

SEQ ID NO: 15                 moltype = DNA   length = 150
FEATURE                       Location/Qualifiers
```

```
source                    1..150
                          mol_type = genomic DNA
                          organism = Sus scrofa
SEQUENCE: 15
gactttagaa gatgttctgc ccatttaagt tccttcactt tgctgtagt cgctgttctc    60
agtgcctgct tggtcacttg taacctagcc cactgtgaca agaaacactg aaaagcaaat   120
aattctcctg aagtctagat agcatctaaa                                    150

SEQ ID NO: 16             moltype = DNA  length = 150
FEATURE                   Location/Qualifiers
source                    1..150
                          mol_type = genomic DNA
                          organism = Sus scrofa
SEQUENCE: 16
gaagatgttc tgcccattta agttccttca cttttgctgt agtcgctgtt ctcagtgcct    60
gcttggtcac tagttctctc ttggtgagta ctttgacaaa tttacttgta acctagccca   120
ctgtgacaag aaacactgaa aagcaaataa                                    150

SEQ ID NO: 17             moltype = DNA  length = 150
FEATURE                   Location/Qualifiers
source                    1..150
                          mol_type = genomic DNA
                          organism = Sus scrofa
SEQUENCE: 17
tttcgcagac tttagaagat gttctgccca tttaagttcc ttcacttttg ctgtagtcgc    60
tgttctcagt gcctgcttgg tgagtacttt gacaaattta cttgtaacct agcccactgt   120
gacaagaaac actgaaaagc aaataattct                                    150

SEQ ID NO: 18             moltype = DNA  length = 150
FEATURE                   Location/Qualifiers
source                    1..150
                          mol_type = genomic DNA
                          organism = Sus scrofa
SEQUENCE: 18
tagaagatgt tctgcccatt taagttcctt cactttgct gtagtcgctg ttctcagtgc     60
ctgcttggtc actaggagta ctttgacaaa tttacttgta acctagccca ctgtgacaag   120
aaacactgaa aagcaaataa ttctcctgaa                                    150

SEQ ID NO: 19             moltype = DNA  length = 82
FEATURE                   Location/Qualifiers
source                    1..82
                          mol_type = other DNA
                          organism = Sus scrofa
SEQUENCE: 19
gttttagagc tagaaatagc aagttaaaat aaggctagtc cgttatcaac ttgaaaaagt    60
ggcaccgagt cggtgctttt tt                                             82

SEQ ID NO: 20             moltype = AA  length = 1380
FEATURE                   Location/Qualifiers
source                    1..1380
                          mol_type = protein
                          organism = Streptococcus pyogenes
SEQUENCE: 20
GMDKKYSIGL DIGTNSVGWA VITDEYKVPS KKFKVLGNTD RHSIKKNLIG ALLFDSGETA    60
EATRLKRTAR RRYTRRKNRI CYLQEIFSNE MAKVDDSFFH RLEESFLVEE DKKHERHPIF   120
GNIVDEVAYH EKYPTIYHLR KKLVDSTDKA DLRLIYLALA HMIKFRGHFL IEGDLNPDNS   180
DVDKLFIQLV QTYNQLFEEN PINASGVDAK AILSARLSKS RRLENLIAQL PGEKKNGLFG   240
NLIALSLGLT PNFKSNFDLA EDAKLQLSKD TYDDDLDNLL AQIGDQYADL FLAAKNLSDA   300
ILLSDILRVN TEITKAPLSA SMIKRYDEHH QDLTLLKAVR RQQLPEKYKE IFFDQSKNGY   360
AGYIDGGASQ EEFYKFIKPI LEKMDGTEEL LVKLNREDLL RKQRTFDNGS IPHQIHLGEL   420
HAILRRQEDF YPFLKDNREK IEKILTFRIP YYVGPLARGN SRFAWMTRKS EETITPWNFE   480
EVVDKGASAQ SFIERMTNFD KNLPNEKVLP KHSLLYEYFT VYNELTKVKY VTEGMRKPAF   540
LSGEQKKAIV DLLFKTNRKV TVKQLKEDYF KKIECFDSVE ISGVEDRFNA SLGTYHDLLK   600
IIKDKDFLDN EENEDILEDI VLTLTLFEDR EMIEERLKTY AHLFDDKVMK QLKRRRYTGW   660
GRLSRKLING IRDKQSGKTI LDFLKSDGFA NRNFMQLIHD DSLTFKEDIQ KAQVSGQGDS   720
LHEHIANLAG SPAIKKGILQ TVKVVDELVK VMGRHKPENI VIEMARENQT TQKGQKNSRE   780
RMKRIEEGIK ELGSQILKEH PVENTQLQNE KLYLYYLQNG RDMYVDQELD INRLSDYDVD   840
HIVPQSFLKD DSIDNKVLTR SDKNRGKSDN VPSEEVVKKM KNYWRQLLNA KLITQRKFDN   900
LTKAERGGLS ELDKAGFIKR QLVETRQITK HVAQILDSRM NTKYDENDKL IREVKVITLK   960
SKLVSDFRKD FQFYKVREIN NYHHAHDAYL NAVVGTALIK KYPKLESEFV YGDYKVYDVR  1020
KMIAKSEQEI GKATAKYFFY SNIMNFFKTE ITLANGEIRK RPLIETNGET GEIVWDKGRD  1080
FATVRKVLSM PQVNIVKKTE VQTGGFSKES ILPKRNSDKL IARKKDWDPK KYGGFDSPTV  1140
AYSVLVVAKV EKGKSKKLKS VKELLGITIM ERSSFEKNPI DFLEAKGYKE VKKDLIIKLP  1200
KYSLFELENG RKRMLASAGE LQKGNELALP SKYVNFLYLA SHYEKLKGSP EDNEQKQLFV  1260
EQHKHYLDEI IEQISEFSKR VILADANLDK VLSAYNKHRD KPIREQAENI IHLFTLTNLG  1320
APAAFKYFDT TIDRKRYTST KEVLDATLIH QSITGLYETR IDLSQLGGDG SGSPKKKRKV  1380

SEQ ID NO: 21             moltype = AA  length = 1400
FEATURE                   Location/Qualifiers
```

```
source                          1..1400
                                mol_type = protein
                                organism = Streptococcus thermophilus
SEQUENCE: 21
SNAMTKPYSI GLDIGTNSVG WAVITDNYKV PSKKMKVLGN TSKKYIKKNL LGVLLFDSGI     60
TAEGRRLKRT ARRRYTRRRN RILYLQEIFS TEMATLDDAF FQRLDDSFLV PDDKRDSKYP    120
IFGNLVEEKV YHDEFPTIYH LRKYLADSTK KADLRLVYLA LAHMIKYRGH FLIEGEFNSK    180
NNDIQKNFQD FLDTYNAIFE SDLSLENSKQ LEEIVKDKIS KLEKKDRILK LFPGEKNSGI    240
FSEFLKLIVG NQADFRKCFN LDEKASLHFS KESYDEDLET LLGYIGDDYS DVFLKAKKLY    300
DAILLSGFLT VTDNETEAPL SSAMIKRYNE HKEDLALLKE YIRNISLKTY NEVFKDDTKN    360
GYAGYIDGKT NQEDFYVYLK NLLAEFEGAD YFLEKIDRED FLRKQRTFDN GSIPYQIHLQ    420
EMRAILDKQA KFYPFLAKNK ERIEKILTFR IPYYVGPLAR GNSDFAWSIR KRNEKITPWN    480
FEDVIDKESS AEAFINRMTS FDLYLPEEKV LPKHSLLYET FNVYNELTKV RFIAESMRDY    540
QFLDSKQKKD IVRLYFKDKR KVTDKDIIEY LHAIYGYDGI ELKGIEKQFN SSLSTYHDLL    600
NIINDKEFLD DSSNEAIIEE IIHTLTIFED REMIKQRLSK FENIFDKSVL KKLSRRHYTG    660
WGKLSAKLIN GIRDEKSGNT ILDYLIDDGI SNRNFMQLIH DDALSFKKKI QKAQIIGDED    720
KGNIKEVVKS LPGSPAIKKG ILQSIKIVDE LVKVMGGRKP ESIVVEMARE NQYTNQGKSN    780
SQQRLKRLEK SLKELGSKIL KENIPAKLSK IDNNALQNDR LYLYYLQNGK DMYTGDDLDI    840
DRLSNYDIDH IIPQAFLKDN SIDNKVLVSS ASNRGKSDDF PSLEVVKKRK TFWYQLLKSK    900
LISQRKFDNL TKAERGGLLP EDKAGFIQRQ LVETRQITKH VARLLDEKFN NKKDENNRAV    960
RTVKIITLKS TLVSQFRKDF ELYKVREIND FHHAHDAYLN AVIASALLKK YPKLEPEFVY   1020
GDYPKYNSFR ERKSATEKVY FYSNIMNIFK KSISLADGRV IERPLIEVNE ETGESVWNKE   1080
SDLATVRRVL SYPQVNVVKK VEEQNHGLDR GKPKGLFNAN LSSKPKPNSN ENLVGAKEYL   1140
DPKKYGGYAG ISNSFAVLVK GTIEKGAKKK ITNVLEFQGI SILDRINYRK DKLNFLLEKG   1200
YKDIELIIEL PKYSLFELSD GSRRMLASIL STNNKRGEIH KGNQIFLSQK FVKLLYHAKR   1260
ISNTINENHR KYVENHKKEF EELFYYILEF NENYVGAKKN GKLLNSAFQS WQNHSIDELC   1320
SSFIGPTGSE RKGLFELTSR GSAADFEFLG VKIPRYRDYT PSSLLKDATL IHQSVTGLYE   1380
TRIDLAKLGE GGSPKKKRKV                                              1400

SEQ ID NO: 22           moltype = DNA  length = 23
FEATURE                 Location/Qualifiers
source                  1..23
                        mol_type = other DNA
                        organism = Sus scrofa
SEQUENCE: 22
gaagcctttc tgtattttg tgg                                              23

SEQ ID NO: 23           moltype = DNA  length = 23
FEATURE                 Location/Qualifiers
source                  1..23
                        mol_type = other DNA
                        organism = Sus scrofa
SEQUENCE: 23
atgattttta gaattcttag tgg                                             23

SEQ ID NO: 24           moltype = DNA  length = 23
FEATURE                 Location/Qualifiers
source                  1..23
                        mol_type = other DNA
                        organism = Sus scrofa
SEQUENCE: 24
tcttagtggt tctcttcttc agg                                             23

SEQ ID NO: 25           moltype = DNA  length = 25
FEATURE                 Location/Qualifiers
source                  1..25
                        mol_type = other DNA
                        organism = Sus scrofa
SEQUENCE: 25
tcttagtggt tctcttcttc aggag                                           25

SEQ ID NO: 26           moltype = DNA  length = 23
FEATURE                 Location/Qualifiers
source                  1..23
                        mol_type = other DNA
                        organism = Sus scrofa
SEQUENCE: 26
ttcttcagga gaacatttct agg                                             23

SEQ ID NO: 27           moltype = DNA  length = 23
FEATURE                 Location/Qualifiers
source                  1..23
                        mol_type = other DNA
                        organism = Sus scrofa
SEQUENCE: 27
tcttcaggag aacatttcta ggg                                             23

SEQ ID NO: 28           moltype = DNA  length = 23
FEATURE                 Location/Qualifiers
```

```
source                      1..23
                            mol_type = other DNA
                            organism = Sus scrofa
SEQUENCE: 28
ataatacaag aagatttaaa tgg                                                  23

SEQ ID NO: 29               moltype = DNA   length = 23
FEATURE                     Location/Qualifiers
source                      1..23
                            mol_type = other DNA
                            organism = Sus scrofa
SEQUENCE: 29
atttaaatgg cataaaacct tgg                                                  23

SEQ ID NO: 30               moltype = DNA   length = 23
FEATURE                     Location/Qualifiers
source                      1..23
                            mol_type = other DNA
                            organism = Sus scrofa
SEQUENCE: 30
aatggcataa aaccttggaa tgg                                                  23

SEQ ID NO: 31               moltype = DNA   length = 23
FEATURE                     Location/Qualifiers
source                      1..23
                            mol_type = other DNA
                            organism = Sus scrofa
SEQUENCE: 31
ttctgagttt gtccattcca agg                                                  23

SEQ ID NO: 32               moltype = DNA   length = 23
FEATURE                     Location/Qualifiers
source                      1..23
                            mol_type = other DNA
                            organism = Sus scrofa
SEQUENCE: 32
tggaatggac aaactcagaa tgg                                                  23

SEQ ID NO: 33               moltype = DNA   length = 25
FEATURE                     Location/Qualifiers
source                      1..25
                            mol_type = other DNA
                            organism = Sus scrofa
SEQUENCE: 33
tggaatggac aaactcagaa tggtg                                                25

SEQ ID NO: 34               moltype = DNA   length = 23
FEATURE                     Location/Qualifiers
source                      1..23
                            mol_type = other DNA
                            organism = Sus scrofa
SEQUENCE: 34
atggtgctac atgaaaactc tgg                                                  23

SEQ ID NO: 35               moltype = DNA   length = 23
FEATURE                     Location/Qualifiers
source                      1..23
                            mol_type = other DNA
                            organism = Sus scrofa
SEQUENCE: 35
catgaaaact ctggatctgc agg                                                  23

SEQ ID NO: 36               moltype = DNA   length = 23
FEATURE                     Location/Qualifiers
source                      1..23
                            mol_type = other DNA
                            organism = Sus scrofa
SEQUENCE: 36
aaaagtgaag gaacttaaat ggg                                                  23

SEQ ID NO: 37               moltype = DNA   length = 23
FEATURE                     Location/Qualifiers
source                      1..23
                            mol_type = other DNA
                            organism = Sus scrofa
SEQUENCE: 37
caaaagtgaa ggaacttaaa tgg                                                  23

SEQ ID NO: 38               moltype = DNA   length = 23
```

```
FEATURE                 Location/Qualifiers
source                  1..23
                        mol_type = other DNA
                        organism = Sus scrofa
SEQUENCE: 38
agcgactaca gcaaaagtga agg                                               23

SEQ ID NO: 39           moltype = DNA   length = 23
FEATURE                 Location/Qualifiers
source                  1..23
                        mol_type = other DNA
                        organism = Sus scrofa
SEQUENCE: 39
cgctgttctc agtgcctgct tgg                                               23

SEQ ID NO: 40           moltype = DNA   length = 23
FEATURE                 Location/Qualifiers
source                  1..23
                        mol_type = other DNA
                        organism = Sus scrofa
SEQUENCE: 40
aagagaacta gtgaccaagc agg                                               23

SEQ ID NO: 41           moltype = DNA   length = 23
FEATURE                 Location/Qualifiers
source                  1..23
                        mol_type = other DNA
                        organism = Sus scrofa
SEQUENCE: 41
tgcttggtca ctagttctct tgg                                               23

SEQ ID NO: 42           moltype = DNA   length = 25
FEATURE                 Location/Qualifiers
source                  1..25
                        mol_type = other DNA
                        organism = Sus scrofa
SEQUENCE: 42
tgcttggtca ctagttctct tggtg                                             25

SEQ ID NO: 43           moltype = DNA   length = 23
FEATURE                 Location/Qualifiers
source                  1..23
                        mol_type = other DNA
                        organism = Sus scrofa
SEQUENCE: 43
tgttacagga ggaaaagaca agg                                               23

SEQ ID NO: 44           moltype = DNA   length = 25
FEATURE                 Location/Qualifiers
source                  1..25
                        mol_type = other DNA
                        organism = Sus scrofa
SEQUENCE: 44
tgttacagga ggaaaagaca aggag                                             25

SEQ ID NO: 45           moltype = DNA   length = 23
FEATURE                 Location/Qualifiers
source                  1..23
                        mol_type = other DNA
                        organism = Sus scrofa
SEQUENCE: 45
gaggaaaaga caaggagctg agg                                               23

SEQ ID NO: 46           moltype = DNA   length = 23
FEATURE                 Location/Qualifiers
source                  1..23
                        mol_type = other DNA
                        organism = Sus scrofa
SEQUENCE: 46
agacaaggag ctgaggctaa cgg                                               23

SEQ ID NO: 47           moltype = DNA   length = 23
FEATURE                 Location/Qualifiers
source                  1..23
                        mol_type = other DNA
                        organism = Sus scrofa
SEQUENCE: 47
gacaaggagc tgaggctaac ggg                                               23
```

```
SEQ ID NO: 48          moltype = DNA    length = 25
FEATURE                Location/Qualifiers
source                 1..25
                       mol_type = other DNA
                       organism = Sus scrofa
SEQUENCE: 48
gacaaggagc tgaggctaac gggtg                                              25

SEQ ID NO: 49          moltype = DNA    length = 23
FEATURE                Location/Qualifiers
source                 1..23
                       mol_type = other DNA
                       organism = Sus scrofa
SEQUENCE: 49
aaggagctga ggctaacggg tgg                                                23

SEQ ID NO: 50          moltype = DNA    length = 25
FEATURE                Location/Qualifiers
source                 1..25
                       mol_type = other DNA
                       organism = Sus scrofa
SEQUENCE: 50
aaggagctga ggctaacggg tggtg                                              25

SEQ ID NO: 51          moltype = DNA    length = 23
FEATURE                Location/Qualifiers
source                 1..23
                       mol_type = other DNA
                       organism = Sus scrofa
SEQUENCE: 51
ggtggtgaaa acaagtgctc tgg                                                23

SEQ ID NO: 52          moltype = DNA    length = 23
FEATURE                Location/Qualifiers
source                 1..23
                       mol_type = other DNA
                       organism = Sus scrofa
SEQUENCE: 52
aaacaagtgc tctggaagag tgg                                                23

SEQ ID NO: 53          moltype = DNA    length = 25
FEATURE                Location/Qualifiers
source                 1..25
                       mol_type = other DNA
                       organism = Sus scrofa
SEQUENCE: 53
aaacaagtgc tctggaagag tggag                                              25

SEQ ID NO: 54          moltype = DNA    length = 23
FEATURE                Location/Qualifiers
source                 1..23
                       mol_type = other DNA
                       organism = Sus scrofa
SEQUENCE: 54
caagtgctct ggaagagtgg agg                                                23

SEQ ID NO: 55          moltype = DNA    length = 25
FEATURE                Location/Qualifiers
source                 1..25
                       mol_type = other DNA
                       organism = Sus scrofa
SEQUENCE: 55
caagtgctct ggaagagtgg aggtg                                              25

SEQ ID NO: 56          moltype = DNA    length = 23
FEATURE                Location/Qualifiers
source                 1..23
                       mol_type = other DNA
                       organism = Sus scrofa
SEQUENCE: 56
aagagtggag gtgaaagtgc agg                                                23

SEQ ID NO: 57          moltype = DNA    length = 25
FEATURE                Location/Qualifiers
source                 1..25
                       mol_type = other DNA
                       organism = Sus scrofa
SEQUENCE: 57
aagagtggag gtgaaagtgc aggag                                              25
```

```
SEQ ID NO: 58          moltype = DNA  length = 23
FEATURE                Location/Qualifiers
source                 1..23
                       mol_type = other DNA
                       organism = Sus scrofa
SEQUENCE: 58
agtggaggtg aaagtgcagg agg                                              23

SEQ ID NO: 59          moltype = DNA  length = 25
FEATURE                Location/Qualifiers
source                 1..25
                       mol_type = other DNA
                       organism = Sus scrofa
SEQUENCE: 59
agtggaggtg aaagtgcagg aggag                                            25

SEQ ID NO: 60          moltype = DNA  length = 23
FEATURE                Location/Qualifiers
source                 1..23
                       mol_type = other DNA
                       organism = Sus scrofa
SEQUENCE: 60
aggtgaaagt gcaggaggag tgg                                              23

SEQ ID NO: 61          moltype = DNA  length = 25
FEATURE                Location/Qualifiers
source                 1..25
                       mol_type = other DNA
                       organism = Sus scrofa
SEQUENCE: 61
aggtgaaagt gcaggaggag tgggg                                            25

SEQ ID NO: 62          moltype = DNA  length = 23
FEATURE                Location/Qualifiers
source                 1..23
                       mol_type = other DNA
                       organism = Sus scrofa
SEQUENCE: 62
ggtgaaagtg caggaggagt ggg                                              23

SEQ ID NO: 63          moltype = DNA  length = 23
FEATURE                Location/Qualifiers
source                 1..23
                       mol_type = other DNA
                       organism = Sus scrofa
SEQUENCE: 63
gtgaaagtgc aggaggagtg ggg                                              23

SEQ ID NO: 64          moltype = DNA  length = 23
FEATURE                Location/Qualifiers
source                 1..23
                       mol_type = other DNA
                       organism = Sus scrofa
SEQUENCE: 64
tggggaactg tgtgtaataa tgg                                              23

SEQ ID NO: 65          moltype = DNA  length = 23
FEATURE                Location/Qualifiers
source                 1..23
                       mol_type = other DNA
                       organism = Sus scrofa
SEQUENCE: 65
gaactgtgtg taataatggc tgg                                              23

SEQ ID NO: 66          moltype = DNA  length = 23
FEATURE                Location/Qualifiers
source                 1..23
                       mol_type = other DNA
                       organism = Sus scrofa
SEQUENCE: 66
aactgtgtgt aataatggct ggg                                              23

SEQ ID NO: 67          moltype = DNA  length = 23
FEATURE                Location/Qualifiers
source                 1..23
                       mol_type = other DNA
                       organism = Sus scrofa
SEQUENCE: 67
```

```
gtgtaataat ggctgggaca tgg                                              23

SEQ ID NO: 68            moltype = DNA   length = 23
FEATURE                  Location/Qualifiers
source                   1..23
                         mol_type = other DNA
                         organism = Sus scrofa
SEQUENCE: 68
taatggctgg gacatggatg tgg                                              23

SEQ ID NO: 69            moltype = DNA   length = 23
FEATURE                  Location/Qualifiers
source                   1..23
                         mol_type = other DNA
                         organism = Sus scrofa
SEQUENCE: 69
atgtggtctc tgttgtttgt agg                                              23

SEQ ID NO: 70            moltype = DNA   length = 23
FEATURE                  Location/Qualifiers
source                   1..23
                         mol_type = other DNA
                         organism = Sus scrofa
SEQUENCE: 70
ctctgttgtt tgtaggcagc tgg                                              23

SEQ ID NO: 71            moltype = DNA   length = 23
FEATURE                  Location/Qualifiers
source                   1..23
                         mol_type = other DNA
                         organism = Sus scrofa
SEQUENCE: 71
tctgttgttt gtaggcagct ggg                                              23

SEQ ID NO: 72            moltype = DNA   length = 23
FEATURE                  Location/Qualifiers
source                   1..23
                         mol_type = other DNA
                         organism = Sus scrofa
SEQUENCE: 72
ccagtggctt tgatagcagt tgg                                              23

SEQ ID NO: 73            moltype = DNA   length = 23
FEATURE                  Location/Qualifiers
source                   1..23
                         mol_type = other DNA
                         organism = Sus scrofa
SEQUENCE: 73
ccaactgcta tcaaagccac tgg                                              23

SEQ ID NO: 74            moltype = DNA   length = 23
FEATURE                  Location/Qualifiers
source                   1..23
                         mol_type = other DNA
                         organism = Sus scrofa
SEQUENCE: 74
ctgctatcaa agccactgga tgg                                              23

SEQ ID NO: 75            moltype = DNA   length = 23
FEATURE                  Location/Qualifiers
source                   1..23
                         mol_type = other DNA
                         organism = Sus scrofa
SEQUENCE: 75
tgctatcaaa gccactggat ggg                                              23

SEQ ID NO: 76            moltype = DNA   length = 23
FEATURE                  Location/Qualifiers
source                   1..23
                         mol_type = other DNA
                         organism = Sus scrofa
SEQUENCE: 76
actaaaatta gcccatccag tgg                                              23

SEQ ID NO: 77            moltype = DNA   length = 23
FEATURE                  Location/Qualifiers
source                   1..23
                         mol_type = other DNA
                         organism = Sus scrofa
```

```
SEQUENCE: 77
ggatgggcta attttagtgc agg                                               23

SEQ ID NO: 78            moltype = DNA   length = 23
FEATURE                  Location/Qualifiers
source                   1..23
                         mol_type = other DNA
                         organism = Sus scrofa
SEQUENCE: 78
gctaatttta gtgcaggttc tgg                                               23

SEQ ID NO: 79            moltype = DNA   length = 23
FEATURE                  Location/Qualifiers
source                   1..23
                         mol_type = other DNA
                         organism = Sus scrofa
SEQUENCE: 79
gtgcaggttc tggacgcatt tgg                                               23

SEQ ID NO: 80            moltype = DNA   length = 23
FEATURE                  Location/Qualifiers
source                   1..23
                         mol_type = other DNA
                         organism = Sus scrofa
SEQUENCE: 80
aggttctgga cgcatttgga tgg                                               23

SEQ ID NO: 81            moltype = DNA   length = 23
FEATURE                  Location/Qualifiers
source                   1..23
                         mol_type = other DNA
                         organism = Sus scrofa
SEQUENCE: 81
atggatcatg tttcttgtcg agg                                               23

SEQ ID NO: 82            moltype = DNA   length = 23
FEATURE                  Location/Qualifiers
source                   1..23
                         mol_type = other DNA
                         organism = Sus scrofa
SEQUENCE: 82
tggatcatgt ttcttgtcga ggg                                               23

SEQ ID NO: 83            moltype = DNA   length = 23
FEATURE                  Location/Qualifiers
source                   1..23
                         mol_type = other DNA
                         organism = Sus scrofa
SEQUENCE: 83
gagggaatga gtcagctctc tgg                                               23

SEQ ID NO: 84            moltype = DNA   length = 23
FEATURE                  Location/Qualifiers
source                   1..23
                         mol_type = other DNA
                         organism = Sus scrofa
SEQUENCE: 84
agggaatgag tcagctctct ggg                                               23

SEQ ID NO: 85            moltype = DNA   length = 23
FEATURE                  Location/Qualifiers
source                   1..23
                         mol_type = other DNA
                         organism = Sus scrofa
SEQUENCE: 85
ctctgggact gcaaacatga tgg                                               23

SEQ ID NO: 86            moltype = DNA   length = 23
FEATURE                  Location/Qualifiers
source                   1..23
                         mol_type = other DNA
                         organism = Sus scrofa
SEQUENCE: 86
gggactgcaa acatgatgga tgg                                               23

SEQ ID NO: 87            moltype = DNA   length = 25
FEATURE                  Location/Qualifiers
source                   1..25
                         mol_type = other DNA
```

```
                            organism = Sus scrofa
SEQUENCE: 87
gggactgcaa acatgatgga tgggg                                              25

SEQ ID NO: 88           moltype = DNA   length = 23
FEATURE                 Location/Qualifiers
source                  1..23
                        mol_type = other DNA
                        organism = Sus scrofa
SEQUENCE: 88
ggactgcaaa catgatggat ggg                                                23

SEQ ID NO: 89           moltype = DNA   length = 23
FEATURE                 Location/Qualifiers
source                  1..23
                        mol_type = other DNA
                        organism = Sus scrofa
SEQUENCE: 89
gactgcaaac atgatggatg ggg                                                23

SEQ ID NO: 90           moltype = DNA   length = 23
FEATURE                 Location/Qualifiers
source                  1..23
                        mol_type = other DNA
                        organism = Sus scrofa
SEQUENCE: 90
gcataactgt actcaccaac agg                                                23

SEQ ID NO: 91           moltype = DNA   length = 23
FEATURE                 Location/Qualifiers
source                  1..23
                        mol_type = other DNA
                        organism = Sus scrofa
SEQUENCE: 91
tgtactcacc aacaggatgc tgg                                                23

SEQ ID NO: 92           moltype = DNA   length = 25
FEATURE                 Location/Qualifiers
source                  1..25
                        mol_type = other DNA
                        organism = Sus scrofa
SEQUENCE: 92
tgtactcacc aacaggatgc tggag                                              25

SEQ ID NO: 93           moltype = DNA   length = 25
FEATURE                 Location/Qualifiers
source                  1..25
                        mol_type = other DNA
                        organism = Sus scrofa
SEQUENCE: 93
aggttactcc agcatcctgt tggtg                                              25

SEQ ID NO: 94           moltype = DNA   length = 23
FEATURE                 Location/Qualifiers
source                  1..23
                        mol_type = other DNA
                        organism = Sus scrofa
SEQUENCE: 94
aggttactcc agcatcctgt tgg                                                23

SEQ ID NO: 95           moltype = DNA   length = 23
FEATURE                 Location/Qualifiers
source                  1..23
                        mol_type = other DNA
                        organism = Sus scrofa
SEQUENCE: 95
gatgctggag taacctgctc agg                                                23

SEQ ID NO: 96           moltype = DNA   length = 23
FEATURE                 Location/Qualifiers
source                  1..23
                        mol_type = other DNA
                        organism = Sus scrofa
SEQUENCE: 96
tgtgtatgtc ttacctgagc agg                                                23

SEQ ID NO: 97           moltype = DNA   length = 23
FEATURE                 Location/Qualifiers
source                  1..23
```

```
                            mol_type = other DNA
                            organism = Sus scrofa
SEQUENCE: 97
atggatctga tttagagatg agg                                           23

SEQ ID NO: 98              moltype = DNA   length = 23
FEATURE                    Location/Qualifiers
source                     1..23
                           mol_type = other DNA
                           organism = Sus scrofa
SEQUENCE: 98
atctgattta gagatgaggc tgg                                           23

SEQ ID NO: 99              moltype = DNA   length = 25
FEATURE                    Location/Qualifiers
source                     1..25
                           mol_type = other DNA
                           organism = Sus scrofa
SEQUENCE: 99
atctgattta gagatgaggc tggtg                                         25

SEQ ID NO: 100             moltype = DNA   length = 23
FEATURE                    Location/Qualifiers
source                     1..23
                           mol_type = other DNA
                           organism = Sus scrofa
SEQUENCE: 100
ttagagatga ggctggtgaa tgg                                           23

SEQ ID NO: 101             moltype = DNA   length = 25
FEATURE                    Location/Qualifiers
source                     1..25
                           mol_type = other DNA
                           organism = Sus scrofa
SEQUENCE: 101
ttagagatga ggctggtgaa tggag                                         25

SEQ ID NO: 102             moltype = DNA   length = 23
FEATURE                    Location/Qualifiers
source                     1..23
                           mol_type = other DNA
                           organism = Sus scrofa
SEQUENCE: 102
gagatgaggc tggtgaatgg agg                                           23

SEQ ID NO: 103             moltype = DNA   length = 23
FEATURE                    Location/Qualifiers
source                     1..23
                           mol_type = other DNA
                           organism = Sus scrofa
SEQUENCE: 103
ggctggtgaa tggaggaaac cgg                                           23

SEQ ID NO: 104             moltype = DNA   length = 25
FEATURE                    Location/Qualifiers
source                     1..25
                           mol_type = other DNA
                           organism = Sus scrofa
SEQUENCE: 104
ggctggtgaa tggaggaaac cggtg                                         25

SEQ ID NO: 105             moltype = DNA   length = 23
FEATURE                    Location/Qualifiers
source                     1..23
                           mol_type = other DNA
                           organism = Sus scrofa
SEQUENCE: 105
aatggaggaa accggtgctt agg                                           23

SEQ ID NO: 106             moltype = DNA   length = 23
FEATURE                    Location/Qualifiers
source                     1..23
                           mol_type = other DNA
                           organism = Sus scrofa
SEQUENCE: 106
cttctattct tcctaagcac cgg                                           23

SEQ ID NO: 107             moltype = DNA   length = 23
FEATURE                    Location/Qualifiers
```

```
source                    1..23
                          mol_type = other DNA
                          organism = Sus scrofa
SEQUENCE: 107
agaatagaag tcaaatttca agg                                              23

SEQ ID NO: 108            moltype = DNA   length = 23
FEATURE                   Location/Qualifiers
source                    1..23
                          mol_type = other DNA
                          organism = Sus scrofa
SEQUENCE: 108
tagaagtcaa atttcaagga cgg                                              23

SEQ ID NO: 109            moltype = DNA   length = 25
FEATURE                   Location/Qualifiers
source                    1..25
                          mol_type = other DNA
                          organism = Sus scrofa
SEQUENCE: 109
tagaagtcaa atttcaagga cggtg                                            25

SEQ ID NO: 110            moltype = DNA   length = 23
FEATURE                   Location/Qualifiers
source                    1..23
                          mol_type = other DNA
                          organism = Sus scrofa
SEQUENCE: 110
aagtcaaatt tcaaggacgg tgg                                              23

SEQ ID NO: 111            moltype = DNA   length = 25
FEATURE                   Location/Qualifiers
source                    1..25
                          mol_type = other DNA
                          organism = Sus scrofa
SEQUENCE: 111
aagtcaaatt tcaaggacgg tgggg                                            25

SEQ ID NO: 112            moltype = DNA   length = 23
FEATURE                   Location/Qualifiers
source                    1..23
                          mol_type = other DNA
                          organism = Sus scrofa
SEQUENCE: 112
agtcaaattt caaggacggt ggg                                              23

SEQ ID NO: 113            moltype = DNA   length = 23
FEATURE                   Location/Qualifiers
source                    1..23
                          mol_type = other DNA
                          organism = Sus scrofa
SEQUENCE: 113
gtcaaatttc aaggacggtg ggg                                              23

SEQ ID NO: 114            moltype = DNA   length = 23
FEATURE                   Location/Qualifiers
source                    1..23
                          mol_type = other DNA
                          organism = Sus scrofa
SEQUENCE: 114
caacataaat catgcttctg tgg                                              23

SEQ ID NO: 115            moltype = DNA   length = 23
FEATURE                   Location/Qualifiers
source                    1..23
                          mol_type = other DNA
                          organism = Sus scrofa
SEQUENCE: 115
ggaagtgctg tcagtttctc tgg                                              23

SEQ ID NO: 116            moltype = DNA   length = 23
FEATURE                   Location/Qualifiers
source                    1..23
                          mol_type = other DNA
                          organism = Sus scrofa
SEQUENCE: 116
ttctctggtt cagctaattt tgg                                              23

SEQ ID NO: 117            moltype = DNA   length = 25
```

```
FEATURE                 Location/Qualifiers
source                  1..25
                        mol_type = other DNA
                        organism = Sus scrofa
SEQUENCE: 117
ttctctggtt cagctaattt tggag                                              25

SEQ ID NO: 118          moltype = DNA   length = 23
FEATURE                 Location/Qualifiers
source                  1..23
                        mol_type = other DNA
                        organism = Sus scrofa
SEQUENCE: 118
ggttcagcta attttggaga agg                                                23

SEQ ID NO: 119          moltype = DNA   length = 23
FEATURE                 Location/Qualifiers
source                  1..23
                        mol_type = other DNA
                        organism = Sus scrofa
SEQUENCE: 119
gctaattttg gagaaggttc tgg                                                23

SEQ ID NO: 120          moltype = DNA   length = 23
FEATURE                 Location/Qualifiers
source                  1..23
                        mol_type = other DNA
                        organism = Sus scrofa
SEQUENCE: 120
gagaaggttc tggaccaatc tgg                                                23

SEQ ID NO: 121          moltype = DNA   length = 23
FEATURE                 Location/Qualifiers
source                  1..23
                        mol_type = other DNA
                        organism = Sus scrofa
SEQUENCE: 121
acaagatcat caaaccagat tgg                                                23

SEQ ID NO: 122          moltype = DNA   length = 23
FEATURE                 Location/Qualifiers
source                  1..23
                        mol_type = other DNA
                        organism = Sus scrofa
SEQUENCE: 122
tttgatgatc ttgtatgcaa tgg                                                23

SEQ ID NO: 123          moltype = DNA   length = 23
FEATURE                 Location/Qualifiers
source                  1..23
                        mol_type = other DNA
                        organism = Sus scrofa
SEQUENCE: 123
atggaaatga gtcagctctc tgg                                                23

SEQ ID NO: 124          moltype = DNA   length = 23
FEATURE                 Location/Qualifiers
source                  1..23
                        mol_type = other DNA
                        organism = Sus scrofa
SEQUENCE: 124
ctctggaact gcaaacatga agg                                                23

SEQ ID NO: 125          moltype = DNA   length = 23
FEATURE                 Location/Qualifiers
source                  1..23
                        mol_type = other DNA
                        organism = Sus scrofa
SEQUENCE: 125
ggaactgcaa acatgaagga tgg                                                23

SEQ ID NO: 126          moltype = DNA   length = 25
FEATURE                 Location/Qualifiers
source                  1..25
                        mol_type = other DNA
                        organism = Sus scrofa
SEQUENCE: 126
ggaactgcaa acatgaagga tgggg                                              25
```

| | | |
|---|---|---|
| SEQ ID NO: 127 | moltype = DNA  length = 23 | |
| FEATURE | Location/Qualifiers | |
| source | 1..23 | |
| | mol_type = other DNA | |
| | organism = Sus scrofa | |
| SEQUENCE: 127 | | |
| gaactgcaaa catgaaggat ggg | | 23 |
| | | |
| SEQ ID NO: 128 | moltype = DNA  length = 23 | |
| FEATURE | Location/Qualifiers | |
| source | 1..23 | |
| | mol_type = other DNA | |
| | organism = Sus scrofa | |
| SEQUENCE: 128 | | |
| aactgcaaac atgaaggatg ggg | | 23 |
| | | |
| SEQ ID NO: 129 | moltype = DNA  length = 23 | |
| FEATURE | Location/Qualifiers | |
| source | 1..23 | |
| | mol_type = other DNA | |
| | organism = Sus scrofa | |
| SEQUENCE: 129 | | |
| gcacaattgt gatcatgctg agg | | 23 |
| | | |
| SEQ ID NO: 130 | moltype = DNA  length = 23 | |
| FEATURE | Location/Qualifiers | |
| source | 1..23 | |
| | mol_type = other DNA | |
| | organism = Sus scrofa | |
| SEQUENCE: 130 | | |
| tgtgatcatg ctgaggatgc tgg | | 23 |
| | | |
| SEQ ID NO: 131 | moltype = DNA  length = 25 | |
| FEATURE | Location/Qualifiers | |
| source | 1..25 | |
| | mol_type = other DNA | |
| | organism = Sus scrofa | |
| SEQUENCE: 131 | | |
| tgtgatcatg ctgaggatgc tggag | | 25 |
| | | |
| SEQ ID NO: 132 | moltype = DNA  length = 23 | |
| FEATURE | Location/Qualifiers | |
| source | 1..23 | |
| | mol_type = other DNA | |
| | organism = Sus scrofa | |
| SEQUENCE: 132 | | |
| agcagacctg aaactgagag tgg | | 23 |
| | | |
| SEQ ID NO: 133 | moltype = DNA  length = 23 | |
| FEATURE | Location/Qualifiers | |
| source | 1..23 | |
| | mol_type = other DNA | |
| | organism = Sus scrofa | |
| SEQUENCE: 133 | | |
| catctaccac tctcagtttc agg | | 23 |
| | | |
| SEQ ID NO: 134 | moltype = DNA  length = 23 | |
| FEATURE | Location/Qualifiers | |
| source | 1..23 | |
| | mol_type = other DNA | |
| | organism = Sus scrofa | |
| SEQUENCE: 134 | | |
| ctgaaactga gagtggtaga tgg | | 23 |
| | | |
| SEQ ID NO: 135 | moltype = DNA  length = 25 | |
| FEATURE | Location/Qualifiers | |
| source | 1..25 | |
| | mol_type = other DNA | |
| | organism = Sus scrofa | |
| SEQUENCE: 135 | | |
| ctgaaactga gagtggtaga tggag | | 25 |
| | | |
| SEQ ID NO: 136 | moltype = DNA  length = 23 | |
| FEATURE | Location/Qualifiers | |
| source | 1..23 | |
| | mol_type = other DNA | |
| | organism = Sus scrofa | |
| SEQUENCE: 136 | | |
| gatggagtca ctgaatgttc agg | | 23 |

```
SEQ ID NO: 137           moltype = DNA   length = 23
FEATURE                  Location/Qualifiers
source                   1..23
                         mol_type = other DNA
                         organism = Sus scrofa
SEQUENCE: 137
cactgaatgt tcaggaagat tgg                                            23

SEQ ID NO: 138           moltype = DNA   length = 23
FEATURE                  Location/Qualifiers
source                   1..23
                         mol_type = other DNA
                         organism = Sus scrofa
SEQUENCE: 138
agattggaag tgaaattcca agg                                            23

SEQ ID NO: 139           moltype = DNA   length = 25
FEATURE                  Location/Qualifiers
source                   1..25
                         mol_type = other DNA
                         organism = Sus scrofa
SEQUENCE: 139
agattggaag tgaaattcca aggag                                          25

SEQ ID NO: 140           moltype = DNA   length = 23
FEATURE                  Location/Qualifiers
source                   1..23
                         mol_type = other DNA
                         organism = Sus scrofa
SEQUENCE: 140
aagtgaaatt ccaaggagaa tgg                                            23

SEQ ID NO: 141           moltype = DNA   length = 25
FEATURE                  Location/Qualifiers
source                   1..25
                         mol_type = other DNA
                         organism = Sus scrofa
SEQUENCE: 141
aagtgaaatt ccaaggagaa tgggg                                          25

SEQ ID NO: 142           moltype = DNA   length = 23
FEATURE                  Location/Qualifiers
source                   1..23
                         mol_type = other DNA
                         organism = Sus scrofa
SEQUENCE: 142
agtgaaattc caaggagaat ggg                                            23

SEQ ID NO: 143           moltype = DNA   length = 23
FEATURE                  Location/Qualifiers
source                   1..23
                         mol_type = other DNA
                         organism = Sus scrofa
SEQUENCE: 143
gtgaaattcc aaggagaatg ggg                                            23

SEQ ID NO: 144           moltype = DNA   length = 23
FEATURE                  Location/Qualifiers
source                   1..23
                         mol_type = other DNA
                         organism = Sus scrofa
SEQUENCE: 144
agattgttcc ccattctcct tgg                                            23

SEQ ID NO: 145           moltype = DNA   length = 23
FEATURE                  Location/Qualifiers
source                   1..23
                         mol_type = other DNA
                         organism = Sus scrofa
SEQUENCE: 145
tggggaacaa tctgtgatga tgg                                            23

SEQ ID NO: 146           moltype = DNA   length = 23
FEATURE                  Location/Qualifiers
source                   1..23
                         mol_type = other DNA
                         organism = Sus scrofa
SEQUENCE: 146
```
gaacaatctg tgatgatggc tgg                                                23

SEQ ID NO: 147          moltype = DNA   length = 23
FEATURE                 Location/Qualifiers
source                  1..23
                        mol_type = other DNA
                        organism = Sus scrofa
SEQUENCE: 147
aacaatctgt gatgatggct ggg                                                23

SEQ ID NO: 148          moltype = DNA   length = 23
FEATURE                 Location/Qualifiers
source                  1..23
                        mol_type = other DNA
                        organism = Sus scrofa
SEQUENCE: 148
ggatagtgat gatgccgctg tgg                                                23

SEQ ID NO: 149          moltype = DNA   length = 23
FEATURE                 Location/Qualifiers
source                  1..23
                        mol_type = other DNA
                        organism = Sus scrofa
SEQUENCE: 149
cagttgctta catgccacag cgg                                                23

SEQ ID NO: 150          moltype = DNA   length = 23
FEATURE                 Location/Qualifiers
source                  1..23
                        mol_type = other DNA
                        organism = Sus scrofa
SEQUENCE: 150
cgctgtggca tgtaagcaac tgg                                                23

SEQ ID NO: 151          moltype = DNA   length = 23
FEATURE                 Location/Qualifiers
source                  1..23
                        mol_type = other DNA
                        organism = Sus scrofa
SEQUENCE: 151
gctgtggcat gtaagcaact ggg                                                23

SEQ ID NO: 152          moltype = DNA   length = 23
FEATURE                 Location/Qualifiers
source                  1..23
                        mol_type = other DNA
                        organism = Sus scrofa
SEQUENCE: 152
ccaatggcag tgacagcagt tgg                                                23

SEQ ID NO: 153          moltype = DNA   length = 23
FEATURE                 Location/Qualifiers
source                  1..23
                        mol_type = other DNA
                        organism = Sus scrofa
SEQUENCE: 153
ccaactgctg tcactgccat tgg                                                23

SEQ ID NO: 154          moltype = DNA   length = 23
FEATURE                 Location/Qualifiers
source                  1..23
                        mol_type = other DNA
                        organism = Sus scrofa
SEQUENCE: 154
actggcgtta actcgaccaa tgg                                                23

SEQ ID NO: 155          moltype = DNA   length = 23
FEATURE                 Location/Qualifiers
source                  1..23
                        mol_type = other DNA
                        organism = Sus scrofa
SEQUENCE: 155
tggtcgagtt aacgccagtg agg                                                23

SEQ ID NO: 156          moltype = DNA   length = 23
FEATURE                 Location/Qualifiers
source                  1..23
                        mol_type = other DNA
                        organism = Sus scrofa

```
SEQUENCE: 156
ggtcgagtta acgccagtga ggg                                                23

SEQ ID NO: 157          moltype = DNA  length = 23
FEATURE                 Location/Qualifiers
source                  1..23
                        mol_type = other DNA
                        organism = Sus scrofa
SEQUENCE: 157
gttaacgcca gtgagggaac tgg                                                23

SEQ ID NO: 158          moltype = DNA  length = 25
FEATURE                 Location/Qualifiers
source                  1..25
                        mol_type = other DNA
                        organism = Sus scrofa
SEQUENCE: 158
aatgtgtcca gttccctcac tggcg                                              25

SEQ ID NO: 159          moltype = DNA  length = 23
FEATURE                 Location/Qualifiers
source                  1..23
                        mol_type = other DNA
                        organism = Sus scrofa
SEQUENCE: 159
aatgtgtcca gttccctcac tgg                                                23

SEQ ID NO: 160          moltype = DNA  length = 23
FEATURE                 Location/Qualifiers
source                  1..23
                        mol_type = other DNA
                        organism = Sus scrofa
SEQUENCE: 160
gtgagggaac tggacacatt tgg                                                23

SEQ ID NO: 161          moltype = DNA  length = 23
FEATURE                 Location/Qualifiers
source                  1..23
                        mol_type = other DNA
                        organism = Sus scrofa
SEQUENCE: 161
cttgacagtg tttcttgcca tgg                                                23

SEQ ID NO: 162          moltype = DNA  length = 23
FEATURE                 Location/Qualifiers
source                  1..23
                        mol_type = other DNA
                        organism = Sus scrofa
SEQUENCE: 162
agagagcaga ctcgtgtcca tgg                                                23

SEQ ID NO: 163          moltype = DNA  length = 23
FEATURE                 Location/Qualifiers
source                  1..23
                        mol_type = other DNA
                        organism = Sus scrofa
SEQUENCE: 163
atggacacga gtctgctctc tgg                                                23

SEQ ID NO: 164          moltype = DNA  length = 23
FEATURE                 Location/Qualifiers
source                  1..23
                        mol_type = other DNA
                        organism = Sus scrofa
SEQUENCE: 164
ggcagtgtag acaccatgaa tgg                                                23

SEQ ID NO: 165          moltype = DNA  length = 25
FEATURE                 Location/Qualifiers
source                  1..25
                        mol_type = other DNA
                        organism = Sus scrofa
SEQUENCE: 165
ggcagtgtag acaccatgaa tgggg                                              25

SEQ ID NO: 166          moltype = DNA  length = 23
FEATURE                 Location/Qualifiers
source                  1..23
                        mol_type = other DNA
```

```
                        organism = Sus scrofa
SEQUENCE: 166
gcagtgtaga caccatgaat ggg                                          23

SEQ ID NO: 167          moltype = DNA   length = 23
FEATURE                 Location/Qualifiers
source                  1..23
                        mol_type = other DNA
                        organism = Sus scrofa
SEQUENCE: 167
cagtgtagac accatgaatg ggg                                          23

SEQ ID NO: 168          moltype = DNA   length = 25
FEATURE                 Location/Qualifiers
source                  1..25
                        mol_type = other DNA
                        organism = Sus scrofa
SEQUENCE: 168
aataatgctt tccccattca tggtg                                        25

SEQ ID NO: 169          moltype = DNA   length = 23
FEATURE                 Location/Qualifiers
source                  1..23
                        mol_type = other DNA
                        organism = Sus scrofa
SEQUENCE: 169
aataatgctt tccccattca tgg                                          23

SEQ ID NO: 170          moltype = DNA   length = 23
FEATURE                 Location/Qualifiers
source                  1..23
                        mol_type = other DNA
                        organism = Sus scrofa
SEQUENCE: 170
tgcaatcata atgaagatgc tgg                                          23

SEQ ID NO: 171          moltype = DNA   length = 25
FEATURE                 Location/Qualifiers
source                  1..25
                        mol_type = other DNA
                        organism = Sus scrofa
SEQUENCE: 171
tgcaatcata atgaagatgc tggtg                                        25

SEQ ID NO: 172          moltype = DNA   length = 23
FEATURE                 Location/Qualifiers
source                  1..23
                        mol_type = other DNA
                        organism = Sus scrofa
SEQUENCE: 172
gatgctggtg tgacatgttc tgg                                          23

SEQ ID NO: 173          moltype = DNA   length = 23
FEATURE                 Location/Qualifiers
source                  1..23
                        mol_type = other DNA
                        organism = Sus scrofa
SEQUENCE: 173
ttttgcagat ggatcagatc tgg                                          23

SEQ ID NO: 174          moltype = DNA   length = 23
FEATURE                 Location/Qualifiers
source                  1..23
                        mol_type = other DNA
                        organism = Sus scrofa
SEQUENCE: 174
gatctggaac tgagacttaa agg                                          23

SEQ ID NO: 175          moltype = DNA   length = 25
FEATURE                 Location/Qualifiers
source                  1..25
                        mol_type = other DNA
                        organism = Sus scrofa
SEQUENCE: 175
gatctggaac tgagacttaa aggtg                                        25

SEQ ID NO: 176          moltype = DNA   length = 23
FEATURE                 Location/Qualifiers
source                  1..23
```

```
                              mol_type = other DNA
                              organism = Sus scrofa
SEQUENCE: 176
ctggaactga gacttaaagg tgg                                              23

SEQ ID NO: 177                moltype = DNA  length = 25
FEATURE                       Location/Qualifiers
source                        1..25
                              mol_type = other DNA
                              organism = Sus scrofa
SEQUENCE: 177
ctggaactga gacttaaagg tggag                                            25

SEQ ID NO: 178                moltype = DNA  length = 23
FEATURE                       Location/Qualifiers
source                        1..23
                              mol_type = other DNA
                              organism = Sus scrofa
SEQUENCE: 178
gaactgagac ttaaaggtgg agg                                              23

SEQ ID NO: 179                moltype = DNA  length = 23
FEATURE                       Location/Qualifiers
source                        1..23
                              mol_type = other DNA
                              organism = Sus scrofa
SEQUENCE: 179
cagccactgt gctgggacag tgg                                              23

SEQ ID NO: 180                moltype = DNA  length = 25
FEATURE                       Location/Qualifiers
source                        1..25
                              mol_type = other DNA
                              organism = Sus scrofa
SEQUENCE: 180
cagccactgt gctgggacag tggag                                            25

SEQ ID NO: 181                moltype = DNA  length = 23
FEATURE                       Location/Qualifiers
source                        1..23
                              mol_type = other DNA
                              organism = Sus scrofa
SEQUENCE: 181
cctccactgt cccagcacag tgg                                              23

SEQ ID NO: 182                moltype = DNA  length = 23
FEATURE                       Location/Qualifiers
source                        1..23
                              mol_type = other DNA
                              organism = Sus scrofa
SEQUENCE: 182
ccactgtgct gggacagtgg agg                                              23

SEQ ID NO: 183                moltype = DNA  length = 25
FEATURE                       Location/Qualifiers
source                        1..25
                              mol_type = other DNA
                              organism = Sus scrofa
SEQUENCE: 183
ccactgtgct gggacagtgg aggtg                                            25

SEQ ID NO: 184                moltype = DNA  length = 23
FEATURE                       Location/Qualifiers
source                        1..23
                              mol_type = other DNA
                              organism = Sus scrofa
SEQUENCE: 184
ctgtgctggg acagtggagg tgg                                              23

SEQ ID NO: 185                moltype = DNA  length = 23
FEATURE                       Location/Qualifiers
source                        1..23
                              mol_type = other DNA
                              organism = Sus scrofa
SEQUENCE: 185
ggaggtggaa attcagaaac tgg                                              23

SEQ ID NO: 186                moltype = DNA  length = 23
FEATURE                       Location/Qualifiers
```

```
source                  1..23
                        mol_type = other DNA
                        organism = Sus scrofa
SEQUENCE: 186
gtggaaattc agaaactggt agg                                           23

SEQ ID NO: 187          moltype = DNA   length = 23
FEATURE                 Location/Qualifiers
source                  1..23
                        mol_type = other DNA
                        organism = Sus scrofa
SEQUENCE: 187
gaaaagtgtg tgatagaagc tgg                                           23

SEQ ID NO: 188          moltype = DNA   length = 25
FEATURE                 Location/Qualifiers
source                  1..25
                        mol_type = other DNA
                        organism = Sus scrofa
SEQUENCE: 188
gaaaagtgtg tgatagaagc tgggg                                         25

SEQ ID NO: 189          moltype = DNA   length = 23
FEATURE                 Location/Qualifiers
source                  1..23
                        mol_type = other DNA
                        organism = Sus scrofa
SEQUENCE: 189
aaaagtgtgt gatagaagct ggg                                           23

SEQ ID NO: 190          moltype = DNA   length = 23
FEATURE                 Location/Qualifiers
source                  1..23
                        mol_type = other DNA
                        organism = Sus scrofa
SEQUENCE: 190
aaagtgtgtg atagaagctg ggg                                           23

SEQ ID NO: 191          moltype = DNA   length = 23
FEATURE                 Location/Qualifiers
source                  1..23
                        mol_type = other DNA
                        organism = Sus scrofa
SEQUENCE: 191
gggactgaaa gaagctgatg tgg                                           23

SEQ ID NO: 192          moltype = DNA   length = 23
FEATURE                 Location/Qualifiers
source                  1..23
                        mol_type = other DNA
                        organism = Sus scrofa
SEQUENCE: 192
aagaagctga tgtggtttgc agg                                           23

SEQ ID NO: 193          moltype = DNA   length = 23
FEATURE                 Location/Qualifiers
source                  1..23
                        mol_type = other DNA
                        organism = Sus scrofa
SEQUENCE: 193
tgatgtggtt tgcaggcagc tgg                                           23

SEQ ID NO: 194          moltype = DNA   length = 23
FEATURE                 Location/Qualifiers
source                  1..23
                        mol_type = other DNA
                        organism = Sus scrofa
SEQUENCE: 194
gatgtggttt gcaggcagct ggg                                           23

SEQ ID NO: 195          moltype = DNA   length = 23
FEATURE                 Location/Qualifiers
source                  1..23
                        mol_type = other DNA
                        organism = Sus scrofa
SEQUENCE: 195
gtttgcaggc agctgggatg tgg                                           23

SEQ ID NO: 196          moltype = DNA   length = 23
```

-continued

```
FEATURE                 Location/Qualifiers
source                  1..23
                        mol_type = other DNA
                        organism = Sus scrofa
SEQUENCE: 196
tcaagtttat tccaaaacca agg                                              23

SEQ ID NO: 197          moltype = DNA   length = 23
FEATURE                 Location/Qualifiers
source                  1..23
                        mol_type = other DNA
                        organism = Sus scrofa
SEQUENCE: 197
aaaccaaggc aacaaacaca tgg                                              23

SEQ ID NO: 198          moltype = DNA   length = 23
FEATURE                 Location/Qualifiers
source                  1..23
                        mol_type = other DNA
                        organism = Sus scrofa
SEQUENCE: 198
cagccatgtg tttgttgcct tgg                                              23

SEQ ID NO: 199          moltype = DNA   length = 23
FEATURE                 Location/Qualifiers
source                  1..23
                        mol_type = other DNA
                        organism = Sus scrofa
SEQUENCE: 199
ctgtttgtaa gcagctgtaa tgg                                              23

SEQ ID NO: 200          moltype = DNA   length = 23
FEATURE                 Location/Qualifiers
source                  1..23
                        mol_type = other DNA
                        organism = Sus scrofa
SEQUENCE: 200
atggaaatga aacttctctt tgg                                              23

SEQ ID NO: 201          moltype = DNA   length = 23
FEATURE                 Location/Qualifiers
source                  1..23
                        mol_type = other DNA
                        organism = Sus scrofa
SEQUENCE: 201
tggaaatgaa acttctcttt ggg                                              23

SEQ ID NO: 202          moltype = DNA   length = 23
FEATURE                 Location/Qualifiers
source                  1..23
                        mol_type = other DNA
                        organism = Sus scrofa
SEQUENCE: 202
ctctttggga ctgcaagaat tgg                                              23

SEQ ID NO: 203          moltype = DNA   length = 23
FEATURE                 Location/Qualifiers
source                  1..23
                        mol_type = other DNA
                        organism = Sus scrofa
SEQUENCE: 203
gggactgcaa gaattggcag tgg                                              23

SEQ ID NO: 204          moltype = DNA   length = 25
FEATURE                 Location/Qualifiers
source                  1..25
                        mol_type = other DNA
                        organism = Sus scrofa
SEQUENCE: 204
gggactgcaa gaattggcag tgggg                                            25

SEQ ID NO: 205          moltype = DNA   length = 23
FEATURE                 Location/Qualifiers
source                  1..23
                        mol_type = other DNA
                        organism = Sus scrofa
SEQUENCE: 205
ggactgcaag aattggcagt ggg                                              23
```

```
SEQ ID NO: 206          moltype = DNA   length = 23
FEATURE                 Location/Qualifiers
source                  1..23
                        mol_type = other DNA
                        organism = Sus scrofa
SEQUENCE: 206
gactgcaaga attggcagtg ggg                                              23

SEQ ID NO: 207          moltype = DNA   length = 25
FEATURE                 Location/Qualifiers
source                  1..25
                        mol_type = other DNA
                        organism = Sus scrofa
SEQUENCE: 207
gactgcaaga attggcagtg gggtg                                            25

SEQ ID NO: 208          moltype = DNA   length = 23
FEATURE                 Location/Qualifiers
source                  1..23
                        mol_type = other DNA
                        organism = Sus scrofa
SEQUENCE: 208
tgcaagaatt ggcagtgggg tgg                                              23

SEQ ID NO: 209          moltype = DNA   length = 23
FEATURE                 Location/Qualifiers
source                  1..23
                        mol_type = other DNA
                        organism = Sus scrofa
SEQUENCE: 209
cttacctgag caggtaattt tgg                                              23

SEQ ID NO: 210          moltype = DNA   length = 23
FEATURE                 Location/Qualifiers
source                  1..23
                        mol_type = other DNA
                        organism = Sus scrofa
SEQUENCE: 210
ggtcgtgttg aagtacaaca tgg                                              23

SEQ ID NO: 211          moltype = DNA   length = 23
FEATURE                 Location/Qualifiers
source                  1..23
                        mol_type = other DNA
                        organism = Sus scrofa
SEQUENCE: 211
ggaactacag tgcggcactg tgg                                              23

SEQ ID NO: 212          moltype = DNA   length = 23
FEATURE                 Location/Qualifiers
source                  1..23
                        mol_type = other DNA
                        organism = Sus scrofa
SEQUENCE: 212
agaggcaatt caatttactt ggg                                              23

SEQ ID NO: 213          moltype = DNA   length = 23
FEATURE                 Location/Qualifiers
source                  1..23
                        mol_type = other DNA
                        organism = Sus scrofa
SEQUENCE: 213
gagaggcaat tcaatttact tgg                                              23

SEQ ID NO: 214          moltype = DNA   length = 23
FEATURE                 Location/Qualifiers
source                  1..23
                        mol_type = other DNA
                        organism = Sus scrofa
SEQUENCE: 214
gtttcttttt acagactgag agg                                              23

SEQ ID NO: 215          moltype = DNA   length = 23
FEATURE                 Location/Qualifiers
source                  1..23
                        mol_type = other DNA
                        organism = Sus scrofa
SEQUENCE: 215
ggttaagagt acaatcatca agg                                              23
```

```
SEQ ID NO: 216            moltype = DNA  length = 23
FEATURE                   Location/Qualifiers
source                    1..23
                          mol_type = other DNA
                          organism = Sus scrofa
SEQUENCE: 216
tgatgattgt actcttaacc tgg                                             23

SEQ ID NO: 217            moltype = DNA  length = 23
FEATURE                   Location/Qualifiers
source                    1..23
                          mol_type = other DNA
                          organism = Sus scrofa
SEQUENCE: 217
cagaaataaa gcagaagaca tgg                                             23

SEQ ID NO: 218            moltype = DNA  length = 23
FEATURE                   Location/Qualifiers
source                    1..23
                          mol_type = other DNA
                          organism = Sus scrofa
SEQUENCE: 218
catgtcttct gctttatttc tgg                                             23

SEQ ID NO: 219            moltype = DNA  length = 23
FEATURE                   Location/Qualifiers
source                    1..23
                          mol_type = other DNA
                          organism = Sus scrofa
SEQUENCE: 219
ctccagatta cagtaaatgg agg                                             23

SEQ ID NO: 220            moltype = DNA  length = 23
FEATURE                   Location/Qualifiers
source                    1..23
                          mol_type = other DNA
                          organism = Sus scrofa
SEQUENCE: 220
gtcctccatt tactgtaatc tgg                                             23

SEQ ID NO: 221            moltype = DNA  length = 23
FEATURE                   Location/Qualifiers
source                    1..23
                          mol_type = other DNA
                          organism = Sus scrofa
SEQUENCE: 221
gtaaatggag gactgagtat agg                                             23

SEQ ID NO: 222            moltype = DNA  length = 23
FEATURE                   Location/Qualifiers
source                    1..23
                          mol_type = other DNA
                          organism = Sus scrofa
SEQUENCE: 222
taaatggagg actgagtata ggg                                             23

SEQ ID NO: 223            moltype = DNA  length = 23
FEATURE                   Location/Qualifiers
source                    1..23
                          mol_type = other DNA
                          organism = Sus scrofa
SEQUENCE: 223
gggctaaaaa gtagagagaa tgg                                             23

SEQ ID NO: 224            moltype = DNA  length = 23
FEATURE                   Location/Qualifiers
source                    1..23
                          mol_type = other DNA
                          organism = Sus scrofa
SEQUENCE: 224
gaatggatgc atattatctg tgg                                             23

SEQ ID NO: 225            moltype = DNA  length = 23
FEATURE                   Location/Qualifiers
source                    1..23
                          mol_type = other DNA
                          organism = Sus scrofa
SEQUENCE: 225
```

```
tccaatgtga tgaatgaagt agg                                               23

SEQ ID NO: 226          moltype = DNA   length = 23
FEATURE                 Location/Qualifiers
source                  1..23
                        mol_type = other DNA
                        organism = Sus scrofa
SEQUENCE: 226
gcctacttca ttcatcacat tgg                                               23

SEQ ID NO: 227          moltype = DNA   length = 23
FEATURE                 Location/Qualifiers
source                  1..23
                        mol_type = other DNA
                        organism = Sus scrofa
SEQUENCE: 227
tgaagtaggc aaatactcaa agg                                               23

SEQ ID NO: 228          moltype = DNA   length = 23
FEATURE                 Location/Qualifiers
source                  1..23
                        mol_type = other DNA
                        organism = Sus scrofa
SEQUENCE: 228
aaagcatgct ccaagaatta tgg                                               23

SEQ ID NO: 229          moltype = DNA   length = 23
FEATURE                 Location/Qualifiers
source                  1..23
                        mol_type = other DNA
                        organism = Sus scrofa
SEQUENCE: 229
aagcatgctc caagaattat ggg                                               23

SEQ ID NO: 230          moltype = DNA   length = 23
FEATURE                 Location/Qualifiers
source                  1..23
                        mol_type = other DNA
                        organism = Sus scrofa
SEQUENCE: 230
cttctggaac ccataattct tgg                                               23

SEQ ID NO: 231          moltype = DNA   length = 23
FEATURE                 Location/Qualifiers
source                  1..23
                        mol_type = other DNA
                        organism = Sus scrofa
SEQUENCE: 231
caagaattat gggttccaga agg                                               23

SEQ ID NO: 232          moltype = DNA   length = 23
FEATURE                 Location/Qualifiers
source                  1..23
                        mol_type = other DNA
                        organism = Sus scrofa
SEQUENCE: 232
aaagtcccag aattgtctcc agg                                               23

SEQ ID NO: 233          moltype = DNA   length = 23
FEATURE                 Location/Qualifiers
source                  1..23
                        mol_type = other DNA
                        organism = Sus scrofa
SEQUENCE: 233
aagtcccaga attgtctcca ggg                                               23

SEQ ID NO: 234          moltype = DNA   length = 23
FEATURE                 Location/Qualifiers
source                  1..23
                        mol_type = other DNA
                        organism = Sus scrofa
SEQUENCE: 234
ccttccctgg agacaattct ggg                                               23

SEQ ID NO: 235          moltype = DNA   length = 23
FEATURE                 Location/Qualifiers
source                  1..23
                        mol_type = other DNA
                        organism = Sus scrofa
```

```
SEQUENCE: 235
cccagaattg tctccaggga agg                                          23

SEQ ID NO: 236           moltype = DNA   length = 23
FEATURE                  Location/Qualifiers
source                   1..23
                         mol_type = other DNA
                         organism = Sus scrofa
SEQUENCE: 236
tccttccctg gagacaattc tgg                                          23

SEQ ID NO: 237           moltype = DNA   length = 23
FEATURE                  Location/Qualifiers
source                   1..23
                         mol_type = other DNA
                         organism = Sus scrofa
SEQUENCE: 237
attgtctcca gggaaggaca ggg                                          23

SEQ ID NO: 238           moltype = DNA   length = 23
FEATURE                  Location/Qualifiers
source                   1..23
                         mol_type = other DNA
                         organism = Sus scrofa
SEQUENCE: 238
gtctccaggg aaggacaggg agg                                          23

SEQ ID NO: 239           moltype = DNA   length = 23
FEATURE                  Location/Qualifiers
source                   1..23
                         mol_type = other DNA
                         organism = Sus scrofa
SEQUENCE: 239
tagacctccc tgtccttccc tgg                                          23

SEQ ID NO: 240           moltype = DNA   length = 23
FEATURE                  Location/Qualifiers
source                   1..23
                         mol_type = other DNA
                         organism = Sus scrofa
SEQUENCE: 240
aggacaggga ggtctagaat cgg                                          23

SEQ ID NO: 241           moltype = DNA   length = 23
FEATURE                  Location/Qualifiers
source                   1..23
                         mol_type = other DNA
                         organism = Sus scrofa
SEQUENCE: 241
gaatcggcta agcccactgt agg                                          23

SEQ ID NO: 242           moltype = DNA   length = 23
FEATURE                  Location/Qualifiers
source                   1..23
                         mol_type = other DNA
                         organism = Sus scrofa
SEQUENCE: 242
ttggtttttc tgcctacagt ggg                                          23

SEQ ID NO: 243           moltype = DNA   length = 23
FEATURE                  Location/Qualifiers
source                   1..23
                         mol_type = other DNA
                         organism = Sus scrofa
SEQUENCE: 243
cttggttttt ctgcctacag tgg                                          23

SEQ ID NO: 244           moltype = DNA   length = 23
FEATURE                  Location/Qualifiers
source                   1..23
                         mol_type = other DNA
                         organism = Sus scrofa
SEQUENCE: 244
ctgtaggcag aaaaaccaag agg                                          23

SEQ ID NO: 245           moltype = DNA   length = 23
FEATURE                  Location/Qualifiers
source                   1..23
                         mol_type = other DNA
```

```
                        organism = Sus scrofa
SEQUENCE: 245
gaaaaaccaa gaggcatgaa tgg                                              23

SEQ ID NO: 246          moltype = DNA  length = 23
FEATURE                 Location/Qualifiers
source                  1..23
                        mol_type = other DNA
                        organism = Sus scrofa
SEQUENCE: 246
gggaagccat tcatgcctct tgg                                              23

SEQ ID NO: 247          moltype = DNA  length = 23
FEATURE                 Location/Qualifiers
source                  1..23
                        mol_type = other DNA
                        organism = Sus scrofa
SEQUENCE: 247
agagagtgaa aagtgagaaa ggg                                              23

SEQ ID NO: 248          moltype = DNA  length = 23
FEATURE                 Location/Qualifiers
source                  1..23
                        mol_type = other DNA
                        organism = Sus scrofa
SEQUENCE: 248
cagagagtga aaagtgagaa agg                                              23

SEQ ID NO: 249          moltype = DNA  length = 23
FEATURE                 Location/Qualifiers
source                  1..23
                        mol_type = other DNA
                        organism = Sus scrofa
SEQUENCE: 249
ctggcttact cctatcatga agg                                              23

SEQ ID NO: 250          moltype = DNA  length = 23
FEATURE                 Location/Qualifiers
source                  1..23
                        mol_type = other DNA
                        organism = Sus scrofa
SEQUENCE: 250
cctatcatga aggaaaatat tgg                                              23

SEQ ID NO: 251          moltype = DNA  length = 23
FEATURE                 Location/Qualifiers
source                  1..23
                        mol_type = other DNA
                        organism = Sus scrofa
SEQUENCE: 251
ccaatatttt ccttcatgat agg                                              23

SEQ ID NO: 252          moltype = DNA  length = 23
FEATURE                 Location/Qualifiers
source                  1..23
                        mol_type = other DNA
                        organism = Sus scrofa
SEQUENCE: 252
aaaaaatagc atttcggtga ggg                                              23

SEQ ID NO: 253          moltype = DNA  length = 23
FEATURE                 Location/Qualifiers
source                  1..23
                        mol_type = other DNA
                        organism = Sus scrofa
SEQUENCE: 253
gaaaaaatag catttcggtg agg                                              23

SEQ ID NO: 254          moltype = DNA  length = 23
FEATURE                 Location/Qualifiers
source                  1..23
                        mol_type = other DNA
                        organism = Sus scrofa
SEQUENCE: 254
acaaagtgaa cacattccct ggg                                              23

SEQ ID NO: 255          moltype = DNA  length = 23
FEATURE                 Location/Qualifiers
source                  1..23
```

```
                            mol_type = other DNA
                            organism = Sus scrofa
SEQUENCE: 255
aacaaagtga acacattccc tgg                                              23

SEQ ID NO: 256              moltype = DNA  length = 23
FEATURE                     Location/Qualifiers
source                      1..23
                            mol_type = other DNA
                            organism = Sus scrofa
SEQUENCE: 256
tcccatgcca tgaagagggt agg                                              23

SEQ ID NO: 257              moltype = DNA  length = 23
FEATURE                     Location/Qualifiers
source                      1..23
                            mol_type = other DNA
                            organism = Sus scrofa
SEQUENCE: 257
ccctaccctc ttcatggcat ggg                                              23

SEQ ID NO: 258              moltype = DNA  length = 23
FEATURE                     Location/Qualifiers
source                      1..23
                            mol_type = other DNA
                            organism = Sus scrofa
SEQUENCE: 258
cccatgccat gaagagggta ggg                                              23

SEQ ID NO: 259              moltype = DNA  length = 23
FEATURE                     Location/Qualifiers
source                      1..23
                            mol_type = other DNA
                            organism = Sus scrofa
SEQUENCE: 259
accctaccct cttcatggca tgg                                              23

SEQ ID NO: 260              moltype = DNA  length = 23
FEATURE                     Location/Qualifiers
source                      1..23
                            mol_type = other DNA
                            organism = Sus scrofa
SEQUENCE: 260
gccatgaaga gggtagggtt agg                                              23

SEQ ID NO: 261              moltype = DNA  length = 23
FEATURE                     Location/Qualifiers
source                      1..23
                            mol_type = other DNA
                            organism = Sus scrofa
SEQUENCE: 261
acctaaccct accctcttca tgg                                              23

SEQ ID NO: 262              moltype = DNA  length = 25
FEATURE                     Location/Qualifiers
source                      1..25
                            mol_type = other DNA
                            organism = Sus scrofa
SEQUENCE: 262
cagaaataaa gcagaagaca tggag                                            25

SEQ ID NO: 263              moltype = DNA  length = 25
FEATURE                     Location/Qualifiers
source                      1..25
                            mol_type = other DNA
                            organism = Sus scrofa
SEQUENCE: 263
catgtcttct gctttatttc tggtg                                            25

SEQ ID NO: 264              moltype = DNA  length = 25
FEATURE                     Location/Qualifiers
source                      1..25
                            mol_type = other DNA
                            organism = Sus scrofa
SEQUENCE: 264
tgactccaga ttacagtaaa tggag                                            25

SEQ ID NO: 265              moltype = DNA  length = 25
FEATURE                     Location/Qualifiers
```

```
source                  1..25
                        mol_type = other DNA
                        organism = Sus scrofa
SEQUENCE: 265
gtcctccatt tactgtaatc tggag                                       25

SEQ ID NO: 266          moltype = DNA   length = 25
FEATURE                 Location/Qualifiers
source                  1..25
                        mol_type = other DNA
                        organism = Sus scrofa
SEQUENCE: 266
gcctacttca ttcatcacat tggag                                       25

SEQ ID NO: 267          moltype = DNA   length = 25
FEATURE                 Location/Qualifiers
source                  1..25
                        mol_type = other DNA
                        organism = Sus scrofa
SEQUENCE: 267
cttctggaac ccataattct tggag                                       25

SEQ ID NO: 268          moltype = DNA   length = 25
FEATURE                 Location/Qualifiers
source                  1..25
                        mol_type = other DNA
                        organism = Sus scrofa
SEQUENCE: 268
attgtctcca gggaaggaca gggag                                       25

SEQ ID NO: 269          moltype = DNA   length = 25
FEATURE                 Location/Qualifiers
source                  1..25
                        mol_type = other DNA
                        organism = Sus scrofa
SEQUENCE: 269
tagacctccc tgtccttccc tggag                                       25

SEQ ID NO: 270          moltype = DNA   length = 25
FEATURE                 Location/Qualifiers
source                  1..25
                        mol_type = other DNA
                        organism = Sus scrofa
SEQUENCE: 270
ccaatatttt ccttcatgat aggag                                       25

SEQ ID NO: 271          moltype = DNA   length = 25
FEATURE                 Location/Qualifiers
source                  1..25
                        mol_type = other DNA
                        organism = Sus scrofa
SEQUENCE: 271
aaaaaatagc atttcggtga gggag                                       25

SEQ ID NO: 272          moltype = DNA   length = 23
FEATURE                 Location/Qualifiers
source                  1..23
                        mol_type = other DNA
                        organism = Sus scrofa
SEQUENCE: 272
gaatcggcta agcccactgt agg                                         23

SEQ ID NO: 273          moltype = DNA   length = 23
FEATURE                 Location/Qualifiers
source                  1..23
                        mol_type = other DNA
                        organism = Sus scrofa
SEQUENCE: 273
cccatgccat gaagagggta ggg                                         23

SEQ ID NO: 274          moltype = DNA   length = 20
FEATURE                 Location/Qualifiers
source                  1..20
                        mol_type = other DNA
                        organism = Sus scrofa
SEQUENCE: 274
aagagaacta gtgaccaagc                                             20

SEQ ID NO: 275          moltype = DNA   length = 20
```

```
FEATURE                 Location/Qualifiers
source                  1..20
                        mol_type = other DNA
                        organism = Sus scrofa
SEQUENCE: 275
tgcttggtca ctagttctct                                                   20

SEQ ID NO: 276          moltype = DNA  length = 20
FEATURE                 Location/Qualifiers
source                  1..20
                        mol_type = other DNA
                        organism = Sus scrofa
SEQUENCE: 276
gaactgtgtg taataatggc                                                   20

SEQ ID NO: 277          moltype = DNA  length = 20
FEATURE                 Location/Qualifiers
source                  1..20
                        mol_type = other DNA
                        organism = Sus scrofa
SEQUENCE: 277
tgctatcaaa gccactggat                                                   20

SEQ ID NO: 278          moltype = DNA  length = 20
FEATURE                 Location/Qualifiers
source                  1..20
                        mol_type = other DNA
                        organism = Sus scrofa
SEQUENCE: 278
gtgcaggttc tggacgcatt                                                   20

SEQ ID NO: 279          moltype = DNA  length = 20
FEATURE                 Location/Qualifiers
source                  1..20
                        mol_type = other DNA
                        organism = Sus scrofa
SEQUENCE: 279
gtgcaggttc tggacgcatt                                                   20

SEQ ID NO: 280          moltype = DNA  length = 20
FEATURE                 Location/Qualifiers
source                  1..20
                        mol_type = other DNA
                        organism = Sus scrofa
SEQUENCE: 280
atggatcatg tttcttgtcg                                                   20

SEQ ID NO: 281          moltype = DNA  length = 20
FEATURE                 Location/Qualifiers
source                  1..20
                        mol_type = other DNA
                        organism = Sus scrofa
SEQUENCE: 281
ggactgcaaa catgatggat                                                   20

SEQ ID NO: 282          moltype = DNA  length = 20
FEATURE                 Location/Qualifiers
source                  1..20
                        mol_type = other DNA
                        organism = Sus scrofa
SEQUENCE: 282
ggactgcaaa catgatggat                                                   20

SEQ ID NO: 283          moltype = DNA  length = 20
FEATURE                 Location/Qualifiers
source                  1..20
                        mol_type = other DNA
                        organism = Sus scrofa
SEQUENCE: 283
agtcaaattt caaggacggt                                                   20

SEQ ID NO: 284          moltype = DNA  length = 20
FEATURE                 Location/Qualifiers
source                  1..20
                        mol_type = other DNA
                        organism = Sus scrofa
SEQUENCE: 284
gctaattttg gagaaggttc                                                   20
```

| | | |
|---|---|---|
| SEQ ID NO: 285<br>FEATURE<br>source | moltype = DNA length = 20<br>Location/Qualifiers<br>1..20<br>mol_type = other DNA<br>organism = Sus scrofa | |
| SEQUENCE: 285<br>gcacaattgt gatcatgctg | | 20 |
| SEQ ID NO: 286<br>FEATURE<br>source | moltype = DNA length = 20<br>Location/Qualifiers<br>1..20<br>mol_type = other DNA<br>organism = Sus scrofa | |
| SEQUENCE: 286<br>ggaactacag tgcggcactg | | 20 |
| SEQ ID NO: 287<br>FEATURE<br>source | moltype = RNA length = 20<br>Location/Qualifiers<br>1..20<br>mol_type = other RNA<br>organism = Sus scrofa | |
| SEQUENCE: 287<br>aagagaacta gtgaccaagc | | 20 |
| SEQ ID NO: 288<br>FEATURE<br>source | moltype = RNA length = 20<br>Location/Qualifiers<br>1..20<br>mol_type = other RNA<br>organism = Sus scrofa | |
| SEQUENCE: 288<br>tgcttggtca ctagttctct | | 20 |
| SEQ ID NO: 289<br>FEATURE<br>source | moltype = RNA length = 20<br>Location/Qualifiers<br>1..20<br>mol_type = other RNA<br>organism = Sus scrofa | |
| SEQUENCE: 289<br>gaactgtgtg taataatggc | | 20 |
| SEQ ID NO: 290<br>FEATURE<br>source | moltype = RNA length = 20<br>Location/Qualifiers<br>1..20<br>mol_type = other RNA<br>organism = Sus scrofa | |
| SEQUENCE: 290<br>tgctatcaaa gccactggat | | 20 |
| SEQ ID NO: 291<br>FEATURE<br>source | moltype = RNA length = 20<br>Location/Qualifiers<br>1..20<br>mol_type = other RNA<br>organism = Sus scrofa | |
| SEQUENCE: 291<br>gtgcaggttc tggacgcatt | | 20 |
| SEQ ID NO: 292<br>FEATURE<br>source | moltype = RNA length = 20<br>Location/Qualifiers<br>1..20<br>mol_type = other RNA<br>organism = Sus scrofa | |
| SEQUENCE: 292<br>gtgcaggttc tggacgcatt | | 20 |
| SEQ ID NO: 293<br>FEATURE<br>source | moltype = RNA length = 20<br>Location/Qualifiers<br>1..20<br>mol_type = other RNA<br>organism = Sus scrofa | |
| SEQUENCE: 293<br>atggatcatg tttcttgtcg | | 20 |
| SEQ ID NO: 294<br>FEATURE<br>source | moltype = RNA length = 20<br>Location/Qualifiers<br>1..20<br>mol_type = other RNA<br>organism = Sus scrofa | |
| SEQUENCE: 294<br>ggactgcaaa catgatggat | | 20 |

```
SEQ ID NO: 295          moltype = RNA   length = 20
FEATURE                 Location/Qualifiers
source                  1..20
                        mol_type = other RNA
                        organism = Sus scrofa
SEQUENCE: 295
ggactgcaaa catgatggat                                                    20

SEQ ID NO: 296          moltype = RNA   length = 20
FEATURE                 Location/Qualifiers
source                  1..20
                        mol_type = other RNA
                        organism = Sus scrofa
SEQUENCE: 296
agtcaaattt caaggacggt                                                    20

SEQ ID NO: 297          moltype = RNA   length = 20
FEATURE                 Location/Qualifiers
source                  1..20
                        mol_type = other RNA
                        organism = Sus scrofa
SEQUENCE: 297
gctaattttg gagaaggttc                                                    20

SEQ ID NO: 298          moltype = RNA   length = 20
FEATURE                 Location/Qualifiers
source                  1..20
                        mol_type = other RNA
                        organism = Sus scrofa
SEQUENCE: 298
gcacaattgt gatcatgctg                                                    20

SEQ ID NO: 299          moltype = RNA   length = 20
FEATURE                 Location/Qualifiers
source                  1..20
                        mol_type = other RNA
                        organism = Sus scrofa
SEQUENCE: 299
ggaactacag tgcggcactg                                                    20

SEQ ID NO: 300          moltype = DNA   length = 157
FEATURE                 Location/Qualifiers
source                  1..157
                        mol_type = genomic DNA
                        organism = Sus scrofa
SEQUENCE: 300
tttcgcagac tttagaagat gttctgccca tttaagttcc ttcacttttg ctgtagtcgc        60
tgttctcagt gcctgcttgg tcactagttc tcttggtgag tactttgaca aatttacttg       120
taacctagcc cactgtgaca agaaacactg aaaagca                                157

SEQ ID NO: 301          moltype = DNA   length = 157
FEATURE                 Location/Qualifiers
source                  1..157
                        mol_type = genomic DNA
                        organism = Sus scrofa
SEQUENCE: 301
tttcgcagac tttagaagat gttctgccca tttaagttcc ttcacttttg ctgtagtcgc        60
tgttctcagt gcctgcttgg tcactagttc tcttggtgag tactttgaca aatttacttg       120
taacctagcc cactgtgaca agaaacactg aaaagca                                157

SEQ ID NO: 302          moltype = DNA   length = 152
FEATURE                 Location/Qualifiers
source                  1..152
                        mol_type = genomic DNA
                        organism = Sus scrofa
SEQUENCE: 302
gtggtgaaaa caagtgctct ggaagagtgg aggtgaaagt gcaggaggag tggggaactg        60
tgtgtaataa tggctgggac atggatgtgg tctctgttgt ttgtaggcag ctgggatgtc       120
caactgctat caaagccact ggatgggcta at                                    152

SEQ ID NO: 303          moltype = DNA   length = 154
FEATURE                 Location/Qualifiers
source                  1..154
                        mol_type = genomic DNA
                        organism = Sus scrofa
SEQUENCE: 303
tggctgggac atggatgtgg tctctgttgt ttgtaggcag ctgggatgtc caactgctat        60
caaagccact ggatgggcta attttagtgc aggttctgga cgcatttgga tgatcatgt       120
```

```
SEQ ID NO: 304          moltype = DNA   length = 151
FEATURE                 Location/Qualifiers
source                  1..151
                        mol_type = genomic DNA
                        organism = Sus scrofa
SEQUENCE: 304
gtaggcagct gggatgtcca actgctatca aagccactgg atgggctaat tttagtgcag   60
gttctggacg catttggatg gatcatgttt cttgtcgagg gaatgagtca gctctctggg  120
actgcaaaca tgatggatgg ggaaagcata a                                 151

SEQ ID NO: 305          moltype = DNA   length = 151
FEATURE                 Location/Qualifiers
source                  1..151
                        mol_type = genomic DNA
                        organism = Sus scrofa
SEQUENCE: 305
gtaggcagct gggatgtcca actgctatca aagccactgg atgggctaat tttagtgcag   60
gttctggacg catttggatg gatcatgttt cttgtcgagg gaatgagtca gctctctggg  120
actgcaaaca tgatggatgg ggaaagcata a                                 151

SEQ ID NO: 306          moltype = DNA   length = 156
FEATURE                 Location/Qualifiers
source                  1..156
                        mol_type = genomic DNA
                        organism = Sus scrofa
SEQUENCE: 306
gtccaactgc tatcaaagcc actgatgggc taattttag tgcaggttct ggacgcattt   60
ggatggatca tgtttcttgt cgagggaatg agtcagctct ctgggactgc aaacatgatg  120
gatggggaaa gcataactgt actcaccaac aggatg                            156

SEQ ID NO: 307          moltype = DNA   length = 153
FEATURE                 Location/Qualifiers
source                  1..153
                        mol_type = genomic DNA
                        organism = Sus scrofa
SEQUENCE: 307
ctggacgcat ttggatggat catgtttctt gtcgagggaa tgagtcagct ctctgggact   60
gcaaacatga tggatgggga aagcataact gtactcacca acaggatgct ggagtaacct  120
gctcaggtaa gacatacaca aataagtcaa gcc                               153

SEQ ID NO: 308          moltype = DNA   length = 153
FEATURE                 Location/Qualifiers
source                  1..153
                        mol_type = genomic DNA
                        organism = Sus scrofa
SEQUENCE: 308
ctggacgcat ttggatggat catgtttctt gtcgagggaa tgagtcagct ctctgggact   60
gcaaacatga tggatgggga aagcataact gtactcacca acaggatgct ggagtaacct  120
gctcaggtaa gacatacaca aataagtcaa gcc                               153

SEQ ID NO: 309          moltype = DNA   length = 153
FEATURE                 Location/Qualifiers
source                  1..153
                        mol_type = genomic DNA
                        organism = Sus scrofa
SEQUENCE: 309
ctctagatgg atctgattta gagatgaggc tggtgaatgg aggaaaccgg tgcttaggaa   60
gaatagaagt caaatttcaa ggacggtggg gaacagtgtg tgatgataac ttcaacataa  120
atcatgcttc tgtggtttgt aaacaacttg aat                               153

SEQ ID NO: 310          moltype = DNA   length = 153
FEATURE                 Location/Qualifiers
source                  1..153
                        mol_type = genomic DNA
                        organism = Sus scrofa
SEQUENCE: 310
cttctgtggt ttgtaaacaa cttgaatgtg gaagtgctgt cagtttctct ggttcagcta   60
attttggaga aggttctgga ccaatctggt ttgatgatct tgtatgcaat ggaaatgagt  120
cagctctctg gaactgcaaa catgaaggat ggg                               153

SEQ ID NO: 311          moltype = DNA   length = 155
FEATURE                 Location/Qualifiers
source                  1..155
                        mol_type = genomic DNA
                        organism = Sus scrofa
SEQUENCE: 311
tgatgatctt gtatgcaatg gaaatgagtc agctctctgg aactgcaaac atgaaggatg   60
```

```
gggaaagcac aattgcgatc atgctgagga tgctggagtg atttgcttaa gtaaggactg    120
acctgggttt gttctgttct ccatgagagg gcaaa                                155
```

SEQ ID NO: 312          moltype = DNA   length = 154
FEATURE                 Location/Qualifiers
source                  1..154
                        mol_type = genomic DNA
                        organism = Sus scrofa
SEQUENCE: 312
```
agacacgtgg ggcaccgtct gtgattctga cttctctctg gaggcggcca gcgtgctgtg    60
cagggaacta cagtgcggca ctgtggtttc cctcctgggg ggagctcact ttggagaagg   120
aagtggacag atctgggctg aagaattcca gtgt                                154
```

SEQ ID NO: 313          moltype = AA   length = 28
FEATURE                 Location/Qualifiers
source                  1..28
                        mol_type = protein
                        organism = Sus scrofa
SEQUENCE: 313
FRRCSAHLSS FTFAVVAVLS ACLVTSSL                                        28

SEQ ID NO: 314          moltype = AA   length = 28
FEATURE                 Location/Qualifiers
source                  1..28
                        mol_type = protein
                        organism = Sus scrofa
SEQUENCE: 314
FRRCSAHLSS FTFAVVAVLS ACLVTSSL                                        28

SEQ ID NO: 315          moltype = AA   length = 50
FEATURE                 Location/Qualifiers
source                  1..50
                        mol_type = protein
                        organism = Sus scrofa
SEQUENCE: 315
GENKCSGRVE VKVQEEWGTV CNNGWDMDVV SVVCRQLGCP TAIKATGWAN                50

SEQ ID NO: 316          moltype = AA   length = 51
FEATURE                 Location/Qualifiers
source                  1..51
                        mol_type = protein
                        organism = Sus scrofa
SEQUENCE: 316
GWDMDVVSVV CRQLGCPTAI KATGWANFSA GSGRIWMDHV SCRGNESALW D              51

SEQ ID NO: 317          moltype = AA   length = 44
FEATURE                 Location/Qualifiers
source                  1..44
                        mol_type = protein
                        organism = Sus scrofa
SEQUENCE: 317
PTAIKATGWA NFSAGSGRIW MDHVSCRGNE SALWDCKHDG WGKH                      44

SEQ ID NO: 318          moltype = AA   length = 44
FEATURE                 Location/Qualifiers
source                  1..44
                        mol_type = protein
                        organism = Sus scrofa
SEQUENCE: 318
PTAIKATGWA NFSAGSGRIW MDHVSCRGNE SALWDCKHDG WGKH                      44

SEQ ID NO: 319          moltype = AA   length = 51
FEATURE                 Location/Qualifiers
source                  1..51
                        mol_type = protein
                        organism = Sus scrofa
SEQUENCE: 319
PTAIKATGWA NFSAGSGRIW MDHVSCRGNE SALWDCKHDG WGKHNCTHQQ D               51

SEQ ID NO: 320          moltype = AA   length = 35
FEATURE                 Location/Qualifiers
source                  1..35
                        mol_type = protein
                        organism = Sus scrofa
SEQUENCE: 320
GRIWMDHVSC RGNESALWDC KHDGWGKHNC THQQD                                35

SEQ ID NO: 321          moltype = AA   length = 35
FEATURE                 Location/Qualifiers

```
source                   1..35
                         mol_type = protein
                         organism = Sus scrofa
SEQUENCE: 321
GRIWMDHVSC RGNESALWDC KHDGWGKHNC THQQD                              35

SEQ ID NO: 322           moltype = AA  length = 48
FEATURE                  Location/Qualifiers
source                   1..48
                         mol_type = protein
                         organism = Sus scrofa
SEQUENCE: 322
GSDLEMRLVN GGNRCLGRIE VKFQGRWGTV CDDNFNINHA SVVCKQLE                48

SEQ ID NO: 323           moltype = AA  length = 50
FEATURE                  Location/Qualifiers
source                   1..50
                         mol_type = protein
                         organism = Sus scrofa
SEQUENCE: 323
SVVCKQLECG SAVSFSGSAN FGEGSGPIWF DDLVCNGNES ALWNCKHEGW              50

SEQ ID NO: 324           moltype = AA  length = 36
FEATURE                  Location/Qualifiers
source                   1..36
                         mol_type = protein
                         organism = Sus scrofa
SEQUENCE: 324
DDLVCNGNES ALWNCKHEGW GKHNCDHAED AGVICL                             36

SEQ ID NO: 325           moltype = AA  length = 51
FEATURE                  Location/Qualifiers
source                   1..51
                         mol_type = protein
                         organism = Sus scrofa
SEQUENCE: 325
DTWGTVCDSD FSLEAASVLC RELQCGTVVS LLGGAHFGEG SGQIWAEEFQ C            51

SEQ ID NO: 326           moltype = AA  length = 21
FEATURE                  Location/Qualifiers
source                   1..21
                         mol_type = protein
                         organism = Sus scrofa
SEQUENCE: 326
FRRCSAHLSS FTFAVVAVLS A                                             21

SEQ ID NO: 327           moltype = AA  length = 21
FEATURE                  Location/Qualifiers
source                   1..21
                         mol_type = protein
                         organism = Sus scrofa
SEQUENCE: 327
FRRCSAHLSS FTFAVVAVLS A                                             21

SEQ ID NO: 328           moltype = AA  length = 24
FEATURE                  Location/Qualifiers
source                   1..24
                         mol_type = protein
                         organism = Sus scrofa
SEQUENCE: 328
GENKCSGRVE VKVQEEWGTV CNNG                                          24

SEQ ID NO: 329           moltype = AA  length = 24
FEATURE                  Location/Qualifiers
source                   1..24
                         mol_type = protein
                         organism = Sus scrofa
SEQUENCE: 329
GWDMDVVSVV CRQLGCPTAI KATG                                          24

SEQ ID NO: 330           moltype = AA  length = 19
FEATURE                  Location/Qualifiers
source                   1..19
                         mol_type = protein
                         organism = Sus scrofa
SEQUENCE: 330
PTAIKATGWA NFSAGSGRI                                                19

SEQ ID NO: 331           moltype = AA  length = 19
```

```
FEATURE                 Location/Qualifiers
source                  1..19
                        mol_type = protein
                        organism = Sus scrofa
SEQUENCE: 331
PTAIKATGWA NFSAGSGRI                                                19

SEQ ID NO: 332          moltype = AA  length = 24
FEATURE                 Location/Qualifiers
source                  1..24
                        mol_type = protein
                        organism = Sus scrofa
SEQUENCE: 332
PTAIKATGWA NFSAGSGRIW MDHV                                          24

SEQ ID NO: 333          moltype = AA  length = 24
FEATURE                 Location/Qualifiers
source                  1..24
                        mol_type = protein
                        organism = Sus scrofa
SEQUENCE: 333
GRIWMDHVSC RGNESALWDC KHDG                                          24

SEQ ID NO: 334          moltype = AA  length = 24
FEATURE                 Location/Qualifiers
source                  1..24
                        mol_type = protein
                        organism = Sus scrofa
SEQUENCE: 334
GRIWMDHVSC RGNESALWDC KHDG                                          24

SEQ ID NO: 335          moltype = AA  length = 22
FEATURE                 Location/Qualifiers
source                  1..22
                        mol_type = protein
                        organism = Sus scrofa
SEQUENCE: 335
GSDLEMRLVN GGNRCLGRIE VK                                            22

SEQ ID NO: 336          moltype = AA  length = 24
FEATURE                 Location/Qualifiers
source                  1..24
                        mol_type = protein
                        organism = Sus scrofa
SEQUENCE: 336
SVVCKQLECG SAVSFSGSAN FGEG                                          24

SEQ ID NO: 337          moltype = AA  length = 24
FEATURE                 Location/Qualifiers
source                  1..24
                        mol_type = protein
                        organism = Sus scrofa
SEQUENCE: 337
DDLVCNGNES ALWNCKHEGW GKHN                                          24

SEQ ID NO: 338          moltype = AA  length = 24
FEATURE                 Location/Qualifiers
source                  1..24
                        mol_type = protein
                        organism = Sus scrofa
SEQUENCE: 338
DTWGTVCDSD FSLEAASVLC RELQ                                          24

SEQ ID NO: 339          moltype = AA  length = 24
FEATURE                 Location/Qualifiers
source                  1..24
                        mol_type = protein
                        organism = Sus scrofa
SEQUENCE: 339
VAVLSACLVT SSWRKRQGAE ANGW                                          24

SEQ ID NO: 340          moltype = AA  length = 20
FEATURE                 Location/Qualifiers
source                  1..20
                        mol_type = protein
                        organism = Sus scrofa
SEQUENCE: 340
VAVLSACLVT CNLAHCDKKH                                               20
```

```
SEQ ID NO: 341          moltype = AA   length = 20
FEATURE                 Location/Qualifiers
source                  1..20
                        mol_type = protein
                        organism = Sus scrofa
SEQUENCE: 341
VAVLSACLVT SSLLEEKTRS                                                    20

SEQ ID NO: 342          moltype = AA   length = 14
FEATURE                 Location/Qualifiers
source                  1..14
                        mol_type = protein
                        organism = Sus scrofa
SEQUENCE: 342
VAVLSACLEE KTRS                                                          14

SEQ ID NO: 343          moltype = AA   length = 20
FEATURE                 Location/Qualifiers
source                  1..20
                        mol_type = protein
                        organism = Sus scrofa
SEQUENCE: 343
VAVLSACLVT RSTLTNLLVT                                                    20

SEQ ID NO: 344          moltype = DNA   length = 33
FEATURE                 Location/Qualifiers
source                  1..33
                        mol_type = other DNA
                        organism = Sus scrofa
SEQUENCE: 344
agttctcttg gtgagtactt tgacaaattt act                                     33

SEQ ID NO: 345          moltype = DNA   length = 16
FEATURE                 Location/Qualifiers
source                  1..16
                        mol_type = other DNA
                        organism = Sus scrofa
SEQUENCE: 345
cactagttct cttggt                                                        16

SEQ ID NO: 346          moltype = DNA   length = 10
FEATURE                 Location/Qualifiers
source                  1..10
                        mol_type = other DNA
                        organism = Sus scrofa
SEQUENCE: 346
ttctcttggt                                                               10

SEQ ID NO: 347          moltype = DNA   length = 23
FEATURE                 Location/Qualifiers
source                  1..23
                        mol_type = other DNA
                        organism = Sus scrofa
SEQUENCE: 347
atgctatttt ttcagcccac agg                                                23

SEQ ID NO: 348          moltype = DNA   length = 23
FEATURE                 Location/Qualifiers
source                  1..23
                        mol_type = other DNA
                        organism = Sus scrofa
SEQUENCE: 348
tttcagccca caggaaaccc agg                                                23

SEQ ID NO: 349          moltype = DNA   length = 23
FEATURE                 Location/Qualifiers
source                  1..23
                        mol_type = other DNA
                        organism = Sus scrofa
SEQUENCE: 349
agcccacagg aaacccaggc tgg                                                23

SEQ ID NO: 350          moltype = DNA   length = 23
FEATURE                 Location/Qualifiers
source                  1..23
                        mol_type = other DNA
                        organism = Sus scrofa
SEQUENCE: 350
aaccagcctg ggtttcctgt ggg                                                23
```

```
SEQ ID NO: 351          moltype = DNA  length = 23
FEATURE                 Location/Qualifiers
source                  1..23
                        mol_type = other DNA
                        organism = Sus scrofa
SEQUENCE: 351
caaccagcct gggtttcctg tgg                                               23

SEQ ID NO: 352          moltype = DNA  length = 23
FEATURE                 Location/Qualifiers
source                  1..23
                        mol_type = other DNA
                        organism = Sus scrofa
SEQUENCE: 352
cacaggaaac ccaggctggt tgg                                               23

SEQ ID NO: 353          moltype = DNA  length = 23
FEATURE                 Location/Qualifiers
source                  1..23
                        mol_type = other DNA
                        organism = Sus scrofa
SEQUENCE: 353
aggaaaccca ggctggttgg agg                                               23

SEQ ID NO: 354          moltype = DNA  length = 23
FEATURE                 Location/Qualifiers
source                  1..23
                        mol_type = other DNA
                        organism = Sus scrofa
SEQUENCE: 354
ggaaacccag gctggttgga ggg                                               23

SEQ ID NO: 355          moltype = DNA  length = 23
FEATURE                 Location/Qualifiers
source                  1..23
                        mol_type = other DNA
                        organism = Sus scrofa
SEQUENCE: 355
gaaacccagg ctggttggag ggg                                               23

SEQ ID NO: 356          moltype = DNA  length = 23
FEATURE                 Location/Qualifiers
source                  1..23
                        mol_type = other DNA
                        organism = Sus scrofa
SEQUENCE: 356
atgtcccctc caaccagcct ggg                                               23

SEQ ID NO: 357          moltype = DNA  length = 23
FEATURE                 Location/Qualifiers
source                  1..23
                        mol_type = other DNA
                        organism = Sus scrofa
SEQUENCE: 357
aatgtcccct ccaaccagcc tgg                                               23

SEQ ID NO: 358          moltype = DNA  length = 23
FEATURE                 Location/Qualifiers
source                  1..23
                        mol_type = other DNA
                        organism = Sus scrofa
SEQUENCE: 358
ggagggaca ttccctgctc tgg                                                23

SEQ ID NO: 359          moltype = DNA  length = 23
FEATURE                 Location/Qualifiers
source                  1..23
                        mol_type = other DNA
                        organism = Sus scrofa
SEQUENCE: 359
acttcaacac gaccagagca ggg                                               23

SEQ ID NO: 360          moltype = DNA  length = 23
FEATURE                 Location/Qualifiers
source                  1..23
                        mol_type = other DNA
                        organism = Sus scrofa
SEQUENCE: 360
```
tacttcaaca cgaccagagc agg                                              23

SEQ ID NO: 361          moltype = DNA   length = 23
FEATURE                 Location/Qualifiers
source                  1..23
                        mol_type = other DNA
                        organism = Sus scrofa
SEQUENCE: 361
ggtcgtgttg aagtacaaca tgg                                              23

SEQ ID NO: 362          moltype = DNA   length = 23
FEATURE                 Location/Qualifiers
source                  1..23
                        mol_type = other DNA
                        organism = Sus scrofa
SEQUENCE: 362
aagtacaaca tggagacacg tgg                                              23

SEQ ID NO: 363          moltype = DNA   length = 23
FEATURE                 Location/Qualifiers
source                  1..23
                        mol_type = other DNA
                        organism = Sus scrofa
SEQUENCE: 363
agtacaacat ggagacacgt ggg                                              23

SEQ ID NO: 364          moltype = DNA   length = 23
FEATURE                 Location/Qualifiers
source                  1..23
                        mol_type = other DNA
                        organism = Sus scrofa
SEQUENCE: 364
gtacaacatg gagacacgtg ggg                                              23

SEQ ID NO: 365          moltype = DNA   length = 23
FEATURE                 Location/Qualifiers
source                  1..23
                        mol_type = other DNA
                        organism = Sus scrofa
SEQUENCE: 365
agagaagtca gaatcacaga cgg                                              23

SEQ ID NO: 366          moltype = DNA   length = 23
FEATURE                 Location/Qualifiers
source                  1..23
                        mol_type = other DNA
                        organism = Sus scrofa
SEQUENCE: 366
ctgtgattct gacttctctc tgg                                              23

SEQ ID NO: 367          moltype = DNA   length = 23
FEATURE                 Location/Qualifiers
source                  1..23
                        mol_type = other DNA
                        organism = Sus scrofa
SEQUENCE: 367
tgattctgac ttctctctgg agg                                              23

SEQ ID NO: 368          moltype = DNA   length = 23
FEATURE                 Location/Qualifiers
source                  1..23
                        mol_type = other DNA
                        organism = Sus scrofa
SEQUENCE: 368
ttctgacttc tctctggagg cgg                                              23

SEQ ID NO: 369          moltype = DNA   length = 23
FEATURE                 Location/Qualifiers
source                  1..23
                        mol_type = other DNA
                        organism = Sus scrofa
SEQUENCE: 369
aggcggccag cgtgctgtgc agg                                              23

SEQ ID NO: 370          moltype = DNA   length = 23
FEATURE                 Location/Qualifiers
source                  1..23
                        mol_type = other DNA
                        organism = Sus scrofa

```
SEQUENCE: 370
ggcggccagc gtgctgtgca ggg                                              23

SEQ ID NO: 371          moltype = DNA   length = 23
FEATURE                 Location/Qualifiers
source                  1..23
                        mol_type = other DNA
                        organism = Sus scrofa
SEQUENCE: 371
tagttccctg cacagcacgc tgg                                              23

SEQ ID NO: 372          moltype = DNA   length = 23
FEATURE                 Location/Qualifiers
source                  1..23
                        mol_type = other DNA
                        organism = Sus scrofa
SEQUENCE: 372
ctgtgcaggg aactacagtg cgg                                              23

SEQ ID NO: 373          moltype = DNA   length = 23
FEATURE                 Location/Qualifiers
source                  1..23
                        mol_type = other DNA
                        organism = Sus scrofa
SEQUENCE: 373
ggaactacag tgcggcactg tgg                                              23

SEQ ID NO: 374          moltype = DNA   length = 23
FEATURE                 Location/Qualifiers
source                  1..23
                        mol_type = other DNA
                        organism = Sus scrofa
SEQUENCE: 374
cggcactgtg gtttccctcc tgg                                              23

SEQ ID NO: 375          moltype = DNA   length = 23
FEATURE                 Location/Qualifiers
source                  1..23
                        mol_type = other DNA
                        organism = Sus scrofa
SEQUENCE: 375
ggcactgtgg tttccctcct ggg                                              23

SEQ ID NO: 376          moltype = DNA   length = 23
FEATURE                 Location/Qualifiers
source                  1..23
                        mol_type = other DNA
                        organism = Sus scrofa
SEQUENCE: 376
gcactgtggt ttccctcctg ggg                                              23

SEQ ID NO: 377          moltype = DNA   length = 23
FEATURE                 Location/Qualifiers
source                  1..23
                        mol_type = other DNA
                        organism = Sus scrofa
SEQUENCE: 377
cactgtggtt tccctcctgg ggg                                              23

SEQ ID NO: 378          moltype = DNA   length = 23
FEATURE                 Location/Qualifiers
source                  1..23
                        mol_type = other DNA
                        organism = Sus scrofa
SEQUENCE: 378
actgtggttt ccctcctggg ggg                                              23

SEQ ID NO: 379          moltype = DNA   length = 23
FEATURE                 Location/Qualifiers
source                  1..23
                        mol_type = other DNA
                        organism = Sus scrofa
SEQUENCE: 379
aaagtgagct cccccagga ggg                                               23

SEQ ID NO: 380          moltype = DNA   length = 23
FEATURE                 Location/Qualifiers
source                  1..23
                        mol_type = other DNA
```

```
                        organism = Sus scrofa
SEQUENCE: 380
caaagtgagc tccccccagg agg                                              23

SEQ ID NO: 381          moltype = DNA   length = 23
FEATURE                 Location/Qualifiers
source                  1..23
                        mol_type = other DNA
                        organism = Sus scrofa
SEQUENCE: 381
ctcctgggggg gagctcactt tgg                                             23

SEQ ID NO: 382          moltype = DNA   length = 23
FEATURE                 Location/Qualifiers
source                  1..23
                        mol_type = other DNA
                        organism = Sus scrofa
SEQUENCE: 382
ctccaaagtg agctcccccc agg                                              23

SEQ ID NO: 383          moltype = DNA   length = 23
FEATURE                 Location/Qualifiers
source                  1..23
                        mol_type = other DNA
                        organism = Sus scrofa
SEQUENCE: 383
gggggagctc actttggaga agg                                              23

SEQ ID NO: 384          moltype = DNA   length = 23
FEATURE                 Location/Qualifiers
source                  1..23
                        mol_type = other DNA
                        organism = Sus scrofa
SEQUENCE: 384
gctcactttg gagaaggaag tgg                                              23

SEQ ID NO: 385          moltype = DNA   length = 23
FEATURE                 Location/Qualifiers
source                  1..23
                        mol_type = other DNA
                        organism = Sus scrofa
SEQUENCE: 385
gagaaggaag tggacagatc tgg                                              23

SEQ ID NO: 386          moltype = DNA   length = 23
FEATURE                 Location/Qualifiers
source                  1..23
                        mol_type = other DNA
                        organism = Sus scrofa
SEQUENCE: 386
agaaggaagt ggacagatct ggg                                              23

SEQ ID NO: 387          moltype = DNA   length = 23
FEATURE                 Location/Qualifiers
source                  1..23
                        mol_type = other DNA
                        organism = Sus scrofa
SEQUENCE: 387
ggctgaagaa ttccagtgtg agg                                              23

SEQ ID NO: 388          moltype = DNA   length = 23
FEATURE                 Location/Qualifiers
source                  1..23
                        mol_type = other DNA
                        organism = Sus scrofa
SEQUENCE: 388
gctgaagaat tccagtgtga ggg                                              23

SEQ ID NO: 389          moltype = DNA   length = 23
FEATURE                 Location/Qualifiers
source                  1..23
                        mol_type = other DNA
                        organism = Sus scrofa
SEQUENCE: 389
ctgaagaatt ccagtgtgag ggg                                              23

SEQ ID NO: 390          moltype = DNA   length = 23
FEATURE                 Location/Qualifiers
source                  1..23
```

```
                            mol_type = other DNA
                            organism = Sus scrofa
SEQUENCE: 390
gggactcgtg cccctcacac tgg                                              23

SEQ ID NO: 391              moltype = DNA  length = 23
FEATURE                     Location/Qualifiers
source                      1..23
                            mol_type = other DNA
                            organism = Sus scrofa
SEQUENCE: 391
tactgggcag agtgaaaggt ggg                                              23

SEQ ID NO: 392              moltype = DNA  length = 23
FEATURE                     Location/Qualifiers
source                      1..23
                            mol_type = other DNA
                            organism = Sus scrofa
SEQUENCE: 392
ctactgggca gagtgaaagg tgg                                              23

SEQ ID NO: 393              moltype = DNA  length = 23
FEATURE                     Location/Qualifiers
source                      1..23
                            mol_type = other DNA
                            organism = Sus scrofa
SEQUENCE: 393
gtgctactgg gcagagtgaa agg                                              23

SEQ ID NO: 394              moltype = DNA  length = 23
FEATURE                     Location/Qualifiers
source                      1..23
                            mol_type = other DNA
                            organism = Sus scrofa
SEQUENCE: 394
cgtcagggcg gggtgctact ggg                                              23

SEQ ID NO: 395              moltype = DNA  length = 23
FEATURE                     Location/Qualifiers
source                      1..23
                            mol_type = other DNA
                            organism = Sus scrofa
SEQUENCE: 395
ccagtagcac cccgccctga cgg                                              23

SEQ ID NO: 396              moltype = DNA  length = 23
FEATURE                     Location/Qualifiers
source                      1..23
                            mol_type = other DNA
                            organism = Sus scrofa
SEQUENCE: 396
ccgtcagggc ggggtgctac tgg                                              23

SEQ ID NO: 397              moltype = DNA  length = 23
FEATURE                     Location/Qualifiers
source                      1..23
                            mol_type = other DNA
                            organism = Sus scrofa
SEQUENCE: 397
cagtagcacc ccgccctgac ggg                                              23

SEQ ID NO: 398              moltype = DNA  length = 23
FEATURE                     Location/Qualifiers
source                      1..23
                            mol_type = other DNA
                            organism = Sus scrofa
SEQUENCE: 398
ctacatgtcc cgtcagggcg ggg                                              23

SEQ ID NO: 399              moltype = DNA  length = 23
FEATURE                     Location/Qualifiers
source                      1..23
                            mol_type = other DNA
                            organism = Sus scrofa
SEQUENCE: 399
gctacatgtc ccgtcagggc ggg                                              23

SEQ ID NO: 400              moltype = DNA  length = 23
FEATURE                     Location/Qualifiers
```

```
source                  1..23
                        mol_type = other DNA
                        organism = Sus scrofa
SEQUENCE: 400
ggctacatgt cccgtcaggg cgg                                         23

SEQ ID NO: 401          moltype = DNA   length = 23
FEATURE                 Location/Qualifiers
source                  1..23
                        mol_type = other DNA
                        organism = Sus scrofa
SEQUENCE: 401
tgtggctaca tgtcccgtca ggg                                         23

SEQ ID NO: 402          moltype = DNA   length = 23
FEATURE                 Location/Qualifiers
source                  1..23
                        mol_type = other DNA
                        organism = Sus scrofa
SEQUENCE: 402
ctgtggctac atgtcccgtc agg                                         23

SEQ ID NO: 403          moltype = DNA   length = 23
FEATURE                 Location/Qualifiers
source                  1..23
                        mol_type = other DNA
                        organism = Sus scrofa
SEQUENCE: 403
acgggacatg tagccacagc agg                                         23

SEQ ID NO: 404          moltype = DNA   length = 23
FEATURE                 Location/Qualifiers
source                  1..23
                        mol_type = other DNA
                        organism = Sus scrofa
SEQUENCE: 404
cgggacatgt agccacagca ggg                                         23

SEQ ID NO: 405          moltype = DNA   length = 23
FEATURE                 Location/Qualifiers
source                  1..23
                        mol_type = other DNA
                        organism = Sus scrofa
SEQUENCE: 405
tgtagccaca gcagggacgt cgg                                         23

SEQ ID NO: 406          moltype = DNA   length = 23
FEATURE                 Location/Qualifiers
source                  1..23
                        mol_type = other DNA
                        organism = Sus scrofa
SEQUENCE: 406
ctacgccgac gtccctgctg tgg                                         23

SEQ ID NO: 407          moltype = DNA   length = 25
FEATURE                 Location/Qualifiers
source                  1..25
                        mol_type = other DNA
                        organism = Sus scrofa
SEQUENCE: 407
cacaggaaac ccaggctggt tggag                                       25

SEQ ID NO: 408          moltype = DNA   length = 25
FEATURE                 Location/Qualifiers
source                  1..25
                        mol_type = other DNA
                        organism = Sus scrofa
SEQUENCE: 408
aggaaaccca ggctggttgg agggg                                       25

SEQ ID NO: 409          moltype = DNA   length = 25
FEATURE                 Location/Qualifiers
source                  1..25
                        mol_type = other DNA
                        organism = Sus scrofa
SEQUENCE: 409
ggtcgtgttg aagtacaaca tggag                                       25

SEQ ID NO: 410          moltype = DNA   length = 25
```

```
FEATURE                 Location/Qualifiers
source                  1..25
                        mol_type = other DNA
                        organism = Sus scrofa
SEQUENCE: 410
aagtacaaca tggagacacg tgggg                                               25

SEQ ID NO: 411          moltype = DNA   length = 25
FEATURE                 Location/Qualifiers
source                  1..25
                        mol_type = other DNA
                        organism = Sus scrofa
SEQUENCE: 411
agagaagtca gaatcacaga cggtg                                               25

SEQ ID NO: 412          moltype = DNA   length = 25
FEATURE                 Location/Qualifiers
source                  1..25
                        mol_type = other DNA
                        organism = Sus scrofa
SEQUENCE: 412
ctgtgattct gacttctctc tggag                                               25

SEQ ID NO: 413          moltype = DNA   length = 25
FEATURE                 Location/Qualifiers
source                  1..25
                        mol_type = other DNA
                        organism = Sus scrofa
SEQUENCE: 413
tgattctgac ttctctctgg aggcg                                               25

SEQ ID NO: 414          moltype = DNA   length = 25
FEATURE                 Location/Qualifiers
source                  1..25
                        mol_type = other DNA
                        organism = Sus scrofa
SEQUENCE: 414
cggcactgtg gtttccctcc tgggg                                               25

SEQ ID NO: 415          moltype = DNA   length = 25
FEATURE                 Location/Qualifiers
source                  1..25
                        mol_type = other DNA
                        organism = Sus scrofa
SEQUENCE: 415
ggcactgtgg tttccctcct ggggg                                               25

SEQ ID NO: 416          moltype = DNA   length = 25
FEATURE                 Location/Qualifiers
source                  1..25
                        mol_type = other DNA
                        organism = Sus scrofa
SEQUENCE: 416
gcactgtggt ttccctcctg ggggg                                               25

SEQ ID NO: 417          moltype = DNA   length = 25
FEATURE                 Location/Qualifiers
source                  1..25
                        mol_type = other DNA
                        organism = Sus scrofa
SEQUENCE: 417
actgtggttt ccctcctggg gggag                                               25

SEQ ID NO: 418          moltype = DNA   length = 25
FEATURE                 Location/Qualifiers
source                  1..25
                        mol_type = other DNA
                        organism = Sus scrofa
SEQUENCE: 418
ctcctggggg gagctcactt tggag                                               25

SEQ ID NO: 419          moltype = DNA   length = 25
FEATURE                 Location/Qualifiers
source                  1..25
                        mol_type = other DNA
                        organism = Sus scrofa
SEQUENCE: 419
ctccaaagtg agctcccccc aggag                                               25
```

```
SEQ ID NO: 420         moltype = DNA   length = 25
FEATURE                Location/Qualifiers
source                 1..25
                       mol_type = other DNA
                       organism = Sus scrofa
SEQUENCE: 420
ggctgaagaa ttccagtgtg agggg                                          25

SEQ ID NO: 421         moltype = DNA   length = 25
FEATURE                Location/Qualifiers
source                 1..25
                       mol_type = other DNA
                       organism = Sus scrofa
SEQUENCE: 421
gtgctactgg gcagagtgaa aggtg                                          25

SEQ ID NO: 422         moltype = DNA   length = 25
FEATURE                Location/Qualifiers
source                 1..25
                       mol_type = other DNA
                       organism = Sus scrofa
SEQUENCE: 422
ctacatgtcc cgtcagggcg gggtg                                          25

SEQ ID NO: 423         moltype = DNA   length = 25
FEATURE                Location/Qualifiers
source                 1..25
                       mol_type = other DNA
                       organism = Sus scrofa
SEQUENCE: 423
ggctacatgt cccgtcaggg cgggg                                          25

SEQ ID NO: 424         moltype = DNA   length = 25
FEATURE                Location/Qualifiers
source                 1..25
                       mol_type = other DNA
                       organism = Sus scrofa
SEQUENCE: 424
tgtggctaca tgtcccgtca gggcg                                          25

SEQ ID NO: 425         moltype = DNA   length = 25
FEATURE                Location/Qualifiers
source                 1..25
                       mol_type = other DNA
                       organism = Sus scrofa
SEQUENCE: 425
tgtagccaca gcagggacgt cggcg                                          25

SEQ ID NO: 426         moltype = DNA   length = 100
FEATURE                Location/Qualifiers
source                 1..100
                       mol_type = other DNA
                       organism = Sus scrofa
SEQUENCE: 426
gaatgaagta ggcaaatact caaaggaaag agaaagcatg ctccaagaat ggtagggtta    60
ggtagtcaca gacatctttt taaagccctg tctccttcca                         100

SEQ ID NO: 427         moltype = DNA   length = 100
FEATURE                Location/Qualifiers
source                 1..100
                       mol_type = other DNA
                       organism = Sus scrofa
SEQUENCE: 427
atgaatgaag taggcaaata ctcaaaggaa agagaaagca tgctccaaga ggtagggtta    60
ggtagtcaca gacatctttt taaagccctg tctccttcca                         100

SEQ ID NO: 428         moltype = DNA   length = 100
FEATURE                Location/Qualifiers
source                 1..100
                       mol_type = other DNA
                       organism = Sus scrofa
SEQUENCE: 428
ggcaaatact caaaggaaag agaaagcatg ctccaagaat tatgggttcc ggtagggtta    60
ggtagtcaca gacatctttt taaagccctg tctccttcca                         100

SEQ ID NO: 429         moltype = DNA   length = 100
FEATURE                Location/Qualifiers
source                 1..100
                       mol_type = other DNA
```

```
                        organism = Sus scrofa
SEQUENCE: 429
agaattatgg gttccagaag gcaaagtccc agaattgtct ccagggaagg ggtagggtta    60
ggtagtcaca gacatctttt taaagccctg tctccttcca                         100

SEQ ID NO: 430          moltype = DNA  length = 100
FEATURE                 Location/Qualifiers
source                  1..100
                        mol_type = other DNA
                        organism = Sus scrofa
SEQUENCE: 430
agaattgtct ccagggaagg acagggaggt ctagaatcgg ctaagcccac ggtagggtta    60
ggtagtcaca gacatctttt taaagccctg tctccttcca                         100

SEQ ID NO: 431          moltype = DNA  length = 100
FEATURE                 Location/Qualifiers
source                  1..100
                        mol_type = other DNA
                        organism = Sus scrofa
SEQUENCE: 431
gaatgaagta ggcaaatact caaaggaaag agaaagcatg ctccaagaat gtagggttag    60
gtagtcacag acatctttt aaagccctgt ctccttccag                          100

SEQ ID NO: 432          moltype = DNA  length = 100
FEATURE                 Location/Qualifiers
source                  1..100
                        mol_type = other DNA
                        organism = Sus scrofa
SEQUENCE: 432
atgaatgaag taggcaaata ctcaaaggaa agagaaagca tgctccaaga gtagggttag    60
gtagtcacag acatctttt aaagccctgt ctccttccag                          100

SEQ ID NO: 433          moltype = DNA  length = 100
FEATURE                 Location/Qualifiers
source                  1..100
                        mol_type = other DNA
                        organism = Sus scrofa
SEQUENCE: 433
ggcaaatact caaaggaaag agaaagcatg ctccaagaat tatgggttcc gtagggttag    60
gtagtcacag acatctttt aaagccctgt ctccttccag                          100

SEQ ID NO: 434          moltype = DNA  length = 100
FEATURE                 Location/Qualifiers
source                  1..100
                        mol_type = other DNA
                        organism = Sus scrofa
SEQUENCE: 434
agaattatgg gttccagaag gcaaagtccc agaattgtct ccagggaagg gtagggttag    60
gtagtcacag acatctttt aaagccctgt ctccttccag                          100

SEQ ID NO: 435          moltype = DNA  length = 100
FEATURE                 Location/Qualifiers
source                  1..100
                        mol_type = other DNA
                        organism = Sus scrofa
SEQUENCE: 435
agaattgtct ccagggaagg acagggaggt ctagaatcgg ctaagcccac gtagggttag    60
gtagtcacag acatctttt aaagccctgt ctccttccag                          100

SEQ ID NO: 436          moltype = DNA  length = 100
FEATURE                 Location/Qualifiers
source                  1..100
                        mol_type = other DNA
                        organism = Sus scrofa
SEQUENCE: 436
gaatgaagta ggcaaatact caaaggaaag agaaagcatg ctccaagaat agagggtagg    60
gttaggtagt cacagacatc tttttaaagc cctgtctcct                         100

SEQ ID NO: 437          moltype = DNA  length = 100
FEATURE                 Location/Qualifiers
source                  1..100
                        mol_type = other DNA
                        organism = Sus scrofa
SEQUENCE: 437
atgaatgaag taggcaaata ctcaaaggaa agagaaagca tgctccaaga agagggtagg    60
gttaggtagt cacagacatc tttttaaagc cctgtctcct                         100

SEQ ID NO: 438          moltype = DNA  length = 100
FEATURE                 Location/Qualifiers
```

```
                        source           1..100
                                         mol_type = other DNA
                                         organism = Sus scrofa
SEQUENCE: 438
ggcaaatact caaaggaaag agaaagcatg ctccaagaat tatgggttcc agagggtagg    60
gttaggtagt cacagacatc tttttaaagc cctgtctcct                         100

SEQ ID NO: 439          moltype = DNA   length = 100
FEATURE                 Location/Qualifiers
source                  1..100
                        mol_type = other DNA
                        organism = Sus scrofa
SEQUENCE: 439
agaattatgg gttccagaag gcaaagtccc agaattgtct ccagggaagg agagggtagg    60
gttaggtagt cacagacatc tttttaaagc cctgtctcct                         100

SEQ ID NO: 440          moltype = DNA   length = 100
FEATURE                 Location/Qualifiers
source                  1..100
                        mol_type = other DNA
                        organism = Sus scrofa
SEQUENCE: 440
agaattgtct ccagggaagg acagggaggt ctagaatcgg ctaagcccac agagggtagg    60
gttaggtagt cacagacatc tttttaaagc cctgtctcct                         100

SEQ ID NO: 441          moltype = DNA   length = 100
FEATURE                 Location/Qualifiers
source                  1..100
                        mol_type = other DNA
                        organism = Sus scrofa
SEQUENCE: 441
atgtcttctg ctttatttct ggtgtgcctt tgactccaga ttacagtaaa ggtagggtta    60
ggtagtcaca gacatctttt taaagccctg tctccttcca                         100

SEQ ID NO: 442          moltype = DNA   length = 100
FEATURE                 Location/Qualifiers
source                  1..100
                        mol_type = other DNA
                        organism = Sus scrofa
SEQUENCE: 442
ttatttctgg tgtgcctttg actccagatt acagtaaatg gaggactgag ggtagggtta    60
ggtagtcaca gacatctttt taaagccctg tctccttcca                         100

SEQ ID NO: 443          moltype = DNA   length = 100
FEATURE                 Location/Qualifiers
source                  1..100
                        mol_type = other DNA
                        organism = Sus scrofa
SEQUENCE: 443
tggaggactg agtatagggc taaaaagtag agagaatgga tgcatattat ggtagggtta    60
ggtagtcaca gacatctttt taaagccctg tctccttcca                         100

SEQ ID NO: 444          moltype = DNA   length = 100
FEATURE                 Location/Qualifiers
source                  1..100
                        mol_type = other DNA
                        organism = Sus scrofa
SEQUENCE: 444
atgcatatta tctgtggtct ccaatgtgat gaatgaagta ggcaaatact ggtagggtta    60
ggtagtcaca gacatctttt taaagccctg tctccttcca                         100

SEQ ID NO: 445          moltype = DNA   length = 100
FEATURE                 Location/Qualifiers
source                  1..100
                        mol_type = other DNA
                        organism = Sus scrofa
SEQUENCE: 445
atgtcttctg ctttatttct ggtgtgcctt tgactccaga ttacagtaaa gtagggttag    60
gtagtcacag acatcttttt aaagccctgt ctccttccag                         100

SEQ ID NO: 446          moltype = DNA   length = 100
FEATURE                 Location/Qualifiers
source                  1..100
                        mol_type = other DNA
                        organism = Sus scrofa
SEQUENCE: 446
ttatttctgg tgtgcctttg actccagatt acagtaaatg gaggactgag gtagggttag    60
gtagtcacag acatcttttt aaagccctgt ctccttccag                         100
```

```
SEQ ID NO: 447          moltype = DNA   length = 100
FEATURE                 Location/Qualifiers
source                  1..100
                        mol_type = other DNA
                        organism = Sus scrofa
SEQUENCE: 447
tggaggactg agtatagggc taaaaagtag agagaatgga tgcatattat gtagggttag    60
gtagtcacag acatctttt aaagccctgt ctccttccag                          100

SEQ ID NO: 448          moltype = DNA   length = 100
FEATURE                 Location/Qualifiers
source                  1..100
                        mol_type = other DNA
                        organism = Sus scrofa
SEQUENCE: 448
atgcatatta tctgtggtct ccaatgtgat gaatgaagta ggcaaatact gtagggttag    60
gtagtcacag acatctttt aaagccctgt ctccttccag                          100

SEQ ID NO: 449          moltype = DNA   length = 100
FEATURE                 Location/Qualifiers
source                  1..100
                        mol_type = other DNA
                        organism = Sus scrofa
SEQUENCE: 449
atgtcttctg ctttatttct ggtgtgcctt tgactccaga ttacagtaaa agagggtagg    60
gttaggtagt cacagacatc ttttaaagc cctgtctcct                          100

SEQ ID NO: 450          moltype = DNA   length = 100
FEATURE                 Location/Qualifiers
source                  1..100
                        mol_type = other DNA
                        organism = Sus scrofa
SEQUENCE: 450
ttatttctgg tgtgcctttg actccagatt acagtaaatg gaggactgag agagggtagg    60
gttaggtagt cacagacatc ttttaaagc cctgtctcct                          100

SEQ ID NO: 451          moltype = DNA   length = 100
FEATURE                 Location/Qualifiers
source                  1..100
                        mol_type = other DNA
                        organism = Sus scrofa
SEQUENCE: 451
tggaggactg agtatagggc taaaaagtag agagaatgga tgcatattat agagggtagg    60
gttaggtagt cacagacatc ttttaaagc cctgtctcct                          100

SEQ ID NO: 452          moltype = DNA   length = 100
FEATURE                 Location/Qualifiers
source                  1..100
                        mol_type = other DNA
                        organism = Sus scrofa
SEQUENCE: 452
atgcatatta tctgtggtct ccaatgtgat gaatgaagta ggcaaatact agagggtagg    60
gttaggtagt cacagacatc ttttaaagc cctgtctcct                          100

SEQ ID NO: 453          moltype = DNA   length = 100
FEATURE                 Location/Qualifiers
source                  1..100
                        mol_type = other DNA
                        organism = Sus scrofa
SEQUENCE: 453
catgaatggc ttcccttcct cacttttcac tctctggctt actcctatca ggtagggtta    60
ggtagtcaca gacatctttt taaagccctg tctccttcca                         100

SEQ ID NO: 454          moltype = DNA   length = 100
FEATURE                 Location/Qualifiers
source                  1..100
                        mol_type = other DNA
                        organism = Sus scrofa
SEQUENCE: 454
ttcccttcct cacttttcac tctctggctt actcctatca tgaaggaaaa ggtagggtta    60
ggtagtcaca gacatctttt taaagccctg tctccttcca                         100

SEQ ID NO: 455          moltype = DNA   length = 100
FEATURE                 Location/Qualifiers
source                  1..100
                        mol_type = other DNA
                        organism = Sus scrofa
SEQUENCE: 455
catgaatggc ttcccttcct cacttttcac tctctggctt actcctatca gtagggttag    60
```

```
SEQ ID NO: 456          moltype = DNA   length = 100
FEATURE                 Location/Qualifiers
source                  1..100
                        mol_type = other DNA
                        organism = Sus scrofa
SEQUENCE: 456
ttccctttct cacttttcac tctctggctt actcctatca tgaaggaaaa gtagggttag    60
gtagtcacag acatcttttt aaagccctgt ctccttccag                         100

SEQ ID NO: 457          moltype = DNA   length = 100
FEATURE                 Location/Qualifiers
source                  1..100
                        mol_type = other DNA
                        organism = Sus scrofa
SEQUENCE: 457
catgaatggc ttccctttct cacttttcac tctctggctt actcctatca agagggtagg    60
gttaggtagt cacagacatc tttttaaagc cctgtctcct                         100

SEQ ID NO: 458          moltype = DNA   length = 100
FEATURE                 Location/Qualifiers
source                  1..100
                        mol_type = other DNA
                        organism = Sus scrofa
SEQUENCE: 458
ttccctttct cacttttcac tctctggctt actcctatca tgaaggaaaa agagggtagg    60
gttaggtagt cacagacatc tttttaaagc cctgtctcct                         100

SEQ ID NO: 459          moltype = DNA   length = 100
FEATURE                 Location/Qualifiers
source                  1..100
                        mol_type = other DNA
                        organism = Sus scrofa
SEQUENCE: 459
tattggaatc atattctccc tcaccgaaat gctattttt cagcccacag gtgattctga     60
cttctctctg gaggcggcca gcgtgctgtg cagggaacta                         100

SEQ ID NO: 460          moltype = DNA   length = 100
FEATURE                 Location/Qualifiers
source                  1..100
                        mol_type = other DNA
                        organism = Sus scrofa
SEQUENCE: 460
tattggaatc atattctccc tcaccgaaat gctattttt cagcccacag gtgaggggca     60
cgagtcccac ctttcactct gcccagtagc accccgccct                         100

SEQ ID NO: 461          moltype = DNA   length = 100
FEATURE                 Location/Qualifiers
source                  1..100
                        mol_type = other DNA
                        organism = Sus scrofa
SEQUENCE: 461
ggaatcatat tctccctcac cgaaatgcta tttttcagc ccacaggaaa tgagggcac      60
gagtcccacc tttcactctg cccagtagca ccccgccctg                         100

SEQ ID NO: 462          moltype = DNA   length = 100
FEATURE                 Location/Qualifiers
source                  1..100
                        mol_type = other DNA
                        organism = Sus scrofa
SEQUENCE: 462
ggaatcatat tctccctcac cgaaatgcta tttttcagc ccacaggaaa tgagggcac      60
gagtcccacc tttcactctg cccagtagca ccccgccctg                         100

SEQ ID NO: 463          moltype = DNA   length = 100
FEATURE                 Location/Qualifiers
source                  1..100
                        mol_type = other DNA
                        organism = Sus scrofa
SEQUENCE: 463
ggaatcatat tctccctcac cgaaatgcta tttttcagc ccacaggaaa tgacgggaca     60
tgtagccaca gcagggacgt cggcgtagtc tgctcaagtg                         100

SEQ ID NO: 464          moltype = DNA   length = 100
FEATURE                 Location/Qualifiers
source                  1..100
                        mol_type = other DNA
                        organism = Sus scrofa
```

-continued

```
SEQUENCE: 464
attctccctc accgaaatgc tattttttca gcccacagga aacccaggct gtgattctga    60
cttctctctg gaggcggcca gcgtgctgtg cagggaacta                         100

SEQ ID NO: 465          moltype = DNA   length = 100
FEATURE                 Location/Qualifiers
source                  1..100
                        mol_type = other DNA
                        organism = Sus scrofa
SEQUENCE: 465
attctccctc accgaaatgc tattttttca gcccacagga aacccaggct gtgaggggca    60
cgagtcccac ctttcactct gcccagtagc accccgccct                         100

SEQ ID NO: 466          moltype = DNA   length = 100
FEATURE                 Location/Qualifiers
source                  1..100
                        mol_type = other DNA
                        organism = Sus scrofa
SEQUENCE: 466
attctccctc accgaaatgc tattttttca gcccacagga aacccaggct ctgacgggac    60
atgtagccac agcagggacg tcggcgtagt ctgctcaagt                         100

SEQ ID NO: 467          moltype = DNA   length = 100
FEATURE                 Location/Qualifiers
source                  1..100
                        mol_type = other DNA
                        organism = Sus scrofa
SEQUENCE: 467
ctccctcacc gaaatgctat tttttcagcc cacaggaaac ccaggctggt gtgattctga    60
cttctctctg gaggcggcca gcgtgctgtg cagggaacta                         100

SEQ ID NO: 468          moltype = DNA   length = 100
FEATURE                 Location/Qualifiers
source                  1..100
                        mol_type = other DNA
                        organism = Sus scrofa
SEQUENCE: 468
ctccctcacc gaaatgctat tttttcagcc cacaggaaac ccaggctggt gtgaggggca    60
cgagtcccac ctttcactct gcccagtagc accccgccct                         100

SEQ ID NO: 469          moltype = DNA   length = 100
FEATURE                 Location/Qualifiers
source                  1..100
                        mol_type = other DNA
                        organism = Sus scrofa
SEQUENCE: 469
ctccctcacc gaaatgctat tttttcagcc cacaggaaac ccaggctggt ctgacgggac    60
atgtagccac agcagggacg tcggcgtagt ctgctcaagt                         100

SEQ ID NO: 470          moltype = DNA   length = 100
FEATURE                 Location/Qualifiers
source                  1..100
                        mol_type = other DNA
                        organism = Sus scrofa
SEQUENCE: 470
tccctcaccg aaatgctatt ttttcagccc acaggaaacc caggctggtt gaggggcac     60
gagtcccacc tttcactctg cccagtagca cccgccctg                          100

SEQ ID NO: 471          moltype = DNA   length = 100
FEATURE                 Location/Qualifiers
source                  1..100
                        mol_type = other DNA
                        organism = Sus scrofa
SEQUENCE: 471
tccctcaccg aaatgctatt ttttcagccc acaggaaacc caggctggtt gaggggcac     60
gagtcccacc tttcactctg cccagtagca cccgccctg                          100

SEQ ID NO: 472          moltype = DNA   length = 100
FEATURE                 Location/Qualifiers
source                  1..100
                        mol_type = other DNA
                        organism = Sus scrofa
SEQUENCE: 472
tccctcaccg aaatgctatt ttttcagccc acaggaaacc caggctggtt gacgggaca     60
tgtagccaca gcagggacgt cggcgtagtc tgctcaagtg                         100

SEQ ID NO: 473          moltype = DNA   length = 100
FEATURE                 Location/Qualifiers
source                  1..100
```

```
                           mol_type = other DNA
                           organism = Sus scrofa
SEQUENCE: 473
atttttcag cccacaggaa acccaggctg gttggagggg acattccctg acatggagac    60
acgtggggca ccgtctgtga ttctgacttc tctctggagg                        100

SEQ ID NO: 474             moltype = DNA  length = 100
FEATURE                    Location/Qualifiers
source                     1..100
                           mol_type = other DNA
                           organism = Sus scrofa
SEQUENCE: 474
atttttcag cccacaggaa acccaggctg gttggagggg acattccctg acgtggggca    60
ccgtctgtga ttctgacttc tctctggagg cggccagcgt                        100

SEQ ID NO: 475             moltype = DNA  length = 100
FEATURE                    Location/Qualifiers
source                     1..100
                           mol_type = other DNA
                           organism = Sus scrofa
SEQUENCE: 475
atttttcag cccacaggaa acccaggctg gttggagggg acattccctg aggcggccag    60
cgtgctgtgc agggaactac agtgcggcac tgtggtttcc                        100

SEQ ID NO: 476             moltype = DNA  length = 100
FEATURE                    Location/Qualifiers
source                     1..100
                           mol_type = other DNA
                           organism = Sus scrofa
SEQUENCE: 476
atttttcag cccacaggaa acccaggctg gttggagggg acattccctg aagtggacag    60
atctgggctg aagaattcca gtgtgagggg cacgagtccc                        100

SEQ ID NO: 477             moltype = DNA  length = 100
FEATURE                    Location/Qualifiers
source                     1..100
                           mol_type = other DNA
                           organism = Sus scrofa
SEQUENCE: 477
atttttcag cccacaggaa acccaggctg gttggagggg acattccctg agcacccgc     60
cctgacggga catgtagcca cagcagggac gtcggcgtag                        100

SEQ ID NO: 478             moltype = DNA  length = 100
FEATURE                    Location/Qualifiers
source                     1..100
                           mol_type = other DNA
                           organism = Sus scrofa
SEQUENCE: 478
atttttcag cccacaggaa acccaggctg gttggagggg acattccctg ctgacgggac    60
atgtagccac agcagggacg tcggcgtagt ctgctcaagt                        100

SEQ ID NO: 479             moltype = DNA  length = 100
FEATURE                    Location/Qualifiers
source                     1..100
                           mol_type = other DNA
                           organism = Sus scrofa
SEQUENCE: 479
tttttcagc ccacaggaaa cccaggctgg ttggagggga cattccctgc tgaggggcac    60
gagtcccacc tttcactctg cccagtagca ccccgccctg                        100

SEQ ID NO: 480             moltype = DNA  length = 100
FEATURE                    Location/Qualifiers
source                     1..100
                           mol_type = other DNA
                           organism = Sus scrofa
SEQUENCE: 480
tttttcagc ccacaggaaa cccaggctgg ttggagggga cattccctgc tgaggggcac    60
gagtcccacc tttcactctg cccagtagca ccccgccctg                        100

SEQ ID NO: 481             moltype = DNA  length = 100
FEATURE                    Location/Qualifiers
source                     1..100
                           mol_type = other DNA
                           organism = Sus scrofa
SEQUENCE: 481
tttttcagc ccacaggaaa cccaggctgg ttggagggga cattccctgc tgacgggaca    60
tgtagccaca gcagggacgt cggcgtagtc tgctcaagtg                        100

SEQ ID NO: 482             moltype = DNA  length = 100
```

```
FEATURE                 Location/Qualifiers
source                  1..100
                        mol_type = other DNA
                        organism = Sus scrofa
SEQUENCE: 482
tttttcagcc cacaggaaac ccaggctggt tggaggggac attccctgct aggcggccag    60
cgtgctgtgc agggaactac agtgcggcac tgtggtttcc                          100

SEQ ID NO: 483          moltype = DNA  length = 100
FEATURE                 Location/Qualifiers
source                  1..100
                        mol_type = other DNA
                        organism = Sus scrofa
SEQUENCE: 483
tttttcagcc cacaggaaac ccaggctggt tggaggggac attccctgct aagtggacag    60
atctgggctg aagaattcca gtgtgagggg cacgagtccc                          100

SEQ ID NO: 484          moltype = DNA  length = 100
FEATURE                 Location/Qualifiers
source                  1..100
                        mol_type = other DNA
                        organism = Sus scrofa
SEQUENCE: 484
tttttcagcc cacaggaaac ccaggctggt tggaggggac attccctgct gaggggcacg    60
agtcccacct ttcactctgc ccagtagcac cccgccctga                          100

SEQ ID NO: 485          moltype = DNA  length = 100
FEATURE                 Location/Qualifiers
source                  1..100
                        mol_type = other DNA
                        organism = Sus scrofa
SEQUENCE: 485
tttttcagcc cacaggaaac ccaggctggt tggaggggac attccctgct agcaccccgc    60
cctgacggga catgtagcca cagcaggac gtcggcgtag                           100

SEQ ID NO: 486          moltype = DNA  length = 100
FEATURE                 Location/Qualifiers
source                  1..100
                        mol_type = other DNA
                        organism = Sus scrofa
SEQUENCE: 486
tttttcagcc cacaggaaac ccaggctggt tggaggggac attccctgct gacgggacat    60
gtagccacag cagggacgtc ggcgtagtct gctcaagtga                          100

SEQ ID NO: 487          moltype = DNA  length = 100
FEATURE                 Location/Qualifiers
source                  1..100
                        mol_type = other DNA
                        organism = Sus scrofa
SEQUENCE: 487
cccaggctgg ttggagggga cattccctgc tctggtcgtg ttgaagtaca gtgattctga    60
cttctctctg gaggcggcca gcgtgctgtg caggaacta                           100

SEQ ID NO: 488          moltype = DNA  length = 100
FEATURE                 Location/Qualifiers
source                  1..100
                        mol_type = other DNA
                        organism = Sus scrofa
SEQUENCE: 488
cccaggctgg ttggagggga cattccctgc tctggtcgtg ttgaagtaca gtgagggca    60
cgagtcccac ctttcactct gcccagtagc accccgccct                          100

SEQ ID NO: 489          moltype = DNA  length = 100
FEATURE                 Location/Qualifiers
source                  1..100
                        mol_type = other DNA
                        organism = Sus scrofa
SEQUENCE: 489
ttggagggga cattccctgc tctggtcgtg ttgaagtaca acatggagac tgaggggcac    60
gagtcccacc tttcactctg cccagtagca ccccgccctg                          100

SEQ ID NO: 490          moltype = DNA  length = 100
FEATURE                 Location/Qualifiers
source                  1..100
                        mol_type = other DNA
                        organism = Sus scrofa
SEQUENCE: 490
ttggagggga cattccctgc tctggtcgtg ttgaagtaca acatggagac tgaggggcac    60
gagtcccacc tttcactctg cccagtagca ccccgccctg                          100
```

```
SEQ ID NO: 491         moltype = DNA  length = 100
FEATURE                Location/Qualifiers
source                 1..100
                       mol_type = other DNA
                       organism = Sus scrofa
SEQUENCE: 491
ttgggaggga cattccctgc tctggtcgtg ttgaagtaca acatggagac tgacgggaca    60
tgtagccaca gcagggacgt cggcgtagtc tgctcaagtg                         100

SEQ ID NO: 492         moltype = DNA  length = 100
FEATURE                Location/Qualifiers
source                 1..100
                       mol_type = other DNA
                       organism = Sus scrofa
SEQUENCE: 492
ggagggaca ttccctgctc tggtcgtgtt gaagtacaac atggagacac gtgattctga    60
cttctctctg gaggcggcca gcgtgctgtg cagggaacta                         100

SEQ ID NO: 493         moltype = DNA  length = 100
FEATURE                Location/Qualifiers
source                 1..100
                       mol_type = other DNA
                       organism = Sus scrofa
SEQUENCE: 493
ggagggaca ttccctgctc tggtcgtgtt gaagtacaac atggagacac gtgaggggca    60
cgagtcccac ctttcactct gcccagtagc accccgccct                         100

SEQ ID NO: 494         moltype = DNA  length = 100
FEATURE                Location/Qualifiers
source                 1..100
                       mol_type = other DNA
                       organism = Sus scrofa
SEQUENCE: 494
ggagggaca ttccctgctc tggtcgtgtt gaagtacaac atggagacac ctgacgggac    60
atgtagccac agcagggacg tcggcgtagt ctgctcaagt                         100

SEQ ID NO: 495         moltype = DNA  length = 100
FEATURE                Location/Qualifiers
source                 1..100
                       mol_type = other DNA
                       organism = Sus scrofa
SEQUENCE: 495
ctgctctggt cgtgttgaag tacaacatgg agacacgtgg ggcaccgtct aggcggccag    60
cgtgctgtgc agggaactac agtgcggcac tgtggtttcc                         100

SEQ ID NO: 496         moltype = DNA  length = 100
FEATURE                Location/Qualifiers
source                 1..100
                       mol_type = other DNA
                       organism = Sus scrofa
SEQUENCE: 496
ctgctctggt cgtgttgaag tacaacatgg agacacgtgg ggcaccgtct aagtggacag    60
atctgggctg aagaattcca gtgtgagggg cacgagtccc                         100

SEQ ID NO: 497         moltype = DNA  length = 100
FEATURE                Location/Qualifiers
source                 1..100
                       mol_type = other DNA
                       organism = Sus scrofa
SEQUENCE: 497
ctgctctggt cgtgttgaag tacaacatgg agacacgtgg ggcaccgtct gaggggcacg    60
agtcccacct ttcactctgc ccagtagcac ccgccctga                          100

SEQ ID NO: 498         moltype = DNA  length = 100
FEATURE                Location/Qualifiers
source                 1..100
                       mol_type = other DNA
                       organism = Sus scrofa
SEQUENCE: 498
ctgctctggt cgtgttgaag tacaacatgg agacacgtgg ggcaccgtct agcacccgc     60
cctgacggga catgtagcca cagcagggac gtcggcgtag                         100

SEQ ID NO: 499         moltype = DNA  length = 100
FEATURE                Location/Qualifiers
source                 1..100
                       mol_type = other DNA
                       organism = Sus scrofa
SEQUENCE: 499
```

-continued

```
ctgctctggt cgtgttgaag tacaacatgg agacacgtgg ggcaccgtct gacgggacat    60
gtagccacag cagggacgtc ggcgtagtct gctcaagtga                          100

SEQ ID NO: 500         moltype = DNA   length = 100
FEATURE                Location/Qualifiers
source                 1..100
                       mol_type = other DNA
                       organism = Sus scrofa
SEQUENCE: 500
tgaagtacaa catggagaca cgtggggcac cgtctgtgat tctgacttct aggcggccag    60
cgtgctgtgc agggaactac agtgcggcac tgtggtttcc                          100

SEQ ID NO: 501         moltype = DNA   length = 100
FEATURE                Location/Qualifiers
source                 1..100
                       mol_type = other DNA
                       organism = Sus scrofa
SEQUENCE: 501
tgaagtacaa catggagaca cgtggggcac cgtctgtgat tctgacttct aagtggacag    60
atctgggctg aagaattcca gtgtgagggg cacgagtccc                          100

SEQ ID NO: 502         moltype = DNA   length = 100
FEATURE                Location/Qualifiers
source                 1..100
                       mol_type = other DNA
                       organism = Sus scrofa
SEQUENCE: 502
tgaagtacaa catggagaca cgtggggcac cgtctgtgat tctgacttct gaggggcacg    60
agtcccacct ttcactctgc ccagtagcac cccgccctga                          100

SEQ ID NO: 503         moltype = DNA   length = 100
FEATURE                Location/Qualifiers
source                 1..100
                       mol_type = other DNA
                       organism = Sus scrofa
SEQUENCE: 503
tgaagtacaa catggagaca cgtggggcac cgtctgtgat tctgacttct agcaccccgc    60
cctgacggga catgtagcca cagcagggac gtcggcgtag                          100

SEQ ID NO: 504         moltype = DNA   length = 100
FEATURE                Location/Qualifiers
source                 1..100
                       mol_type = other DNA
                       organism = Sus scrofa
SEQUENCE: 504
tgaagtacaa catggagaca cgtggggcac cgtctgtgat tctgacttct gacgggacat    60
gtagccacag cagggacgtc ggcgtagtct gctcaagtga                          100

SEQ ID NO: 505         moltype = DNA   length = 100
FEATURE                Location/Qualifiers
source                 1..100
                       mol_type = other DNA
                       organism = Sus scrofa
SEQUENCE: 505
tccctcaccg aaatgctatt ttttcagccc acaggaaacc caggctggtt ctgtggtttc    60
cctcctgggg ggagctcact ttggagaagg aagtggacag                          100

SEQ ID NO: 506         moltype =       length =
SEQUENCE: 506
000

SEQ ID NO: 507         moltype = AA    length = 4
FEATURE                Location/Qualifiers
source                 1..4
                       mol_type = protein
                       organism = Sus scrofa
SEQUENCE: 507
AHRK                                                                 4

SEQ ID NO: 508         moltype = AA    length = 7
FEATURE                Location/Qualifiers
source                 1..7
                       mol_type = protein
                       organism = Sus scrofa
SEQUENCE: 508
AHRKPRL                                                              7

SEQ ID NO: 509         moltype = AA    length = 8
FEATURE                Location/Qualifiers
```

```
source                      1..8
                            mol_type = protein
                            organism = Sus scrofa
SEQUENCE: 509
AHRKPRLV                                                                        8

SEQ ID NO: 510              moltype = AA   length = 13
FEATURE                     Location/Qualifiers
source                      1..13
                            mol_type = protein
                            organism = Sus scrofa
SEQUENCE: 510
AHRKPRLVGG DIP                                                                 13

SEQ ID NO: 511              moltype = AA   length = 14
FEATURE                     Location/Qualifiers
source                      1..14
                            mol_type = protein
                            organism = Sus scrofa
SEQUENCE: 511
AHRKPRLVGG DIPC                                                                14

SEQ ID NO: 512              moltype = AA   length = 21
FEATURE                     Location/Qualifiers
source                      1..21
                            mol_type = protein
                            organism = Sus scrofa
SEQUENCE: 512
AHRKPRLVGG DIPCSGRVEV Q                                                        21

SEQ ID NO: 513              moltype = AA   length = 24
FEATURE                     Location/Qualifiers
source                      1..24
                            mol_type = protein
                            organism = Sus scrofa
SEQUENCE: 513
AHRKPRLVGG DIPCSGRVEV QHGD                                                     24

SEQ ID NO: 514              moltype = AA   length = 25
FEATURE                     Location/Qualifiers
source                      1..25
                            mol_type = protein
                            organism = Sus scrofa
SEQUENCE: 514
AHRKPRLVGG DIPCSGRVEV QHGDT                                                    25

SEQ ID NO: 515              moltype = AA   length = 29
FEATURE                     Location/Qualifiers
source                      1..29
                            mol_type = protein
                            organism = Sus scrofa
SEQUENCE: 515
AHRKPRLVGG DIPCSGRVEV QHGDTWGTV                                                29

SEQ ID NO: 516              moltype = AA   length = 29
FEATURE                     Location/Qualifiers
source                      1..29
                            mol_type = protein
                            organism = Sus scrofa
SEQUENCE: 516
AHRKPRLVGG DIPCSGRVEV QHGDTWGTV                                                29

SEQ ID NO: 517              moltype = AA   length = 34
FEATURE                     Location/Qualifiers
source                      1..34
                            mol_type = protein
                            organism = Sus scrofa
SEQUENCE: 517
AHRKPRLVGG DIPCSGRVEV QHGDTWGTVC DSDF                                          34

SEQ ID NO: 518              moltype = AA   length = 64
FEATURE                     Location/Qualifiers
source                      1..64
                            mol_type = protein
                            organism = Sus scrofa
SEQUENCE: 518
AHRKPRLVTV VSLLGGAHFG EGSGQIWAEE FQCEGHESHL SLCPVAPRPD GTCSHSRDVG              60
VVCS                                                                           64
```

-continued

```
SEQ ID NO: 519            moltype = AA   length = 1010
FEATURE                   Location/Qualifiers
source                    1..1010
                          mol_type = protein
                          organism = Sus scrofa
SEQUENCE: 519
MDKLRMVLHE NSGSADFRRC SAHLSSFTFA VVAVLSACLV TSSLGGKDKE LRLTGGENKC    60
SGRVEVKVQE EWGTVCNNGW DMDVVSVVCR QLGCPTAIKA TGWANFSAGS GRIWMDHVSC   120
RGNESALWDC KHDGWGKHNC THQQDAGVTC SDGSDLEMRL VNGGNRCLGR IEVKFQGRWG   180
TVCDDNFNIN HASVVCKQLE CGSAVSFSGS ANFGEGSGPI WFDDLVCNGN ESALWNCKHE   240
GWGKHNCDHA EDAGVICLNG ADLKLRVVDG VTECSGRLEV KFQGEWGTIC DDGWDSDDAA   300
VACKQLGCPT AVTAIGRVNA SEGTGHIWLD SVSCHGHESA LWQCRHHEWG KHYCNHNEDA   360
GVTCSDGSDL ELRLKGGGSH CAGTVEVEIQ KLVGKVCDRS WGLKEADVVC RQLGCGSALK   420
TSYQVYSKTK ATNTWLFVSS CNGNETSLWD CKNWQWGGLS CDHYDEAKIT CSGYTQIRLV   480
NGKTPCEGRV ELNILGSWGS LCNSHWDMED AHVLCQQLKC GVALSIPRGA PFGKGSEQVW   540
RHMFHCTGTE KHMGDCSVTA LGASLCSSGQ VASVICSGNQ SQTLSPCNSS SSDPSSSIIS   600
EENGVACIGS GQLRLVDGGG RCAGRVEVYH EGSWGTICDD SWDLNDAHVV CKQLSCGWAI   660
NATGSAHFGE GTGPIWLDEI NCNGKESHIW QCHSHGWGRH NCRHKEDAGV ICSEFMSLRL   720
ISENSRETCA GRLEVFYNGA WGSVGRNSMS PATVGVVCRQ LGCADRGDIS PASSDKTVSR   780
HMWVDNVQCP KGPDTLWQCP SSPWKKRLAS PSEETWITCA NKIRLQEGNT NCSGRVEIWY   840
GGSWGTVCDD SWDLEDAQVV CRQLGCGSAL EAGKEAAFGQ GTGPIWLNEV KCKGNETSLW   900
DCPARSWGHS DCGHKEDAAV TCSEIAKSRE SLHATGRSSF VALAIFGVIL LACLIAFLIW   960
TQKRRQRQRL SVFSGGENSV HQIQYREMNS CLKADETDML NPSGDHSEVQ            1010

SEQ ID NO: 520            moltype = DNA   length = 101
FEATURE                   Location/Qualifiers
source                    1..101
                          mol_type = other DNA
                          organism = Sus scrofa
SEQUENCE: 520
ctcacttttc actctctggc ttactcctat caagagggta gggttaggta gtcacagaca    60
tctttttaaa gccctgtctc cttccaggat acacacaaat c                      101

SEQ ID NO: 521            moltype = DNA   length = 100
FEATURE                   Location/Qualifiers
source                    1..100
                          mol_type = other DNA
                          organism = Sus scrofa
SEQUENCE: 521
ctcacttttc actctctggc ttactcctat cagagggtag ggttaggtag tcacagacat    60
cttttttaaag ccctgtctcc ttccaggata cacacaaatc                       100

SEQ ID NO: 522            moltype = DNA   length = 98
FEATURE                   Location/Qualifiers
source                    1..98
                          mol_type = other DNA
                          organism = Sus scrofa
SEQUENCE: 522
ctcacttttc actctctggc ttactcctat cagggtaggg ttaggtagtc acagacatct    60
ttttaaagcc ctgtctcctt ccaggataca cacaaatc                           98

SEQ ID NO: 523            moltype = DNA   length = 108
FEATURE                   Location/Qualifiers
source                    1..108
                          mol_type = other DNA
                          organism = Sus scrofa
SEQUENCE: 523
ctcacttttc actctctggc ttactcctat catggcatgg gagggtaggg ttaggtagtc    60
acagacatct ttttaaagcc ctgtctcctt ccaggataca cacaaatc               108

SEQ ID NO: 524            moltype = DNA   length = 72
FEATURE                   Location/Qualifiers
source                    1..72
                          mol_type = other DNA
                          organism = Sus scrofa
SEQUENCE: 524
ctcacttttc agggttaggt agtcacagac atctttttaa agccctgtct ccttccagga    60
tacacacaaa tc                                                       72

SEQ ID NO: 525            moltype = DNA   length = 90
FEATURE                   Location/Qualifiers
source                    1..90
                          mol_type = other DNA
                          organism = Sus scrofa
SEQUENCE: 525
ctcacttttc actctctggc ttactcctag ggttaggtag tcacagacat cttttaaag    60
ccctgtctcc ttccaggata cacacaaatc                                    90

SEQ ID NO: 526            moltype = DNA   length = 75
```

```
FEATURE                 Location/Qualifiers
source                  1..75
                        mol_type = other DNA
                        organism = Sus scrofa
SEQUENCE: 526
ctcactttc actctctggc ttactcccca gacatctttt taaagccctg tctccttcca    60
ggatacacac aaatc                                                    75

SEQ ID NO: 527          moltype = DNA  length = 96
FEATURE                 Location/Qualifiers
source                  1..96
                        mol_type = other DNA
                        organism = Sus scrofa
SEQUENCE: 527
ctcactttc actctctggc ttactccaga gggtagggtt aggtagtcac agacatcttt    60
ttaaagccct gtctccttcc aggatacaca caaatc                             96

SEQ ID NO: 528          moltype = DNA  length = 97
FEATURE                 Location/Qualifiers
source                  1..97
                        mol_type = other DNA
                        organism = Sus scrofa
SEQUENCE: 528
ctcactttc actctctggc ttactcctat caggtagggt taggtagtca cagacatctt    60
tttaaagccc tgtctccttc caggatacac acaaatc                            97

SEQ ID NO: 529          moltype = DNA  length = 90
FEATURE                 Location/Qualifiers
source                  1..90
                        mol_type = other DNA
                        organism = Sus scrofa
SEQUENCE: 529
ctcactttc actctctggc ttactcctag ggttaggtag tcacagacat cttttttaaag    60
ccctgtctc ttccaggata cacacaaatc                                     90

SEQ ID NO: 530          moltype = DNA  length = 99
FEATURE                 Location/Qualifiers
source                  1..99
                        mol_type = other DNA
                        organism = Sus scrofa
SEQUENCE: 530
ctcactttc actctctggc ttactcctat caagggtagg gttaggtagt cacagacatc    60
ttttaaagc cctgtctcct tccaggatac acacaaatc                           99

SEQ ID NO: 531          moltype = DNA  length = 93
FEATURE                 Location/Qualifiers
source                  1..93
                        mol_type = other DNA
                        organism = Sus scrofa
SEQUENCE: 531
ctcactttc actctctggc ttactcctat cagggttagg tagtcacaga catcttttta    60
aagccctgtc tccttccagg atacacacaa atc                                93

SEQ ID NO: 532          moltype = DNA  length = 92
FEATURE                 Location/Qualifiers
source                  1..92
                        mol_type = other DNA
                        organism = Sus scrofa
SEQUENCE: 532
ctcactttc actctctggc ttactccggt agggttaggt agtcacagac atcttttaa     60
agccctgtct ccttccagga tacacacaaa tc                                 92

SEQ ID NO: 533          moltype = DNA  length = 98
FEATURE                 Location/Qualifiers
source                  1..98
                        mol_type = other DNA
                        organism = Sus scrofa
SEQUENCE: 533
ctcactttc actctctggc ttactcctat caaggtaggg ttaggtagtc acagacatct    60
ttttaaagcc ctgtctcctt ccaggataca cacaaatc                           98

SEQ ID NO: 534          moltype = DNA  length = 99
FEATURE                 Location/Qualifiers
source                  1..99
                        mol_type = other DNA
                        organism = Sus scrofa
SEQUENCE: 534
ctcactttc actctctggc ttactcctat cacaggtagg gttaggtagt cacagacatc    60
ttttaaagc cctgtctcct tccaggatac acacaaatc                           99
```

```
SEQ ID NO: 535            moltype = DNA  length = 95
FEATURE                   Location/Qualifiers
source                    1..95
                          mol_type = other DNA
                          organism = Sus scrofa
SEQUENCE: 535
ctcactttc actctctggc ttactcctat ggtagggtta ggtagtcaca gacatctttt    60
taaagccctg tctccttcca ggatacacac aaatc                              95

SEQ ID NO: 536            moltype = DNA  length = 125
FEATURE                   Location/Qualifiers
source                    1..125
                          mol_type = other DNA
                          organism = Sus scrofa
SEQUENCE: 536
gcaaagtccc agaattgtct ccagggaagg acagggaggt ctagaatcgg ctaagcccac    60
ggtagggtta ggtagtcaca gacatctttt taaagccctg tctccttcca ggatacacac   120
aaatc                                                              125

SEQ ID NO: 537            moltype = DNA  length = 124
FEATURE                   Location/Qualifiers
source                    1..124
                          mol_type = other DNA
                          organism = Sus scrofa
SEQUENCE: 537
gcaaagtccc agaattgtct ccagggaagg acagggaggt ctagaatcgg ctaagccac     60
gtagggttag gtagtcacag acatctttt aaagccctgt ctccttccag gatacacaca   120
aatc                                                               124

SEQ ID NO: 538            moltype = DNA  length = 123
FEATURE                   Location/Qualifiers
source                    1..123
                          mol_type = other DNA
                          organism = Sus scrofa
SEQUENCE: 538
gcaaagtccc agaattgtct ccagggaagg acagggaggt ctagaatcgg ctaagcccat    60
tagggttagg tagtcacaga catctttta aagccctgtc tccttccagg atacacacaa   120
atc                                                                123

SEQ ID NO: 539            moltype = DNA  length = 114
FEATURE                   Location/Qualifiers
source                    1..114
                          mol_type = other DNA
                          organism = Sus scrofa
SEQUENCE: 539
gcaaagtccc agaattgtct ccagggaagg acagggaggt ctagaatcgg ctagggttag    60
gtagtcacag acatcttttt aaagccctgt ctccttccag gatacacaca aatc         114

SEQ ID NO: 540            moltype = DNA  length = 123
FEATURE                   Location/Qualifiers
source                    1..123
                          mol_type = other DNA
                          organism = Sus scrofa
SEQUENCE: 540
gcaaagtccc agaattgtct ccagggaagg acagggaggt ctagaatcgg ctaagcccac    60
tagggttagg tagtcacaga catctttta aagccctgtc tccttccagg atacacacaa   120
atc                                                                123

SEQ ID NO: 541            moltype = DNA  length = 116
FEATURE                   Location/Qualifiers
source                    1..116
                          mol_type = other DNA
                          organism = Sus scrofa
SEQUENCE: 541
gcaaagtccc agaattgtct ccagggaagg acagggaggt ctagaatcgg ctaagcccac    60
aggtagtcac agacatcttt ttaaagccct gtctccttcc aggatacaca caaatc      116

SEQ ID NO: 542            moltype = DNA  length = 124
FEATURE                   Location/Qualifiers
source                    1..124
                          mol_type = other DNA
                          organism = Sus scrofa
SEQUENCE: 542
gcaaagtccc agaattgtct ccagggaagg acagggaggt ctagaatcgg ctaagcccag    60
gtagggttag gtagtcacag acatctttt aaagccctgt ctccttccag gatacacaca   120
aatc                                                               124

SEQ ID NO: 543            moltype = DNA  length = 122
```

```
FEATURE              Location/Qualifiers
source               1..122
                     mol_type = other DNA
                     organism = Sus scrofa
SEQUENCE: 543
gcaaagtccc agaattgtct ccagggaagg acagggaggt ctagaatcgg ctaagcccat    60
ggggttaggt agtcacagac atcttttta agccctgtct ccttccagga tacacacaaa   120
tc                                                                  122

SEQ ID NO: 544       moltype = DNA   length = 113
FEATURE              Location/Qualifiers
source               1..113
                     mol_type = other DNA
                     organism = Sus scrofa
SEQUENCE: 544
gcaaagtccc agaattgtct ccagggaagg acagggaggt ctagaatcgg tagggttagg    60
tagtcacaga catctttta aagccctgtc tccttccagg atacacacaa atc           113

SEQ ID NO: 545       moltype = DNA   length = 113
FEATURE              Location/Qualifiers
source               1..113
                     mol_type = other DNA
                     organism = Sus scrofa
SEQUENCE: 545
atttctggtg tgcctttgac tccagattac agtaaatgga ggactgaggg tagggttagg    60
tagtcacaga catctttta aagccctgtc tccttccagg atacacacaa atc           113

SEQ ID NO: 546       moltype = DNA   length = 117
FEATURE              Location/Qualifiers
source               1..117
                     mol_type = other DNA
                     organism = Sus scrofa
SEQUENCE: 546
atttctggtg tgcctttgac tccagattac agtaaatgga ggactgagag agggtagggt    60
taggtagtca cagacatctt tttaaagccc tgtctccttc caggatacac acaaatc     117

SEQ ID NO: 547       moltype = DNA   length = 106
FEATURE              Location/Qualifiers
source               1..106
                     mol_type = other DNA
                     organism = Sus scrofa
SEQUENCE: 547
atttctggtg tgcctttgac tccagattac agtaaatgga gggtagggtt aggtagtcac    60
agacatcttt ttaaagccct gtctccttcc aggatacaca caaatc                 106

SEQ ID NO: 548       moltype = DNA   length = 112
FEATURE              Location/Qualifiers
source               1..112
                     mol_type = other DNA
                     organism = Sus scrofa
SEQUENCE: 548
atttctggtg tgcctttgac tccagattac agtaaatgga ggactgaggg tgggttaggt    60
agtcacagac atcttttta agccctgtct ccttccagga tacacacaaa tc           112

SEQ ID NO: 549       moltype = DNA   length = 117
FEATURE              Location/Qualifiers
source               1..117
                     mol_type = other DNA
                     organism = Sus scrofa
SEQUENCE: 549
atttctggtg tgcctttgac tccagattac agtaaatgga ggactgagag aggatagggt    60
taggtagtca cagacatctt tttaaagccc tgtctccttc caggatacac acaaatc     117

SEQ ID NO: 550       moltype = DNA   length = 90
FEATURE              Location/Qualifiers
source               1..90
                     mol_type = other DNA
                     organism = Sus scrofa
SEQUENCE: 550
gaaagagaaa gcatgctcca agaatggtag ggttaggtag tcacagacat cttttaaag    60
ccctgtctcc ttccaggata cacacaaatc                                    90

SEQ ID NO: 551       moltype = DNA   length = 89
FEATURE              Location/Qualifiers
source               1..89
                     mol_type = other DNA
                     organism = Sus scrofa
SEQUENCE: 551
gaaagagaaa gcatgctcca agaaggtagg gttaggtagt cacagacatc ttttaaagc    60
```

```
cctgtctcct tccaggatac acacaaatc                                          89

SEQ ID NO: 552          moltype = DNA   length = 91
FEATURE                 Location/Qualifiers
source                  1..91
                        mol_type = other DNA
                        organism = Sus scrofa
SEQUENCE: 552
gaaagagaaa gcatgctcca agaatgggta gggttaggta gtcacagaca tcttttttaaa       60
gccctgtctc cttccaggat acacacaaat c                                       91

SEQ ID NO: 553          moltype = DNA   length = 87
FEATURE                 Location/Qualifiers
source                  1..87
                        mol_type = other DNA
                        organism = Sus scrofa
SEQUENCE: 553
gaaagagaaa gcatgctcca agagtagggt taggtagtca cagacatctt tttaaagccc        60
tgtctccttc caggatacac acaaatc                                            87

SEQ ID NO: 554          moltype = DNA   length = 97
FEATURE                 Location/Qualifiers
source                  1..97
                        mol_type = other DNA
                        organism = Sus scrofa
SEQUENCE: 554
gaaagagaaa gcatgctcca agaatccaag agggtagggt taggtagtca cagacatctt        60
tttaaagccc tgtctccttc caggatacac acaaatc                                 97

SEQ ID NO: 555          moltype = DNA   length = 92
FEATURE                 Location/Qualifiers
source                  1..92
                        mol_type = other DNA
                        organism = Sus scrofa
SEQUENCE: 555
gaaagagaaa gcatgctcca agaatagggt agggttaggt agtcacagac atcttttttaa       60
agccctgtct ccttccagga tacacacaaa tc                                      92

SEQ ID NO: 556          moltype = DNA   length = 21
FEATURE                 Location/Qualifiers
source                  1..21
                        mol_type = other DNA
                        organism = Sus scrofa
SEQUENCE: 556
ctaagcccac tgtaggcaga a                                                  21

SEQ ID NO: 557          moltype = DNA   length = 21
FEATURE                 Location/Qualifiers
source                  1..21
                        mol_type = other DNA
                        organism = Sus scrofa
SEQUENCE: 557
ctgggtttcc tgtgggctga a                                                  21

SEQ ID NO: 558          moltype = DNA   length = 24
FEATURE                 Location/Qualifiers
source                  1..24
                        mol_type = other DNA
                        organism = Sus scrofa
SEQUENCE: 558
tggcttactc ctatcatgaa ggaa                                               24

SEQ ID NO: 559          moltype = DNA   length = 21
FEATURE                 Location/Qualifiers
source                  1..21
                        mol_type = other DNA
                        organism = Sus scrofa
SEQUENCE: 559
atgtagccac agcagggacg t                                                  21

SEQ ID NO: 560          moltype = DNA   length = 22
FEATURE                 Location/Qualifiers
source                  1..22
                        mol_type = other DNA
                        organism = Sus scrofa
SEQUENCE: 560
ccaagcggat ttgtgtgtat cc                                                 22

SEQ ID NO: 561          moltype = DNA   length = 28
```

```
FEATURE             Location/Qualifiers
source              1..28
                    mol_type = other DNA
                    organism = Sus scrofa
SEQUENCE: 561
ttcccatgcc atgaagaggg tagggtta                                      28

SEQ ID NO: 562      moltype = DNA  length = 21
FEATURE             Location/Qualifiers
source              1..21
                    mol_type = other DNA
                    organism = Sus scrofa
SEQUENCE: 562
gctaagccca ctgtaggcag a                                             21

SEQ ID NO: 563      moltype = DNA  length = 21
FEATURE             Location/Qualifiers
source              1..21
                    mol_type = other DNA
                    organism = Sus scrofa
SEQUENCE: 563
gcggatttgt gtgtatcctg g                                             21

SEQ ID NO: 564      moltype = DNA  length = 24
FEATURE             Location/Qualifiers
source              1..24
                    mol_type = other DNA
                    organism = Sus scrofa
SEQUENCE: 564
tggcttactc ctatcaggta gggt                                          24
```

METHODS FOR IMPROVING THE HEALTH OF PORCINE SPECIES BY TARGETED INACTIVATION OF CD163

CROSS REFERENCE TO RELATED APPLICATIONS

This application claims the benefit of and priority to U.S. application Ser. No. 17/581,239 filed on Jan. 21, 2022 (U.S. Pat. No. 11,535,850) and U.S. Non-Provisional application Ser. No. 17/515,139, filed Oct. 29, 2021. Ser. No. 17/515,139 in turn claims priority to U.S. Non-Provisional application Ser. No. 17/307,369, filed May 4, 2021 (now U.S. Pat. No. 11,208,659). Ser. No. 17/307,369 claims priority to U.S. Provisional Application 63/020,128 filed on May 5, 2020 and to U.S. Provisional Application 63/021,370 filed on May 7, 2020. Each application is hereby incorporated by reference, each in their entirety.

REFERENCE TO SEQUENCE LISTING SUBMITTED ELECTRONICALLY

The official copy of the sequence listing is submitted electronically via EFS-Web as an XML ST_26 formatted sequence listing with a file named TD-12-2020-US6-SE-QLST, created on Mar. 2, 2023, and having a size of 511,102 bytes is filed concurrently with the specification. The sequence listing contained in this XML formatted document is part of the specification and is herein incorporated by reference in its entirety.

FIELD

The present disclosure relates to methods for improving the health of porcine species. In particular, the present disclosure relates to methods of protecting *Sus scrofa* animals and elite lines from infection by porcine reproductive and respiratory syndrome virus (PRRSv) through targeted polynucleotide edits of CD163 to prevent infection and generate resistant animals, herds, and cell lines.

BACKGROUND

Viral infections are a major source of morbidity and mortality in the livestock industry. In particular, Porcine Reproductive and Respiratory Syndrome (PRRS) is a panzootic infectious disease of pigs, causing major economic losses to the world-wide pig industry. PRRS manifests in pigs of all ages but primarily causes late-term abortions and stillbirths in sows and respiratory disease in piglets. The causative agent of the disease is the positive-strand RNA PRRS virus (PRRSv). PRRS is the most economically important disease of domestic swine in North America, Europe and Asia, costing producers in North America more than $600 million annually.

Currently, there are no effective treatment programs for acute PRRS. As a result, when incidence of PRRS is detected on a farm, depopulation, sufficient cleaning/disinfection, and proper disposal of the carcasses must be used to eliminate the virus. In more extreme cases, whole herd depopulation-repopulation has been documented as an effective method of eliminating the PRRSv from endemically infected herds; however, this method results in significant loss.

Vaccines for PRRSv do exist; however, these vaccines have been unable to control the disease largely due to the genetic diversity within the structural proteins of the virus. Consequently, prevention of infection is currently the best control measure. As a prophylactic measure, farms in a country or zone where PRRSv exists must use stringent control measures, involving an assessment of the health status of replacement gilts and boars, as well as 45-60 days of isolation and acclimatization for incoming stock.

In recent years, more attention has been given to the role CD163 may play in the occurrence of PRRS. Despite the significant heterogeneity in strains of PRRSv, strains of PRRSv all share a tropism for CD163-positive cells. Although CD163 is a virus receptor, the CD163 scavenger receptor is also involved in the adhesion of monocytes to endothelial cells. Functions and a detailed description of CD163 are provided in Onofre, Gabriela et al., *ACTA MEDICA*, 2009, 52, 57-61.

CD163 is a 130 kDa type 1 membrane protein considered to be a fusion receptor for the PRRS virus; it is mapped to chromosome 5 in pigs. The basic transcript encodes for a protein of 1076 amino acids. There are five reported isoforms of CD163; three of the isoforms display different splicing forms of their cytoplasmic domains. Generally, however, the genomic molecule sequence of CD163 comprises 17 exons coding for a peptide signal sequence, nine scavenger receptor cysteine-rich (SRCR) domains, two proline serine threonine (PST) linker domains, a cytoplasmic domain, and a short cytoplasmic tail. CD163 has been described as the receptor for PRRSv. Domain 5 (SRCR5) of the protein is the interaction site for the virus. Exon 7 of CD163 encodes the SRCR domain 5 (SRCR5) that serves as an interaction site for the PRRSv in vitro. Burkard (Burkard, C., PLoS Pathog. 2017, 23, 13, e1006206) demonstrated that removal of CD163 exon 7 confers PRRSv resistance to porcine macrophages. The guides used in that work (set forth as targeting sequences including the PAM in SEQ ID NOs: 272 and 273), however, may lack sufficient activity and specificity for gene editing as part of a commercial breeding program. Further work by Whitworth and colleagues included creating a 123 bp deletion in Exon 7 using guides as set forth (including the PAM) in SEQ ID NO: 354 and SEQ ID NO: 211 (Whitworth, K. M., Biol. Reprod., 2014, 91, 1-13). Whitworth et al. (Whitworth, K. M., Nature Biotechnology, 2016, 34, 20-22) reported the preparation of PRRSv resistant pigs by knocking out the function of CD163.

Genome editing includes altering the genome by deleting, inserting, or substituting specific nucleic acid sequences. The alteration can be gene- or location-specific. Genome editing can use site-directed nucleases, such as Cas proteins and their cognate polynucleotides.

Clustered regularly interspaced short palindromic repeats (CRISPR) and CRISPR-associated proteins (Cas) constitute the CRISPR-Cas system.

Cas9 is an exemplary Type II CRISPR Cas protein. Cas9 is an endonuclease that can be programmed by the tracrRNA/crRNA to cleave, in a site-specific manner, a DNA target sequence using two distinct endonuclease domains (HNH and RuvC/RNase H-like domains) (see U.S. Patent Application Publication No. 2014-0068797, published 6 Mar. 2014; see also Jinek, M., et al., *Science*, 337:816-821 (2012) and Karvelis et al. *Genome Biology* (2015) 16:253.

The foregoing CD163 edits, while demonstrating some indication of efficacy against PRRSv, cannot be made as precisely and effectively as the edits disclosed herein. There is a need to improve the health of a porcine herd by editing the CD163 gene using guides for improved editing activity and reduced unintended edits, while conferring resistance to PRRSv.

SUMMARY

The present specification provides for and includes edited CD163 genes that confer PRRSv resistance on pigs comprising the edited gene.

In various embodiments, the present teachings can include a pig whose genome comprises a CD163 gene comprising the nucleic acid sequence of SEQ ID NO: 453, wherein the CD163 gene expresses a modified CD163 protein that exhibits reduced uptake of the porcine reproductive and respiratory syndrome virus (PRRSV) relative to a wild-type CD163 protein. In some configuration, the present teachings can include a cell isolated from the pig of the present teachings. In various configurations, the present teachings can include an isolated cell line obtained from the pig of the present teachings. In various configurations, the present teachings can include an isolated fibroblast cell line obtained from the pig of the present teachings.

In various configurations, the CD163 gene can be heterozygous for the nucleic acid sequence of SEQ ID NO: 453. In some configuration, the present teachings can include a cell isolated from the pig of the present teachings. In various configurations, the present teachings can include an isolated cell line obtained from the pig of the present teachings. In various configurations, the present teachings can include an isolated fibroblast cell line obtained from the pig of the present teachings.

In various configurations, the CD163 gene can be homozygous for the nucleic acid sequence of SEQ ID NO: 453. In some configuration, the present teachings can include a cell isolated from the pig of the present teachings. In various configurations, the present teachings can include an isolated cell line obtained from the pig of the present teachings. In various configurations, the present teachings can include an isolated fibroblast cell line obtained from the pig of the present teachings.

In various embodiments, the present teachings can include method of producing one or more pigs whose genome comprises a CD163 gene comprising the nucleic acid sequence of SEQ ID NO: 453, wherein the CD163 gene expresses a CD163 protein that exhibits reduced uptake of the porcine reproductive and respiratory syndrome virus (PRRSV) relative to a wild-type CD163 protein, the method comprising: a) introducing: i) a Cas9 protein or a nucleic acid sequence encoding a Cas9 protein; ii) a guide RNA (gRNA) comprising the nucleic acid sequence of SEQ ID NO: 249; and iii) a gRNA comprising the nucleic acid sequence of SEQ ID NO: 256 into an isolated pig cell; b) producing a pig from the isolated pig cell. In various configurations, the isolated pig cell can be a fertilized oocyte and the producing can comprise implanting the fertilized oocyte into a surrogate mother. In various configurations, the method can further comprise breeding the pig to a wild-type pig to create a plurality of first-generation progeny. In some configurations, the method can further comprise breeding the plurality of first-generation progeny to produce a plurality of second-generation progeny. In some configurations, individuals from the plurality of second-generation progeny can be homozygous for the nucleic acid sequence of SEQ ID NO: 453.

In some configurations, the isolated pig cell is a fibroblast cell. In various configurations, the present teachings can include a pig produced by a method of the present teachings.

In various configurations, the producing can comprise nuclear transfer of the isolated pig cell or a cell derived therefrom to produce a pig embryo. In various configurations, the isolated pig cell can be a pig embryo or zygote. In some configurations, the method may further comprise implanting the pig embryo or zygote into a surrogate mother. In various configurations, the may further comprise implanting the pig embryo obtained from the nuclear transfer into a surrogate mother.

In some embodiments, the present teachings provide for and include a CD163 gene edited to confer PRRSv resistance in *Sus scrofa* wherein the edit excises exon 7 and the edited gene can comprise a repaired genomic sequence as set forth in any one of SEQ ID NOs: 426-458 and 520-555. In some configurations, the edited gene can comprise a repaired genomic sequence selected from the group consisting of SEQ ID NOs: 426-458. In various configurations, the repaired gene sequence can comprise SEQ ID NO: 426, SEQ ID NO: 427, SEQ ID NO: 428, SEQ ID NO: 429, SEQ ID NO: 430, SEQ ID NO: 431, SEQ ID NO: 432, SEQ ID NO: 433, SEQ ID NO: 434, SEQ ID NO: 435, SEQ ID NO: 436, SEQ ID NO: 437, SEQ ID NO: 438, SEQ ID NO: 439, SEQ ID NO: 440, SEQ ID NO: 441, SEQ ID NO: 442, SEQ ID NO: 443, SEQ ID NO: 444, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 520, SEQ ID NO: 521, SEQ ID NO: 522, SEQ ID NO: 523, SEQ ID NO: 524, SEQ ID NO: 525, SEQ ID NO: 526, SEQ ID NO: 527, SEQ ID NO: 528, SEQ ID NO: 529, SEQ ID NO: 530, SEQ ID NO: 531, SEQ ID NO: 532, SEQ ID NO: 533, SEQ ID NO: 534, SEQ ID NO: 535, SEQ ID NO: 536, SEQ ID NO: 537, SEQ ID NO: 538, SEQ ID NO: 539, SEQ ID NO: 540, SEQ ID NO: 541, SEQ ID NO: 542, SEQ ID NO: 543, SEQ ID NO: 544, SEQ ID NO: 545, SEQ ID NO: 546, SEQ ID NO: 547, SEQ ID NO: 548, SEQ ID NO: 549, SEQ ID NO: 550, SEQ ID NO: 551, SEQ ID NO: 552, SEQ ID NO: 553, SEQ ID NO: 554, or SEQ ID NO: 555. In various configurations, the edit can be created using a pair of gRNAs, wherein the pair of gRNAs can be SEQ ID NOs: 229 and 256, SEQ ID NOs: 230 and 256, SEQ ID NOs: 231 and 256, SEQ ID NOs: 237 and 256, SEQ ID NOs: 241 and 256, SEQ ID NOs: 229 and 258, SEQ ID NOs: 230 and 258, SEQ ID NOs: 231 and 258, SEQ ID NOs: 237 and 258, SEQ ID NOs: 241 and 258, SEQ ID NOs: 229 and 261, SEQ ID NOs: 230 and 261, SEQ ID NOs: 231 and 261, SEQ ID NOs: 237 and 261, SEQ ID NOs: 241 and 261, SEQ ID NOs: 219 and 256, SEQ ID NOs: 221 and 256, SEQ ID NOs: 224 and 256, SEQ ID NOs: 227 and 256, SEQ ID NOs: 219 and 258, SEQ ID NOs: 221 and 258, SEQ ID NOs: 224 and 258, SEQ ID NOs: 227 and 258, SEQ ID NOs: 219 and 261, SEQ ID NOs: 221 and 261, SEQ ID NOs: 224 and 261, SEQ ID NOs: 227 and 261, SEQ ID NOs: 249 and 256, SEQ ID NOs: 250 and 256, SEQ ID NOs: 249 and 258, SEQ ID NOs: 250 and 258, SEQ ID NOs: 249 and 261, or SEQ ID NOs: 250 and 261. In various configurations, the edit can be created using a pair of gRNAs, wherein the pair of targeting regions can be SEQ ID NOs: 229 and 256, SEQ ID NOs: 230 and 256, SEQ ID NOs: 231 and 256, SEQ ID NOs: 241 and 256, SEQ ID NOs: 229 and 258, SEQ ID NOs: 231 and 258, SEQ ID NOs: 241 and 258, SEQ ID NOs: 219 and 256, SEQ ID NOs: 221 and 256, SEQ ID NOs: 224 and 256, SEQ ID NOs: 227 and 256, SEQ ID NOs: 227 and 258, SEQ ID NOs: 221 and 261, SEQ ID NOs: 249 and 256, SEQ ID NOs: 250 and 256, SEQ ID NOs: 249 and 258, or SEQ ID NOs: 249 and 261.

In various configurations, the edit can be created using a pair of gRNAs wherein the pair of gRNAs can be SEQ ID NOs: 229 and 256. In various configurations, the edit can be created using a pair of gRNAs wherein the pair of gRNAs can be SEQ ID NOs: 230 and 256. In various configurations, the edit can be created using a pair of gRNAs wherein the pair of gRNAs can be SEQ ID NOs: 231 and 256. In various configurations, the edit can be created using a pair of gRNAs wherein the pair of gRNAs can be SEQ ID NOs: 237 and 256. In various configurations, the edit can be created using a pair of gRNAs wherein the pair of gRNAs can be SEQ ID NOs: 241 and 256. In various configurations, the edit can be created using a pair of gRNAs wherein the pair of gRNAs can be SEQ ID NOs: 229 and 258. In various configurations, the edit can be created using a pair of gRNAs wherein the pair of gRNAs can be SEQ ID NOs: 230 and 258. In various configurations, the edit can be created using a pair of gRNAs wherein the pair of gRNAs wherein the pair of targeting regions can be SEQ ID NOs: 231 and 258. In various configurations, the edit can be created using a pair of gRNAs wherein the pair of gRNAs can be SEQ ID NOs: 237 and 258. In various configurations, the edit can be created using a pair of gRNAs wherein the pair of gRNAs can be SEQ ID NOs: 241 and 258. In various configurations, the edit can be created using a pair of gRNAs wherein the pair of gRNAs can be SEQ ID NOs: 229 and 261. In various configurations, the edit can be created using a pair of gRNAs wherein the pair of gRNAs can be SEQ ID NOs: 230 and 261. In various configurations, the edit can be a pair of gRNAs wherein the pair of gRNAs can be SEQ ID NOs: 231 and 261. In various configurations, the edit can be created using a pair of gRNAs wherein the pair of gRNAs can be SEQ ID NOs: 237 and 261. In various configurations, the edit can be created using a pair of gRNAs wherein the pair of gRNAs can be SEQ ID NOs: 241 and 261. In various configurations, the edit can be created using a pair of gRNAs wherein the pair of gRNAs can be SEQ ID NOs: 219 and 256. In various configurations, the edit can be created using a pair of gRNAs wherein the pair of gRNAs can be SEQ ID NOs: 221 and 256. In various configurations, the edit can be created using a pair of gRNAs wherein the pair of gRNAs can be SEQ ID NOs: 224 and 256. In various configurations, the edit can be created using a pair of gRNAs wherein the pair of gRNAs can be SEQ ID NOs: 227 and 256. In various configurations, the edit can be created using a pair of gRNAs wherein the pair of gRNAs can be SEQ ID NOs: 219 and 258. In various configurations, the edit can be created using a pair of gRNAs wherein the pair of gRNAs can be SEQ ID NOs: 221 and 258. In various configurations, the edit can be created using a pair of gRNAs wherein the pair of gRNAs can be SEQ ID NOs: 224 and 258. In various configurations, the edit can be created using a pair of gRNAs wherein the pair of gRNAs can be SEQ ID NOs: 227 and 258. In various configurations, the edit can be created using a pair of gRNAs wherein the pair of gRNAs can be SEQ ID NOs: 219 and 261. In various configurations, the edit can be created using a pair of gRNAs wherein the pair of gRNAs can be SEQ ID NOs: 221 and 261. In various configurations, the edit can be created using a pair of gRNAs wherein the pair of gRNAs can be SEQ ID NOs: 224 and 261. In various configurations, the edit can be created using a pair of gRNAs wherein the pair of gRNAs can be SEQ ID NOs: 227 and 261. In various configurations, the edit can be created using a pair of gRNAs wherein the pair of gRNAs can be SEQ ID NOs: 249 and 256. In various configurations, the edit can be created using a pair of gRNAs wherein the pair of gRNAs can be SEQ ID NOs: 250 and 256. In various configurations, the edit can be created using a pair of gRNAs wherein the pair of gRNAs can be SEQ ID NOs: 249 and 258. In various configurations, the edit can be created using a pair of gRNAs wherein the pair of gRNAs can be SEQ ID NOs: 250 and 258. In various configurations, the edit can be created a pair of gRNAs wherein the pair of gRNAs can be SEQ ID NOs: 249 and 261. In various configurations, the edit can be created using a pair of gRNAs wherein the pair of gRNAs can be SEQ ID NOs: 250 and 261. In various configurations, the repaired genomic sequence can comprise SEQ ID NO: 453 and the edit can be created using sequences set forth in SEQ ID NOs: 249 and 256.

In various configurations, the instant disclosure provides for and includes a *Sus scrofa* cell that can comprise the CD163 gene of the present teachings. In some configurations, the present teachings further provide for and include a cell line that can comprise a plurality of the *Sus scrofa* cell. In some configurations, the cell line can be a fibroblast cell line. In various configurations, the cell, plurality of cells, or cell line can be derived from PIC line 2, PIC line 3, PIC line 15, PIC line 19, PIC line 27, PIC line 62, or PIC line 65. The present teachings further provide for an embryo, piglet, or mature adult that can comprise a plurality of the cell.

The present disclosure also provides for a CD163 gene edited to confer PRRSv resistance in *Sus scrofa* wherein the edit creates a stop codon resulting in a predicted exon 7 amino acid sequence that can be selected from the group consisting of 506-517. In various configurations, the amino acid sequence can be set forth in SEQ ID NO: 506, SEQ ID NO: 507, SEQ ID NO: 508, SEQ ID NO: 509, SEQ ID NO: 510, SEQ ID NO: 511, SEQ ID NO: 512, SEQ ID NO: 513, SEQ ID NO: 514, SEQ ID NO: 515, SEQ ID NO: 516, or SEQ ID NO: 517. In various configurations, the predicted amino acid sequence of exon 7 can be set forth in SEQ ID NO: 513. In some configurations, the edit can be created using gRNAs selected from the group consisting of SEQ ID NOs: 351 and 365, SEQ ID NOs: 351 and 387, SEQ NOs.: 348 and 390, SEQ ID NOs: 348 and 388, SEQ ID NOs: 348 and 395, SEQ ID NOs: 352 and 365, SEQ ID NOs: 352 and 387, SEQ ID NOs: 352 and 399, SEQ ID NOs: 353 and 365, SEQ ID NOs: 353 and 387, SEQ ID NOs: 353 and 399, SEQ ID NOs:354 and 390, SEQ ID NOs: 354 and 388, SEQ ID NOs: 354 and 395, SEQ ID NOs: 358 and 361, SEQ ID NOs: 358 and 362, SEQ ID NOs: 358 and 368, SEQ ID NOs: 358 and 384, SEQ ID NOs: 358 and 394, SEQ ID NOs: 358 and 399, SEQ ID NOs: 359 and 390, SEQ ID NOs: 359 and 388, SEQ ID NOs: 359 and 395, SEQ ID NOs: 360 and 368, SEQ ID NOs: 360 and 384, SEQ ID NOs: 360 and 389, SEQ ID NOs: 360 and 394, SEQ ID NOs: 360 and 397, SEQ ID NOs: 361 and 365, SEQ ID NOs: 361 and 387, SEQ ID NOs: 362 and 390, SEQ ID NOs: 362 and 388, SEQ ID NOs: 362 and 395, SEQ ID NOs. 364 and 365, SEQ ID NOs: 364 and 387, SEQ ID NOs: 364 and 399, SEQ ID NOs: 365 and 368, SEQ ID NOs: 365 and 384, SEQ ID NOs: 365 and 389, SEQ ID NOs: 365 and 394, SEQ ID NOs: 365 and 397, SEQ ID NOs: 366 and 368, SEQ ID NOs: 366 and 384, SEQ ID NOs: 366 and 389, SEQ ID NOs: 366 and 394, and SEQ ID NOs: 366 and 397. In various configurations, the edit can be created using gRNAs selected from the group consisting of SEQ ID NOs: 351 and 365, SEQ ID NOs: 348 and 390, SEQ ID NOs: 348 and 388, SEQ ID NOs: 354 and 390, SEQ ID NOs: 358 and 394, SEQ ID NOs: 362 and 390, and SEQ ID NOs: 366 and 394. In various configurations, the gRNAs used to create the edit can be SEQ ID NOs: 351 and 365. In various configurations, the gRNAs used to create the edit can be SEQ ID NOs: 351 and 387. In various configurations, the gRNAs used to create the edit can be SEQ ID NOs: 348 and 390. In various configurations, the gRNAs used to create the edit can be SEQ ID NOs: 348 and 388. In various configurations, the gRNAs used to create the edit can be SEQ ID NOs: 348 and 395. In various configurations, the gRNAs used to create the edit can be SEQ ID NOs: 352 and 365. In various configurations, the gRNAs used to create the edit can be SEQ ID NOs: 352 and 387. In various configurations, the gRNAs used to create the edit can be SEQ ID NOs: 352 and 399. In various configurations, the gRNAs used to create the edit can be SEQ ID NOs: 353 and 365. In various configurations, the gRNAs used to create the edit can be SEQ ID NOs: 353 and 387. In various configurations, the gRNAs used to create the edit can be SEQ ID NOs: 353 and 399. In various configurations, the gRNAs used to create the edit can be SEQ ID NOs: 354 and 390. In various configurations, the gRNAs used to create the edit can be SEQ ID NOs: 354 and 388. In various configurations, the gRNAs used to create the edit can be SEQ ID NOs: 354 and 395. In various configurations, the gRNAs used to create the edit can be SEQ ID NOs: 358 and 361. In various configurations, the gRNAs used to create the edit can be SEQ ID NOs: 358 and 362. In various configurations, the gRNAs used to create the edit can be SEQ ID NOs: 358 and 368. In various configurations, the gRNAs used to create the edit can be SEQ ID NOs: 358 and 384. In various configurations, the gRNAs used to create the edit can be SEQ ID NOs: 358 and 394. In various configurations, the gRNAs used to create the edit can be SEQ ID NOs: 358 and 399. In various configurations, the gRNAs used to create the edit can be SEQ ID NOs: 359 and 390. In various configurations, the gRNAs used to create the edit can be SEQ ID NOs: 359 and 388. In various configurations, the gRNAs used to create the edit can be SEQ ID NOs: 359 and 395. In various configurations, the gRNAs used to create the edit can be SEQ ID NOs: 360 and 368. In various configurations, the gRNAs used to create the edit can be SEQ ID NOs: 360 and 384. In various configurations, the gRNAs used to create the edit can be SEQ ID NOs: 360 and 389. In various configurations, the gRNAs used to create the edit can be SEQ ID NOs: 360 and 394. In various configurations, the gRNAs used to create the edit can be SEQ ID NOs: 360 and 397. In various configurations, the gRNAs used to create the edit can be SEQ ID NOs: 361 and 365. In various configurations, the gRNAs used to create the edit can be SEQ ID NOs: 361 and 387. In various configurations, the gRNAs used to create the edit can be SEQ ID NOs: 362 and 390. In various configurations, the gRNAs used to create the edit can be SEQ ID NOs: 362 and 388. In various configurations, the gRNAs used to create the edit can be SEQ ID NOs: 362 and 395. In various configurations, the gRNAs used to create the edit can be SEQ ID NOs: 364 and 365. In various configurations, the gRNAs used to create the edit can be SEQ ID NOs: 364 and 387. In various configurations, the gRNAs used to create the edit can be SEQ ID NOs: 364 and 399. In various configurations, the gRNAs used to create the edit can be SEQ ID NOs: 365 and 368. In various configurations, the gRNAs used to create the edit can be SEQ ID NOs: 365 and 384. In various configurations, the gRNAs used to create the edit can be SEQ ID NOs: 365 and 389. In various configurations, the gRNAs used to create the edit can be SEQ ID NOs: 365 and 394. In various configurations, the gRNAs used to create the edit can be SEQ ID NOs: 365 and 397. In various configurations, the gRNAs used to create the edit can be SEQ ID NOs: 366 and 368. In various configurations, the gRNAs used to create the edit can be SEQ ID NOs: 366 and 384. In various configurations, the gRNAs used to create the edit can be SEQ ID NOs: 366 and 389. In various configurations, the gRNAs used to create the edit can be SEQ ID NOs: 366 and 394. In various configurations, the gRNAs used to create the edit can be SEQ ID NOs: 366 and 397.

In various configurations, the edited CD163 gene can have a nucleic acid sequence selected from the group consisting of SEQ ID NO: 459-504. In various configurations, the repaired gene can have a nucleic acid sequence set forth in SEQ ID NO: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, or 504. In various configurations, the repaired gene can have a nucleic acid sequence as set forth in SEQ ID NO: 489. In various configurations the predicted amino acid sequence of exon 7 can be as set forth in SEQ ID NO: 513. In various configurations, the predicted amino acid sequence of the gene can be SEQ ID NO: 513, the repaired gene can have a nucleic acid sequence set forth in SEQ ID NO: 489, and the edit can be created using sequences set forth in SEQ ID NOs: 362 and 390.

The present disclosure provides for and includes a *Sus scrofa* cell that can comprise the CD163 gene edited to comprise an exogenous stop codon as described supra. The present disclosure also provides for a cell line that can comprise a plurality of the cell comprising the CD163 gene edited to comprise an exogenous stop codon. In some configurations, the cell line can be a fibroblast cell line. In various configurations, the cell can be derived from PIC line 2, PIC line 3, PIC line 15, PIC line 19, PIC line 27, PIC line 62, or PIC line 65. The present disclosure also provides for and includes an embryo, piglet, or mature adult comprising a plurality of the cell that can comprise the CD163 gene edited to comprise an exogenous stop codon.

In various embodiments, the present teachings provide for and include a pair of gRNAs for editing a *Sus scrofa* CD163 gene having a sequence as set forth in SEQ ID NOs: 229 and 256, SEQ ID NOs: 230 and 256, SEQ ID NOs: 231 and 256, SEQ ID NOs: 237 and 256, SEQ ID NOs: 241 and 256, SEQ ID NOs: 229 and 258, SEQ ID NOs: 230 and 258, SEQ ID NOs: 231 and 258, SEQ ID NOs: 237 and 258, SEQ ID NOs: 241 and 258, SEQ ID NOs: 229 and 261, SEQ ID NOs: 230 and 261, SEQ ID NOs: 231 and 261, SEQ ID NOs: 237 and 261, SEQ ID NOs: 241 and 261, SEQ ID NOs: 219 and 256, SEQ ID NOs: 221 and 256, SEQ ID NOs: 224 and 256, SEQ ID NOs: 227 and 256, SEQ ID NOs: 219 and 258, SEQ ID NOs: 221 and 258, SEQ ID NOs: 224 and 258, SEQ ID NOs: 227 and 258, SEQ ID NOs: 219 and 261, SEQ ID NOs: 221 and 261, SEQ ID NOs: 224 and 261, SEQ ID NOs: 227 and 261, SEQ ID NOs: 249 and 256, SEQ ID NOs: 250 and 256, SEQ ID NOs: 249 and 258, SEQ ID NOs: 250 and 258, SEQ ID NOs: 249 and 261, SEQ ID NOs: 250 and 261, SEQ ID NOs: 351 and 365, SEQ ID NOs: 351 and 387, SEQ NOs: 348 and 390, SEQ ID NOs: 348 and 388, SEQ ID NOs: 348 and 395, SEQ ID NOs: 352 and 365, SEQ ID NOs: 352 and 387, SEQ ID NOs: 352 and 399, SEQ ID NOs: 353 and 365, SEQ ID NOs: 353 and 387, SEQ ID NOs: 353 and 399, SEQ ID NOs: 354 and 390, SEQ ID NOs: 354 and 388, SEQ ID NOs: 354 and 395, SEQ ID NOs: 358 and 361, SEQ ID NOs: 358 and 362, SEQ ID NOs: 358 and 368, SEQ ID NOs: 358 and 384, SEQ ID NOs: 358 and 394, SEQ ID NOs: 358 and 399, SEQ ID NOs: 359 and 390, SEQ ID NOs: 359 and 388, SEQ ID NOs: 359 and 395, SEQ ID NOs: 360 and 368, SEQ ID NOs: 360 and 384, SEQ ID NOs: 360 and 389, SEQ ID NOs: 360 and 394, SEQ ID NOs: 360 and 397, SEQ ID NOs: 361 and 365, SEQ ID NOs: 361 and 387, SEQ ID NOs: 362 and 390, SEQ ID NOs: 362 and 388, SEQ ID NOs: 362 and 395, SEQ ID NOs: 364 and 365, SEQ ID NOs: 364 and 387, SEQ ID NOs: 364 and 399, SEQ ID NOs: 365 and 368, SEQ ID NOs: 365 and 384, SEQ ID NOs: 365 and 389, SEQ ID NOs: 365 and 394, SEQ ID NOs: 365 and 397, SEQ ID NOs: 366 and 368, SEQ ID NOs: 366 and 384, SEQ ID NOs: 366 and 389, SEQ ID NOs: 366 and 394, or SEQ ID NOs: 366 and 397. In some configurations, the pair of gRNAs can have a sequence as set forth in SEQ ID NOs: 229 and 256, SEQ ID NOs: 230 and 256, SEQ ID NOs: 231 and 256, SEQ ID NOs: 241 and 256, SEQ ID NOs: 229 and 258, SEQ ID NOs: 231 and 258, SEQ ID NOs: 241 and 258, SEQ ID NOs: 219 and 256, SEQ ID NOs: 221 and 256, SEQ ID NOs: 224 and 256, SEQ ID NOs: 227 and 256, SEQ ID NOs: 227 and 258, SEQ ID NOs: 221 and 261, SEQ ID NOs: 249 and 256, SEQ ID NOs: 250 and 256, SEQ ID NOs: 249 and 258, SEQ ID NOs: 249 and 261, SEQ ID NOs: 351 and 365, SEQ ID NOs: 348 and 390, SEQ ID NOs: 348 and 388, SEQ ID NOs: 354 and 390, SEQ ID NOs: 358 and 394, SEQ ID NOs: 362 and 390, or SEQ ID NOs: 366 and 394. In various configurations, the pair of gRNAs can have a sequence as set forth in SEQ ID NOs: 249 and 256. In various configurations, the pair of gRNAs can have a sequence as set forth in SEQ ID NOs: 362 and 390.

The present disclosure provides for and includes a CRISPR complex for editing a CD163 gene of *Sus scrofa* comprising a pair of gRNAs of the present teachings.

The present disclosure provides for and includes a method for editing a CD163 gene of *Sus scrofa* comprising using a CRISPR-CAS complex comprising a pair of gRNAs of the present teachings.

The present disclosure provides for and includes a method for preparing a PRSSV resistant *Sus scrofa* cell by using a CRISPR-CAS complex comprising the pair of gRNAs of the present teachings.

The present disclosure provides for and includes a method of producing PRRSv resistant *Sus scrofa* animals, comprising: a) editing a CD163 gene of a *Sus scrofa* cell or a plurality of *Sus scrofa* cells using a CRISPR complex comprising a pair of gRNAs of the present teachings; and b) producing an animal from the cell or plurality of cells.

The present disclosure provides for and includes the use of a cell line according to the present teachings in producing PRRSv resistant animals.

The present disclosure also provides for and includes an embryo, piglet, or mature adult comprising a plurality of the cell according to the present teachings.

In various embodiments the present disclosure provides for and includes a method of determining the presence or absence of an edited sequence having 90% or 95% identity with a sequence set forth in SEQ ID NO: 453 comprising performing real time PCR with a) differentially labeled probes of sequences set forth in SEQ ID NO: 564 and SEQ ID NO: 558 or 561; b) a primer pair set forth in SEQ ID NOs: 562 and 563; and c) a primer pair set forth in SEQ ID NOs: 556 and 557 or SEQ ID NOs: 559 and 560. In some configurations, the edited sequence can have 100% identity with the sequence set forth in SEQ ID NO: 453. In some configurations, the edited sequence can have 90% identity with the sequence set forth in SEQ ID NO: 453. In some configurations, the edited sequence can have 95% identity with the sequence set forth in SEQ ID NO: 453.

In various embodiments, the present teachings provide for and include a PCR primer selected from the group consisting of SEQ ID NO: 556, SEQ ID NO: 557, SEQ ID NO: 559, SEQ ID NO: 560, SEQ ID NO: 562, and SEQ ID NO: 563. In some configurations, the PCR primer can have a sequence as set forth in SEQ ID NO: 556. In various configurations, the PCR primer can have a sequence as set forth in SEQ ID NO: 557. In various configurations, the PCR primer can have a sequence as set forth in SEQ ID NO: 559. In various configurations, the PCR primer can have a sequence as set forth in SEQ ID NO: 560. In various configurations, the PCR primer can have a sequence as set forth in SEQ ID NO: 562. In various configurations, the PCR primer can have a sequence as set forth in SEQ ID NO: 563.

In some embodiments, the present disclosure provides for and includes a real time PCR probe selected from the group consisting of SEQ ID NO: 558, SEQ ID NO: 561, and SEQ ID NO: 564. In some configurations, the probe has a sequence as set forth in SEQ ID NO: 558. In various configurations, the probe has a sequence as set forth in SEQ ID NO: 561. In various configurations, the probe has a sequence as set forth in SEQ ID NO: 564.

In various embodiments, the present teachings provide for and include the use of PCR primers set forth in a) SEQ ID NO: 556 and 557 and SEQ ID NO: 562 and 563 or b) SEQ ID NO: 559 and 560 and SEQ ID NO: 562 and 563 to determine the presence or absence of an edited genome sequence set forth in SEQ ID NO: 453.

In various embodiments, the present teachings provide for and include the use of PCR probes set forth in a) SEQ ID NOs: 558 and 564 or b) SEQ ID NOs: 561 and 564 to determine the presence or absence of an edited genome sequence set forth in SEQ ID NO: 453.

In various embodiments, the present teachings provide for and include a method of creating a PRRSv resistant pig comprising editing the pig's genome to comprise a genomic sequence as set forth in SEQ ID NO: 453. In some configurations, the editing the pig's genome can comprise administering gRNAs having sequences set forth in SEQ ID NOs: 249 and 256. In various configurations, the administering comprises injecting pre-formed RNP complexes comprising the gRNAs and a CAS protein into a zygote, embryo, or MII oocyte. In various configurations, the pig is a PIC™ line 2 (Pig Improvement Company, Ltd, Basingstoke, UK), PIC™ line 3, PIC™ line 15, PIC™ line 19, PIC™ line 27, PIC™ line 62, or PIC™ line 65 pig.

In various embodiments, the present disclosure provides for and includes, a *Sus scrofa* animal comprising an edited gene that confers PRRSv resistance in *Sus scrofa* wherein the edit excises exon 7 and the edited gene comprises a repaired genomic sequence set forth in SEQ ID NO: 453. In some configurations, the edit can be made with guideRNAs (gRNAs) having sequences set forth in SEQ ID NOs: 249 and 256. In various configurations, the animal can be an edited animal of PIC™ line 2, PIC™ line 3, PIC™ line 15, PIC™ line 19, PIC™ line 27, PIC™ line 62, or PIC™ line 65. In various configurations, the present disclosure provides for and includes a cell prepared from the animal of the present teachings. In various configurations, the present disclosure provides for and includes a cell line prepared from the cell according to the present teachings. In some configurations, the cell line can be a fibroblast cell line.

In some embodiments, the present teachings provide for and include a CD163 gene edited to confer PRRSv resistance in *Sus scrofa* wherein the edit excises exon 7 and the edited gene comprises a repaired genomic sequence set forth in SEQ ID NO: 453. In some configurations, the edit is created using sequences set forth in SEQ ID NOs: 249 and 256. In various configurations, the present disclosure provides for a *Sus scrofa* cell comprising the CD163 gene according to the present teachings. In some configurations, the present disclosure provides for a cell line comprising a plurality of the cell according to the present teachings. In some configurations, the cell line can be a fibroblast cell line.

In various configurations, the cell can be isolated from PIC line 2, PIC line 3, PIC line 15, PIC line 19, PIC line 27, PIC line 62, or PIC line 65.

In various embodiments, the present disclosure provides for and includes a pair of gRNAs for editing a *Sus scrofa* CD163 gene comprising the guide sequences set forth in SEQ ID NOs: 249 and 256.

In various embodiments, the present teachings provide for and include a method of creating a PRRSv resistant pig comprising editing the pig's genome to comprise a genomic sequence as set forth in SEQ ID NO: 453. In some configurations, editing the pig's genome can comprise administering gRNAs having sequences set forth in SEQ ID NOs: 249 and 256. In some configurations, the administering can comprise injecting pre-formed RNP complexes comprising the gRNAs and a CAS protein into a zygote, embryo, or MII oocyte. In various configurations, the pig can be a PIC™ line 2, PIC™ line 3, PIC™ line 15, PIC™ line 19, PIC™ line 27, PIC™ line 62, or PIC™ line 65 pig.

DETAILED DESCRIPTION

The aspects of the present teachings include, but are not limited to, particular methods of improving the health of a porcine species by targeted inactivation of CD163, which can vary and are understood by skilled artisans. It is further to be understood that all terminology used herein is for the purpose of describing particular aspects only, and is not intended to be limiting in any manner or scope. For example, as used in this specification and the appended claims, the singular forms "a," "an," and "the" can include plural referents unless the content clearly indicates otherwise. Further, all units, prefixes, and symbols may be denoted in their SI accepted forms. Numeric ranges recited within the specification are inclusive of the numbers defining the range and include each integer within the defined range.

So that the present application may be more readily understood, certain terms are first defined. Unless defined otherwise, all technical and scientific terms used herein have the same meaning as commonly understood by one of ordinary skill in the art to which aspects of the present application pertain. Many methods and materials similar, modified, or equivalent to those described herein can be used in the practice of the aspects of the present application without undue experimentation, the preferred materials and methods are described herein. In describing and claiming the aspects of the present application, the following terminology will be used in accordance with the definitions set out below.

As used herein, "animal cell" means a cell, including, but not limited to, a somatic cell, culture cell, gamete cell, blood cell, zygote, and embryonic cell. These animal cells can be reproductive or non-reproductive cells. As used herein, cells may be isolated from an animal or embryo and maintained in tissue culture. Also included are mixed cultures that can comprise gene edited cells of the present specification and a non-gene edited support cell or feeder cell.

As used herein, the terms "gene edited," "genetically edited," and "genome-edited," refer to the use of homing technology with naturally occurring or artificially engineered endonucleases, often referred to as "homing endonucleases," or "targeting endonucleases." "Genome-editing" and "gene editing," refer to altering the genome by deleting, inserting, or substituting specific nucleic acid sequences. The altering can be gene or location specific, but need not be altering the sequence of a gene per se. Genome editing can use endonucleases such as the CRISPR system to cut a nucleic acid, thereby generating a site for the alteration.

Other endonucleases are available and are suitable for use; however, off-site cutting and specificity can be significant problems. In systems like CRISPR and others, the nuclease can be directed to the target site by complexing with a polynucleotide, herein called a "target sequence," to introduce a site specific DSB. Not to be limited by theory, the DSB can then be repaired by endogenous non-homologous end joining (NHEJ) machinery.

A number of endonucleases are known that are suitable for, and have been adapted to, gene editing. Gene editing methods are known in the art, including Clustered Regularly Interspaced Short Palindromic Repeats (CRISPR) systems (e.g., the CRISPR/Cas9 system), Transcription Activator-Like Effector Nucleases (TALENs), and Gene editing nucleases including Zinc Finger Nucleases (ZFNs). Gene edited animals can be distinguished from transgenic animals by the incorporation of exogenous DNA sequences, particularly sequences having identity with sequences from foreign species in the latter. Here, the terms include, and provide for, small deletions and insertions that do not introduce more than 10 nucleotides. The terms also encompass progeny animals such as those created by sexual crosses or asexual propagation from the initial gene edited animal.

As used herein, the term "repair template" or "repair sequences" refers to a polynucleotide introduced into a cell undergoing DSB repair at nuclease targeted locations in the genome to guide the repair and provide accurate and selective editing. Repair templates can be used to selectively change or delete sequences at a locus having a DSB and generally comprise a 5' genome hybridizing region and a 3' genome hybridizing region. In an aspect, the 5' genome hybridizing and 3' genome hybridizing regions can share at least 80% homology. In an aspect, the 5' genome hybridizing and 3' genome hybridizing regions can share identity. Further descriptions of the repair templates of the present disclosure are provided below. For deletion templates, a contiguous region of the genome can be separated by the deletion of one or more nucleotides. Targeted editing of individual bases can be prepared using repair templates comprising a contiguous region of a genome and having one or more base changes, including addition of a stop codon. The percentage identity of a repair template to a contiguous region of the genome can be between 80% and 100% using an ungapped alignment. As provided herein, a core region of identity within a repair template is provided that may be flanked by a flanking homology region sharing between 80% and 100% homology to the targeted chromosomal region. Not to be limited by theory, the core region identity can increase the fidelity of the repair process while extended regions of homology on either side increase the efficiency and allow for genotypic variation among cells targeted for editing.

As used herein, the term "wild type" or "WT" refers to a phenotype, genotype, or gene that predominates in a natural population of pigs or line of pigs. When used to compare phenotypes and genotypes of gene edited cells and animals of specific lines, the term "wild type" refers to non-gene edited cells and animals of the same line. In an aspect, the present disclosure provides for comparison of edited pigs to non-edited pigs of a similar breed having a similar genetic background. In an aspect, the present disclosure provides for comparison of edited pigs to non-edited pigs of the same breeding line.

As used herein, the term "knock-out" refers to the disruption of gene function by reduction or elimination of its expression. Knock-outs may be generated through the creation of double-strand breaks (DSBs) in the chromosome which can then be repaired using either non-homologous end joining (NHEJ) or homologous recombination of DNA repair templates or targeting vectors by homology-directed repair (HDR). Not to be limited by theory, HDR knock-outs may also be prepared by microhomology-mediated end joining providing a repair template to insert, delete, or edit genomic sequences. Knock-outs may also be generated through replacement vectors, or hit-and-run vectors, or random insertion of a gene trap vector resulting in complete, partial, or conditional loss of gene function.

References herein to a deletion in a nucleotide sequence spanning a range are inclusive of all nucleotides in the listed range. For example, a 5 base pair deletion from nucleotide "a" to nucleotide "e" means that each of nucleotides "a," "b," "c," "d," and "e" have been deleted (where "b," "c," and "d" are between "a" and "e").

As used herein, the term "edit" includes alterations in the nucleotide sequence of a polynucleotide, such as, for example, a gene, coding DNA sequence (CDS), or non-coding DNA sequence, compared to the wild-type sequence. The term "edits" may include insertions, deletions, splice-donor site edits, point-edits, and the like.

As used herein, the term "clustered regularly interspaced short palindromic repeats" or "CRISPR" refers to a gene editing system utilizing a CRISPR segment of genetic material, and the RNA segments and enzymes it produces, to identify and modify specific DNA sequences in the genome of other organisms. CRISPR systems include Type I, Type II, and Type III CRISPR systems. As used herein, the term "CRISPR associated protein" or "Cas" refers to a protein family that can be strictly associated with CRISPR elements and always occurs near a repeat cluster of CRISPR segments. For example, Cas proteins can include, but are not limited to, Cas9 family member proteins, Cas6 family member proteins (e.g., Csy4 and Cas6), and Cas5 family member proteins. Examples of Cas protein families and methods of identifying the same have been disclosed in Haft, Daniel H., et al., *PLoS Comput. Bio.*, 2005, 1, e60.

While not being limited by any particular scientific theory, a CRISPR nuclease can form a complex with a guide RNA (gRNA), which hybridizes with a complementary target nucleic acid molecule, thereby guiding the CRISPR nuclease to the target nucleic acid molecule. The crRNA comprises a repeat sequence and a spacer sequence which can be complementary to a specific protospacer sequence in an invading pathogen. It is the spacer sequence that can be designed to be complementary to target sequences in a eukaryotic genome. CRISPR nucleases can associate with their respective crRNAs in their active forms. The present specification provides for, and includes a crRNA that can comprise an RNA spacer comprising the first 20 nucleotides of each of SEQ ID NOs: 22 to 271 and 347 to 425. As used herein, each of SEQ ID NOs: 22 to 271 and 347 to 425 provides for, and includes, the corresponding RNA sequence substituting uridine for the thymidine and ribose for deoxyribose. Also, as used herein, the SEQ ID NOs include the PAM (see below) which is present in the genome sequence targeted. Skilled artisans will recognize that the gRNA targeting this sequence would not include the PAM, and therefore would recognize that a gRNA having a sequence set forth in these SEQ ID NOs would only include the first 20 nucleotides, thus excluding the PAM.

Some CRISPR nucleases, such as CasX and Cas9, can require another non-coding RNA component, referred to as a trans-activating crRNA (tracrRNA), to have functional activity. A crRNA comprising a spacer sequence selected from the group consisting of the first 20 nucleotides of each of SEQ ID NOs: 22 to 271 and the first 20 nucleotides of each of SEQ ID NOs: 347 to 425 can be covalently linked to the 5' end of a tracrRNA into one nucleic acid molecule in what is herein referred to as a "single guide RNA" (sgRNA), as described in Jinek, et al., *Science*, 337, 2012, 816-821. As used herein, the tracrRNA is also referred to as "guide RNA backbone" or "the backbone" sequence. As used herein, gRNA includes both a single guide RNA or separate molecules comprising the spacer sequence in the crRNA for use with a separate tracrRNA. The gRNA can guide the active Cas complex to a target site complementary to the spacer sequence in the crRNA, where the Cas nuclease can cleave the target site. The crRNA can have a region of complementarity to a potential DNA target sequence and a second region that can form base-pair hydrogen bonds with the tracrRNA to form a secondary structure, typically to form at least one stem structure. The region of complementarity to the DNA target sequence can be the spacer or spacer sequence. The tracrRNA and a crRNA can interact through a number of base-pair hydrogen bonds to form secondary RNA structures. Complex formation between tracrRNA/crRNA and Cas9 protein can result in a conformational change of the Cas9 protein that facilitates binding to DNA, endonuclease activities of the Cas9 protein, and crRNA-guided site-specific DNA cleavage by the endonuclease Cas9 (Svitashev et al., Nature Communications, 2016, 7, 113274). In practice, the 20 nucleotides and the guide RNA backbone can be DNA (that can be expressed from a promoter to be transcribed in vivo (in cells) or in vitro (via T7 polymerase) to form an RNA guide or the guide RNA backbone can be chemically synthesized dual (crRNA and trRNA) guide or single guide RNA.

For a Cas9 protein/tracrRNA/crRNA complex to cleave a double-stranded DNA target sequence, the DNA target sequence can be adjacent to a cognate protospacer adjacent motif (PAM). By designing a crRNA to have an appropriate spacer sequence, the complex can be targeted to cleave at a locus of interest, e.g., a locus at which sequence modification is desired.

A variety of Type II CRISPR-Cas system crRNA and tracrRNA sequences, and associated predicted secondary structures are known in the art (see, e.g., Ran, F. A., et al., *Nature*, 2015, 520, 186-191; Fonfara et al., *Nucleic Acids Research*, 2014, 42, 2577-2590). The Type II CRISPR-Cas system of Ran et al., is provided herein in an aspect.

The spacer of Type II CRISPR-Cas systems can hybridize to a nucleic acid target sequence that is located 5' or 3' of a PAM, depending upon the Cas protein to be used. A PAM can vary depending upon the Cas polypeptide to be used. For example, if Cas9 from *S. pyogenes* is used, the PAM can be a sequence in the nucleic acid target sequence that comprises the sequence 5'-NRR-3', wherein R can be either A or G, N is any nucleotide, and N is immediately 3' of the nucleic acid target sequence targeted by the nucleic acid target binding sequence. Preferably, the PAM of *S. pyogenes* comprises 5'-NGG-3'. In another example, if Cas9 from *S. thermophilus* CRISPR3 (Sther CR3) is used, the PAM can be a sequence in the nucleic acid target sequence that comprises the sequence 5'-nGGnG-3'. (See Sapranauskas et al., *Nucleic Acids Research*, 2011, 39, 9275-9282).

Other Cas proteins recognize other PAMs, and one of skill in the art can determine the PAM for any particular Cas protein. A growing number of CAS proteins and systems are known in the art that are suitable for use with the targeting sequences of the present specification. See Shah et al., *RNA*

Biol., 2013, 10, 891-899. A representative sample of CAS systems and their PAM sequences is provided in Table 1 below.

TABLE 1

Exemplary CRISPR/Cas Systems

| Species/Variant of Cas9 | PAM Sequence | |
|---|---|---|
| Streptococcus pyogenes (SP); SpCas9 | 3' NGG | Wu et al., Nat Biotechnol., 2014, 32, 670-676 |
| SpCas9 D1135E variant | 3' NGG (reduced NAG binding) | Nishimasu et al., Science, 2018, 361, 1259-1262. |
| SpCas9 VRER variant | 3' NGCG | Nishimasu et al. (2018) |
| SpCas9 EQR variant | 3' NGAG | Nishimasu et al. (2018) |
| SpCas9 VQR variant | 3' NGAN or NGNG | Nishimasu et al. (2018) |
| Staphylococcus aureus (SA); SaCas9 | 3' NNGRRT or NNGRR(N) | Kleinstiver et al., Nature, 2015, 523, 481-485 |
| Acidaminococcus sp. (AsCpf1) and Lachnospiraceae bacterium (LbCpf1) | 5' TTTV | Fagerlund, R., et al., 2015, Genome Biology, 16, 251 |
| AsCpf1 RR variant | 5' TYCV | Nishimasu et al., Mol Cell., 2017, 67, 139-147 |
| LbCpf1 RR variant | 5' TYCV | Nishimasu et al. (2017) |
| AsCpf1 RVR variant | 5' TATV | Nishimasu et al. (2017) |
| Neisseria meningitidis (NM) | 3' NNNNGAT | Hou et al., 2013, Proc. Natl. Acad. Sci. USA, 110, 15644-156449 |
| Treponema denticola (TD) | 3' NAAAAC | Sun et al., Biotechnol J., 2018, 13, e1700588 |
| Campylobacter jejuni (Cj) | NNNNRYAC | Kim, et al., Nat Commun., 2017, 8, 14500. |
| Streptococcus thermophilus CR1 (St) | NNAGAAW | Toth et al., 2016, Biol Direct., 11, 46 |
| Streptococcus thermophilus CR3 | nGGnG | Müller et al., Mol Ther., 2016, 24,636-644 |

Methods that rely on any CRISPR/CAS system can have a PAM sequence of NRR (e.g., NGG and NAA) as provided below for the S. pyogenes sequences or can have a PAM sequence of NGGNG as provided for the S. thermophilus sequences. Table 3 and the sequence listing provide the targeting sequences and chromosomal locations. It will also be appreciated by those of skill in the art that known CAS systems having different PAM requirements can be engineered to recognize and utilize the target sequences disclosed herein. Examples of modifications are presented in Table 1.

The terms "CRISPR/CasN or "CRISPR/CasN system" refer to a programmable nuclease system for genetic editing that includes a CasN (e.g., Cas2, Cas5, Cas6, Cas9, etc.) protein, or derivative thereof, and one or more non-coding RNAs that can provide the function of a CRISPR RNA (crRNA) and trans-activating RNA (tracrRNA) for the CasN. The crRNA and tracrRNA can be used individually or can be combined to produce a "guide RNA" (gRNA). The crRNA or gRNA can provide a sequence that is complementary to the genomic target.

The term "Cpf1" or "CAS12" refers to another programmable RNA-guided endonuclease of a class 2 CRISPR-Cas system, described and used for gene editing purposes (Zetsche et al., Cell, 163:759-771, 2015). This system can use a non-specific endonuclease unit from the Cpf1 protein family, with a specificity of cleavage conferred by a single crRNA (lacking tracrRNA). Similar to Cas9, the Cpf1 coding sequence can be fused to UTR sequences described herein to improve its stability, and thus the efficiency of the resulting gene editing method.

As used herein, the terms "transcription activator-like effector nucleases" or "TALENS" refer to nucleases engineered to enable the targeted alteration of a given DNA sequence. TALENs can comprise a non-specific DNA-cleaving nuclease fused to a TALE DNA-binding domain that can be engineered to allow targeted gene editing. A "TALE DNA-binding domain" or "TALE" can be a polypeptide comprising one or more TALE repeat domains/units. The repeat domains can be involved in binding of the TALE to its cognate target DNA sequence. A single "repeat unit" (also referred to as a "repeat") can be 33-35 amino acids in length and exhibits at least some sequence homology with other TALE repeat sequences within a naturally occurring TALE protein. A "designed" DNA binding protein can be a protein not occurring in nature whose design/composition results principally from rational criteria. TALENS are discussed and disclosed in Joung et al., Nat. Rev. Mol. Cell. Biol., 2013, 14, 49-55. A "selected TALE" can be a protein not found in nature whose production results primarily from an empirical process such as phage display, interaction trap, or hybrid selection. The present specification provides for, and includes, the use of TALENS to the pigs described herein.

"Resistance" or "disease resistance" refers to the extent to which an organism can defend itself from and/or withstand the attack of a pathogen and remain unaffected. An organism may demonstrate complete resistance, meaning it remains virtually unaffected by a pathogen. Alternatively, an organism may demonstrate partial resistance, wherein the extent to which the pathogen affects the organisms can be less than a comparable organism with no resistance. Resistance may stem from a particular characteristic of the organism, allowing the organism to avoid the outcome of organism-pathogen interactions. Resistance can be demonstrated by the extent to which an organism can avoid the disease symptoms associated with, or reduce the incidence/severity of clinical signs, or reduce the clinical symptoms associated with a pathogen.

The terms "increased resistance" and "reduced susceptibility" refer to a statistically significant reduction of the incidence and/or severity of clinical signs or clinical symptoms which are associated with infection by a given pathogen. For example, "increased resistance" or "reduced susceptibility" refer to a statistically significant reduction of the incidence and/or severity of clinical signs or clinical symptoms which are associated with infection by PRRSv in an animal comprising a deleted or inactivated chromosomal sequence in a CD163 gene protein as compared to a control animal having an unmodified chromosomal sequence. The term "statistically significant reduction of clinical symptoms" means, but is not limited to, the frequency in the incidence of at least one clinical symptom in the modified group of subjects and, in some aspects, clinical symptoms may be statistically reduced by at least 80% lower than in the non-modified control group after the challenge with the infectious agent.

As used herein, the terms "reduction of the incidence and/or severity of clinical signs" or "reduction of clinical symptoms" mean reducing the number of infected subjects in a group, reducing or eliminating the number of subjects exhibiting clinical signs of infection, or reducing the severity of any clinical signs that are present in one or more subjects, in comparison to wild-type infection in an otherwise similar genetic background. For example, these terms encompass any clinical signs of infection, lung pathology, viremia, antibody production, reduction of pathogen load, pathogen shedding, reduction in pathogen transmission, or reduction of any clinical sign symptomatic of PRRS when compared to an otherwise similar background. Comparisons of clinical signs between non-edited CD163 pigs and CD163 edited pigs can be individually or between herds. In an aspect, an individual pig does not present clinical signs. In an aspect, a herd of CD163 edited pigs present reduced clinical signs. In an aspect, the size of the herd can be at least 100 animals. In an aspect, CD163 edited pigs of the present specification can have reduced clinical signs of reproductive syndrome. In an aspect, a herd of CD163 edited pigs can have a reduced number of premature farrowings, reduced numbers of stillborn or mummified piglets, reduced numbers of PRRSv-positive piglets, or reductions in delays to return to service of sow. In an aspect, CD163 edited pigs of the present specification can have reduced clinical signs in sows and gilts including, but not limited to, reduced anorexia, reduced fever, reduced lethargy, reduced pneumonia, reduced agalactica, and reduced subcutaneous and hind limb edema. In an aspect, gilts and sows that are CD163 edited pigs of the present specification can have reduced red/blue discoloration of the ears and vulva. In an aspect, CD163 edited sows can exhibit reduced delays to return to estrus after weaning. The present specification provides for, and includes, reduced deaths among a herd of CD163 edited gilts and sows. Also included and provided for by the present specification are reduced clinical signs in finishing pigs. In an aspect, a herd of CD163 edited finishing pigs can have reduced respiratory clinical signs selected from the group consisting of fever, sneezing, hyperpnoea, dyspnea, coughing, pneumonia, lethargy, periocular edema, and oculo-nasal discharge. Preferably these clinical signs can be reduced in one or more animals of the present teachings by at least 10% in comparison to subjects not having a modification in the CD163 gene and having a similar background and that become infected. In an aspect, clinical signs can be reduced in subjects of the present teachings by at least 80%. In another aspect, clinical signs can be reduced in pigs of the present teachings by at least 85%. In a further aspect, clinical signs can be reduced in pigs of the present teachings by at least 90%. In yet another aspect, clinical signs can be reduced in pigs of the present teachings by at least 95%. In aspects according to the present disclosure, clinical signs can be reduced by 80% to 100% relative to non-edited CD163 pigs.

The term "breeding" as used herein refers to a process comprising the selection of superior male and superior female animals use for creation of the next generation of offspring. This process further comprises the union of male and female gametes so that fertilization occurs. Such a union may be brought about by mating (copulation) or by in vitro or in vivo artificial methods. Such artificial methods can include, but are not limited to, artificial insemination, surgical assisted artificial insemination, in vitro fertilization, intracytoplasmic sperm injection, zona drilling, in vitro culture of fertilized oocytes, ovary transfer, and ovary splitting. The term "breeding" as used herein also can include transferring of a fertilized oocyte into the reproductive tract of a female animal in order to allow for more offspring from a particular elite female.

As used herein, "reference sequence" is a defined sequence used as a basis for sequence comparison. A reference sequence may be a subset or the entirety of a specified sequence; for example, as a segment of a full-length promoter sequence, or the complete promoter sequence. In an aspect, the reference sequence can be the Sscrofal 1.1 reference genome (GenBank accession: GCA_000003025.6).

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity can be determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence can be equal to the number of identical positions between the two sequences divided by the total number of positions in the query sequence over its length (or a comparison window), which is then multiplied by 100%. When percentage of sequence identity is used in reference to proteins, it is recognized that residue positions which are not identical often can differ by conservative amino acid substitutions, where amino acid residues can be substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

For optimal alignment of sequences to calculate their percent identity, various pair-wise or multiple sequence alignment algorithms and programs are known in the art, such as ClustalW or Basic Local Alignment Search Tool (BLAST®, National Library of Medicine, Bethesda, MD), etc., that can be used to compare the sequence identity or similarity between two or more nucleotide or protein sequences. Although other alignment and comparison methods are known in the art, the alignment and percent identity between two sequences (including the percent identity ranges described above) can be as determined by the ClustalW algorithm, see, e.g., Chenna, R., et al., *Nucleic Acids Research*, 2003, 31, 3497-3500; Thompson, J. D., et al., *Nucleic Acids Research*, 1994, 22, 4673-4680; Larkin M A et al., *Bioinformatics*, 2007, 23, 2947-2948; and Altschul, S. F., et al., *J. Mol. Biol.*, 1990, 215, 403-410.

Identity to a sequence used herein can be expressed in terms of a percent identity between two sequences as determined according to alignment of the two sequences. The present specification provides for repair template sequences that can have at least 80% identity to a contiguous region of a genome. In an aspect, the repair template can have a 5' region and a 3' region sharing at least 80% identity to a contiguous region of the genome and a core region having identity to the chromosome sequences flanking the intended gene edit site.

The present specification provides for, and includes, but is not limited to, target sequences that can be 100% identical to the target sequences selected from the group consisting of SEQ ID NOs: 22 to 271 and 347 to 425. These target sequences can comprise a PAM sequence such as those listed on Table 1. Accordingly, when incorporated into a guide RNA, in an aspect the spacer region can share 100% identity to a sequence selected from the group of the first 20 nucleotides of each of SEQ ID NOs: 22 to 271 and the first 20 nucleotides of each of SEQ ID NOs: 347 to 425. Also included are spacer sequences that can have from 15 to 20 nucleotides of each of SEQ ID NOs: 22 to 271 or from 15 to 20 nucleotides of each of SEQ ID NOs: 347 to 425. (The remainder of the sequence can comprise the PAM sequence which can be present in the genome, but not the gRNA molecules.) Also included and provided for are guide RNA spacer sequences that can have one or more mismatches to the target sequence. In an aspect, the mismatch can be at the distal end of the sequence target sequence to ensure that identity at the endonuclease cleavage site is maintained. Typically, the mismatches can occur at the 5' end of the target sequence relative to the nuclease site at the 3' end. In an aspect, a target sequence, or the spacer sequences of a guide RNA prepared therefrom, may have a single mismatch. In another aspect, a target sequence, or the spacer sequences of a guide RNA prepared therefrom, may have two (2) mismatches. In another aspect, a sequence, or the spacer sequences of a guide RNA prepared therefrom, may have three (3) mismatches. In another aspect, a sequence, or the spacer sequences of a guide RNA prepared therefrom, that may have less than four (4) mismatches are included. In some aspects, the mismatch regions can be limited to terminal nucleotides distal to the PAM sequences and cleavage site.

In an aspect, the target sequences and the spacer sequence of the gRNA guide can have at least 90% identity to a sequence selected from the group consisting of the first 20 nucleotides of each of SEQ ID NOs: 22 to 271 and the first 20 nucleotides of each of SEQ ID NOs: 347 to 425. In a further aspect, the RNA guide can have at least 90% identity and 100% identity at 15 nucleotides at the 3' end of the sequence. In an aspect, the target sequences and the RNA guide can have at least 95% identity. In a further aspect, the RNA guide can have at least 95% identity or 100% identity at 15 nucleotides at the 3' end of the sequence. In an aspect, the target sequences and the RNA guide can have at least 96% identity. In a further aspect, the RNA guide can have at least 96% identity or 100% identity at 15 nucleotides at the 3' end of the sequence. In an aspect, the target sequences and the RNA guide can have at least 97% identity. In a further aspect, the RNA guide can have at least 97% identity or 100% identity at 15 nucleotides at the 3' end of the sequence. In an aspect, the target sequences and the RNA guide can have at least 98% identity. In a further aspect, the RNA guide can have at least 98% identity or 100% identity at 15 nucleotides at the 3' end of the sequence. In an aspect, the target sequences and the RNA guide can have at least 99% identity. In a further aspect, the RNA guide can have at least 99% identity or 100% identity at 15 nucleotides at the 3' end of the sequence. In an aspect, the target sequences and the RNA guide can have at least 100% identity. Also included and provided for by the present specification are spacer sequences that can comprise the first 15 nucleotides each of SEQ ID NOs: 22 to 271 or the first 15 nucleotides each of SEQ ID NOs: 347 to 425. In an aspect, the spacer sequences can comprise the first 16 nucleotides in each of SEQ ID NOs: 22 to 271 or the first 16 nucleotides in each of SEQ ID NOs: 347 to 425. In another aspect, the spacer sequences can comprise the first 17 nucleotides in each of SEQ ID NOs: 22 to 271 or the first 17 nucleotides in each of SEQ ID NOs: 347 to 425. In an aspect, the spacer sequences can comprise the first 18 nucleotides in each of SEQ ID NOs: 22 to 271 or the first 18 nucleotides in each of SEQ ID NOs: 347 to 425. In yet another aspect, the spacer sequences can comprise the first 19 nucleotides in each of SEQ ID NOs: 22 to 271 or the first 19 nucleotides in each of SEQ ID NOs: 347 to 425.

The preferred meaning of "fertilization" as used herein to refer to pig breeding encompasses any technique that produces a viable embryo. Fertilization can include both insemination of female pigs, and in vitro or ex vivo fertilization. There are three commonly available ways to inseminate a sow, namely traditional artificial insemination (AI), intrauterine insemination (IUI), and deep intrauterine insemination (DIUI). These techniques all rely on providing a dose of semen, typically fresh and unfrozen, for insemination. In vitro fertilization (IVF) can be the harvesting of unfertilized oocytes(s) and the subsequent fertilization of those oocytes with semen in vitro (i.e., in the laboratory) instead of in vivo (i.e., in the live animal; insemination discussed above) as in standard ET. The fertilized oocytes(s) or embryo(s) from the oocyte donor can then be transferred into another female (embryo recipient). Embryo transfer (ET) can be the harvesting of fertilized oocytes(s) or embryo(s) from one female (embryo donor) and transfer of those embryo(s) into another female (embryo recipient) whose reproductive status can be synchronized with that of the donor.

As described in Cameron et. al. (*Nat Methods,* 2017, 14, 600-606), the CRISPR-Cas9 system can be used for genome editing in both basic research and biotechnology. The application of CRISPR and related technologies to gene or genome editing can be accompanied by unwanted off-target cleavage activity and possible pathogenic and other negative phenotypic consequences. To minimize off-target cleavage, a variety of genome-wide experimental methods have been recently developed but some methods are potentially biased due to cellular context or inefficiencies in recovering relevant cleavage sites. On approach, the SITE-SEQ® assay (Caribou Biosciences, Inc., Berkeley CA) disclosed in Cameron et. al. enables one to comprehensively list Cas9 cleavage sites in a sample genome, then probe those sites for cellular off-target editing in follow-up experiments through (1) extraction and purification of high-molecular weight genomic DNA, (2) execution of Cas9 Ribonucleoprotein (RNP) cleavage in vitro, (3) fragmentation, adapter ligation, and affinity purification to enrich for Cas9 cleaved fragments, and (4) amplification and indexing of SITE-SEQ® libraries for ILLUMINA® (ILLUMINA®, San Diego, CA) sequencing. (See Cameron et al., *Nat Methods,* 2017, 14, 600-606.) Various other methods of discovering and reducing the number of potential off-target edits are known in the genome editing arts. While such bioinformatics tools can be invaluable for identifying suitable target sequences, the error rate is generally higher than desired and the approach can be limited when the system lacks extensive sequence data. Further, the fidelity of DSB break repair can vary, thus confounding the ability to predict and prevent unwanted off target effects. Further testing of in silico selected target sequences can identify select sequences that have higher efficiencies and fewer off target cuts. Testing in cell culture systems combined with high-throughput sequencing methods can be used to identify poor performing target constructs.

For example, the type II CRISPR system, which is derived from *Streptococcus pyogenes* (*S. pyogenes*), can be reconstituted in mammalian cells using Cas9, a specificity-determining CRISPR RNA (crRNA) comprising a backbone sequence and a sequence selected from the group consisting of the first twenty nucleotides of each of SEQ ID NOs: 22 to 271 and the first twenty nucleotides of each of SEQ ID NOs: 347 to 425, and an auxiliary trans-activating RNA (tracrRNA). The term "off target effect" broadly refers to any impact distinct from and not intended as a result of the on-target treatment or procedure. Examples of off-target edits can include double strand breaks at unintended locations that lead to DNA insertions of unintended nucleotides or repair templates, deletions, or rearrangements. For some systems, for example the *S. pyogenes* and *S. thermophilus* CRISPR system, the crRNA and tracrRNA duplexes can be fused to generate a single-guide RNA (sgRNA). The first 20 nucleotides of the sgRNA can be complementary to the target DNA sequence and can be the spacer region, and those 20 nucleotides can be followed at the 3' end by a protospacer adjacent motif (PAM) in the genome (but not the guide). In an aspect, the first 20 nucleotides of the sgRNA and PAM sequence can be a sequence selected from the group consisting of SEQ ID NOs: 22 to 271 and 347 to 425. Accordingly, as provided below at Table 2 and SEQ ID NOs: 22 to 271 and 347 to 425, specific targeting of the Cas nuclease from either *S. pyogenes* or *S. thermophilus* can be accomplished combining the crRNAs with a backbone sequence. Although the 20-nucleotide guide sequence plus PAM sequence (e.g., 23 to 25 nucleotides) of the sgRNA can provide tightly controlled targeting and cleavage, it has been discovered that off-target cleavage activity can still occur on DNA sequences with between 3-5 base pair mismatches in the PAM-distal part of the sgRNA-guiding sequence. Further, different types of guide RNA structures actually affect the cleavage precision, increasing or decreasing cleave on off-target sites. Various techniques, as well as a further description of off-target cleavage, are reviewed in Zhang et al., *Mol Ther Nucleic Acids*, 2015, 4, e264. The mechanisms and effects of off-target cleavage are still poorly understood, meaning it can be difficult to predict and to compensate for its effects. However, the consequences can be severe; off-target cleavage can ultimately lead to genomic instability and disrupt the functionality of otherwise normal genes.

The present specification provides for, and includes, pigs that can have inactivating edits in both alleles of the CD163 gene and that can be resistant to infection with PRRSv. The CD163 pigs disclosed herein further do not comprise new sequences or polypeptides, nor do they comprise non-native amino acids resulting from frameshifts or missense mutations.

The gene edits disclosed herein allow for the protection of CD163-positive fetuses (e.g., fetuses that have one or two wild-type CD163 alleles). CD163-positive fetuses can be protected from PRRSv infection while in utero so long as the dam possesses inactivating edits in both alleles of her CD163 genes (PCT/US2018/027944). For example, dams having inactivating edits in both alleles of the CD163 gene can be mated with males having two wild-type CD163 alleles, and the resulting heterozygous fetuses will be protected from PRRSv infection in utero.

In an aspect, pigs having inactivating edits in one allele of CD163 can be generated using the methods of the present specification. These pigs having heterozygous CD163 alleles (one edited, one wild-type) can be bred with other pigs also having heterozygous CD163 alleles or homozygous edited CD163 alleles, and offspring from this breeding having homozygous edited CD163 alleles can be selected for resistance to infection with PRRSv. The present disclosure also provides for, and includes, porcine animals and populations, and methods for creating or improving porcine animals and populations, in which the animals can be homozygous for one or more particular genetic markers or alleles. In various aspects, the present disclosure provides for, and includes, animals, and methods for creating or improving crossing porcine animals and populations, by generating animals that can be heterozygous for one or more particular genetic markers or alleles, and crossing said animals with other animals heterozygous for one or more of the particular genetic markers or alleles to produce animals that can be homozygous for the one or more particular genetic markers or alleles. In some aspects, multiple rounds of crossing and/or back-crossing may be required to obtain homozygosity for each of the particular genetic markers and alleles. In other aspects, a single cross may be sufficient to obtain homozygosity.

Various techniques known in the art can be used to inactivate genes to make knock-out animals and/or to introduce edited genes into animals to produce founder animals and to make animal lines, in which the knockout or nucleic acid construct can be integrated into the genome. Such techniques can include, without limitation, pronuclear microinjection (U.S. Pat. No. 4,873,191), retrovirus mediated gene transfer into germ lines (Van der Putten et al., *Proc. Natl. Acad. Sci. USA*, 1985, 82, 6148-1652), gene targeting into embryonic stem cells (Thompson et al., *Cell*, 1989, 56, 313-321), electroporation of embryos (Lo, *Mol. Cell. Biol.*, 1983, 3, 1803-1814), sperm-mediated gene transfer (Lavitrano et al., *Proc. Natl. Acad. Sci. USA*, 2002, 99, 14230-14235; Lavitrano et al., *Reprod. Fert. Develop.*, 2006, 18, 19-23), and in vitro transformation of somatic cells, such as cumulus or mammary cells, or adult, fetal, or embryonic stem cells, followed by nuclear transplantation (Wilmut et al., *Nature*, 1997, 385, 810-813 and Wakayama et al., *Nature*, 1998, 394, 369-374). Pronuclear microinjection, sperm mediated gene transfer, and somatic cell nuclear transfer can be other useful techniques. An animal can be genomically edited in that all of its cells have the edit, including its germ line cells. When methods are used that produce an animal that is mosaic in its modification, the animals may be mosaic and can be further inbred and progeny that are genomically edited can be produced and selected using standard methods. Cloning, for instance, may be used to make a mosaic animal if its cells are edited at the blastocyst stage, or genomic modification can take place when a single-cell is edited. In an aspect, an inactivated knock-out edit can be homozygous.

In an embryo/zygote microinjection aspect, a nucleic acid construct, mRNA, protein, polynucleotides, or combinations thereof, can be introduced into a fertilized egg. In an aspect, one or two cell fertilized eggs can be used. One and two cell fertilized eggs can provide a visible nuclear structure containing the genetic material from the sperm head and the egg within the protoplasm. In an aspect, pronuclear staged fertilized eggs can be obtained in vitro or in vivo (i.e., surgically recovered from the oviduct of donor animals). In another aspect, in vitro fertilized eggs can be produced, for example, from collected swine ovaries by follicles aspirated using methods known in the art. See, e.g., Agung et al., *J Reprod Dev.*, 2013, 59, 103-106 and Appeltant et al., *J Reprod Dev.*, 2016, 62, 439-449. In an aspect, mature oocytes can be provided for use in the in vitro fertilization methods. In another aspect, mature oocytes can be injected with the CRISPR/Cas gene editing system of the present specification.

The present specification further provides for in vitro fertilization of mature oocytes. In an aspect, the oocytes can be matured in vitro as provided above. In another aspect, mature oocytes can be collected from gilts. In vitro fertilization is performed according to established methods. See Appeltant et al., *J Reprod Dev.*, 2011, 57, 9-16, and Fowler et al., *Reprod Biol.*, 2018, 18, 203-211.

Zygotes or embryos can be obtained for germline editing by artificial insemination and flushing. The collected zygotes or embryos can then be edited using the methods provided herein. In an aspect, linearized nucleic acid constructs, mRNA, proteins, polynucleotides or combinations thereof can be injected or otherwise introduced, for example, by electroporation, into one of the pronuclei or into the cytoplasm of a zygote or embryo post-fertilization, or into a gamete cell pre-fertilization. In an aspect, a pre-formed RNP complex comprising the Cas nuclease protein and a guide RNA comprising a backbone of SEQ ID NO: 19 and a targeting sequence selected from any one of SEQ ID NOs: 22 to 271 and 347 to 425 can be prepared and injected into the embryo, zygote, or oocyte. In another aspect, a pre-formed RNP complex comprising the Cas nuclease and a guide RNA comprising a backbone of SEQ ID NO: 19 and a spacer sequence selected from an RNA sequence of a sequence selected from the group consisting of the first 20 nucleotides of each of SEQ ID NOs: 22 to 271 can be prepared and injected into the embryo, zygote, or oocyte, together with a repair template comprising SEQ ID NOs: 1 to 13 listed in Table 6. Also included, and provided for, by the present specification are the combinations of spacer sequences and repair templates that can have the sequences of SEQ ID NOs:1 to 13 as recited in Table 6. In an aspect, the injected zygotes or embryos can be transferred to a recipient female (e.g., into the oviducts of a recipient female) and allowed to develop in the recipient female to produce the transgenic or gene edited animals. In an aspect, the methods further provide for in vitro or in vivo fertilized zygotes or embryos that can be centrifuged at 15,000×g for 5 minutes to sediment lipids allowing visualization of the pronucleus. The zygotes or embryos can be injected with using an EPPENDORF® FEMTOJET® (EPPENDORF® AG, Germany) injector and can be cultured until blastocyst formation. Rates of embryo cleavage and blastocyst formation and quality can be recorded.

In an aspect, the CRISPR/Cas editing system and gRNA can be provided as a nucleic acid construct. In another aspect, the Cas nuclease may be provided as an mRNA together with a guide RNA comprising a backbone sequence and a targeting sequence selected from the group consisting of the first 20 nucleotides of each of SEQ ID NOs: 22 to 271 and the first 20 nucleotides of each of SEQ ID NOs: 347 to 425. In another aspect, the Cas nuclease may be provided as an mRNA together with a guide RNA comprising a backbone sequence and a targeting sequence selected from the group consisting of the first 20 nucleotides of each of SEQ ID NOs: 22 to 271 together with a repair template listed in Table 6 and selected from the group consisting of SEQ ID NOs: 1 to 13. In a further aspect, the gene targeting complex can be provided by microinjection of a transcribable DNA encoding a Cas nuclease and a guide RNA comprising a backbone sequence and a targeting sequence selected from the group consisting of the first 20 nucleotides of each of SEQ ID NOs: 22 to 271 and the first 20 nucleotides of each of SEQ ID NOs: 347 to 425. In aspects according the present specification, the backbone sequence can be a sequence of SEQ ID NO: 19. Also included and provided for by the present specification are the combinations of targeting sequences and repair templates that can have one of the sequences recited in SEQ ID NOs: 1 to 13. It would be understood by persons of skill in the art that various combinations of nuclease, gRNA, and optionally repair template sequences, can be introduced into oocytes, zygotes, blastula, and embryos to achieve the goals of the present methods. It will be further understood that other backbone sequences can be used in conjunction with the targeting sequences of SEQ ID NOs: 22 to 271 and SEQ ID NOs: 347 to 425 for use with other Cas nucleases. Any Cas nuclease having a PAM sequence of NGG or NGGNG can be suitable for the preparation of a backbone sequence for combination with the targeting sequences of the present specification. In various aspects, the desired edit can have a final genomic sequence of SEQ ID NOs: 426 to 505. In some configurations, the desired edit lacks exon 7 and can have a final nucleotide sequence as set forth in SEQ ID NOs: 426 to 458. In various configurations, the final genomic sequence can include an exogenous stop codon and can have a final genomic sequence as set forth in SEQ ID NOs: 459-504. In various configurations, these partial CD163 genes can have an exon 7 amino acid sequence as set forth in SEQ ID NOs: 506 to 517.

In an aspect, the injected zygotes or embryos can be transferred to a recipient female (e.g., into the oviducts of a recipient female) and allowed to develop in the recipient female to produce the transgenic or gene edited animals. In an aspect, the methods further provide for in vitro or in vivo fertilized zygotes or embryos that can be centrifuged at 15,000×g for 5 minutes to sediment lipids allowing visualization of the pronucleus. The zygotes or embryos can be injected using, for example, an EPPENDORF® FEMTOJET® injector and can be cultured until blastocyst formation. Rates of embryo cleavage and blastocyst formation and quality can be recorded.

The present specification provides for, and includes, a recipient sow having one or more embryos that can be injected with a CRISPR/Cas/gRNA combination according to the present disclosure. In an aspect, a pre-formed RNP complex can be provided comprising the Cas nuclease and a guide RNA comprising a backbone of SEQ ID NO: 19 and a spacer sequence selected from the group consisting of the first 20 nucleotides of each of SEQ ID NOs: 22 to 271 and the first 20 nucleotides of each of SEQ ID NOs: 347 to 425. In various aspects, two pre-formed RNP complexes can be provided comprising the Cas nuclease and a guide RNA comprising a backbone of SEQ ID NO: 19 and each comprising a different spacer sequence selected from the group consisting of the first 20 nucleotides of each of SEQ ID NOs: 22 to 271 and the first 20 nucleotides of each of SEQ ID NOs: 347 to 425. Also provided for, and included, are recipient sows that can have one or more embryos injected with a pre-formed RNP complex that can comprise the Cas nuclease and a guide RNA comprising a targeting sequence selected from the group consisting of the first 20 nucleotides of each of SEQ ID NOs: 22 to 271 and the first 20 nucleotides of each of SEQ ID NOs: 347-425. In an aspect, the pre-formed RNP complex can be prepared and injected into the embryo, zygote, or oocyte, together with a repair template listed in Table 6 (SEQ ID NOs: 1 to 13). In an aspect, a recipient sow can be a sow of a different line than the donor embryos.

Embryos or zygotes can be surgically transferred into uteri of synchronous recipients. Typically, 100-200 (or 150-200) embryos or zygotes can be deposited into the ampulla-isthmus junction of the oviduct using a catheter. After surgery, real-time ultrasound examination of pregnancy can be performed. In an aspect, the present specification can include a recipient sow having 1 to 100, but more typically 30 to 60 CRISPR/Cas/gRNA combination treated embryos wherein said embryos can comprise a gene edited CD163 gene comprising a sequence of SEQ ID NOs: 1 to 18 or 426 to 505. In an aspect, the transferred embryos can comprise a mosaic of edited cells. Also included are CD163 gene edited embryos that can be non-mosaic.

Methods of improving the health of a livestock animal or herd of livestock can comprise modifying a target sequence in the genome of an animal cell to form a truncated CD163 polypeptide. Also provided for, and included, are improved animals that can have truncated CD163 polypeptides. In some aspects, the predicted truncated polypeptides do not include non-native amino acids. Without being bound by theory, the truncated gene product can be rapidly digested in vivo by cellular proteases. In an aspect of the present specification, the truncated CD163 can result in the complete elimination of the protein. In a further aspect, the truncated CD163 can be non-detectable in vivo. In an aspect, the truncated CD163 can be non-detectable by immunofluorescence labelling and FACS analysis. In yet another aspect, the truncated CD163 can be non-detectable when using any of the expression analysis methods provided in the specification, including those provided in Example 5. In yet another aspect, the truncated CD163 can be non-detectable when using any of the expression analysis methods provided in the specification, including those provided in Example 8.

In another aspect, a gene edited CD163 pig can comprise a truncated CD163 gene with no more than 25 non-native amino acids. Not to be limited by theory, truncated CD163 proteins can be destabilized and targeted for degradation within the cell. Accordingly, CD163 protein sequences and CD163 polypeptides comprising non-native amino acids can be non-detectable. In another aspect, the predicted truncated CD163 protein can comprise no more than 211 amino acids of the native protein. In an aspect, the truncated CD163 protein can be predicted to comprise no more than 144 amino acids of the native protein. In an aspect, the truncated CD163 protein can be predicted to comprise no more than 133 amino acids of the native protein. In yet another aspect, the truncated CD163 protein can be predicted to comprise no more than 129 amino acids of the native protein. In an aspect, the truncated CD163 protein can be predicted to comprise no more than 113 amino acids of the native protein. In yet another aspect, the truncated CD163 protein can be predicted to comprise no more than 108 amino acids of the native protein. In a further aspect, the truncated CD163 protein can be predicted to comprise no more than 93 amino acids of the native protein. In yet another aspect, the truncated CD163 protein can be predicted to comprise no more than 74 amino acids of the native protein. As provided herein, truncated CD163 proteins can comprise between 32 to 211 amino acids of native CD163 polypeptide sequences and no more than 25 non-native amino acids and can be undetectable in cells and cell extracts.

In other aspects, altered CD163 protein can have a truncation with a single amino acid substitution. In some aspects, the altered CD163 protein can have a predicted amino acid sequence of no more than 1,010 amino acids.

The present specification provides for, and includes, gene edited CD163 pigs that can have truncations of the CD163 protein (e.g., amino acids 1 to 40 of CD163 reference sequence NP_999141). Not to be limited by theory, it is believed that truncations within the signal peptide (also known as the signal sequence) can result in a failure of the protein to translocate to the cellular membrane and the polypeptide is subsequently degraded within the cell. Accordingly, CD163 proteins having signal peptide truncations can result in CD163 null animals that are resistant to infection by PRRSv. In an aspect, the gene edited CD163 animals having proteins truncated in the signal sequence can comprise no more than 25 amino acids of non-native amino acid sequences. In an aspect, the gene edited pigs can comprise no more than the first 39 amino acids of the native CD163 protein. In an aspect, the gene edited pigs can comprise no more than the first 39 amino acids of the native CD163 protein and no more than 15 non-native amino acids. Also included, and provided for, by the present specification are gene edited pigs that can be predicted to comprise no more than the first 38 amino acids of the native CD163 protein. In an aspect, the gene edited pigs can comprise no more than the first 38 amino acids of the native CD163 protein and no more than 15 non-native amino acids. Also included, and provided for, by the present specification are gene edited pigs that can be predicted to comprise no more than the first 36 amino acids of the native CD163 protein. In an aspect, the gene edited pigs can comprise no more than the first 36 amino acids of the native CD163 protein and no more than 15 non-native amino acids. Truncated proteins can be non-detectable using methods known to those of skill in the art.

In an aspect, the gene edited pigs can be predicted to comprise no more than the first 34 amino acids of the native CD163 protein and no more than 15 non-native amino acids. In an aspect, the gene edited pigs can be predicted to comprise no more than the first 32 amino acids of the native CD163 protein and no more than 15 non-native amino acids. Truncated proteins can be non-detectable using methods known to those of skill in the art.

Further, the present disclosure provides for and includes truncations of the CD163 protein that can include deletion of exon 7 (SEQ ID NOs: 426-458), sequences where an exogenous stop codon is introduced into exon 7 (SEQ ID NO: 459-504). These truncations can include CD163 proteins comprising no more than 1,010 amino acids.

Breeding techniques can be used to create animals that are homozygous for the inactivated gene from the initial homozygous or heterozygous founder or other heterozygous animals. Homozygous animals can be generated. Gene edited pigs described herein can be bred with other edited or wild-type pigs of interest to ultimately generate pigs that are homozygous or heterozygous for the edited gene. In an aspect, the homozygous animal can be an animal of any one of the lines generated by crosses with PIC™ elite porcine lines 2, 3, 15, 19, 27, 62, 65, and combinations thereof. In an aspect, the homozygous animal can be a hybrid animal prepared by a cross between animals of Line 2 and Line 3.

Gene editing has been used to address various diseases, including PRRS, in swine. While there have been several gene editing technologies developed over the past 15 years, generally these platforms can be designed to introduce a double-stranded break at a specific region of a genome. The introduced break can then be repaired by the cell's own machinery.

One repair pathway, non-homologous end-joining (NHEJ), is evolutionarily conserved throughout all kingdoms of life and is the predominant double-strand break repair pathway in mammalian cells. This repair process can result in the random insertion or deletion of nucleotides across the cut site. As a practical matter, this incomplete fidelity can be used to advantage by providing in trans a DNA repair template. In an aspect, a DNA repair template carrying an alternative allele of the targeted site (for example, a single base polymorphism or a single or multiple base insertion or deletion) can be co-delivered with the gene editing reagents, and through the use of the cell's homologous recombination machinery, the DNA repair template can direct the repair to generate a new allele. In aspects according to the present specification, DNA repair templates can be designed and selected based on the location of high efficiency of CRISPR/CAS cleavage (e.g., high editing frequency from Table 3) and the ability to introduce deletions that can result in truncated proteins that comprise only wild type sequences. Repair templates can increase the efficiency and accuracy of gene editing. DNA repair templates suitable for the methods of the present application can include SEQ ID NOs: 1 to 13. In an aspect, the DNA repair templates can be paired with a guide sequence as described below in Table 6. Unlike transgenesis, genome editing according to the present specification does not result in the introduction of foreign DNA sequences into the genome.

However, as these exogenously added DNA repair templates have the possibility to randomly integrate in the genome, it is also advantageous to identify and use guide pairs that result in the deletion of DNA sequences such that the joined ends can result in the generation of an in-frame translational stop codon across the joined ends; when the cut sites of two guides are repaired by NHEJ in an end-to-end manner, this new DNA sequence, when transcribed into mRNA and translated into protein could terminate the production of the CD163 protein. Although function of this terminated CD163 protein can be lost, often, but not always, premature termination of protein synthesis can result in an unstable polypeptide that can be degraded and not detectable by standard methods. Guide pairs that cut exon 7 of the CD163 gene such that the joined ends form an exogenous stop codon can include SEQ ID NOs: 351 and 365, SEQ ID NOs: 351 and 387, SEQ NOs: 348 and 390, SEQ ID NOs: 348 and 388, SEQ ID NOs: 348 and 395, SEQ ID NOs: 352 and 365, SEQ ID NOs: 352 and 387, SEQ ID NOs: 352 and 399, SEQ ID NOs: 353 and 365, SEQ ID NOs: 353 and 387, SEQ ID NOs: 353 and 399, SEQ ID NOs: 354 and 390, SEQ ID NOs: 354 and 388, SEQ ID NOs: 354 and 395, SEQ ID NOs: 358 and 361, SEQ ID NOs: 358 and 362, SEQ ID NOs: 358 and 368, SEQ ID NOs: 358 and 384, SEQ ID NOs: 358 and 394, SEQ ID NOs: 358 and 399, SEQ ID NOs: 359 and 390, SEQ ID NOs: 359 and 388, SEQ ID NOs: 359 and 395, SEQ ID NOs: 360 and 368, SEQ ID NOs: 360 and 384, SEQ ID NOs: 360 and 389, SEQ ID NOs: 360 and 394, SEQ ID NOs: 360 and 397, SEQ ID NOs: 361 and 365, SEQ ID NOs: 361 and 387, SEQ ID NOs: 362 and 390, SEQ ID NOs: 362 and 388, SEQ ID NOs: 362 and 395, SEQ ID NOs: 364 and 365, SEQ ID NOs: 364 and 387, SEQ ID NOs: 364 and 399, SEQ ID NOs: 365 and 368, SEQ ID NOs: 365 and 384, SEQ ID NOs: 365 and 389, SEQ ID NOs: 365 and 394, SEQ ID NOs: 365 and 397, SEQ ID NOs: 366 and 368, SEQ ID NOs: 366 and 384, SEQ ID NOs: 366 and 389, SEQ ID NOs: 366 and 394, and SEQ ID NOs: 366 and 397.

In one aspect, the present teachings can involve a simple, precise and reproducible single CD163 loss of function edit in elite pigs such that the edit occurs early in the CD163 gene. A single guide RNA-Cas protein combination and DNA repair template can be selected for directing a specific gene edit in elite pigs, based on several considerations and approaches: efficient cutting near the 5' end of the CD163 gene in tissue culture, bioinformatic review identifying guides with few mismatches in the pig genome, high specificity of on-target cutting as determined by biochemical prescreen, and the ability to target specific gene edits at an intended site in pig embryo-like cells. Examples of specific gene edits of CD163 are discussed in detail below. In an aspect, a specific gene edit according to the present specification can include a CD163 gene comprising a sequence selected from the group consisting of SEQ ID NOs: 1 to 18 and 426 to 505. In an aspect, cells comprising an edited CD163 gene can comprise at least one allele having a sequence selected from the group consisting of SEQ ID NOs:1 to 18 and 426 to 505. In an aspect, cells comprising two gene edited alleles of the CD163 gene can comprise, at both alleles, a sequence selected from the group consisting of SEQ ID NOs: 1 to 18 and 426 to 505. In an aspect, both gene edited CD163 genes can comprise the same sequence selected from the group consisting of SEQ ID NOs: 1 to 18 and 426-505 (e.g., two alleles of SEQ ID NO: 1 or two alleles of SEQ ID NO: 2, etc.). In an aspect, the genome of a cell can comprise gene edited CD163 genes comprising one each of a sequence selected from the group consisting of SEQ ID NOs:1 to 18 and 426-505 (e.g., an allele of SEQ ID NO: 1 with an allele of SEQ ID NO: 2, and all combinations thereof).

Also provided for, and included, are mixtures of cells that can comprise CD163 edited cells and non-gene edited cells. In an aspect, the mixture can be an embryo. In another aspect, the mixture can be a cell culture. In a further aspect, the mixture of cells does not comprise a reproductive cell. In an aspect, the present specification can provide for, and includes, a tissue culture of CD163 edited cells and methods to prepare such cultures. Cultures according to the present specification can include mixtures of CD163 edited cells (e.g., cells having an allele of SEQ ID NO: 1 with cells having an allele of SEQ ID NO: 2, cells having an allele of SEQ ID NO: 1 with cells having an allele of SEQ ID NO: 3, and all combinations thereof). In an aspect, the tissue culture of non-reproductive cells can include cells comprising a single CD163 edit. In a further aspect, cells of a single CD163 edit in culture may comprise one or both edited alleles.

Specific examples of endonuclease and guide RNA backbone sequences that can be used in the products and methods of the present teachings are listed in Table 2.

TABLE 2

| Endonuclease and Guide Backbone Sequences | |
| --- | --- |
| Sequence Identity | SEQ ID NO: |
| Guide RNA Backbone (DNA sequence shown) | 19 |
| *Streptococcus pyogenes* endonuclease protein sequence | 20 |
| *Streptococcus thermophilus* CR3 endonuclease protein sequence | 21 |

Elite porcine nucleus lines can be sequenced and aligned against a public reference for the CD163 gene. These data can be used for the development of gene editing reagents for the PRRS-resistance project. These sequences can be scanned for the presence of conserved RNA-guided CRISPR-Cas9 recognition sites which can consist of the 3 nucleotide or 5 nucleotide motif, nGG (AGG, CGG, TGG, GGG), nGGnG (AGGTG, CGGTG, TGGTG, GGGTG, AGGGG, CGGGG, TGGGG, GGGGG, AGGAG, CGGAG, TGGAG, GGGAG, AGGCG, CGGCG, TGGCG, GGGCG), respectively. This motif, called the PAM sequence, can be located adjacent to, and 3' of, a 20 nucleotide spacer sequence which can be used for base-pairing with the RNA. Suitable sites can be identified, and crRNA guide or single guide sequences can be prepared, and are presented below in Table 3.

While not limited to any particular theory, when complexed, the guideRNA-Cas9 protein can recognize a DNA site for cleavage, which can then be repaired by cellular components by either non-homologous end joining (random repair) or by a DNA template repair pathway (homology directed repair, HDR).

Guide RNAs (gRNA) can be generated across exons 1 to exons 7 of CD163. Edits in the virus binding domain (Domain 5) of the CD163 protein can inhibit the ability of the virus to bind to the protein, thus preventing uptake of the virus into pig lung macrophages. When the edit in CD163 is homozygous in pigs, the animals can be resistant to PRRS infection. The present specification provides for, and includes, gRNA sequences including the crRNA sequences listed in Table 3 that can be selected from the group consisting of the first 20 nucleotides of each of SEQ ID NOs: 22 to 271 and 347 to 425. SEQ ID NOs: 22 to 271 and 347 to 425 are shown as DNA sequences. The corresponding RNA counterpart, and the presence of the PAM motif which is generally not included in gRNAs, would be apparent to a person of skill in the art. Also provided herein, are RNA sequences that can comprise sequences selected from the group consisting of the first 20 nucleotides of each of SEQ ID NOs: 22 to 271 and 347 to 425. SEQ ID NOs: 22 to 271 and 347 to 425 can be combined with the gRNA backbone sequence and expressed as RNA for use in the preparation of a gRNA and then mixed with the Cas nuclease to prepare an active ribonucleotide protein complex (sgRNP). The sgRNP complex can then be injected into a mature oocyte, a zygote, or early embryo, either alone or together with a repair template selected from the group consisting of SEQ ID NOs:1 to 13. After cleavage and template directed repair, the CD163 gene can be edited to incorporate the repair template sequences, and the edited genome of a CD163 gene edited cell can comprise a sequence selected from the group consisting of SEQ ID NOs: 1 to 13.

In one aspect, the present disclosure can include a simple, precise, and reproducible single CD163 loss of function edit in elite pigs such that the edit occurs early in the CD163 gene (exons 1-7). In an aspect, a pig can have a CD163 gene comprising a sequence selected from the group consisting of SEQ ID NOs: 1 to 18 and 426 to 505. Also included and provided for is a pig that can comprise SEQ ID NOs: 1 to 18 and 425 to 505 in a genomic region comprising the markers of Table 8. Also included and provided for is a pig that can comprise SEQ ID NO: 2 in a genomic region comprising the markers of Table 8. Also included and provided for is a pig that can comprise SEQ ID NO: 426-458 in a genomic region comprising the markers of Table 8. Also included and provided for is a pig that can comprise SEQ ID NO: 459-504 in a genomic region comprising the markers of Table 8. Using porcine embryonic fibroblast cell lines derived from these elite pigs, 250 guide RNA and Cas9 protein combinations can be tested to identify gene editing pairs that efficiently cut and generate edits in the CD163 gene. Selected specific guides and endonuclease protein combinations found are listed in Table 3, along with the location of the target, their endonuclease activity (average editing frequency), and the position on CD163 of the edit. Greater average editing frequency combinations are preferred because they have more effective editing activity. Combinations having an average editing frequency greater than 1 are desired. In an aspect, combinations can have an average editing frequency greater than 5. In another aspect, combinations can have an average editing frequency greater than 10. In yet another aspect, combinations can have an average editing frequency greater than 15. The present disclosure provides for, and includes, combinations that can have an average editing frequency greater than 20. In an aspect, combinations can have an average editing frequency greater than 25. In yet another aspect, combinations can have an average editing frequency greater than 30.

As shown in Table 3, the average editing frequency varied greatly between target sequences. Moreover, sequences targeting overlapping sequences resulted in different editing frequencies depending on the Cas protein source. For example, SEQ ID NOs: 24 and 25 targeted overlapping locations and had a 10-fold difference in editing frequency. At this site, with these sequences, *S. pyogenes* provided a nearly a 20-fold higher editing frequency. In contrast, RNPs incorporating SEQ ID NOs: 33 and 34 resulted in indistinguishable average editing frequencies between the Cas proteins. While RNPs incorporating a Cas9 nuclease from *S. pyogenes* can provide superior average editing frequencies, that is not always the case. As shown for SEQ ID NOs: 60 and 61, RNPs incorporating the Cas9 protein from *S. thermophilus* resulted in superior editing frequencies (e.g., 3.9 vs. 22.0). Accordingly, the present specification provides for efficient guide RNA sequences or efficient targeting sequences for targeting CD163 using the CRISPR/Cas system. In an aspect, RNPs can comprise a sequence selected from the group consisting of the first 20 nucleotides of each of SEQ ID NOs: 22 to 271 and 347 to 425.

All position designations herein refer to the Sscrofa11.1 reference genome (GenBank accession: GCA_000003025.6).

Target site sequences SEQ ID NOs: 22 to 271 and 347 to 425 can be editing target sequences within the porcine CD163 gene. In each target site sequence, the first 20 nucleotides can correspond to the guide RNA spacer, and the remaining 3 or 5 nucleotides can be the PAM sequences for *S. pyogenes* or *S. thermophilus*, respectively. The first 20 bases of SEQ ID NOs: 22 to 271 and 347 to 425 correspond to the DNA equivalent guide RNA sequences, with the appropriate ribonuclease bases substituted for deoxyribonuclease bases, although the DNA bases can be used instead of RNA bases as guides. Guide RNA sequences can be paired with *S. pyogenes* or *S. thermophilus* endonucleases to direct DNA breaks in the porcine genome in either coding or non-coding regions of the CD163 gene, which can result in DNA deletions and/or DNA nucleotide insertions. Depending on the locations of the target sites as disclosed in Table 3, pairs of guide/endonuclease combinations can be selected to delete regions of the CD163 gene between the pairs of guide/endonuclease combinations.

Target site sequences SEQ ID NOs: 212 to 271 and 347 to 425 are targeting sequences that can be used to design guides for deletion of exon 7 of the CD163 gene. Pairing of intron 6 targeting guides SEQ ID NOs: 212 to 253, and 262 to 271 with intron 7 targeting guides SEQ ID NOs: 254 to 261 using *S. pyogenes* can cause two double strand breaks on the CD163 gene, resulting in excision of exon 7. Pairing of targeting guides SEQ ID NOs: 249 and 256 also can result in excision of Exon 7. Pairing of some guides can result in the introduction of a stop codon in Exon 7, including SEQ ID NOs: 351 and 365, SEQ ID NOs: 351 and 387, SEQ NOs.: 348 and 390, SEQ ID NOs: 348 and 388, SEQ ID NOs: 348 and 498, SEQ ID NOs: 352 and 365, SEQ ID NOs:

352 and 387, SEQ ID NOs: 352 and 399, SEQ ID NOs: 353 and 365, SEQ ID NOs: 353 and 387, SEQ ID NOs: 353 and 399, SEQ ID NOs: 354 and 390, SEQ ID NOs: 354 and 388, SEQ ID NOs: 354 and 395, SEQ ID NOs: 358 and 361, SEQ ID NOs: 358 and 362, SEQ ID NOs: 358 and 368, SEQ ID NOs: 358 and 384, SEQ ID NOs: 358 and 394, SEQ ID NOs: 358 and 399, SEQ ID NOs: 359 and 390, SEQ ID NOs: 359 and 388, SEQ ID NOs: 359 and 395, SEQ ID NOs: 360 and 368, SEQ ID NOs: 360 and 384, SEQ ID NOs: 360 and 389, SEQ ID NOs: 360 and 394, SEQ ID NOs: 360 and 397, SEQ ID NOs: 361 and 365, SEQ ID NOs: 361 and 387, SEQ ID NOs: 362 and 390, SEQ ID NOs: 362 and 388, SEQ ID NOs: 362 and 395, SEQ ID NOs. 364 and 365, SEQ ID NOs: 364 and 387, SEQ ID NOs: 364 and 399, SEQ ID NOs: 365 and 368, SEQ ID NOs: 365 and 384, SEQ ID NOs: 365 and 389, SEQ ID NOs: 365 and 394, SEQ ID NOs: 365 and 397, SEQ ID NOs: 366 and 368, SEQ ID NOs: 366 and 384, SEQ ID NOs: 366 and 389, SEQ ID NOs: 366 and 394, or SEQ ID NOs: 366 and 397.

For each targeting sequence, Table 3 lists its SEQ ID No., the species of CAS9 nuclease homing arm used, the location of the targeting sequence on the *Sus scrofa* genome including the PAM sequence, the editing efficiency as measured by the average fraction of edits for a particular guide in fetal fibroblast cell assays, and the exon on CD163 targeted.

TABLE 3

List of target sequences and editing activities in porcine fetal fibroblasts

| SEQ ID NO: | Cas9 Nuclease | Location of target | Average edited fraction | Position on CD163 |
|---|---|---|---|---|
| 22 | S. pyogenes | chr5: 63300192-63300214 | 12.9 | Exon 1/15 |
| 23 | S. pyogenes | chr5: 63300222-63300244 | 1.4 | Exon 1/15 |
| 24 | S. pyogenes | chr5: 63300236-63300258 | 5.8 | Exon 1/15 |
| 25 | S. thermophilus | chr5: 63300236-63300260 | 0.3 | Exon 1/15 |
| 26 | S. pyogenes | chr5: 63300250-63300272 | 8.6 | Exon 1/15 |
| 27 | S. pyogenes | chr5: 63300251-63300273 | 0.1 | Exon 1/15 |
| 28 | S. pyogenes | chr5: 63300275-63300297 | 25.7 | Exon 1/15 |
| 29 | S. pyogenes | chr5: 63300288-63300310 | 24.9 | Exon 1/15 |
| 30 | S. pyogenes | chr5: 63300293-63300315 | 12.8 | Exon 1/15 |
| 31 | S. pyogenes | chr5: 63300305-63300327 | 0.4 | Exon 1/15 |
| 32 | S. pyogenes | chr5: 63300308-63300330 | 3.4 | Exon 1/15 |
| 33 | S. thermophilus | chr5: 63300308-63300332 | 3.7 | Exon 1/15 |
| 34 | S. pyogenes | chr5: 63300327-63300349 | 5.3 | Exon 1/15 |
| 35 | S. pyogenes | chr5: 63300336-63300358 | 3.5 | Exon 1/15 |
| 36 | S. pyogenes | chr5: 63301950-63301972 | 14.4 | Exon 2/15 |
| 37 | S. pyogenes | chr5: 63301951-63301973 | 16.3 | Exon 2/15 |
| 38 | S. pyogenes | chr5: 63301962-63301984 | 13.6 | Exon 2/15 |
| 39 | S. pyogenes | chr5: 63301981-63302003 | 3.6 | Exon 2/15 |
| 40 | S. pyogenes | chr5: 63301995-63302017 | 21.8 | Exon 2/15 |
| 41 | S. pyogenes | chr5: 63301997-63302019 | 8.2 | Exon 2/15 |
| 42 | S. thermophilus | chr5: 63301997-63302021 | 10.1 | Exon 2/15 |
| 43 | S. pyogenes | chr5: 63303121-63303143 | 16.4 | Exon 3/15 |
| 44 | S. thermophilus | chr5: 63303121-63303145 | 16.1 | Exon 3/15 |
| 45 | S. pyogenes | chr5: 63303129-63303151 | 31.4 | Exon 3/15 |
| 46 | S. pyogenes | chr5: 63303136-63303158 | 22.8 | Exon 3/15 |
| 47 | S. pyogenes | chr5: 63303137-63303159 | 42.9 | Exon 3/15 |
| 48 | S. thermophilus | chr5: 63303137-63303161 | 10.7 | Exon 3/15 |
| 49 | S. pyogenes | chr5: 63303140-63303162 | 36.7 | Exon 3/15 |
| 50 | S. thermophilus | chr5: 63303140-63303164 | 32.6 | Exon 3/15 |
| 51 | S. pyogenes | chr5: 63303158-63303180 | 21.1 | Exon 3/15 |
| 52 | S. pyogenes | chr5: 63303166-63303188 | 23.6 | Exon 3/15 |
| 53 | S. thermophilus | chr5: 63303166-63303190 | 22.1 | Exon 3/15 |
| 54 | S. pyogenes | chr5: 63303169-63303191 | 40.0 | Exon 3/15 |
| 55 | S. thermophilus | chr5: 63303169-63303193 | 19.5 | Exon 3/15 |
| 56 | S. pyogenes | chr5: 63303181-63303203 | 9.9 | Exon 3/15 |
| 57 | S. thermophilus | chr5: 63303181-63303205 | 10.4 | Exon 3/15 |
| 58 | S. pyogenes | chr5: 63303184-63303206 | 20.6 | Exon 3/15 |
| 59 | S. thermophilus | chr5: 63303184-63303208 | 2.8 | Exon 3/15 |
| 60 | S. pyogenes | chr5: 63303189-63303211 | 3.9 | Exon 3/15 |
| 61 | S. thermophilus | chr5: 63303189-63303213 | 22.0 | Exon 3/15 |
| 62 | S. pyogenes | chr5: 63303190-63303212 | 18.1 | Exon 3/15 |
| 63 | S. pyogenes | chr5: 63303191-63303213 | 23.5 | Exon 3/15 |
| 64 | S. pyogenes | chr5: 63303209-63303231 | 23.6 | Exon 3/15 |
| 65 | S. pyogenes | chr5: 63303213-63303235 | 4.1 | Exon 3/15 |
| 66 | S. pyogenes | chr5: 63303214-63303236 | 16.2 | Exon 3/15 |
| 67 | S. pyogenes | chr5: 63303220-63303242 | 14.6 | Exon 3/15 |
| 68 | S. pyogenes | chr5: 63303226-63303248 | 15.4 | Exon 3/15 |
| 69 | S. pyogenes | chr5: 63303243-63303265 | 21.6 | Exon 3/15 |
| 70 | S. pyogenes | chr5: 63303250-63303272 | 1.5 | Exon 3/15 |
| 71 | S. pyogenes | chr5: 63303251-63303273 | 30.3 | Exon 3/15 |
| 72 | S. pyogenes | chr5: 63303278-63303300 | 20.1 | Exon 3/15 |
| 73 | S. pyogenes | chr5: 63303278-63303300 | 1.5 | Exon 3/15 |
| 74 | S. pyogenes | chr5: 63303282-63303304 | 23.9 | Exon 3/15 |
| 75 | S. pyogenes | chr5: 63303283-63303305 | 20.8 | Exon 3/15 |
| 76 | S. pyogenes | chr5: 63303294-63303316 | 33.8 | Exon 3/15 |
| 77 | S. pyogenes | chr5: 63303299-63303321 | 8.2 | Exon 3/15 |
| 78 | S. pyogenes | chr5: 63303305-63303327 | 6.1 | Exon 3/15 |
| 79 | S. pyogenes | chr5: 63303315-63303337 | 25.2 | Exon 3/15 |
| 80 | S. pyogenes | chr5: 63303319-63303341 | 28.7 | Exon 3/15 |
| 81 | S. pyogenes | chr5: 63303338-63303360 | 4.5 | Exon 3/15 |
| 82 | S. pyogenes | chr5: 63303339-63303361 | 2.8 | Exon 3/15 |
| 83 | S. pyogenes | chr5: 63303357-63303379 | 18.3 | Exon 3/15 |
| 84 | S. pyogenes | chr5: 63303358-63303380 | 26.6 | Exon 3/15 |
| 85 | S. pyogenes | chr5: 63303374-63303396 | 16.1 | Exon 3/15 |
| 86 | S. pyogenes | chr5: 63303378-63303400 | 35.4 | Exon 3/15 |
| 87 | S. thermophilus | chr5: 63303378-63303402 | 40.0 | Exon 3/15 |
| 88 | S. pyogenes | chr5: 63303379-63303401 | 24.4 | Exon 3/15 |
| 89 | S. pyogenes | chr5: 63303380-63303402 | 25.6 | Exon 3/15 |
| 90 | S. pyogenes | chr5: 63303406-63303428 | 28.1 | Exon 3/15 |
| 91 | S. pyogenes | chr5: 63303413-63303435 | 13.7 | Exon 3/15 |
| 92 | S. thermophilus | chr5: 63303413-63303437 | 19.0 | Exon 3/15 |
| 93 | S. thermophilus | chr5: 63303419-63303443 | 15.2 | Exon 3/15 |
| 94 | S. pyogenes | chr5: 63303421-63303443 | 16.5 | Exon 3/15 |
| 95 | S. pyogenes | chr5: 63303428-63303450 | 35.8 | Exon 3/15 |
| 96 | S. pyogenes | chr5: 63303441-63303463 | 3.4 | Exon 3/15 |
| 97 | S. pyogenes | chr5: 63306087-63306109 | 19.8 | Exon 4/15 |
| 98 | S. pyogenes | chr5: 63306091-63306113 | 4.5 | Exon 4/15 |
| 99 | S. thermophilus | chr5: 63306091-63306115 | 3.1 | Exon 4/15 |
| 100 | S. pyogenes | chr5: 63306098-63306120 | 29.9 | Exon 4/15 |
| 101 | S. thermophilus | chr5: 63306098-63306122 | 31.5 | Exon 4/15 |
| 102 | S. pyogenes | chr5: 63306101-63306123 | 29.2 | Exon 4/15 |
| 103 | S. pyogenes | chr5: 63306108-63306130 | 6.9 | Exon 4/15 |
| 104 | S. thermophilus | chr5: 63306108-63306132 | 14.7 | Exon 4/15 |
| 105 | S. pyogenes | chr5: 63306116-63306138 | 21.6 | Exon 4/15 |
| 106 | S. pyogenes | chr5: 63306127-63306149 | 26.4 | Exon 4/15 |
| 107 | S. pyogenes | chr5: 63306140-63306162 | 6.9 | Exon 4/15 |
| 108 | S. pyogenes | chr5: 63306144-63306166 | 35.2 | Exon 4/15 |
| 109 | S. thermophilus | chr5: 63306144-63306168 | 3.3 | Exon 4/15 |
| 110 | S. pyogenes | chr5: 63306147-63306169 | 8.8 | Exon 4/15 |
| 111 | S. thermophilus | chr5: 63306147-63306171 | 3.2 | Exon 4/15 |
| 112 | S. pyogenes | chr5: 63306148-63306170 | 5.2 | Exon 4/15 |
| 113 | S. pyogenes | chr5: 63306149-63306171 | 28.0 | Exon 4/15 |
| 114 | S. pyogenes | chr5: 63306193-63306215 | 9.3 | Exon 4/15 |
| 115 | S. pyogenes | chr5: 63306236-63306258 | 14.2 | Exon 4/15 |
| 116 | S. pyogenes | chr5: 63306251-63306273 | 26.3 | Exon 4/15 |
| 117 | S. thermophilus | chr5: 63306251-63306275 | 4.4 | Exon 4/15 |
| 118 | S. pyogenes | chr5: 63306257-63306279 | 1.3 | Exon 4/15 |
| 119 | S. pyogenes | chr5: 63306263-63306285 | 7.8 | Exon 4/15 |
| 120 | S. pyogenes | chr5: 63306273-63306295 | 35.0 | Exon 4/15 |
| 121 | S. pyogenes | chr5: 63306287-63306309 | 13.4 | Exon 4/15 |
| 122 | S. pyogenes | chr5: 63306296-63306318 | 2.0 | Exon 4/15 |
| 123 | S. pyogenes | chr5: 63306315-63306337 | 31.2 | Exon 4/15 |
| 124 | S. pyogenes | chr5: 63306332-63306354 | 10.1 | Exon 4/15 |
| 125 | S. pyogenes | chr5: 63306336-63306358 | 31.1 | Exon 4/15 |
| 126 | S. thermophilus | chr5: 63306336-63306360 | 52.8 | Exon 4/15 |
| 127 | S. pyogenes | chr5: 63306337-63306359 | 30.3 | Exon 4/15 |
| 128 | S. pyogenes | chr5: 63306338-63306360 | 43.2 | Exon 4/15 |
| 129 | S. pyogenes | chr5: 63306364-63306386 | 2.5 | Exon 4/15 |
| 130 | S. pyogenes | chr5: 63306371-63306393 | 0.2 | Exon 4/15 |
| 131 | S. thermophilus | chr5: 63306371-63306395 | 0.3 | Exon 4/15 |
| 132 | S. pyogenes | chr5: 63309028-63309050 | 4.5 | Exon 5/15 |
| 133 | S. pyogenes | chr5: 63309034-63309056 | 5.1 | Exon 5/15 |
| 134 | S. pyogenes | chr5: 63309035-63309057 | 41.8 | Exon 5/15 |
| 135 | S. thermophilus | chr5: 63309035-63309059 | 21.9 | Exon 5/15 |
| 136 | S. pyogenes | chr5: 63309053-63309075 | 15.1 | Exon 5/15 |

TABLE 3-continued

List of target sequences and editing activities in porcine fetal fibroblasts

| SEQ ID NO: | Cas9 Nuclease | Location of target | Average edited fraction | Position on CD163 |
|---|---|---|---|---|
| 137 | S. pyogenes | chr5: 63309061-63309083 | 0.2 | Exon 5/15 |
| 138 | S. pyogenes | chr5: 63309077-63309099 | 15.7 | Exon 5/15 |
| 139 | S. thermophilus | chr5: 63309077-63309101 | 11.2 | Exon 5/15 |
| 140 | S. pyogenes | chr5: 63309084-63309106 | 10.1 | Exon 5/15 |
| 141 | S. thermophilus | chr5: 63309084-63309108 | 23.8 | Exon 5/15 |
| 142 | S. pyogenes | chr5: 63309085-63309107 | 11.3 | Exon 5/15 |
| 143 | S. pyogenes | chr5: 63309086-63309108 | 23.4 | Exon 5/15 |
| 144 | S. pyogenes | chr5: 63309094-63309116 | 13.8 | Exon 5/15 |
| 145 | S. pyogenes | chr5: 63309104-63309126 | 7.8 | Exon 5/15 |
| 146 | S. pyogenes | chr5: 63309108-63309130 | 1.4 | Exon 5/15 |
| 147 | S. pyogenes | chr5: 63309109-63309131 | 7.0 | Exon 5/15 |
| 148 | S. pyogenes | chr5: 63309130-63309152 | 24.8 | Exon 5/15 |
| 149 | S. pyogenes | chr5: 63309144-63309166 | 20.8 | Exon 5/15 |
| 150 | S. pyogenes | chr5: 63309145-63309167 | 0.1 | Exon 5/15 |
| 151 | S. pyogenes | chr5: 63309146-63309168 | 37.4 | Exon 5/15 |
| 152 | S. pyogenes | chr5: 63309173-63309195 | 2.5 | Exon 5/15 |
| 153 | S. pyogenes | chr5: 63309173-63309195 | 2.3 | Exon 5/15 |
| 154 | S. pyogenes | chr5: 63309189-63309211 | 11.5 | Exon 5/15 |
| 155 | S. pyogenes | chr5: 63309193-63309215 | 2.7 | Exon 5/15 |
| 156 | S. pyogenes | chr5: 63309194-63309216 | 10.4 | Exon 5/15 |
| 157 | S. pyogenes | chr5: 63309200-63309222 | 3.8 | Exon 5/15 |
| 158 | S. thermophilus | chr5: 63309205-63309229 | 19.0 | Exon 5/15 |
| 159 | S. pyogenes | chr5: 63309207-63309229 | 21.0 | Exon 5/15 |
| 160 | S. pyogenes | chr5: 63309210-63309232 | 19.0 | Exon 5/15 |
| 161 | S. pyogenes | chr5: 63309233-63309255 | 8.3 | Exon 5/15 |
| 162 | S. pyogenes | chr5: 63309250-63309272 | 13.6 | Exon 5/15 |
| 163 | S. pyogenes | chr5: 63309252-63309274 | 23.0 | Exon 5/15 |
| 164 | S. pyogenes | chr5: 63309273-63309295 | 2.3 | Exon 5/15 |
| 165 | S. thermophilus | chr5: 63309273-63309297 | 34.4 | Exon 5/15 |
| 166 | S. pyogenes | chr5: 63309274-63309296 | 15.1 | Exon 5/15 |
| 167 | S. pyogenes | chr5: 63309275-63309297 | 19.4 | Exon 5/15 |
| 168 | S. thermophilus | chr5: 63309284-63309308 | 14.4 | Exon 5/15 |
| 169 | S. pyogenes | chr5: 63309286-63309308 | 7.0 | Exon 5/15 |
| 170 | S. pyogenes | chr5: 63309308-63309330 | 0.5 | Exon 5/15 |
| 171 | S. thermophilus | chr5: 63309308-63309332 | 2.4 | Exon 5/15 |
| 172 | S. pyogenes | chr5: 63309323-63309345 | 16.0 | Exon 5/15 |
| 173 | S. pyogenes | chr5: 63309841-63309863 | 0.1 | Exon 6/15 |
| 174 | S. pyogenes | chr5: 63309857-63309879 | 8.4 | Exon 6/15 |
| 175 | S. thermophilus | chr5: 63309857-63309881 | 8.0 | Exon 6/15 |
| 176 | S. pyogenes | chr5: 63309860-63309882 | 40.3 | Exon 6/15 |
| 177 | S. thermophilus | chr5: 63309860-63309884 | 32.3 | Exon 6/15 |
| 178 | S. pyogenes | chr5: 63309863-63309885 | 37.2 | Exon 6/15 |
| 179 | S. pyogenes | chr5: 63309886-63309908 | 4.7 | Exon 6/15 |
| 180 | S. thermophilus | chr5: 63309886-63309910 | 3.5 | Exon 6/15 |
| 181 | S. pyogenes | chr5: 63309889-63309911 | 38.1 | Exon 6/15 |
| 182 | S. pyogenes | chr5: 63309889-63309911 | 34.1 | Exon 6/15 |
| 183 | S. thermophilus | chr5: 63309889-63309913 | 17.5 | Exon 6/15 |
| 184 | S. pyogenes | chr5: 63309892-63309914 | 4.9 | Exon 6/15 |
| 185 | S. pyogenes | chr5: 63309907-63309929 | 13.5 | Exon 6/15 |
| 186 | S. pyogenes | chr5: 63309911-63309933 | 5.5 | Exon 6/15 |
| 187 | S. pyogenes | chr5: 63309933-63309955 | 0.7 | Exon 6/15 |
| 188 | S. thermophilus | chr5: 63309933-63309957 | 10.0 | Exon 6/15 |
| 189 | S. pyogenes | chr5: 63309934-63309956 | 6.4 | Exon 6/15 |
| 190 | S. pyogenes | chr5: 63309935-63309957 | 18.7 | Exon 6/15 |
| 191 | S. pyogenes | chr5: 63309955-63309977 | 12.0 | Exon 6/15 |
| 192 | S. pyogenes | chr5: 63309963-63309985 | 5.6 | Exon 6/15 |
| 193 | S. pyogenes | chr5: 63309970-63309992 | 0.5 | Exon 6/15 |
| 194 | S. pyogenes | chr5: 63309971-63309993 | 12.5 | Exon 6/15 |
| 195 | S. pyogenes | chr5: 63309977-63309999 | 5.3 | Exon 6/15 |
| 196 | S. pyogenes | chr5: 63310021-63310043 | 2.2 | Exon 6/15 |
| 197 | S. pyogenes | chr5: 63310035-63310057 | 10.3 | Exon 6/15 |
| 198 | S. pyogenes | chr5: 63310038-63310060 | 0.2 | Exon 6/15 |
| 199 | S. pyogenes | chr5: 63310058-63310080 | 8.2 | Exon 6/15 |
| 200 | S. pyogenes | chr5: 63310077-63310099 | 6.2 | Exon 6/15 |
| 201 | S. pyogenes | chr5: 63310078-63310100 | 8.6 | Exon 6/15 |
| 202 | S. pyogenes | chr5: 63310092-63310114 | 2.7 | Exon 6/15 |
| 203 | S. pyogenes | chr5: 63310098-63310120 | 11.1 | Exon 6/15 |
| 204 | S. thermophilus | chr5: 63310098-63310122 | 8.0 | Exon 6/15 |
| 205 | S. pyogenes | chr5: 63310099-63310121 | 12.2 | Exon 6/15 |
| 206 | S. pyogenes | chr5: 63310100-63310122 | 21.1 | Exon 6/15 |
| 207 | S. thermophilus | chr5: 63310100-63310124 | 0.1 | Exon 6/15 |
| 208 | S. pyogenes | chr5: 63310103-63310125 | 3.3 | Exon 6/15 |
| 209 | S. pyogenes | chr5: 63310152-63310174 | 4.8 | Exon 6/15 |
| 210 | S. pyogenes | chr5: 63323061-63323083 | 32.8 | Exon 7/15 |
| 211 | S. pyogenes | chr5: 63323147-63323169 | 17.0 | Exon 7/15 |
| 212 | S. pyogenes | chr5: 63322548-63322570 | 13.6 | Intron 6 |
| 213 | S. pyogenes | chr5: 63322549-63322571 | 1.7 | Intron 6 |
| 214 | S. pyogenes | chr5: 63322566-63322588 | 15.6 | Intron 6 |
| 215 | S. pyogenes | chr5: 63322594-63322616 | 0.0 | Intron 6 |
| 216 | S. pyogenes | chr5: 63322597-63322619 | 0.0 | Intron 6 |
| 217 | S. pyogenes | chr5: 63322646-63322668 | 21.1 | Intron 6 |
| 218 | S. pyogenes | chr5: 63322647-63322669 | 12.6 | Intron 6 |
| 219 | S. pyogenes | chr5: 63322681-63322703 | 44.3 | Intron 6 |
| 220 | S. pyogenes | chr5: 63322683-63322705 | 3.9 | Intron 6 |
| 221 | S. pyogenes | chr5: 63322693-63322715 | 33.9 | Intron 6 |
| 222 | S. pyogenes | chr5: 63322694-63322716 | 26.1 | Intron 6 |
| 223 | S. pyogenes | chr5: 63322714-63322736 | 5.7 | Intron 6 |
| 224 | S. pyogenes | chr5: 63322731-63322753 | 42.8 | Intron 6 |
| 225 | S. pyogenes | chr5: 63322756-63322778 | 5.8 | Intron 6 |
| 226 | S. pyogenes | chr5: 63322757-63322779 | 21.2 | Intron 6 |
| 227 | S. pyogenes | chr5: 63322770-63322792 | 36.1 | Intron 6 |
| 228 | S. pyogenes | chr5: 63322799-63322821 | 29.9 | Intron 6 |
| 229 | S. pyogenes | chr5: 63322800-63322822 | 43.2 | Intron 6 |
| 230 | S. pyogenes | chr5: 63322809-63322831 | 33.3 | Intron 6 |
| 231 | S. pyogenes | chr5: 63322810-63322832 | 46.8 | Intron 6 |
| 232 | S. pyogenes | chr5: 63322834-63322856 | 7.8 | Intron 6 |
| 233 | S. pyogenes | chr5: 63322835-63322857 | 18.3 | Intron 6 |
| 234 | S. pyogenes | chr5: 63322839-63322861 | 18.8 | Intron 6 |
| 235 | S. pyogenes | chr5: 63322839-63322861 | 13.2 | Intron 6 |
| 236 | S. pyogenes | chr5: 63322840-63322862 | 2.8 | Intron 6 |
| 237 | S. pyogenes | chr5: 63322845-63322867 | 55.3 | Intron 6 |
| 238 | S. pyogenes | chr5: 63322848-63322870 | 27.2 | Intron 6 |
| 239 | S. pyogenes | chr5: 63322852-63322874 | 24.4 | Intron 6 |
| 240 | S. pyogenes | chr5: 63322859-63322881 | 22.2 | Intron 6 |
| 241 | S. pyogenes | chr5: 63322875-63322897 | 25.3 | Intron 6 |
| 242 | S. pyogenes | chr5: 63322887-63322909 | 4.2 | Intron 6 |
| 243 | S. pyogenes | chr5: 63322888-63322910 | 3.5 | Intron 6 |
| 244 | S. pyogenes | chr5: 63322891-63322913 | 44.3 | Intron 6 |
| 245 | S. pyogenes | chr5: 63322900-63322922 | 58.2 | Intron 6 |
| 246 | S. pyogenes | chr5: 63322906-63322928 | 3.7 | Intron 6 |
| 247 | S. pyogenes | chr5: 63322926-63322948 | 38.1 | Intron 6 |
| 248 | S. pyogenes | chr5: 63322927-63322949 | 0.5 | Intron 6 |
| 249 | S. pyogenes | chr5: 63322947-63322969 | 31.7 | Intron 6 |
| 250 | S. pyogenes | chr5: 63322957-63322979 | 50.0 | Intron 6 |
| 251 | S. pyogenes | chr5: 63322957-63322979 | 11.0 | Intron 6 |
| 252 | S. pyogenes | chr5: 63322991-63323013 | 4.5 | Intron 6 |
| 253 | S. pyogenes | chr5: 63322992-63323014 | 0.5 | Intron 6 |
| 254 | S. pyogenes | chr5: 63323338-63323360 | 19.8 | Intron 7 |
| 255 | S. pyogenes | chr5: 63323339-63323361 | 8.1 | Intron 7 |
| 256 | S. pyogenes | chr5: 63323361-63323383 | 21.1 | Intron 7 |
| 257 | S. pyogenes | chr5: 63323362-63323384 | 30.4 | Intron 7 |
| 258 | S. pyogenes | chr5: 63323362-63323384 | 5.6 | Intron 7 |
| 259 | S. pyogenes | chr5: 63323363-63323385 | 2.8 | Intron 7 |
| 260 | S. pyogenes | chr5: 63323367-63323389 | 23.2 | Intron 7 |
| 261 | S. pyogenes | chr5: 63323368-63323390 | 26.2 | Intron 7 |
| 262 | S. thermophilus | chr5: 63322644-63322668 | Activity not tested | Intron 6 |
| 263 | S. thermophilus | chr5: 63322647-63322671 | Activity not tested | Intron 6 |
| 264 | S. thermophilus | chr5: 63322678-63322702 | Activity not tested | Intron 6 |
| 265 | S. thermophilus | chr5: 63322681-63322705 | Activity not tested | Intron 6 |
| 266 | S. thermophilus | chr5: 63322755-63322779 | Activity not tested | Intron 6 |
| 267 | S. thermophilus | chr5: 63322807-63322831 | Activity not tested | Intron 6 |
| 268 | S. thermophilus | chr5: 63322845-63322869 | Activity not tested | Intron 6 |
| 269 | S. thermophilus | chr5: 63322850-63322874 | Activity not tested | Intron 6 |
| 270 | S. thermophilus | chr5: 63322955-63322979 | Activity not tested | Intron 6 |
| 271 | S. thermophilus | chr5: 63322989-63323013 | Activity not tested | Intron 6 |
| 347 | S. pyogenes | chr5: 63323002-63323024 | 2.1 | Exon 7 |
| 348 | S. pyogenes | chr5: 63323011-63323033 | 31.9 | Exon 7 |
| 349 | S. pyogenes | chr5: 63323015-63323037 | 7.7 | Exon 7 |

TABLE 3-continued

List of target sequences and editing activities in porcine fetal fibroblasts

| SEQ ID NO: | Cas9 Nuclease | Location of target | Average edited fraction | Position on CD163 |
|---|---|---|---|---|
| 350 | S. pyogenes | chr5: 63323017-63323039 | 56.5 | Exon 7 |
| 351 | S. pyogenes | chr5: 63323018-63323040 | 74.3 | Exon 7 |
| 352 | S. pyogenes | chr5: 63323019-63323041 | 52.3 | Exon 7 |
| 353 | S. pyogenes | chr5: 63323022-63323044 | 44.0 | Exon 7 |
| 354 | S. pyogenes | chr5: 63323023-63323045 | 61.6 | Exon 7 |
| 355 | S. pyogenes | chr5: 63323024-63323046 | 49.4 | Exon 7 |
| 356 | S. pyogenes | chr5: 63323028-63323050 | 3.1 | Exon 7 |
| 357 | S. pyogenes | chr5: 63323029-63323051 | 0.8 | Exon 7 |
| 358 | S. pyogenes | chr5: 63323040-63323062 | 42.4 | Exon 7 |
| 359 | S. pyogenes | chr5: 63323052-63323074 | 66.7 | Exon 7 |
| 360 | S. pyogenes | chr5: 63323053-63323075 | 13.4 | Exon 7 |
| 361 | S. pyogenes | chr5: 63323061-63323083 | 77.9 | Exon 7 |
| 362 | S. pyogenes | chr5: 63323071-63323093 | 60.8 | Exon 7 |
| 363 | S. pyogenes | chr5: 63323072-63323094 | 70.6 | Exon 7 |
| 364 | S. pyogenes | chr5: 63323073-63323095 | 75.2 | Exon 7 |
| 365 | S. pyogenes | chr5: 63323098-63323120 | 64.4 | Exon 7 |
| 366 | S. pyogenes | chr5: 63323102-63323124 | 55.0 | Exon 7 |
| 367 | S. pyogenes | chr5: 63323105-63323127 | 51.2 | Exon 7 |
| 368 | S. pyogenes | chr5: 63323108-63323130 | 58.3 | Exon 7 |
| 369 | S. pyogenes | chr5: 63323125-63323147 | 14.5 | Exon 7 |
| 370 | S. pyogenes | chr5: 63323126-63323148 | 22.6 | Exon 7 |
| 371 | S. pyogenes | chr5: 63323131-63323153 | 49.9 | Exon 7 |
| 372 | S. pyogenes | chr5: 63323139-63323161 | 68.9 | Exon 7 |
| 373 | S. pyogenes | chr5: 63323147-63323169 | 57.4 | Exon 7 |
| 374 | S. pyogenes | chr5: 63323159-63323181 | 12.9 | Exon 7 |
| 375 | S. pyogenes | chr5: 63323160-63323182 | 19.7 | Exon 7 |
| 376 | S. pyogenes | chr5: 63323161-63323183 | 33.6 | Exon 7 |
| 377 | S. pyogenes | chr5: 63323162-63323184 | 65.3 | Exon 7 |
| 378 | S. pyogenes | chr5: 63323163-63323185 | 51.4 | Exon 7 |
| 379 | S. pyogenes | chr5: 63323173-63323195 | 57.6 | Exon 7 |
| 380 | S. pyogenes | chr5: 63323174-63323196 | 52.1 | Exon 7 |
| 381 | S. pyogenes | chr5: 63323175-63323197 | 48.2 | Exon 7 |
| 382 | S. pyogenes | chr5: 63323177-63323199 | 33.7 | Exon 7 |
| 383 | S. pyogenes | chr5: 63323181-63323203 | 18.3 | Exon 7 |
| 384 | S. pyogenes | chr5: 63323187-63323209 | 57.0 | Exon 7 |
| 385 | S. pyogenes | chr5: 63323197-63323219 | 33.3 | Exon 7 |
| 386 | S. pyogenes | chr5: 63323198-63323220 | 58.3 | Exon 7 |
| 387 | S. pyogenes | chr5: 63323219-63323241 | 20.7 | Exon 7 |
| 388 | S. pyogenes | chr5: 63323220-63323242 | 42.2 | Exon 7 |
| 389 | S. pyogenes | chr5: 63323221-63323243 | 43.4 | Exon 7 |
| 390 | S. pyogenes | chr5: 63323231-63323253 | 21.8 | Exon 7 |
| 391 | S. pyogenes | chr5: 63323251-63323273 | 46.8 | Exon 7 |
| 392 | S. pyogenes | chr5: 63323252-63323274 | 42.6 | Exon 7 |
| 393 | S. pyogenes | chr5: 63323255-63323277 | 22.8 | Exon 7 |
| 394 | S. pyogenes | chr5: 63323267-63323289 | 85.4 | Exon 7 |
| 395 | S. pyogenes | chr5: 63323268-63323290 | 41.1 | Exon 7 |
| 396 | S. pyogenes | chr5: 63323268-63323290 | 53.6 | Exon 7 |
| 397 | S. pyogenes | chr5: 63323269-63323291 | 32.1 | Exon 7 |
| 398 | S. pyogenes | chr5: 63323277-63323299 | 16.6 | Exon 7 |
| 399 | S. pyogenes | chr5: 63323278-63323300 | 39.0 | Exon 7 |
| 400 | S. pyogenes | chr5: 63323279-63323301 | 11.7 | Exon 7 |
| 401 | S. pyogenes | chr5: 63323282-63323304 | 48.9 | Exon 7 |
| 402 | S. pyogenes | chr5: 63323283-63323305 | n/a | Exon 7 |
| 403 | S. pyogenes | chr5: 63323287-63323309 | 11.6 | Exon 7 |
| 404 | S. pyogenes | chr5: 63323288-63323310 | 69.3 | Exon 7 |
| 405 | S. pyogenes | chr5: 63323295-63323317 | 46.0 | Exon 7 |
| 406 | S. pyogenes | chr5: 63323300-63323322 | 54.2 | Exon 7 |
| 407 | S. thermophilus | chr5: 63323019-63323043 | 25.5 | Exon 7 |
| 408 | S. thermophilus | chr5: 63323022-63323046 | 24.7 | Exon 7 |
| 409 | S. thermophilus | chr5: 63323061-63323085 | 37.8 | Exon 7 |
| 410 | S. thermophilus | chr5: 63323071-63323095 | 30.4 | Exon 7 |
| 411 | S. thermophilus | chr5: 63323096-63323120 | 33.4 | Exon 7 |
| 412 | S. thermophilus | chr5: 63323102-63323126 | 19.8 | Exon 7 |
| 413 | S. thermophilus | chr5: 63323105-63323129 | 0.6 | Exon 7 |
| 414 | S. thermophilus | chr5: 63323159-63323183 | 14.8 | Exon 7 |
| 415 | S. thermophilus | chr5: 63323160-63323184 | 7.8 | Exon 7 |
| 416 | S. thermophilus | chr5: 63323161-63323185 | 3.6 | Exon 7 |
| 417 | S. thermophilus | chr5: 63323163-63323187 | 7.9 | Exon 7 |
| 418 | S. thermophilus | chr5: 63323175-63323199 | 33.8 | Exon 7 |
| 419 | S. thermophilus | chr5: 63323175-63323199 | 11.5 | Exon 7 |
| 420 | S. thermophilus | chr5: 63323219-63323243 | 8.1 | Exon 7 |
| 421 | S. thermophilus | chr5: 63323253-63323277 | 32.6 | Exon 7 |
| 422 | S. thermophilus | chr5: 63323275-63323299 | 0.2 | Exon 7 |
| 423 | S. thermophilus | chr5: 63323277-63323301 | 12.3 | Exon 7 |
| 424 | S. thermophilus | chr5: 63323280-63323304 | 26.0 | Exon 7 |
| 425 | S. thermophilus | chr5: 63323295-63323319 | 30.5 | Exon 7 |

Efficient guideRNA-Cas9 pairs which cut sites early in the CD163 gene (exons 1-4) were selected and further screened for potential off-target binding within the pig genome.

In some instances, the use of guide RNA and endonuclease has been observed to result in cleavage of DNA at unintended locations in the genome. Because the repair process for dsDNA breaks can be random, off-target cleavage events can result in undesirable changes to coding or regulatory regions in the genome. Therefore, in instances where a number of single or paired guides can perform an intended edit with similar editing frequencies, it is advantageous to consider off-target cleavage in choosing a guide or guide pair for editing experiments.

A number of computational and biochemical approaches for elucidating off-targets have been developed. Computational approaches can include, but are not limited to, Cas-OFFinder (Bae, S., et al., Bioinformatics, 2014, 30, 1473-1475), CRISPR-offinder (Zhao, C., et al., Int. J. Biol. Sci., 2017, 13, 1470-1478), and CRISPR-OFF (Alkan, F., et al., Genome Biol., 2018, 19, 177). Other computational approaches are readily available to those skilled in the art. Biochemical approaches can include, but are not limited to, GUIDE-Seq (Tsai, S. Q., et al., Nat Biotechnol. 2015, 33, 187-197), SITE-SEQ® (Cameron, P., et al., Nat Methods 2017, 14, 600-606), and CIRCLE-seq (Tsai, S. Q., et al., Nat. Methods, 2017, 14, 607-614). Other biochemical approaches are readily available to those skilled in the art. While computational methods are relatively fast and inexpensive compared to biochemical ones, biochemical approaches have been shown to be superior in identifying validated off-target edits.

A subset of guideRNAs that have demonstrated a high frequency of intended edits in porcine fetal fibroblasts, as described above, were assayed for specificity using SITE-SEQ®. Using naked gDNA and RNP editing reagents in vitro, SITE-SEQ® can provide a list of potential cleavage sites. Off-target cleavage in a cellular environment can be more complicated than that simulated biochemically in vitro. Factors such as effective RNP concentration and target availability due to chromatin state, among other factors, can contribute to the number of off-target edits realized in porcine cells or in edited pigs. Fortunately, biochemical methods such as SITE-SEQ® can provide researchers a list of sites to interrogate. These sites can be interrogated by methods that include, but are not limited to, TOPO cloning and sequencing of TOPO clones, ILLUMINA® amplicon sequencing, Nanopore sequencing, other NGS sequencing methods, and sequence capture (Gnirke, A., et al., Nat. Biotechnol., 2009, 27, 182-189).

Screening was performed for biochemically-identified off-target sites in edited porcine fibroblasts and subsequently in injected embryos. Guides with validated off-target edits were de-prioritized for use in generating edited pigs. Animals generated using guides with known off-targets can be interrogated for the presence of off-target edits using the strategies outlined above. Animals that do contain off-target edits can either be removed from the breeding program or the off-target edits can be removed via breeding. This screening can include bioinformatic methods, such as BLAST® searching, to identify sequences in the *Sus scrofa* genome that contain 1-5 mismatches with the guideRNA, that could therefore allow for off-target binding. The number of potential off-target binding sites in the genome when allowing these mismatches in the computer algorithm is detailed below in Table 4.

TABLE 4

Mismatch Detection

| SITE | LOCATION- Spy coordinates | SEQ ID SEQ ID Spy | SEQ ID Stherm | MISMATCHES ≤ 5 Spy | Stherm C3 |
|---|---|---|---|---|---|
| 1  | chr5: 63300236-63300258 | 19  | 20  | 920  | 142 |
| 2  | chr5: 63300308-63300330 | 32  | 33  | 625  | 51  |
| 3  | chr5: 63301997-63302019 | 41  | 42  | 506  | 37  |
| 4  | chr5: 63303121-63303143 | 43  | 44  | 1625 | 201 |
| 5  | chr5: 63303137-63303159 | 47  | 48  | 474  | 32  |
| 6  | chr5: 63303140-63303162 | 49  | 50  | 548  | 49  |
| 7  | chr5: 63303166-63303188 | 52  | 53  | 692  | 92  |
| 8  | chr5: 63303169-63303191 | 54  | 55  | 782  | 94  |
| 9  | chr5: 63303181-63303203 | 56  | 57  | 1346 | 200 |
| 10 | chr5: 63303184-63303206 | 58  | 59  | 1873 | 382 |
| 11 | chr5: 63303189-63303211 | 60  | 61  | 1642 | 240 |
| 12 | chr5: 63303378-63303400 | 86  | 87  | 588  | 53  |
| 13 | chr5: 63303413-63303435 | 91  | 92  | 545  | 50  |
| 14 | chr5: 63306108-63306130 | 103 | 104 | 480  | 49  |
| 15 | chr5: 63306144-63306166 | 108 | 109 | 344  | 21  |
| 16 | chr5: 63306147-63306169 | 110 | 111 | 451  | 44  |
| 17 | chr5: 63306251-63306273 | 116 | 117 | 1343 | 65  |
| 18 | chr5: 63306336-63306358 | 125 | 126 | 718  | 66  |
| 19 | chr5: 63306371-63306393 | 130 | 131 | 1310 | 131 |
| 20 | chr5: 63309035-63309057 | 134 | 135 | 690  | 83  |
| 21 | chr5: 63309077-63309099 | 138 | 139 | 949  | 95  |
| 22 | chr5: 63309084-63309106 | 140 | 141 | 1234 | 99  |
| 23 | chr5: 63309273-63309295 | 164 | 165 | 418  | 47  |
| 24 | chr5: 63309308-63309330 | 170 | 171 | 747  | 95  |
| 25 | chr5: 63309857-63309879 | 174 | 175 | 795  | 47  |
| 26 | chr5: 63309860-63309882 | 176 | 177 | 736  | 94  |
| 27 | chr5: 63309886-63309908 | 179 | 180 | 1829 | 124 |
| 28 | chr5: 63309889-63309911 | 182 | 183 | 1575 | 94  |
| 29 | chr5: 63309933-63309955 | 187 | 188 | 871  | 95  |
| 30 | chr5: 63310098-63310120 | 203 | 204 | 533  | 73  |
| 31 | chr5: 63310100-63310122 | 206 | 207 | 537  | 53  |

One of the factors that contributes to cutting at these off-target sites can be whether the gene editing components are delivered as a DNA vector or as an RNA-protein complex; sites that may have as few as 1 or 2 base mismatches can be faithfully discriminated from the intended target site when the Cas9 and guide RNA can be delivered as a single guide ribonucleotide protein complex (sgRNP) rather than delivered on a DNA vector.

A second consideration to maximize specificity of a Cas9 guide-RNA reagent can be to prescreen guide RNA-protein pairs using in vitro biochemical methods. Several laboratories have published methods to screen for off-target edit sites. These biochemical approaches can identify potential off-target Cas9 cleavage sites in purified genomic DNA. Using these assays, genomic DNA can be digested with a range of sgRNP concentrations, from limiting to saturating, thus permitting the recovery of both high- and low-cleavage-sensitivity off-target sites. See, e.g., Cameron et al., "SITE-SEQ®: A Genome-wide Method to Measure Cas9 Cleavage," Protocol Exchange (2017).

The off-target sites identified by off-target screening can be used to guide careful and comprehensive examination of possible off-target sites in cells, measuring both editing frequency and functional cellular consequence. Several selected guide RNA-Cas protein pairs can be screened, and the screening can demonstrate: 1) efficient cutting nearer to the 5' end of the CD163 gene, and 2) few mismatch sequences as determined by bioinformatic methods.

Using this guide selection criteria, several guide RNA-Cas protein pairs can be selected for cutting activity in porcine parthenotes. Porcine oocytes can be doubled using an electric current, injected with guide RNA-Cas protein, allowed to develop for 7 days, then harvested and DNA sequenced across the intended target site. Several guide RNA-Cas protein pairs can be identified to confer edits at a high frequency in parthenotes and are selected for further development.

The present specification provides for, and includes, methods for identifying and selecting optimal target sites for CRISPR/Cas mediated cleavage and gene editing. In an aspect, the method can comprise identifying a target region of a genome for editing; identifying all 20 nucleotide sequences in the target region; performing a bioinformatic screen to identify and remove sequences that match non-target sites in the pig genome that contain 1 to 4 mismatches and have a suitable PAM sequence based on the Cas protein; preparing CRISPR/Cas RNP complexes comprising a guide RNA backbone and target sequences, introducing the CRISPR/Cas RNP complexes into a porcine cell in culture, and determining the average editing frequency of the guide RNA/Cas combination. In an aspect, determining the average editing frequency of the guide RNA/Cas combination can comprise amplifying, by PCR, a region surrounding the target site, performing amplicon deep sequencing, and comparing it to untreated cells. In an aspect, the method provides for selecting preferred target sequences that can have an average editing frequency of at least 15. Also provided for are methods for identifying and selecting optimal target sites for CRISPR/Cas mediated cleavage and gene editing wherein the guide RNA and Cas proteins can be provided as part of an expression vector or vectors. Suitable cells are known to persons of skill in the art and can include, but are not limited to, primary fetal fibroblasts of an intended porcine breeding line.

Multiple repair templates can be designed to generate in-frame stop codons. The repair templates listed, when used with appropriate guide RNAs in an endonuclease system, can generate an in-frame termination codon (TAA, TGA, TAG) after repair. Different lengths of repair templates can be used, having sequence identity on either side of the edit site. In an aspect, a repair template can share at least 15 nucleotides on either side of the CRISPR/Cas endonuclease cleavage site (e.g., 15~15 nucleotides). In other aspects, repair templates can share more than 100 nucleotides on either side of the edit site (e.g., >100~>100). Repair templates can be single, double, or staggered strands of complementary DNA using overhangs on the ends. In addition, these templates are not limited to DNA but also could be RNA or modified nucleotides (inosine, for example) or a mixture of these bases and have 5' and or 3' ends protected from degradation. Because there are exonucleases that cleave nucleotides from the ends, protecting the ends with modified bases can prevent exonuclease digestion in the cell of both DNA and RNA. Not to be limited by theory, increasing the length of the region of identity on both sides of the edit site can increase the efficiency and specificity of the repair process (e.g., homology arms). Included and provided for by the present specification are repair templates that can have 100% identity over at least 25 nucleotides on both sides of the edit site. This core identity region ensures that the desired edit (for example, deletions for SEQ ID NOs: 1 to 13) is accurate and efficient. In an aspect, the core identity region can be at least 40 nucleotides flanking the edit site. In yet another aspect, the core identity region can be at least 50 nucleotides on both sides of the edit site. In an aspect, the flanking core region can comprise 60 nucleotides of 100% identity. Also included in an aspect are repair templates that can have 70 identical nucleotides to the chromosomal region flanking the edit site. In an aspect, the core identity region can comprise 75 nucleotides of identity to the chromosomal region flanking the edit site. In an aspect, the core identity region can comprise 25 to 40 flanking nucleotides. In a further aspect, the core identity region can comprise 40 to 75 flanking nucleotides.

In some aspects, the core identity region can be further flanked by additional regions of homology to the target site (the "flanking homology regions"). As provided herein, in an aspect, the flanking homology regions can comprise 100% identity to the target site. As examples, SEQ ID NOs: 1 to 13 shared 100% homology to the CD163 region on either side of the targeted edit site as found in lines 2, 3, 15, 19, 27, 62, or 65 (e.g., 100% homology in the core region and the flanking homology regions). Also included are repair templates that can comprise SEQ ID NOs: 1 to 13, wherein the core identity region can comprise 100% identity to 25 nucleotides of the genome on either side of the desired edit (e.g., bases 50 to 100) and can be flanked by at least 80% identity to the genome on either side of the core region (e.g., nucleotides 1 to 49 and 101 to 150 of SEQ ID NOs: 1 to 18). In another aspect, the core region can have 100% homology and the flanking homology regions can share 85% homology. In a further aspect, the core region can have 100% homology and the flanking homology regions can share 90% homology. In yet another aspect, the core region can have 100% homology and the flanking homology regions can share 95% homology. Also included in an aspect are repair templates that can have a core region that has 100% homology and the flanking homology regions share 97% homology. In some aspects, the flanking homology regions can share 99% homology. Not to be limited by theory, it is thought that increasing the length of the flanking homology regions can introduce the desired CD163 edits into related animals without further modifying the genome. That is, specific repair sequences incorporating polymorphisms or changes in the CD163 genome of other pigs are specifically included and provided for.

The present specification includes, and provides for, flanking homology regions that can have greater than 50 nucleotides on each side of the edit site. In an aspect, the flanking homology regions can have greater than 75 nucleotides on each side of the edit site. In an aspect, the flanking homology regions can have greater than 100 nucleotides on each side of the edit site. Also included are flanking homology regions that can have greater than 200 nucleotides on each side of the edit site. In aspects, the flanking homology regions can have between 30 and 1000 nucleotides on each side of the edit site.

The present specification includes, and provides for, additional modifications at the 5' and 3' ends of repair template. Repair templates are not limited to DNA but also could be RNA or modified nucleotides (inosine, for example) or a mixture of these bases and can have 5' and or 3' ends protected from degradation. Because there are exonucleases that cleave nucleotides from the ends, protecting the ends with modified bases can prevent exonuclease digestion in the cell of both DNA and RNA. Accordingly, as provided herein, the 5' and 3' ends of a repair template comprising a flanking homology region can be modified to prevent degradation.

The present specification provides for, and includes, ribonucleoprotein (RNP) complexes that can comprise a guide polynucleotide and a Cas protein. In an aspect, the Cas protein can be a S. thermophilus Cas9. In another aspect, the Cas protein can be Cas9 from S. pyogenes. Other suitable Cas proteins are known in the art and exemplary Cas systems are described above in Table 1. The selection of suitable Cas proteins depends on the required PAM sequence combination, and methods of identifying Cas proteins and modifying Pam sequences are known. Similarly, Cas systems differ in their requirements for guide RNA backbone sequences (e.g., tracrRNA sequences). In an aspect, the RNP complex can comprise a Cas protein and a guide nucleotide having at least 98% sequence identity to an RNA sequence selected from the group consisting of the first 20 nucleotides of each of SEQ ID NOs: 22 to 271 and 347 to 425. In another aspect, the RNP complex can comprise a guide RNA comprising a sequence selected from the group consisting of the first 20 nucleotides of each of SEQ ID NOs: 22 to 271 and 347 to 425. In an aspect, the RNP complex can comprise a guide polynucleotide having 99% identity to a sequence selected from the group consisting of the first 20 nucleotides of each of SEQ ID NOs: 22 to 271 and 347 to 425. In an aspect, the guide polynucleotide of the RNP complex can comprise a sequence selected from the group consisting of the first 20 nucleotides of each of SEQ ID NOs: 22 to 271 and 347 to 425. As provided herein, the RNP complex can comprise the sequences of any one of SEQ ID NOs: 22 to 271 and 347 to 425 combined with an RNA backbone as part of an sgRNA. In an aspect, the RNP complex can be pre-formed prior to injection into a target cell or can be injected or introduced separately.

Also provided for, and included, in the present specification are isolated guide RNAs that can comprise a spacer selected from the group consisting of the first 20 nucleotides of each of SEQ ID NOs: 22 to 271 and the first 20 nucleotides of each of SEQ ID NOs: 347 to 425. In an aspect, the Cas protein can be a protein comprising SEQ ID NOs: 20 or 21.

The present specification also includes, and provides for, DNA vectors that can encode guide RNAs for the preparation of CRISPR/Cas RNPs. In general, a vector encoding a guide RNA can comprise a sequence selected from the group consisting of the first 20 nucleotides of each of SEQ ID NOs: 22 to 271 or SEQ ID NOs: 347 to 425 and a guide RNA backbone arranged in cis and as part of a single transcription unit. Upon expression in a suitable cell, the DNA vector can produce an sgRNA of the present specification. Suitable expression vector backbones, including promoters, selectable markers and replication origins, are well known to persons of skill in the art. In practice, the 20 nucleotides and the guide RNA backbone can be DNA (when expressed from a promoter to be transcribed in vivo (in cells) or in vitro (via T7 polymerase) to form an RNA guide or the backbone can be chemically synthesized dual (crRNA and trRNA) guide or single guide RNA.

Specific guideRNAs can be paired to excise parts of the CD163 gene by using paired guideRNAs to delete sections of the gene located between those guides. Exemplary pairs of guideRNAs (listed as DNA sequences) are provided in Table 5. Guide pairs without an exon 7 amino acid sequence listed remove the entire exon. The complete amino acid sequence for these deletions is set forth in SEQ ID NO: 553. All guides in Table 5 can create the desired sequence by excising the DNA in between the two guides and NHEJ repair between the cut sites without the use of a DNA repair template. The guide pairs that result in the amino acid sequences set forth in SEQ TD NOs. 506-517 can introduce an exogenous stop codon across the cut ends of the DNA introduced by the guide.

TABLE 5

Exemplary Guide RNA Pairs

| SEQ ID NO: (5') | Cut site (5') | SEQ ID NO: (3') | Cut site (3') | Deletion size (bp) | Repaired Sequence SEQ ID | Exon 7AA SEQ ID |
|---|---|---|---|---|---|---|
| 229 | 63322816 | 256 | 63323377 | 561 | 426 | N/A |
| 230 | 63322814 | 256 | 63323377 | 562 | 427 | N/A |
| 231 | 63322826 | 256 | 63323377 | 551 | 428 | N/A |
| 237 | 63322861 | 256 | 63323377 | 516 | 429 | N/A |
| 241 | 63322891 | 256 | 63323377 | 486 | 430 | N/A |
| 229 | 63322816 | 258 | 63323378 | 562 | 431 | N/A |
| 230 | 63322814 | 258 | 63323378 | 563 | 432 | N/A |
| 231 | 63322826 | 258 | 63323378 | 552 | 433 | N/A |
| 237 | 63322861 | 258 | 63323378 | 517 | 434 | N/A |
| 241 | 63322891 | 258 | 63323378 | 487 | 435 | N/A |
| 229 | 63322816 | 261 | 63323373 | 558 | 436 | N/A |
| 230 | 63322814 | 261 | 63323373 | 559 | 437 | N/A |
| 231 | 63322826 | 261 | 63323373 | 548 | 438 | N/A |
| 237 | 63322861 | 261 | 63323373 | 513 | 439 | N/A |
| 241 | 63322891 | 261 | 63323373 | 483 | 440 | N/A |
| 219 | 63322697 | 256 | 63323377 | 680 | 441 | N/A |
| 221 | 63322709 | 256 | 63323377 | 668 | 442 | N/A |
| 224 | 63322747 | 256 | 63323377 | 630 | 443 | N/A |
| 227 | 63322786 | 256 | 63323377 | 591 | 444 | N/A |
| 219 | 63322697 | 258 | 63323378 | 681 | 445 | N/A |
| 221 | 63322709 | 258 | 63323378 | 669 | 446 | N/A |
| 224 | 63322747 | 258 | 63323378 | 631 | 447 | N/A |
| 227 | 63322786 | 258 | 63323378 | 592 | 448 | N/A |
| 219 | 63322697 | 261 | 63323373 | 677 | 449 | N/A |
| 221 | 63322709 | 261 | 63323373 | 665 | 450 | N/A |
| 224 | 63322747 | 261 | 63323373 | 627 | 451 | N/A |
| 227 | 63322786 | 261 | 63323373 | 588 | 452 | N/A |
| 249 | 63322963 | 256 | 63323377 | 414 | 453 | N/A |
| 250 | 63322973 | 256 | 63323377 | 404 | 454 | N/A |
| 249 | 63322963 | 258 | 63323378 | 415 | 455 | N/A |
| 250 | 63322973 | 258 | 63323378 | 405 | 456 | N/A |
| 249 | 63322963 | 261 | 63323373 | 411 | 457 | N/A |
| 250 | 63322973 | 261 | 63323373 | 401 | 458 | N/A |
| 351 | 63323023 | 365 | 63323103 | 80 | 459 | 506 |
| 351 | 63323023 | 387 | 63323235 | 212 | 460 | 506 |
| 348 | 63323027 | 390 | 63323236 | 209 | 461 | 507 |
| 348 | 63323027 | 388 | 63323236 | 209 | 462 | 507 |
| 348 | 63323027 | 395 | 63323284 | 257 | 463 | 507 |
| 352 | 63323035 | 365 | 63323103 | 68 | 464 | 508 |
| 352 | 63323035 | 387 | 63323235 | 200 | 465 | 508 |
| 352 | 63323035 | 399 | 63323283 | 248 | 466 | 508 |
| 353 | 63323038 | 365 | 63323103 | 65 | 467 | 509 |
| 353 | 63323038 | 387 | 63323235 | 197 | 468 | 509 |
| 353 | 63323038 | 399 | 63323283 | 245 | 469 | 509 |
| 354 | 63323039 | 390 | 63323236 | 197 | 470 | 509 |
| 354 | 63323039 | 388 | 63323236 | 197 | 471 | 509 |
| 354 | 63323039 | 395 | 63323284 | 245 | 472 | 509 |
| 358 | 63323056 | 361 | 63323077 | 21 | 473 | 510 |
| 358 | 63323056 | 362 | 63323087 | 31 | 474 | 510 |
| 358 | 63323056 | 368 | 63323124 | 68 | 475 | 510 |
| 358 | 63323056 | 384 | 63323203 | 147 | 476 | 510 |
| 358 | 63323056 | 394 | 63323272 | 216 | 477 | 510 |
| 358 | 63323056 | 399 | 63323283 | 227 | 478 | 511 |

TABLE 5-continued

Exemplary Guide RNA Pairs

| SEQ ID NO: (5') | Cut site (5') | SEQ ID NO: (3') | Cut site (3') | Deletion size (bp) | Repaired Sequence SEQ ID | Exon 7AA SEQ ID |
|---|---|---|---|---|---|---|
| 359 | 63323057 | 390 | 63323236 | 179 | 479 | 511 |
| 359 | 63323057 | 388 | 63323236 | 179 | 480 | 511 |
| 359 | 63323057 | 395 | 63323284 | 227 | 481 | 511 |
| 360 | 63323058 | 368 | 63323124 | 66 | 482 | 511 |
| 360 | 63323058 | 384 | 63323203 | 145 | 483 | 511 |
| 360 | 63323058 | 389 | 63323237 | 179 | 484 | 511 |
| 360 | 63323058 | 394 | 63323272 | 214 | 485 | 511 |
| 360 | 63323058 | 397 | 63323285 | 227 | 486 | 511 |
| 361 | 63323077 | 365 | 63323103 | 26 | 487 | 512 |
| 361 | 63323077 | 387 | 63323235 | 158 | 488 | 512 |
| 362 | 63323087 | 390 | 63323236 | 149 | 489 | 513 |
| 362 | 63323087 | 388 | 63323236 | 149 | 490 | 512 |
| 362 | 63323087 | 395 | 63323284 | 197 | 491 | 513 |
| 364 | 63323089 | 365 | 63323103 | 14 | 492 | 514 |
| 364 | 63323089 | 387 | 63323235 | 146 | 493 | 514 |
| 364 | 63323089 | 399 | 63323283 | 194 | 494 | 514 |
| 365 | 63323103 | 368 | 63323124 | 21 | 495 | 515 |
| 365 | 63323103 | 384 | 63323203 | 100 | 496 | 516 |
| 365 | 63323103 | 389 | 63323237 | 134 | 497 | 516 |
| 365 | 63323103 | 394 | 63323272 | 169 | 498 | 516 |
| 365 | 63323103 | 397 | 63323285 | 182 | 499 | 516 |
| 366 | 63323118 | 368 | 63323124 | 6 | 500 | 517 |
| 366 | 63323118 | 384 | 63323203 | 85 | 501 | 517 |
| 366 | 63323118 | 389 | 63323237 | 119 | 502 | 517 |
| 366 | 63323118 | 394 | 63323272 | 154 | 503 | 517 |
| 366 | 63323118 | 397 | 63323285 | 167 | 504 | 517 |
| 354 | 63323039 | 211 | 63323163 | 123 | 505 | 518 |

In aspects, the guide RNA-Cas protein pairs can further comprise a DNA repair template. Exemplary guides and repair templates creating stop codons are listed in Table 6. These and other guides can be paired with other repair templates to generate in-frame stop codons or perturb, interfere, or eliminate splicing of exons, as examples of disrupting CD163 mRNA translation or processing. Other examples can include, but are not limited to, the elimination of the start ATG codon, or programming repair outcomes when using paired guide RNAs where a repair template could promote a single repair outcome over random non-homologous end joining when paired nucleases remove an exon (e.g., deletion of exon 7 corresponding to domain 5) in CD163. Without being limited by theory, analysis reveals consistent reduction of bioinformatic mismatches with inclusion of the extra nG in the PAM (nGGnG) as well as reduced off-target cutting in vitro and in vivo. Reduction of mismatches can include those from an alignment perspective (whether the DNA sequence has mismatches with the RNA guide sequence). See Table 4. A mismatch may not be an off-target edit (cutting or presence of indel, in vitro or in vivo, respectively), but an off-target edit is likely due to a mismatch. In the most preferred aspects, the methods disclosed herein produce no off-target edits in pigs, and the pigs disclosed herein have no off-target edits in their genomes.

TABLE 6

Guide RNAs and repair templates for editing CD163

| | Region Chr5 Location of guide RNAs binding site | | | | | | |
|---|---|---|---|---|---|---|---|
| | 63301998-02017 | 63301997-02016 | 63303213-03232 | 63303283-03302 | 63303315-03334 | 63303315-03334 | 63303338-03357 |
| Repair template SEQ ID NO | 1 | 2 | 3 | 4 | 5 | 6 | 7 |

TABLE 6-continued

Guide RNAs and repair templates for editing CD163

| | | | | | | | |
|---|---|---|---|---|---|---|---|
| Guide RNA spacer (DNA) SEQ ID NO | 274 | 275 | 276 | 277 | 278 | 279 | 280 |
| Guide RNA spacer (RNA) SEQ ID NO | 287 | 288 | 289 | 290 | 291 | 292 | 293 |
| WT Region SEQ ID NO. | 300 | 301 | 302 | 303 | 304 | 305 | 306 |
| Trans-lation of WT region | 313 | 314 | 315 | 316 | 317 | 318 | 319 |
| Translation of Deletion | 326 | 327 | 328 | 329 | 330 | 331 | 332 |
| Base deletion coordinates | chr5: 63301999-63302005 | chr5: 63301999-63302005 | chr5 63303234-63303235 | chr5: 63303304-63303307 | chr5: 63303336-63303336 | chr5: 63303337-63303337 | chr5: 63303351-63303356 |
| Deleted bases (#) | CTT GGT C (7) | CTT GGT C (7) | GG (2) | GGC T (4) | G (1) | G (1) | CTT GTC (6) |

Region Chr5 Location of guide RNAs binding site

| | 63303379-63303398 | 63303379-63303398 | 63306148-06167 | 63306263-06282 | 63306364-06383 | 63323147-23166 |
|---|---|---|---|---|---|---|
| Repair template SEQ ID NO | 8 | 9 | 10 | 11 | 12 | 13 |
| Guide RNA spacer (DNA) SEQ ID NO | 281 | 282 | 283 | 284 | 285 | 286 |
| Guide RNA spacer (RNA) SEQ ID NO | 294 | 295 | 296 | 297 | 298 | 299 |
| WT Region SEQ ID NO. | 307 | 308 | 309 | 310 | 311 | 312 |
| Trans-lation of WT region | 320 | 321 | 322 | 323 | 324 | 325 |
| Translation of Deletion | 333 | 334 | 335 | 336 | 337 | 338 |
| Base deletion coordinates | chr5 63303399-63303401 | chr5: 63303400-63303402 | chr5:6 3306156-63306158 | chr5: 63306282-63306284 | chr5: 63306373-63306377 | chr5: 63323159-63323162 |
| Deleted bases (#) | GGG (3) | GGG (3) | TTC (3) | CTC (3) | CGA TC (5) | CGG C (4) |

The stochastic natural cellular repair process of non-homologous end joining (NHEJ) repair sometimes involves inserting or deleting single or multiple nucleotides at the double-strand break. As a consequence of this repair process, if a double-strand break occurs in the coding region of a gene, a shift in the translational reading frame of the encoded mRNA can result until an in-frame stop codon, terminating protein translation. Although the translation of this naturally, accidentally mutated gene can produce a shortened protein relative to the protein product of an unmodified version, the amino acid sequence of this newly encoded polypeptide would be unique, possibly reducing or even improving the fitness of cells within the target organism. In an aspect, to preclude the creation of frame shifting mutations and the translation of this set of undesirable polypeptides, edited pigs can be screened for formation of an in-frame translational stop codon at or near the endonuclease cut site that is a consequence of a separate, naturally occurring NHEJ repair.

The excision of genomic DNA sequence using two intronic guideRNAs in conjunction with an endonuclease can be accomplished by NHEJ repairs that include, but are not limited to, the end-to-end joining of nuclease cut sites. Because introns are non-coding, NHEJ repair outcomes that include indels around the nuclease cut sites can accomplish the excision of the intended region of DNA which can include intron and/or exon sequences. Because some NHEJ repair outcomes occur more frequently than others, it is advantageous to consider repair outcome frequency when choosing a guideRNA pair for use in gene editing experiments. SEQ ID NO: 520-555 illustrate repair outcomes of exon 7 excisions observed in blastocysts from guide pairs as set forth in Table 7. The designed repair outcome for these guide pairs is listed in Table 5.

TABLE 7

Observed Repair Outcomes in Blastocysts

| SEQ ID NO: (5') | SEQ ID NO: (3') | Repair outcome SEQ ID |
|---|---|---|
| 249 | 261 | 520 |
| 249 | 261 | 521 |
| 249 | 261 | 522 |
| 249 | 261 | 523 |
| 249 | 261 | 524 |
| 249 | 261 | 525 |
| 249 | 261 | 526 |
| 249 | 261 | 527 |
| 249 | 256 | 528 |
| 249 | 256 | 529 |
| 249 | 256 | 530 |
| 249 | 256 | 531 |
| 249 | 256 | 532 |
| 249 | 256 | 533 |
| 249 | 256 | 534 |
| 249 | 256 | 535 |
| 241 | 258 | 536 |
| 241 | 258 | 537 |
| 241 | 258 | 538 |
| 241 | 258 | 539 |
| 241 | 258 | 540 |
| 241 | 258 | 541 |
| 241 | 258 | 542 |
| 241 | 258 | 543 |
| 241 | 258 | 544 |
| 221 | 261 | 545 |
| 221 | 261 | 546 |
| 221 | 261 | 547 |
| 221 | 261 | 548 |
| 221 | 261 | 549 |
| 229 | 256 | 550 |
| 229 | 256 | 551 |
| 229 | 256 | 552 |
| 229 | 256 | 553 |
| 229 | 256 | 554 |
| 229 | 256 | 555 |

In another aspect, during gene editing, in-frame stop codons that do not result in the addition of new amino acids can be created by including a DNA repair template together with the guide RNA-Cas protein pair. In an aspect, a DNA repair template can be a dsDNA. In another aspect, the DNA repair template can be a ssDNA. Co-introduction of a double- or single-stranded DNA repair template can be used to either delete or insert DNA nucleotides to form an in-frame translational stop codon (TAA, TGA, TAG) at or near the double-strand break site initiated by the endonuclease. DNA repair templates can further comprise polynucleotide modification templates containing several nucleotide changes in comparison to the native sequence, which can directly edit the target DNA sequence and can be co-transfected with the endonuclease editing reagents to generate edited CD163 genes with in-frame stop codons. In an aspect, the encoded proteins from these gene edited CD163 genes, when transcribed into mRNA and then translated into protein, can only synthesize a shortened and non-functional form of the CD163 polypeptide. Not to be limited by theory, DNA repair templates having longer regions of sequence homology can be more efficient. In certain embodiments, DNA repair templates can contain regions of sequence identity (homology arms) within the DNA repair template which can flank the sequence change and can range from fewer than 50 nucleotides to greater than 1000 nucleotides.

Several aspects of Cas9-protein/guide RNA combinations together with DNA repair templates are shown in Table 6. As provided in Table 6, several Cas9-protein/guide RNA combinations can be paired with DNA repair templates having, but not being limited to, 75 bases of sequence homology on each side of the targeted deletion (50 core homology bases and flanking homology regions of 50 on either side). In an aspect, the protein-guide RNA complexes and template combinations can be transfected into cells. Without being limited by theory, repair of the double-strand break using the DNA repair template can direct the formation of an in-frame translational stop codon as the result of deletion of single or multiple nucleotides at or adjacent to the break site. Animals and cells obtained from this method demonstrate that endonuclease-directed double-strand breaks at the porcine CD163 gene can be repaired using a co-introduced DNA repair template. As provided herein, repair templates having a sequence of SEQ ID NOs: 1 to 13 can introduce an in-frame translational stop codon in Exon 2, thereby producing a shortened and non-functional CD163 protein.

Use of a DNA repair template according to the present specification is not limited to abolishing the function of CD163. The present specification further includes, and provides for, a repair template that can direct the removal or addition of nucleotides to the gene. In an aspect, the stability or half-life modulation of the encoded CD163 mRNA can be modulated by editing according to the present methods. In yet another aspect, DNA sequences which encode amino acids of the mature protein responsible for binding PRRS virus can be removed or replaced. In an aspect, CD163 expression and or activity can be reduced by at least 90% but not abolished. In an aspect of the present teachings, using the spacer sequences described with other repair templates would be contemplated by those skilled in the art to allow for the formation of an in frame stop codon by the removal of bases and the introduction of bases or a combination thereof.

Included, and provided for, by the present specification are pigs derived from elite porcine lines comprising edited CD163 genes. In aspects, the elite porcine lines can be PIC™ Line 15, PIC™ Line 17, PIC™ Line 27, PIC™ Line 65, PIC™ Line 14, PIC™ Line 62, PIC337, PIC800, PIC280, PIC327, PIC408, PIC™ 399, PIC410, PIC415, PIC359, PIC380, PIC837, PIC260, PIC265, PIC210, PIC™ Line 2, PIC™ Line 3, PIC™ Line 4, PIC™ Line 5, PIC™ Line 18, PIC™ Line 19, PIC™ Line 92, PIC95, PIC™ CAMBOROUGH® (Pig Improvement Company, Limited, Basingstoke, UK), PIC1070, PIC™ CAMBOROUGH®40, PIC™ CAMBOROUGH® 22, PIC1050, PIC™ CAMBOROUGH® 29, PIC™ CAMBOROUGH® 48, or PIC™ CAMBOROUGH® x54. In various aspects, the elite porcine lines can be PIC™ elite porcine lines 2, 3, 15, 19, 27, 62, or 65. In another aspect, the pigs can comprise edited CD163 genes derived from elite porcine lines. In aspects, the pigs can comprise an edited CD163 in a CD163 genomic region having the genotypes shown in Table 8 to Table 14. Table 8 to Table 14 present each position on chromosome 5 in the vicinity of the CD163 gene in which a single nucleotide polymorphism exists.

Each table presents alleles that are homozygous in that line and provides a distinguishing genetic signature of the line, as well as its unique genome edited region. All the genetic signatures are based on the Sscrofa11.1 reference genome (GenBank accession: GCA_000003025.6). Accordingly, the transmission of the edited CD163 line can be followed, and animals comprising an edited CD163 gene obtained from the line can be identified. Pigs of other lines are heterozygous or opposite genotype at multiple alleles when compared to the lines of Table 8 to Table 14. In this way, the combination of genetic signatures in each line can be used to distinguish between pigs belonging to a particular line and pigs not belonging to a particular line. In an aspect, the genetic signatures provide for methods to breed and track the CD163 edited genomes from generation to generation. In an aspect, progeny generations that comprise the CD163 edited genomes having a genetic signature according to Table 8 to Table 14 can be prepared.

TABLE 8

Line 2 Genetic Signatures

| Position | Genotype | Position | Genotype | Position | Genotype | Position | Genotype |
|---|---|---|---|---|---|---|---|
| 60306428 | C/C | 60354925 | C/C | 63553656 | G/G | 65411831 | C/C |
| 60306527 | C/C | 60355415 | G/G | 63558087 | G/G | 65411848 | G/G |
| 60308030 | C/C | 60355420 | T/T | 63640722 | G/G | 65411854 | T/T |
| 60320580 | C/C | 60355448 | G/G | 63792071 | T/T | 65411966 | C/C |
| 60322529 | A/A | 60355529 | A/A | 64009226 | C/C | 65412729 | G/G |
| 60324162 | T/T | 60355530 | A/A | 64459105 | T/T | 65413215 | G/G |
| 60327987 | C/C | 60355774 | C/C | 64460101 | A/A | 65413759 | C/C |
| 60328009 | T/T | 60356277 | C/C | 64527707 | A/A | 65417199 | A/A |
| 60335421 | T/T | 60356351 | C/C | 64577968 | C/C | 65417256 | G/G |
| 60338654 | G/G | 60356575 | C/C | 64943306 | T/T | 65417261 | A/A |
| 60344946 | A/A | 60356578 | T/T | 65242696 | T/T | 65417273 | C/C |
| 60345163 | C/C | 60356861 | G/G | 65242725 | A/A | 65417287 | G/G |
| 60345689 | G/G | 60356885 | T/T | 65242729 | A/A | 65417716 | G/G |
| 60345715 | G/G | 60356898 | T/T | 65242736 | G/G | 65417797 | C/C |
| 60345722 | A/A | 60356914 | C/C | 65249484 | T/T | 65417800 | C/C |
| 60345749 | G/G | 60357001 | T/T | 65260283 | T/T | 65419169 | G/G |
| 60345775 | A/A | 60357014 | T/T | 65269510 | C/C | 65419410 | G/G |
| 60345825 | A/A | 60358409 | C/C | 65273886 | T/T | 65420017 | T/T |
| 60346409 | G/G | 60358449 | G/G | 65276133 | C/C | 65420184 | G/G |
| 60346607 | A/A | 60358469 | T/T | 65277053 | T/T | 65420415 | A/A |
| 60346641 | G/G | 60358475 | T/T | 65277156 | C/C | 65420591 | G/G |
| 60346691 | T/T | 60358551 | A/A | 65277320 | G/G | 65420680 | C/C |
| 60346734 | A/A | 60358568 | G/G | 65280282 | A/A | 65420681 | A/A |
| 60347297 | G/G | 60358641 | C/C | 65282683 | C/C | 65420693 | G/G |
| 60350295 | C/C | 60358704 | T/T | 65283434 | C/C | 65420947 | G/G |
| 60350343 | G/G | 60358714 | T/T | 65283970 | C/C | 65420949 | T/T |
| 60350448 | C/C | 60368913 | C/C | 65284829 | C/C | 65421133 | G/G |
| 60350470 | T/T | 60368916 | A/A | 65285100 | C/C | 65421195 | G/G |
| 60350475 | C/C | 60368921 | T/T | 65285902 | G/G | 65421255 | G/G |
| 60350564 | A/A | 60368940 | G/G | 65285914 | T/T | 65421365 | G/G |
| 60350571 | A/A | 60368963 | C/C | 65286400 | C/C | 65421421 | C/C |
| 60350572 | A/A | 60416097 | G/G | 65294497 | T/T | 65422005 | G/G |
| 60350911 | C/C | 60543479 | C/C | 65383805 | C/C | 65422008 | G/G |
| 60351055 | G/G | 60614797 | G/G | 65405986 | C/C | 65422057 | T/T |
| 60351604 | C/C | 60614964 | C/C | 65410118 | C/C | 65422141 | C/C |
| 60351855 | T/T | 60920926 | G/G | 65410147 | G/G | 65422701 | C/C |
| 60351857 | C/C | 61479206 | C/C | 65410198 | C/C | 65422725 | C/C |
| 60351972 | G/G | 61479353 | T/T | 65410435 | C/C | 65425730 | G/G |
| 60352165 | C/C | 61653091 | C/C | 65410440 | T/T | 65601310 | C/C |
| 60352923 | C/C | 61783688 | A/A | 65410441 | C/C | 65602328 | C/C |
| 60353408 | A/A | 62091204 | A/A | 65410443 | C/C | 65711602 | C/C |
| 60353562 | T/T | 62416522 | A/A | 65410447 | C/C | 65761990 | C/C |
| 60353576 | C/C | 62476273 | C/C | 65411265 | C/C | 66293766 | G/G |
| 60353659 | T/T | 62687883 | C/C | 65411431 | G/G | 66296268 | A/A |
| 60353721 | G/G | 63044336 | A/A | 65411524 | C/C | | |
| 60354428 | G/G | 63546615 | C/C | 65411698 | G/G | | |

TABLE 9

Line 3 Genetic Signatures

| Position | Genotype | Position | Genotype | Position | Genotype | Position | Genotype |
|---|---|---|---|---|---|---|---|
| 60414864 | T/T | 64555715 | G/G | 64774093 | G/G | 66035868 | A/A |
| 60415813 | C/C | 64561148 | G/G | 64775512 | G/G | 66042409 | C/C |
| 60415854 | G/G | 64561209 | C/C | 64775565 | C/C | 66042542 | C/C |
| 60572371 | A/A | 64561659 | G/G | 64780089 | T/T | 66042551 | C/C |
| 60663464 | C/C | 64561828 | T/T | 64780152 | C/C | 66042557 | A/A |
| 60663499 | A/A | 64561873 | G/G | 64780196 | C/C | 66042563 | G/G |
| 61016527 | G/G | 64561935 | C/C | 64783169 | C/C | 66155827 | A/A |
| 61442674 | T/T | 64562021 | C/C | 64783774 | C/C | 66155859 | A/A |
| 61870484 | C/C | 64562771 | C/C | 64783896 | G/G | 66155863 | T/T |

TABLE 9-continued

Line 3 Genetic Signatures

| Position | Genotype | Position | Genotype | Position | Genotype | Position | Genotype |
|---|---|---|---|---|---|---|---|
| 61989476 | G/G | 64563462 | G/G | 64784000 | T/T | 66156160 | A/A |
| 62510031 | G/G | 64682243 | C/C | 64784139 | C/C | 66156183 | G/G |
| 62602514 | T/T | 64682929 | G/G | 64784235 | T/T | 66156533 | G/G |
| 63044336 | A/A | 64685072 | T/T | 64784410 | A/A | 66167582 | C/C |
| 63345577 | G/G | 64692673 | G/G | 64784653 | A/A | 66167809 | C/C |
| 63452493 | A/A | 64692905 | T/T | 64784725 | C/C | 66167823 | T/T |
| 63669675 | G/G | 64693058 | T/T | 64784844 | A/A | 66167877 | A/A |
| 63754659 | T/T | 64705228 | G/G | 64784875 | T/T | 66167888 | C/C |
| 63810627 | C/C | 64720067 | A/A | 64785001 | A/A | 66167905 | A/A |
| 63810632 | G/G | 64722426 | T/T | 64785078 | C/C | 66168135 | C/C |
| 63810707 | T/T | 64722539 | C/C | 64813032 | G/G | 66168261 | C/C |
| 63810733 | G/G | 64726936 | G/G | 64819974 | C/C | 66168311 | G/G |
| 63810819 | C/C | 64729340 | C/C | 64893099 | G/G | 66168615 | G/G |
| 63810857 | C/C | 64730596 | G/G | 64899922 | A/A | 66168688 | G/G |
| 63810861 | G/G | 64736752 | G/G | 64934758 | C/C | 66168742 | G/G |
| 64010555 | T/T | 64761650 | G/G | 65348500 | G/G | 66168880 | G/G |
| 64010599 | A/A | 64767369 | G/G | 65546268 | A/A | 66168947 | T/T |
| 64452338 | A/A | 64768411 | G/G | 65546327 | G/G | 66168952 | A/A |
| 64455982 | C/C | 64769978 | T/T | 65841270 | T/T | 66168993 | A/A |
| 64457532 | T/T | 64769989 | C/C | 65858531 | G/G | | |
| 64458163 | T/T | 64770307 | G/G | 65979134 | G/G | | |
| 64458711 | G/G | 64773053 | A/A | 65985520 | C/C | | |

TABLE 10

Line 15 Genetic Signatures

| Position | Genotype | Position | Genotype | Position | Genotype | Position | Genotype |
|---|---|---|---|---|---|---|---|
| 60391943 | G/G | 61515967 | T/T | 63367266 | G/G | 64537982 | T/T |
| 60392234 | T/T | 61759785 | C/C | 63424311 | T/T | 64893205 | A/A |
| 60394009 | A/A | 61759821 | C/C | 63535058 | T/T | 64916422 | G/G |
| 60414796 | T/T | 61865586 | A/A | 63653754 | G/G | 65039734 | C/C |
| 60601475 | A/A | 61867498 | C/C | 63655538 | T/T | 65175496 | C/C |
| 60630898 | A/A | 62192420 | G/G | 63669242 | A/A | 65177506 | G/G |
| 60630910 | A/A | 62195570 | A/A | 63669944 | C/C | 65294016 | C/C |
| 60786421 | G/G | 62196101 | C/C | 63669946 | G/G | 65571397 | A/A |
| 60787517 | G/G | 62442547 | G/G | 63900332 | A/A | 65573608 | T/T |
| 60792231 | G/G | 62509196 | T/T | 64138082 | C/C | 65576707 | C/C |
| 60795724 | C/C | 62675268 | G/G | 64171653 | C/C | 65984917 | G/G |
| 60915211 | C/C | 62843969 | G/G | 64471845 | G/G | 65984984 | T/T |
| 61016227 | A/A | 62852334 | A/A | 64472363 | A/A | 65985058 | T/T |
| 61086145 | T/T | 63025151 | A/A | 64472504 | T/T | 65985392 | C/C |
| 61275101 | C/C | 63025152 | C/C | 64472616 | T/T | 66042472 | C/C |
| 61396087 | A/A | 63168616 | A/A | 64523343 | A/A | 66099282 | A/A |
| 61434042 | G/G | 63266682 | T/T | 64536599 | G/G | 66119075 | T/T |

TABLE 11

Line 19 Genetic Signatures

| Position | Genotype | Position | Genotype | Position | Genotype | Position | Genotype |
|---|---|---|---|---|---|---|---|
| 60320100 | A/A | 61390748 | C/C | 63174233 | T/T | 65031621 | C/C |
| 60320144 | C/C | 61465215 | T/T | 63174257 | A/A | 65031630 | C/C |
| 60320580 | C/C | 61567329 | C/C | 63393845 | G/G | 65031684 | T/T |
| 60507836 | C/C | 61567357 | A/A | 63393849 | T/T | 65222383 | T/T |
| 60512716 | G/G | 61567365 | A/A | 63393851 | T/T | 65222385 | A/A |
| 60564418 | A/A | 61567410 | C/C | 63860532 | A/A | 65242693 | C/C |
| 60666662 | T/T | 61567494 | C/C | 63861247 | A/A | 65497229 | C/C |
| 60683738 | T/T | 61567594 | G/G | 63862368 | T/T | 65499233 | C/C |
| 60782197 | T/T | 61975156 | G/G | 64138082 | C/C | 65502398 | G/G |
| 60782278 | T/T | 61975367 | G/G | 64171653 | C/C | 65562917 | C/C |
| 60782642 | A/A | 61975382 | A/A | 64181448 | G/G | 65566225 | T/T |
| 60782683 | G/G | 61975388 | C/C | 64402245 | T/T | 65567066 | T/T |
| 60782756 | G/G | 62363513 | T/T | 64455172 | G/G | 65894449 | C/C |
| 60782997 | G/G | 62367647 | G/G | 64514012 | C/C | 65904537 | T/T |
| 60783031 | C/C | 62378299 | G/G | 64514013 | A/A | 65959573 | A/A |

TABLE 11-continued

Line 19 Genetic Signatures

| Position | Genotype | Position | Genotype | Position | Genotype | Position | Genotype |
|---|---|---|---|---|---|---|---|
| 60783198 | G/G | 62610431 | T/T | 64522169 | G/G | 65998062 | C/C |
| 61131519 | G/G | 62952267 | T/T | 64522173 | T/T | 66158553 | A/A |
| 61131736 | C/C | 62965473 | T/T | 64522177 | T/T | 66158950 | C/C |
| 61189029 | C/C | 63108711 | G/G | 64522178 | C/C | 66159103 | A/A |
| 61359517 | A/A | 63109224 | T/T | 64794635 | G/G | 66159212 | G/G |

TABLE 12

Line 27 Genetic Signatures

| Position | Genotype | Position | Genotype | Position | Genotype | Position | Genotype |
|---|---|---|---|---|---|---|---|
| 60347934 | A/A | 62159353 | T/T | 62918655 | T/T | 64582272 | A/A |
| 60356984 | C/C | 62313847 | C/C | 63042154 | C/C | 64600735 | G/G |
| 60692943 | C/C | 62315464 | A/A | 63043261 | G/G | 65056396 | A/A |
| 60693260 | G/G | 62570257 | C/C | 63046692 | G/G | 65056671 | T/T |
| 60693769 | G/G | 62570793 | A/A | 63433705 | G/G | 65332987 | A/A |
| 60938885 | T/T | 62571313 | T/T | 63490990 | A/A | 65335837 | C/C |
| 60960728 | A/A | 62917536 | G/G | 63626018 | A/A | 65390844 | A/A |
| 61436306 | G/G | 62917597 | T/T | 63626423 | T/T | 65404042 | A/A |
| 61464114 | C/C | 62917618 | C/C | 63626826 | C/C | 65404045 | A/A |
| 61468375 | G/G | 62917629 | T/T | 63630149 | A/A | 65404063 | C/C |
| 61736415 | A/A | 62917780 | G/G | 63631098 | C/C | 65705261 | G/G |
| 61736429 | G/G | 62917866 | T/T | 63977777 | A/A | 65740018 | T/T |
| 61757961 | G/G | 62917889 | T/T | 63977821 | G/G | 65740030 | A/A |
| 61820110 | A/A | 62918448 | G/G | 64460204 | C/C | 66235840 | G/G |
| 61822513 | T/T | 62918456 | A/A | 64582243 | C/C | | |
| 61858837 | G/G | 62918465 | A/A | 64582246 | G/G | | |

TABLE 13

Line 62 Genetic Signatures

| Position | Genotype | Position | Genotype | Position | Genotype | Position | Genotype |
|---|---|---|---|---|---|---|---|
| 60336383 | A/A | 61760230 | C/C | 62483897 | T/T | 64484177 | T/T |
| 60343172 | A/A | 61927492 | T/T | 62847072 | G/G | 64689271 | A/A |
| 60345254 | G/G | 61927506 | A/A | 62874766 | G/G | 64758235 | C/C |
| 60447765 | G/G | 62006220 | T/T | 62897778 | A/A | 64790188 | C/C |
| 60452143 | C/C | 62115641 | T/T | 63100290 | C/C | 64895383 | C/C |
| 60452167 | T/T | 62169134 | T/T | 63219344 | G/G | 64991645 | A/A |
| 60462769 | T/T | 62368918 | C/C | 63361759 | G/G | 65045805 | T/T |
| 60653700 | T/T | 62471593 | C/C | 63388357 | C/C | 65146186 | C/C |
| 60654939 | A/A | 62474001 | A/A | 63442314 | G/G | 65368620 | C/C |
| 60654943 | A/A | 62474006 | C/C | 63590333 | T/T | 65432698 | C/C |
| 61085770 | A/A | 62474365 | A/A | 63670724 | G/G | 65542716 | A/A |
| 61108831 | G/G | 62480042 | A/A | 63714834 | A/A | 65637507 | G/G |
| 61117357 | A/A | 62480261 | G/G | 63792005 | T/T | 65771614 | C/C |
| 61234908 | C/C | 62480699 | A/A | 63985848 | A/A | 65771615 | G/G |
| 61331270 | A/A | 62480892 | A/A | 63985923 | G/G | 65772162 | T/T |
| 61388824 | G/G | 62481902 | G/G | 64131088 | C/C | 66033248 | T/T |
| 61755575 | C/C | 62482914 | T/T | 64471400 | C/C | 66033476 | C/C |
| 61759095 | C/C | 62483893 | C/C | 64483848 | G/G | 66033484 | C/C |

TABLE 14

Line 65 Genetic Signatures

| Position | Genotype | Position | Genotype | Position | Genotype | Position | Genotype |
|---|---|---|---|---|---|---|---|
| 60322300 | C/C | 60783031 | C/C | 63383925 | A/A | 64759492 | T/T |
| 60411747 | A/A | 60783198 | G/G | 63392495 | T/T | 64795760 | T/T |
| 60412758 | G/G | 60791719 | T/T | 63549670 | C/C | 64797970 | A/A |
| 60412775 | A/A | 60900261 | G/G | 63593491 | G/G | 64798690 | G/G |
| 60412826 | C/C | 60911551 | A/A | 63609938 | A/A | 64860395 | G/G |

TABLE 14-continued

Line 65 Genetic Signatures

| Position | Genotype | Position | Genotype | Position | Genotype | Position | Genotype |
|---|---|---|---|---|---|---|---|
| 60413294 | G/G | 60912669 | A/A | 63641998 | C/C | 64860396 | C/C |
| 60459719 | A/A | 61223574 | A/A | 63678793 | G/G | 64862131 | C/C |
| 60462179 | C/C | 61486607 | C/C | 63784770 | G/G | 65371202 | T/T |
| 60492928 | A/A | 61756324 | G/G | 63810897 | C/C | 65371472 | G/G |
| 60492938 | T/T | 61832527 | C/C | 63810903 | C/C | 65371901 | G/G |
| 60666662 | T/T | 61895566 | C/C | 63810920 | G/G | 65371970 | C/C |
| 60722708 | C/C | 61895833 | A/A | 63810922 | T/T | 65372072 | A/A |
| 60770183 | G/G | 62354225 | C/C | 63810928 | G/G | 65409493 | A/A |
| 60770197 | C/C | 62364072 | G/G | 63872757 | C/C | 65437347 | G/G |
| 60777431 | C/C | 62383525 | G/G | 63944636 | G/G | 65573362 | T/T |
| 60781592 | T/T | 62399452 | T/T | 63944765 | C/C | 65601655 | G/G |
| 60782197 | T/T | 62404734 | A/A | 64138639 | C/C | 65747069 | T/T |
| 60782278 | T/T | 62432982 | C/C | 64194054 | G/G | 65843843 | A/A |
| 60782642 | A/A | 62841388 | G/G | 64242768 | T/T | 65849424 | T/T |
| 60782683 | G/G | 62931496 | T/T | 64270989 | G/G | 66248756 | A/A |
| 60782756 | G/G | 63156406 | C/C | 64753488 | G/G | | |
| 60782997 | G/G | 63156417 | T/T | 64758888 | A/A | | |
| 60783006 | G/G | 63266198 | A/A | 64758900 | C/C | | |

Elite PIC™ lines 2, 3, 15, 19, 27, 62 and 65 are lines selected for superior commercial phenotypes. In an aspect, the CD163 gene edited cells and animals can be free of deleterious alleles that are present in wild populations and in many commercial herds. In aspects, CD163 gene edited cells and animals can be free of one of more of the deleterious alleles selected from the group consisting of epetheliogenesis imperfecta, melanotic skin tumors, dermatosis vegetans, abnormal mamae, shortened vertebral column, kinky tail, rudimentary tail, Hairlessness, Hairlessness (2), Woolly hair, Hydrocephalus, Tassels, Legless, Three-legged, Syndactyly, Polydactyly, Pulawska factor, Heterochromia iridis, Congenital tremor A III, Congenital tremor A IV, Congenital ataxia, Hind leg paralysis, Bentleg, Thickleg, Malignant hyperthermia, Hemophilia (von Willebrand's disease), Leukemia, Hemolytic disease, edema, Acute respiratory distress ("barker"), Rickets, 25 Renal hypoplasia, Renal cysts, Uterus aplasia, Porcine Stress Syndrome (PSS), halothane (HAL), Dipped Shoulder (Humpy Back, Kinky Back, Kyphosis), Hyperostosis, Mammary Hypoplasia, and Undeveloped Udder. As provided herein, the improved methods of preparing CD163 gene edited animals can avoid introducing new mutations at the deleterious loci or generating new amorphic, hypomorphic, hypermorphic, neomorphic, antimorphic mutations at non-target sites. These latter changes can be particularly undesirable in elite lines as they can interfere with genes involved in desirable traits that can be controlled by multiple loci in a continuous, quantitative way in a population. Many such Quantitative Trait Loci (QTL) are known and can be typically characterized by a bell-shaped curve the trait value can be plotted against the number of observed animals. Such polygenic inheritance of traits can be common among traits recognized as commercially important such as, but not limited to, backfat, average daily feed intake, lifetime daily gain, and loin depth.

Similarly, traits associated with productivity can be multigenic and controlled by multiple QTLs. These traits were typically measured by visual inspection but methods now can include ultrasound to measure backfat thickness (bfp), loin depth (ldp) and intramuscular fat (uip). As provided in Table 15, elite lines can have desirable phenotypic traits including high backfat and loin depth while having high lifetime daily gain. Similarly, the sows of the elite lines can be fecund and have large litters, few stillborn, and sufficient teats to ween and nurse the piglets.

TABLE 15

Desirable Phenotypic Traits

| LINE | TRT | average | standard deviation |
|---|---|---|---|
| 2 | Backfat, mm | 7.8 | 1.81 |
| 3 | Backfat, mm | 9.44 | 2.77 |
| 15 | Backfat, mm | 8.16 | 2.03 |
| 65 | Backfat, mm | 7.45 | 1.88 |
| 2 | Average Daily Feed Intake, kg | 1.99 | 0.24 |
| 3 | Average Daily Feed Intake, kg | 2.13 | 0.25 |
| 15 | Average Daily Feed Intake, kg | 2.22 | 0.24 |
| 65 | Average Daily Feed Intake, kg | 2.2 | 0.27 |
| 2 | Lifetime Daily Gain, grams/day | 683.83 | 73.53 |
| 3 | Lifetime Daily Gain, grams/day | 704.23 | 80.15 |
| 15 | Lifetime Daily Gain, grams/day | 755.61 | 69.32 |
| 65 | Lifetime Daily Gain, grams/day | 800.6 | 84.48 |
| 2 | Loin depth, mm | 65.31 | 7.09 |
| 3 | Loin depth, mm | 62.61 | 7.14 |
| 15 | Loin depth, mm | 67.17 | 7.15 |
| 65 | Loin depth, mm | 81.2 | 8 |
| 2 | Total Born per litter | 13.71 | 3.191 |
| 3 | Total Born per litter | 15.06 | 3.41 |
| 15 | Total Born per litter | 10.39 | 2.71 |
| 65 | Total Born per litter | 10.31 | 2.52 |
| 2 | Still born per litter | 1.19 | 1.43 |
| 3 | Still born per litter | 1.25 | 1.50 |
| 15 | Still born per litter | 1.22 | 1.37 |
| 65 | Still born per litter | 0.77 | 1.16 |
| 2 | Teat number | 15.43 | 1.27 |
| 3 | Teat number | 15.44 | 1.29 |

The present specification provides for, and includes, gene edited pigs of selected elite lines that can be homozygous for CD163 knockout edits (CD163$^{-/-}$). In an aspect, the line can be selected from the group consisting of PIC™ Line 2, Line 3, Line 15, Line 19, Line 27, Line 62, Line 65, and progeny thereof comprising the edited CD163 genes described herein. Gene edited lines 2, 3, 15, 19, 27, 62, and 65 can comprise CD163 genomic regions as provided at Table 8 to Table 14, and can be readily distinguished from each other, from unimproved lines, and from other elite lines. In aspects according to the present specification, the heterozygous and homozygous pigs of the present specification can be free of off-site mutations. The present specification provides for, and includes, pigs and cells that can have edited CD163 genes comprising SEQ ID NOs: 1 to 18 and 426 to 505 and that can share a genetic signature comprising at least 90% of the genotypic markers of Table 8 to Table 14. The present specification provides for, and includes, pigs and cells that can have edited CD163 genes comprising SEQ ID NO: 2 and sharing a genetic signature comprising at least 90% of the genotypic markers of Table 8 to Table 14. In an aspect, the genetic signature of a CD163 edited pig or cell can share a genetic signature comprising at least 95% of the genotypic markers of Table 8 to Table 14. Also included are CD163 edited pigs or cells that can share a genetic signature comprising at least 97% of the genotypic markers of Table 8 to Table 14. In an aspect, the CD163 edited pigs or cells can share a genetic signature comprising at least 98% of the genotypic markers of Table 8 to Table 14. Another aspect provides for CD163 edited pigs or cells that can share a genetic signature comprising at least 99% of the genotypic markers of Table 8 to Table 14.

As provided herein, the gene-edited CD163$^{-/-}$ animals and cells of Lines 2, 3, 15, 19, 27, 62, and 65, can retain desirable commercial traits and can be free of deleterious off-target mutations and can comprise an edited CD163 gene comprising any of SEQ ID NOs: 1 to 18 and 426-505. In aspects of the present disclosure, the gene-edited CD163$^{-/-}$ animals and cells of Lines 2, 3, 15, 19, 27, 62, and 65, can comprise at least 90% of the loin depth of the non-edited pig line and can comprise an edited CD163 gene comprising any of SEQ ID NOs: 1 to 18 and 426-505. In aspects of the present disclosure, the gene-edited CD163$^{-/-}$ animals and cells of Lines 2, 3, 15, 19, 27, 62, and 65, can comprise at least 90% of the lifetime daily gain of the non-edited pig line. In aspects of the present disclosure, the gene-edited CD163$^{-/-}$ animals and cells of Lines 2, 3, 15, 19, 27, 62, and 65, can comprise at least 90% of the average daily feed intake of the non-edited pig line. The present specification provides for, and includes, pigs and cells that can have edited CD163 genes comprising SEQ ID NOs: 1 to 18 and 426 to 505 and can share a genetic signature comprising at least 90% of the genotypic markers of Table 8 to Table 14.

As provided herein, the gene-edited CD163$^{-/-}$ animals and cells of Lines 2, 3, 15, 19, 27, 62, and 65, can retain desirable reproductive traits. In aspects of the present disclosure, the gene-edited CD163$^{-/-}$ animals and cells of Lines 2, 3, 15, 19, 27, 62, and 65, comprising a gene-edited CD163$^{-/-}$ of SEQ ID NOs:1 to 18 or 426 to 505 can comprise at least 90% of the total born per litter of the non-edited pig line. In aspects of the present disclosure, the gene-edited CD163$^{-/-}$ animals and cells of Lines 2, 3, 15, 19, 27, 62, and 65, comprising a gene-edited CD163$^{-/-}$ of SEQ ID NOs:1 to 18 or 426 to 505 can comprise no more than 110% of the number of still born piglets compared to the non-edited pig line. In aspects of the present disclosure, the gene-edited CD163$^{-/-}$ animals and cells of Lines 2, 3, 15, 19, 27, 62, and 65, comprising a gene-edited CD163$^{-/-}$ of SEQ ID NOs:1 to 18 or 426 to 505 can comprise at least 90% of the average number of teats compared to the non-edited pig line.

In an aspect, the gene edited CD163$^{-/-}$ animals and cells of Line 2 having a gene-edited CD163$^{-/-}$ of SEQ ID NOs:1 to 18 or 426 to 505 can have backfat that is at least 90% of the amount found in unedited Line 2 animals. In an aspect, gene edited CD163$^{-/-}$ animals and cells of Line 2 can have backfat that is at least 97% of the unedited Line 2 animal.

In an aspect, the gene edited CD163$^{-/-}$ animals and cells of Line 3 having a gene-edited CD163$^{-/-}$ of SEQ ID NOs:1 to 18 or 426 to 505 can have backfat that is at least 90% of the amount found in unedited Line 3 animals. In an aspect, gene edited CD163$^{-/-}$ animals and cells of Line 3 can have backfat that is at least 95% of the unedited Line 3 animal. In an aspect, gene edited CD163$^{-/-}$ animals and cells of Line 3 can have backfat that is at least 97% of the unedited Line 2 animal.

In an aspect, the gene edited CD163$^{-/-}$ animals and cells of Line 15 having a gene-edited CD163$^{-/-}$ of SEQ ID NOs:1 to 18 or 426 to 505 can have backfat that is at least 90% of the amount found in unedited Line 15 animals. In an aspect, gene edited CD163$^{-/-}$ animals and cells of Line 15 can have backfat that is at least 95% of the unedited Line 15 animal. In an aspect, gene edited CD163$^{-/-}$ animals and cells of Line 15 can have backfat that is at least 97% of the unedited Line 2 animal.

In an aspect, the gene edited CD163$^{-/-}$ animals and cells of Line 19 having a gene-edited CD163$^{-/-}$ of SEQ ID NOs:1 to 18 or 426 to 505 can have backfat that is at least 90% of the amount found in unedited Line 19 animals. In an aspect, gene edited CD163$^{-/-}$ animals and cells of Line 19 can have backfat that is at least 95% of the unedited Line 19 animal. In an aspect, gene edited CD163$^{-/-}$ animals and cells of Line 19 have can backfat that is at least 97% of the unedited Line 2 animal.

In an aspect, the gene edited CD163$^{-/-}$ animals and cells of Line 27 having a gene-edited CD163$^{-/-}$ of SEQ ID NOs:

1 to 18 or 426 to 505 can have backfat that is at least 90% of the amount found in unedited Line 27 animals. In an aspect, gene edited CD163$^{-/-}$ animals and cells of Line 27 can have backfat that is at least 95% of the unedited Line 27 animal. In an aspect, gene edited CD163$^{-/-}$ animals and cells of Line 27 can have backfat that is at least 97% of the unedited Line 2 animal.

In an aspect, the gene edited CD163$^{-/-}$ animals and cells of Line 62 having a gene-edited CD163$^{-/-}$ of SEQ ID NOs:1 to 18 or 426 to 505 can have backfat that is at least 90% of the amount found in unedited Line 62 animals. In an aspect, gene edited CD163$^{-/-}$ animals and cells of Line 62 can have backfat that is at least 95% of the unedited Line 62 animal. In an aspect, the gene edited CD163$^{-/-}$ animals and cells of Line 62 having a gene-edited CD163$^{-/-}$ of SEQ ID NO: 2 can have backfat that is at least 95% of the amount found in unedited Line 62 animals. In an aspect, gene edited CD163$^{-/-}$ animals and cells of Line 62 can have backfat that is at least 97% of the unedited Line 2 animal.

In an aspect, the gene edited CD163$^{-/-}$ animals and cells of Line 65 having a gene-edited CD163$^{-/-}$ of SEQ ID NOs:1 to 18 or 426 to 505 can have backfat that is at least 90% of the amount found in unedited Line 65 animals. In an aspect, gene edited CD163$^{-/-}$ animals and cells of Line 65 can have backfat that is at least 95% of the unedited Line 65 animal. In an aspect, gene edited CD163$^{-/-}$ animals and cells of Line 65 can have backfat that is at least 97% of the unedited Line 2 animal.

In an aspect, the gene edited CD163$^{-/-}$ animals and cells of Line 2 having a gene-edited CD163$^{-/-}$ of SEQ ID NOs:1 to 18 or 426 to 505 can have a number of total born per litter that is at least 90% of the amount found in unedited Line 2 animals. In an aspect, gene edited CD163$^{-/-}$ animals and cells of Line 2 can have a number of total born per litter that is at least 95% of the unedited Line 2 animal. In an aspect, gene edited CD163$^{-/-}$ animals and cells of Line 2 can have a number of total born per litter that is at least 97% of the unedited Line 2 animal.

In an aspect, the gene edited CD163$^{-/-}$ animals and cells of Line 3 having a gene-edited CD163$^{-/-}$ of SEQ ID NOs: 1 to 18 or 426 to 505 can have a number of total born per litter that is at least 90% of the amount found in unedited Line 3 animals. In an aspect, gene edited CD163$^{-/-}$ animals and cells of Line 3 can have a number of total born per litter that is at least 95% of the unedited Line 3 animal. In an aspect, gene edited CD163$^{-/-}$ animals and cells of Line 3 can have a number of total born per litter that is at least 97% of the unedited Line 3 animal.

In an aspect, the gene edited CD163$^{-/-}$ animals and cells of Line 15 having a gene-edited CD163$^{-/-}$ of SEQ ID NOs: 1 to 18 or 426 to 505 can have a number of total born per litter that is at least 90% of the amount found in unedited Line 15 animals. In an aspect, gene edited CD163$^{-/-}$ animals and cells of Line 15 can have a number of total born per litter that is at least 95% of the unedited Line 15 animal. In an aspect, gene edited CD163$^{-/-}$ animals and cells of Line 15 can have a number of total born per litter that is at least 97% of the unedited Line 15 animal.

In an aspect, the gene edited CD163$^{-/-}$ animals and cells of Line 19 having a gene-edited CD163$^{-/-}$ of SEQ ID NOs:1 to 18 or 426 to 505 can have a number of total born per litter that is at least 90% of the amount found in unedited Line 19 animals. In an aspect, gene edited CD163$^{-/-}$ animals and cells of Line 19 can have a number of total born per litter that is at least 95% of the unedited Line 19 animal. In an aspect, gene edited CD163$^{-/-}$ animals and cells of Line 19 can have a number of total born per litter that is at least 97% of the unedited Line 19 animal.

In an aspect, the gene edited CD163$^{-/-}$ animals and cells of Line 27 having a gene-edited CD163$^{-/-}$ of SEQ ID NOs:1 to 18 or 426 to 505 can have a number of total born per litter that is at least 90% of the amount found in unedited Line 27 animals. In an aspect, gene edited CD163$^{-/-}$ animals and cells of Line 27 can have a number of total born per litter that is at least 95% of the unedited Line 27 animal. In an aspect, gene edited CD163$^{-/-}$ animals and cells of Line 27 can have a number of total born per litter that is at least 97% of the unedited Line 27 animal.

In an aspect, the gene edited CD163$^{-/-}$ animals and cells of Line 62 having a gene-edited CD163$^{-/-}$ of SEQ ID NOs:1 to 18 or 426 to 505 can have a number of total born per litter that is at least 90% of the amount found in unedited Line 62 animals. In an aspect, gene edited CD163$^{-/-}$ animals and cells of Line 62 can have a number of total born per litter that is at least 95% of the unedited Line 62 animal. In an aspect, gene edited CD163$^{-/-}$ animals and cells of Line 62 can have a number of total born per litter that is at least 97% of the unedited Line 62 animal.

In an aspect, the gene edited CD163$^{-/-}$ animals and cells of Line 65 having a gene-edited CD163$^{-/-}$ of SEQ ID NOs:1 to 18 or 426 to 505 can have a number of total born per litter that is at least 90% of the amount found in unedited Line 65 animals. In an aspect, gene edited CD163$^{-/-}$ animals and cells of Line 65 can have a number of total born per litter that is at least 95% of the unedited Line 65 animal. In an aspect, gene edited CD163$^{-/-}$ animals and cells of Line 65 can have a number of total born per litter that is at least 97% of the unedited Line 65 animal.

The present specification provides for and includes CD163 edited animals comprising the germplasm of PIC™ Line 15, PIC™ Line 17, PIC™ Line 27, PIC™ Line 65, PIC™ Line 14, PIC™ Line 62, PIC337, PIC800, PIC280, PIC327, PIC408, PIC™ 399, PIC410, PIC415, PIC359, PIC380, PIC837, PIC260, PIC265, PIC210, PIC™ Line 2, PIC™ Line 3, PIC™ Line 4, PIC™ Line 5, PIC™ Line 18, PIC™ Line 19, PIC™ Line 92, PIC95, PIC™ CAMBOROUGH®, PIC1070, PIC™ CAMBOROUGH® 40, PIC™ CAMBOROUGH® 22, PIC1050, PIC™ CAMBOROUGH® 29, PIC™ CAMBOROUGH® 48, or PIC™ CAMBOROUGH® x54. As used herein, the term germplasm includes an intact genome present in cells or nuclei and comprising chromosomes. The term germplasm may include any gamete, germ cell, or any somatic cell from which an animal can be cloned. The edited germplasm can comprise an edit having an edited genomic sequence of any one of SEQ ID NOs: 426 to 505. The edited germplasm can comprise an edit having an edited genomic sequence of any one of SEQ ID NOs: 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, or 505. The edited germplasm can comprise a genome that is 80%, 85%, 90%, 95% similar or identical to PIC™ Line 15. The edited germplasm can comprise a genome that is 80%, 85%, 90%, 95% similar or identical to PIC™ Line 17. The edited germplasm can comprise a genome that is 80%, 85%, 90%, 95% similar or identical to PIC™ Line 27. The edited germplasm can comprise a genome that is 80%, 85%, 90%, 95% similar or identical to PIC™ Line 65. The edited germplasm can comprise a genome that is 80%, 85%, 90%, 95% similar or identical to PIC™ Line 14. The edited germplasm can comprise a genome that is 80%, 85%, 90%, 95% similar or identical to PIC™ Line 62. The edited germplasm can comprise a genome that is 80%, 85%, 90%, 95% similar or identical to PIC337. The edited germplasm can comprise a genome that is 80%, 85%, 90%, 95% similar or identical to PIC800. The edited germplasm can comprise a genome that is 80%, 85%, 90%, 95% similar or identical to PIC280. The edited germplasm can comprise a genome that is 80%, 85%, 90%, 95% similar or identical to PIC327. The edited germplasm can comprise a genome that is 80%, 85%, 90%, 95% similar or identical to PIC408. The edited germplasm can comprise a genome that is 80%, 85%, 90%, 95% similar or identical to PIC™ 399. The edited germplasm can comprise a genome that is 80%, 85%, 90%, 95% similar or identical to PIC410. The edited germplasm can comprise a genome that is 80%, 85%, 90%, 95% similar or identical to PIC415. The edited germplasm can comprise a genome that is 80%, 85%, 90%, 95% similar or identical to PIC359. The edited germplasm can comprise a genome that is 80%, 85%, 90%, 95% similar or identical to PIC380. The edited germplasm can comprise a genome that is 80%, 85%, 90%, 95% similar or identical to PIC837. The edited germplasm can comprise a genome that is 80%, 85%, 90%, 95% similar or identical to PIC260. The edited germplasm can comprise a genome that is 80%, 85%, 90%, 95% similar or identical to PIC265. The edited germplasm can comprise a genome that is 80%, 85%, 90%, 95% similar or identical to PIC210. The edited germplasm can comprise a genome that is 80%, 85%, 90%, 95% similar or identical to PIC™ Line 2. The edited germplasm can comprise a genome that is 80%, 85%, 90%, 95% similar or identical to PIC™ Line 3. The edited germplasm can comprise a genome that is 80%, 85%, 90%, 95% similar or identical to PIC™ Line 4. The edited germplasm can comprise a genome that is 80%, 85%, 90%, 95% similar or identical to PIC™ Line 5. The edited germplasm can comprise a genome that is 80%, 85%, 90%, 95% similar or identical to PIC™ Line 18. The edited germplasm can comprise a genome that is 80%, 85%, 90%, 95% similar or identical to PIC™ Line 19. The edited germplasm can comprise a genome that is 80%, 85%, 90%, 95% similar or identical to PIC™ Line 92. The edited germplasm can comprise a genome that is 80%, 85%, 90%, 95% similar or identical to PIC95. The edited germplasm can comprise a genome that is 80%, 85%, 90%, 95% similar or identical to PIC™ CAMBOROUGH®. The edited germplasm can comprise a genome that is 80%, 85%, 90%, 95% similar or identical to PIC1070. The edited germplasm can comprise a genome that is 80%, 85%, 90%, 95% similar or identical to PIC™ CAMBOROUGH® 40. The edited germplasm can comprise a genome that is 80%, 85%, 90%, 95% similar or identical to PIC™ CAMBOROUGH® 22. The edited germplasm can comprise a genome that is 80%, 85%, 90%, 95% similar or identical to PIC1050. The edited germplasm can comprise a genome that is 80%, 85%, 90%, 95% similar or identical to PIC™ CAMBOROUGH® 29. The edited germplasm can comprise a genome that is 80%, 85%, 90%, 95% similar or identical to PIC™ CAMBOROUGH® 48. The edited germplasm can comprise a genome that is 80%, 85%, 90%, 95% similar or identical to PIC™ CAMBOROUGH® x54.

The present specification provides for and includes CD163 edited animals comprising the germplasm of PIC™ Line 2, Line 3, Line 15, Line 19, Line 27, Line 62, or Line 65. The edited germplasm can comprise an edit having an edited genomic sequence of any one of SEQ ID NOs: 426 to 505. The edited germplasm can comprise an edit having an edited genomic sequence of any one of SEQ ID NOs: 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, or 505. The edited germplasm can comprise an edit having an edited genomic sequence as set forth in SEQ ID NO: 453. The edited germplasm can comprise a genome that is 80%, 85%, 90%, 95% similar or identical to PIC™ Line 2 with a CD163 edited sequence comprising SEQ ID NO: 453. The edited germplasm can comprise a genome that is 80%, 85%, 90%, 95% similar or identical to PIC™ Line 3 with a CD163 edited sequence comprising SEQ ID NO: 453. The edited germplasm can comprise a genome that is 80%, 85%, 90%, 95% similar or identical to PIC™ Line 15 with a CD163 edited sequence comprising SEQ ID NO: 453. The edited germplasm can comprise a genome that is 80%, 85%, 90%, 95% similar or identical to PIC™ Line 19 with a CD163 edited sequence comprising SEQ ID NO: 453. The edited germplasm can comprise a genome that is 80%, 85%, 90%, 95% similar or identical to 80%, 85%, 90%, 95% similar or identical to PIC™ Line 27 with a CD163 edited sequence comprising SEQ ID NO: 453. The edited germplasm can comprise a genome that is 80%, 85%, 90%, 95% similar or identical to PIC™ Line 62 with a CD163 edited sequence comprising SEQ ID NO: 453. The edited germplasm can comprise a genome that is 80%, 85%, 90%, 95% similar or identical to PIC™ Line 65 with a CD163 edited sequence comprising SEQ ID NO: 453.

The edited germplasm can comprise an edit having an edited genomic sequence as set forth in SEQ ID NO: 489. The edited germplasm can comprise a genome that is 80%, 85%, 90%, 95% similar or identical to PIC™ Line 2 with a CD163 edited sequence comprising SEQ ID NO: 489. The edited germplasm can comprise a genome that is 80%, 85%, 90%, 95% similar or identical to PIC™ Line 3 with a CD163 edited sequence comprising SEQ ID NO: 489. The edited germplasm can comprise a genome that is 80%, 85%, 90%, 95% similar or identical to PIC™ Line 15 with a CD163 edited sequence comprising SEQ ID NO: 489. The edited germplasm can comprise a genome that is 80%, 85%, 90%, 95% similar or identical to PIC™ Line 19 with a CD163 edited sequence comprising SEQ ID NO: 489. The edited germplasm can comprise a genome that is 80%, 85%, 90%, 95% similar or identical to 80%, 85%, 90%, 95% similar or identical to PIC™ Line 27 with a CD163 edited sequence comprising SEQ ID NO: 489. The edited germplasm can comprise a genome that is 80%, 85%, 90%, 95% similar or identical to PIC™ Line 62 with a CD163 edited sequence comprising SEQ ID NO: 489. The edited germplasm can comprise a genome that is 80%, 85%, 90%, 95% similar or identical to PIC™ Line 65 with a CD163 edited sequence comprising SEQ ID NO: 489. The edited germplasm can have a predicted exon 7 amino acid sequence from any one of SEQ ID NOs: 506-517. The edited germplasm can have a predicted exon 7 amino acid sequence as set forth in SEQ ID NO: 513.

The edited germplasm can comprise an edit having an edited genomic sequence as set forth in SEQ ID NO: 505. The edited germplasm can comprise a genome that is 80%, 85%, 90%, 95% similar or identical to PIC™ Line 2 with a CD163 edited sequence comprising SEQ ID NO: 505. The edited germplasm can comprise a genome that is 80%, 85%, 90%, 95% similar or identical to PIC™ Line 3 with a CD163 edited sequence comprising SEQ ID NO: 505. The edited germplasm can comprise a genome that is 80%, 85%, 90%, 95% similar or identical to PIC™ Line 15 with a CD163 edited sequence comprising SEQ ID NO: 505. The edited germplasm can comprise a genome that is 80%, 85%, 90%, 95% similar or identical to PIC™ Line 19 with a CD163 edited sequence comprising SEQ ID NO: 505. The edited germplasm can comprise a genome that is 80%, 85%, 90%, 95% similar or identical to 80%, 85%, 90%, 95% similar or identical to PIC™ Line 27 with a CD163 edited sequence comprising SEQ ID NO: 505. The edited germplasm can comprise a genome that is 80%, 85%, 90%, 95% similar or identical to PIC™ Line 62 with a CD163 edited sequence comprising SEQ ID NO: 505. The edited germplasm can comprise a genome that is 80%, 85%, 90%, 95% similar or identical to PIC™ Line 65 with a CD163 edited sequence comprising SEQ ID NO: 505. The edited germplasm can have a predicted exon 7 amino acid sequence as set forth in SEQ ID NO: 518.

The present specification also provides for and includes cells of PIC™ Line 2, Line 3, Line 15, Line 19, Line 27, Line 62, or Line 65. In some embodiments, a cell of PIC™ Line 2 can comprise an edited genomic sequence of any one of SEQ ID NOs: 426 to 505. The cell of PIC™ Line 2 can comprise an editing genomic sequence as set forth in SEQ ID NO: 453. In some embodiments, a cell of PIC™ Line 3 can comprise an edited genomic sequence of any one of SEQ ID NOs: 426 to 505. The cell of PIC™ Line 3 can comprise an editing genomic sequence as set forth in SEQ ID NO: 453. In some embodiments, a cell of PIC™ Line 15 can comprise an edited genomic sequence of any one of SEQ ID NOs: 426 to 505. The cell of PIC™ Line 15 can comprise an edited genomic sequence as set forth in SEQ Id NO: 453. In some embodiments, a cell of PIC™ Line 19 can comprise an edited genomic sequence of any one of SEQ ID NOs: 426 to 505. The cell of PIC™ Line 19 can comprise an editing genomic sequence as set forth in SEQ Id NO: 453. In some embodiments, a cell of PIC™ Line 27 can comprise an edited genomic sequence of any one of SEQ ID NOs: 426 to 505. The cell of PIC™ Line 27 can comprise an editing genomic sequence as set forth in SEQ ID NO: 453. In some embodiments, a cell of PIC™ Line 62 can comprise an edited genomic sequence of any one of SEQ ID NOs: 426 to 505. The cell of PIC™ Line 62 can comprise an editing genomic sequence as set forth in SEQ Id NO: 453. In some embodiments, a cell of PIC™ Line 65 can comprise an edited genomic sequence of any one of SEQ ID NOs: 426 to 505. The cell of PIC™ Line 65 can comprise an editing genomic sequence as set forth in SEQ Id NO: 453. The edited germplasm can have a predicted exon 7 amino acid sequence as set forth in SEQ ID NO: 513.

The present specification provides for, and includes, hybrid animals that can comprise the CD163 gene edits characterized by SEQ ID NOs: 1 to 18 and 426 to 505. In some configurations, gene edit can comprise SEQ ID NO: 453. In an aspect, the hybrid animal can be a CD163$^{-/-}$ hybrid animal of the CAMBOROUGH® (PIC™ UK Limited, Basingstoke, UK) line. CAMBOROUGH® pigs are hybrids that can be prepared by a cross between Line 2 and Line 3. In an aspect, the hybrid animal can be a CD163$^{-/-}$ hybrid animal of the CAMBOROUGH® line having an edited CD163 gene of SEQ ID NO: 2. In an aspect, the hybrid animal can be a CD163$^{-/-}$ hybrid animal of the CAMBOROUGH® line having an edited CD163 gene of SEQ ID NO: 426-458. In various aspects, the hybrid animal can be a CD163$^{-/-}$ hybrid animal of the CAMBOROUGH® line having an edited CD163 gene of SEQ ID NO: 453. In an aspect, the hybrid animal can be a CD163$^{-/-}$ hybrid animal of the CAMBOROUGH® line having an edited CD163 gene of SEQ ID NO: 459-504. In various aspects, the hybrid animal can be a CD163$^{-/-}$ hybrid animal of the CAMBOROUGH® line having an edited CD163 gene sequence of SEQ ID NO: 489. CAMBOROUGH® hybrid pigs are pigs that have large litters with uniform and vigorous piglets. CAMBOROUGH® hybrid pigs have a long productive life and have a low mortality. CAMBOROUGH® CD163$^{-/-}$ hybrid pigs retain these desirable commercial traits. In an aspect, CAMBOROUGH® CD163$^{-/-}$ hybrid pigs have litter sizes that are indistinguishable from non-gene edited CAMBOROUGH® hybrid pigs. In aspects according to the present specification, the heterozygous and homozygous pigs of the present specification are free of off-site mutations.

The present specification further provides, and includes, methods for preparing CD163 gene edited hybrid animals. In an aspect, a first parent can comprise a CD163 gene edited boar, gilt, or sow of one of PIC™ Line 2, Line 3, Line 15, Line 19, Line 27, Line 62, or Line 65 for crossing to a second parent. In an aspect, the genome of a gene edited first parent can comprise a sequence selected from the group consisting of SEQ ID NOs: 1 to 18 or 426 to 505. In some aspects, the genome can comprise SEQ ID NO: 453. In various aspects, the genome can comprise SEQ ID NO: 489. In various aspects, the genome can comprise SEQ ID NO: 505. In an aspect, the method can comprise a second parent selected from the group consisting of a CD163 gene edited boar, gilt, or sow of one of PIC™ Line 2, Line 3, Line 15, Line 19, Line 27, Line 62, or Line 65. Also provided for, and included, by the present specification are methods of preparing CD163 edited animals that can comprise crossing a progeny of any one of PIC™ Line 2, Line 3, Line 15, Line 19, Line 27, Line 62, or Line 65.

In an aspect, the present specification provides for heterozygous pigs from lines 2, 3, 15, and 65 (Table 8, Table 9, Table 10, and Table 14, respectively) that can have at least one copy of the CD163 gene successfully edited in a knock-out edit. These edited pigs can exhibit a healthy phenotype with no noticeable deleterious effects from the edit. In another aspect, the specification provides for pigs from lines 19, 27, and 62 (Table 11, Table 12, and Table 13, respectively) that can be edited using the methods disclosed herein to generate edited pigs with healthy phenotypes. The heterozygous pigs can be crossed with non-edited animals of the corresponding line to produce F1 heterozygous pigs. In an embodiment, heterozygous pigs of lines 2, 3, 15, and 65 can be crossed to a second heterozygous pig of lines 2, 3, 15, and 65, and homozygous CD163 edited pigs can be produced in Mendelian proportions. Notably, the gene edits can be unique and identifiable using SEQ ID NOs: 1 to 18 and 426 to 505 and share genetic signatures comprising at least 90% of the genotypic markers of Table 8 to Table 14, thereby enabling the detection and breeding of the CD163 gene edited genomes in any progeny generation. In an aspect, the genetic signatures can share 95% or more of the genotypic markers of Table 8 to Table 14. In another aspect, the genetic signatures share 97% or more of the genotypic markers of Table 8 to Table 14. Also included are genetic signatures that can share 98% or more of the genotypic markers of Table 8 to Table 14. Importantly, the linkage of the CD163 edits to the genomic regions identifiable using the genotypic markers of Table 8 to Table 14 can enable the preparation of any progeny animal having the desired edits and the tracking of the edited regions in any number of progeny generations. In aspects according to the present specification, the heterozygous and homozygous pigs of the present specification can be free of off-site mutations.

The present specification provides for, and includes, an embryo or zygote that can be obtained from an elite line of pigs. In an aspect, the embryo or zygote can be obtained from an elite porcine line selected from the group consisting of PIC™ Line 2, Line 3, Line 15, Line 19, Line 27, Line 62, or Line 65. In an aspect, the embryo or zygote can be a frozen embryo or zygote. In another aspect, the embryo or zygote can be a frozen blastocyst. As provided herein, the embryos can be prepared from in vitro matured oocytes collected from estrus synchronized gilts. The surrounding cumulus cells can be removed from the in vitro matured oocytes and incubated with washed boar spermatozoa and incubated. After incubation, presumptive zygotes can be microinjected with an RNP mixture comprising the CRISPR-Cas endonuclease and guide RNA combinations comprising the first 20 nucleotides of SEQ ID NOs: 22 to 271 or 347 to 425 listed in Table 3. Injected embryos can be transferred to a surrogate female at the 1 to 4 cell stage. In an aspect, the RNP mixture can further include repair templates listed in Table 6 (SEQ ID NOs: 1 to 13). In an aspect, injected zygotes can be surgically implanted into the oviducts of estrus synchronized, un-mated surrogate females by a mid-line laparotomy under general anesthesia (each surrogate receives 40-60 injected embryos).

The present specification provides for, and includes, gene edited pigs of selected elite lines that can be CD163$^{-/-}$. In an aspect, the line can be PIC™ Line 15, PIC™ Line 17, PIC™ Line 27, PIC™ Line 65, PIC™ Line 14, PIC™ Line 62, PIC337, PIC800, PIC280, PIC327, PIC408, PIC™ 399, PIC410, PIC415, PIC359, PIC380, PIC837, PIC260, PIC265, PIC210, PIC™ Line 2, PIC™ Line 3, PIC™ Line 4, PIC™ Line 5, PIC™ Line 18, PIC™ Line 19, PIC™ Line 92, PIC95, PIC™ CAMBOROUGH®, PIC1070, PIC™ CAMBOROUGH® 40, PIC™ CAMBOROUGH® 22, PIC1050, PIC™ CAMBOROUGH® 29, PIC™ CAMBOROUGH® 48, or PIC™ CAMBOROUGH® x54. In an aspect, the line can be selected from the group consisting of PIC™ Line 2, Line 3, Line 15, Line 19, Line 27, Line 62, Line 65, and progeny thereof comprising the edited CD163 genes described herein. Gene edited lines 2, 3, 15, 19, 27, 62, and 65 comprise CD163 genomic regions as provided above at Table 8 to Table 14, and can be readily distinguished from each other, from unimproved lines, and from other elite lines. Similarly, progeny of lines 2, 3, 15, 19, 27, 62, and 65 comprising the CD163$^{-/-}$ genomic regions as provided in Table 8 to Table 14 can be identified. Accordingly, the present specification provides for progeny pigs that can have a CD163$^{-/-}$ genomic region.

The present specification provides for and includes hybrid porcine lines comprising an edited CD163 gene of the present teachings. In some aspects, the hybrid porcine line can be produced by crossing an edited PIC™ line with at least one other edited PIC™ line. In some aspects, the porcine line can be produced by serial crosses to introduce germplasm from three or more porcine lines. In an aspect, the line can be PIC™ Line 15, PIC™ Line 17, PIC™ Line 27, PIC™ Line 65, PIC™ Line 14, PIC™ Line 62, PIC337, PIC800, PIC280, PIC327, PIC408, PIC™ 399, PIC410, PIC415, PIC359, PIC380, PIC837, PIC260, PIC265, PIC210, PIC™ Line 2, PIC™ Line 3, PIC™ Line 4, PIC™ Line 5, PIC™ Line 18, PIC™ Line 19, PIC™ Line 92, PIC95, PIC™ CAMBOROUGH®, PIC1070, PIC™ CAMBOROUGH® 40, PIC™ CAMBOROUGH® 22, PIC1050, PIC™ CAMBOROUGH® 29, PIC™ CAMBOROUGH® 48, or PIC™ CAMBOROUGH® x54.

In various aspects, PIC™ Line 65 is sold under the trade name PIC337. In various aspects, PIC™ line 62 is sold under the tradename PIC408. In various aspects, hybrid pigs made by crossing PIC™ lines 15 and 17 are sold under the tradenames PIC800 or PIC280. In various aspects, PIC™ Line 27 is sold under the tradename PIC327. In various aspects, hybrids created from crossing PIC™ Line 65 and PIC™ Line 62 is sold under the tradenames PIC399, PIC410 or PIC415. In various aspects, hybrids created from crossing PIC™ Line 65 and Pic Line 27 are sold under the tradename PIC359. In various aspects, hybrids prepared from crossing PIC™ Line 800 pigs (which is a hybrid of PIC™ Line 15 and PIC™ Line 17) to PIC™ Line 65 pigs are sold under the tradenames PIC380 or PIC837. In various aspects, PIC™ Line 14 is sold under the trade name PIC260. In various aspects, hybrids created from crossing PIC™ Line 14 and PIC™ Line 65 are sold under the tradename PIC265. In various aspects, hybrids created by crossing PIC™ Line 2 and PIC™ Line 3 are sold under the tradenames PIC210, PIC™ CAMBOROUGH®, and PIC1050. In various aspects, hybrids of PIC™ Line 3 and PIC™ Line 92 are sold under the tradename PIC95. In various configurations, hybrids made from crossing PIC™ Line 19 and PIC™ Line 3 are sold under the tradename PIC1070. In various aspects, hybrids created by crossing PIC™ Line 18 and PIC™ Line 3 are sold under the tradename PIC™ CAMBOROUGH® 40. In various aspects, hybrids created from crossing PIC™ Line 19 and PIC1050 (which is itself a hybrid of PIC™ lines 2 and 3) are sold under the tradename PIC™ CAMBOROUGH® 22. In various aspects, hybrids created from crossing PIC™ Line 2 and PIC1070 (which is itself a hybrid of PIC™ lines 19 and 3) are sold under the tradename PIC™ CAMBOROUGH® 29. In various aspects, hybrids created from crossing PIC™ Line 18 and PIC1050 (which is itself a hybrid of PIC™ lines 2 and 3) are sold under the tradename PIC™ CAMBOROUGH® 48. In various aspects, hybrids created from crossing PIC™ Line 4 and PIC™ Line 5 are sold under the tradename PIC™ CAMBOROUGH® x54. The present teachings provide for and include pigs of any of the forgoing lines or hybrids comprising a CD163 edit of the present teachings.

In various aspects, the present teachings provide for an include pigs comprising an edited CD163 gene comprising an edited sequence set forth in SEQ ID NOs: 453, 489, or 505 wherein the pig can be a pig of PIC™ Line 15, PIC™ Line 17, PIC™ Line 27, PIC™ Line 65, PIC™ Line 14, PIC™ Line 62, PIC™ Line 2, PIC™ Line 3, PIC™ Line 4, PIC™ Line 5, PIC™ Line 18, PIC™ Line 19, PIC™ Line 92, or a hybrid of two or more of these lines. In various aspects, the hybrid pig can be a cross of PIC™ Line 15 and PIC™ Line 17, PIC™ Line 65 and PIC™ Line 62, PIC™ Line 65 and PIC™ Line 27, a serial hybrid of PIC™ Line 15 and PIC™ Line 17, wherein the hybrid offspring is then crossed to PIC™ Line 65, PIC™ Line 14 and PIC™ Line 65, PIC™ Line 2 and PIC™ Line 3, PIC™ Line 3 and PIC™ Line 92, PIC™ Line 19 and PIC™ Line 3, PIC™ Line 18 and PIC™ Line 3, a serial hybrid between a hybrid pig of PIC™ Line 2 and PIC™ Line 3 and a pig of PIC™ Line 19, a serial hybrid between a hybrid pig of PIC™ Line 19 and PIC™ Line 3 and a pig of PIC™ Line 2, a serial hybrid between a hybrid of PIC™ Line 2 and PIC™ Line 3 crossed to a pig of PIC™ Line 18, or a hybrid of PIC™ Line 4 and PIC™ Line 5.

In various aspects, the hybrid line comprising an edited CD163 gene can be produced by crossing two or more of lines 2, 3, 15, 19, 27, 62, or 65. In some aspects, the hybrid line comprising an edited CD163 gene can be a CAMBOROUGH® line. CAMBOROUGH® pigs are hybrids that can be prepared by a cross between Line 2 and Line 3. In various aspects, the hybrid line can comprise a PIC™ 837 hybrid line comprising an edited CD163 gene. PIC™ 837 pigs are hybrids that can be prepared by crossing PIC™ Line 800 pigs to PIC™ Line 65 pigs.

The present specification provides for, and includes, hybrid CD163$^{-/-}$ progeny lines comprising one CD163$^{-/-}$ genomic region that can be obtained from lines 2, 3, 15, 19, 27, 62, or 65, and a second CD163$^{-/-}$ genomic region that can be obtained from a different line selected from lines 2, 3, 15, 19, 27, 62, or 65. In an aspect, a hybrid CD163$^{-/-}$ progeny line can comprise a CD163$^{-/-}$ allele in a genomic region according to Table 8 and a CD163$^{-/-}$ allele in a genomic region according to Table 10. In an aspect, a hybrid CD163$^{-/-}$ progeny line can comprise a CD163$^{-/-}$ allele in a genomic region according to Table 8 and a CD163$^{-/-}$ allele in a genomic region according to Table 14. In an aspect, a hybrid CD163$^{-/-}$ progeny line can comprise a CD163$^{-/-}$ allele in a genomic region according to Table 9 and a CD163$^{-/-}$ allele in a genomic region according to Table 10. In an aspect, a hybrid CD163$^{-/-}$ progeny line can comprise a CD163$^{-/-}$ allele in a genomic region according to Table 9 and a CD163$^{-/-}$ allele in a genomic region according to Table 14.

The present specification provides for, and includes, hybrid animals that can comprise the CD163 gene edits characterized by SEQ ID NOs: 1 to 18 and 426 to 505. In an aspect, the hybrid animals comprising the CD163 gene edits can be characterized by SEQ ID NO: 2. In an aspect, the hybrid animals comprising the CD163 gene edits can be characterized by SEQ ID NO: 426-458. In an aspect, the hybrid animals comprising the CD163 gene edits can be characterized by SEQ ID NO: 453. In an aspect, the hybrid animals comprising the CD163 gene edits can be characterized by SEQ ID NO: 459-504. In an aspect, the hybrid animals comprising the CD163 gene edits can be characterized by SEQ ID NO: 489. In an aspect, the hybrid animal can be a CD163$^{-/-}$ hybrid animals of the CAMBOROUGH® line. CAMBOROUGH® pigs are hybrids that can be prepared by a cross between Line 2 and Line 3.

In various aspects, the hybrid pig can comprise SEQ ID NO: 2 in a genomic region according to Table 8 and SEQ ID NO: 2 in a genomic region according to Table 10. In an aspect, the hybrid pig can comprise SEQ ID NO: 453 in a genomic region according to Table 8 and SEQ ID NO: 453 in a genomic region according to Table 10. In an aspect, the hybrid pig can comprise SEQ ID NO: 489 in a genomic region according to Table 8 and SEQ ID NO: 489 in a genomic region according to Table 10. In an aspect, a hybrid CD163$^{-/-}$ progeny line can comprise SEQ ID NO: 2 in a genomic region according to Table 8 and SEQ ID NO: 2 in a genomic region according to Table 14. In an aspect, a hybrid CD163$^{-/-}$ progeny line can comprise SEQ ID NO: 453 in a genomic region according to Table 8 and SEQ ID NO: 453 in a genomic region according to Table 14. In an aspect, a hybrid CD163$^{-/-}$ progeny line can comprise SEQ ID NO: 489 in a genomic region according to Table 8 and SEQ ID NO: 489 in a genomic region according to Table 14. In an aspect, a hybrid CD163$^{-/-}$ progeny line can comprise SEQ ID NO: 2 in a genomic region according to Table 9 and SEQ ID NO: 2 in a genomic region according to Table 10. In an aspect, a hybrid CD163$^{-/-}$ progeny line can comprise SEQ ID NO: 453 in a genomic region according to Table 9 and SEQ ID NO: 453 in a genomic region according to Table 10. In an aspect, a hybrid CD163$^{-/-}$ progeny line can comprise SEQ ID NO: 489 in a genomic region according to Table 9 and SEQ ID NO: 489 in a genomic region according to Table 10. In an aspect, a hybrid CD163$^{-/-}$ progeny line can comprise SEQ ID NO: 489 in a genomic region according to Table 9 and SEQ ID NO: 489 in a genomic region according to Table 10. In an aspect, a hybrid CD163$^{-/-}$ progeny line can comprise SEQ ID NO: 2 in a genomic region according to Table 8 and SEQ ID NO: 2 in a genomic region according to Table 10. In an aspect, the hybrid pig can comprise SEQ ID NO: 453 in a genomic region according to Table 8 and SEQ ID NO: 453 in a genomic region according to Table 10. In an aspect, the hybrid pig can comprise SEQ ID NO: 489 in a genomic region according to Table 8 and SEQ ID NO: 489 in a genomic region according to Table 10. In an aspect, a hybrid CD163$^{-/-}$ progeny line can comprise SEQ ID NO: 2 in a genomic region according to Table 8 and SEQ ID NO: 2 in a genomic region according to Table 14. In an aspect, a hybrid CD163$^{-/-}$ progeny line can comprise SEQ ID NO: 453 in a genomic region according to Table 8 and SEQ ID NO: 453 in a genomic region according to Table 14. In an aspect, a hybrid CD163$^{-/-}$ progeny line can comprise SEQ ID NO: 489 in a genomic region according to Table 8 and SEQ ID NO: 489 in a genomic region according to Table 14. In an aspect, a hybrid CD163$^{-/-}$ progeny line can comprise SEQ ID NO: 2 in a genomic region according to Table 9 and SEQ ID NO: 2 in a genomic region according to Table 10. In an aspect, a hybrid CD163$^{-/-}$ progeny line can comprise SEQ ID NO: 453 in a genomic region according to Table 9 and SEQ ID NO: 453 in a genomic region according to Table 10. In an aspect, a hybrid CD163$^{-/-}$ progeny line can comprise SEQ ID NO: 489 in a genomic region according to Table 9 and SEQ ID NO: 489 in a genomic region according to Table 10. In aspects according to the present specification, the heterozygous and homozygous pigs of the present specification can be free of off-site mutations.

In an aspect, the hybrid animal can be a CD163$^{-/-}$ hybrid animals of the CAMBOROUGH® line. CAMBOROUGH® pigs are hybrids that can be prepared by a cross between Line 2 and Line 3. In an aspect, the hybrid pig can comprise SEQ ID NO: 426 to 505 in a genomic region according to Table 8 and SEQ ID NO: 426-505 in a genomic region according to Table 10. In an aspect, the hybrid pig can comprise SEQ ID NO: 453 in a genomic region according to Table 8 and SEQ ID NO: 453 in a genomic region according to Table 10. In an aspect, the hybrid pig can comprise SEQ ID NO: 489 in a genomic region according to Table 8 and SEQ ID NO: 489 in a genomic region according to Table 10. In an aspect, a hybrid CD163$^{-/-}$ progeny line can comprise SEQ ID NO: 426 to 505 in a genomic region according to Table 8 and SEQ ID NO: 426 to 505 in a genomic region according to Table 14. In an aspect, a hybrid CD163$^{-/-}$ progeny line can comprise SEQ ID NO: 453 in a genomic region according to Table 8 and SEQ ID NO: 489 in a genomic region according to Table 14. In an aspect, a hybrid CD163$^{-/-}$ progeny line can comprise SEQ ID NO: 489 in a genomic region according to Table 8 and SEQ ID NO: 453 in a genomic region according to Table 14. In an aspect, a hybrid CD163$^{-/-}$ progeny line can comprise SEQ ID NO: 426 to 505 in a genomic region according to Table 9 and SEQ ID NO: 426 to 505 in a genomic region according to Table 10. In an aspect, a hybrid CD163$^{-/-}$ progeny line can comprise SEQ ID NO: 453 in a genomic region according to Table 9 and SEQ ID NO: 453 in a genomic region according to Table 10. In an aspect, a hybrid CD163$^{-/-}$ progeny line can comprise SEQ ID NO: 489 in a genomic region according to Table 9 and SEQ ID NO: 489 in a genomic region according to Table 10.

In various aspects, an edited pig of PIC™ line 2, PIC™ line 3, PIC™ line 15, PIC™ line 19, PIC™ line 27, PIC™ line 62, or PIC™ line 65 can have a CD163 gene comprising a predicted amino acid sequence as set forth in SEQ ID NO: 518. In various aspects, the edited CD163 gene can have a 123 bp deletion as set forth in SEQ ID NO: 505. In various configurations, this deletion can have an Exon 7 Amino Acid sequence of AHRKPRLV-TVVSLLGGAHFGEGSGQIWA-EEFQCEGHESHLSLCPVAPRPDGTCSHSRDVGVVCS (SEQ ID NO: 518). In various aspects, a pig having an edited CD163 gene comprising an amino acid sequence set forth in SEQ ID NO: 518 can be a hybrid offspring between two PIC™ lines. In various aspects, the pig can have an edited CD163 Exon 7 sequence comprising a nucleotide sequence set forth in SEQ ID NO: 505. In various aspects, the pig can be an offspring of a cross between PIC™ line 2 and PIC™ line 3. In aspects according to the present specification, the heterozygous and homozygous pigs of the present specification can be free of off-site mutations.

Importantly, the CD163 edited pigs and cells of the present specification retain their desirable commercial phenotypes. The edited pigs can exhibit a healthy phenotype with no noticeable acute deleterious effects from the edit. In an aspect, the pigs of lines 2, 3, 15, 19, 27, 62, and 65, can retain the commercially desirable phenotypes as provided in Table 15.

Methods for improving the health of existing herds of livestock can comprise modifying the CD163 gene locus using the methods described above. In an aspect, the method can comprise introducing into a pig cell an endonuclease or a polynucleotide encoding said endonuclease, and a guide polynucleotide comprising a sequence selected from the group consisting of the first 20 nucleotides of each of SEQ ID NOs: 22 to 271 or the first 20 nucleotides of each of 347 to 425, incubating the cell under conditions that permit the endonuclease to act upon the DNA at, or near, the target sequence and thereby induce recombination, homology-directed repair, or non-homologous end joining at or near the target site, identifying at least one cell having a modification at said target sequence, and producing an animal from an animal cell. In aspects of the present specification, the endonuclease can be an RNP complex of a guide RNA and a Cas protein from *S. thermophilus*. In another aspect, the endonuclease can be an RNP complex of a guide RNA and a Cas protein from *S. pyogenes*.

In an aspect, the method can further comprise providing to the cell a repair guide comprising a sequence selected from the group consisting of nucleotides 50 to 100 of SEQ ID NOs: 1 to 13. In another aspect, a repair guide can comprise a sequence selected from the group consisting of nucleotides 50 to 100 of SEQ ID NOs: 1 to 13 and can further comprise 85% homology to nucleotides 1 to 49 and 101 to 150 of SEQ ID NOs: 1 to 13. In an aspect, the repair guide can comprise a sequence selected from the group consisting of SEQ ID NOs: 1 to 13. As provided herein, the method for improving the health of existing herds provides for the maintenance of desirable commercial phenotypes as discussed above. In an aspect, the desirable commercial phenotypes can be at least 90% of the phenotypes observed in herds of non-edited pigs having a similar genetic background.

The CD163 gene edited locus can be introduced into the herd by conventional breeding or by methods incorporating artificial insemination. To prepare homozygous animals, crosses between parents having at least one gene edited CD163 locus comprising a sequence of SEQ ID NOs: 1 to 18 or 426 to 505 can be performed and homozygous progeny (present at a 1:4 Mendelian ratio) can be selected. As provided herein, a combination of parents and one gene edited CD163 locus can be suitable for improving the herd. Further breeding of animals having the CD163 gene edited loci can improve the health of the herd until all the animals of the herd comprise a CD163 gene edited locus as described. Notably, the health of the herd can improve significantly well before the herd has been bred fully to a CD163 gene edited herd. Specifically, and as discussed above, pig fetuses in a PRRSv resistant gene edited CD163 sow are themselves protected from PRRSv. Further, one of ordinary skill in the art would know that, as the numbers of homozygous CD163 edited animals increase, suitable pig vectors for PRRSv transmission decrease (e.g., herd immunity develops). Accordingly, the present methods can provide for improving a herd by introducing herd immunity.

One useful method of detecting the desired edit is to use real-time PCR. PCR primers flanking the region of interest and a probe that specifically anneals to the region of interest. The probe is labelled with both a fluorophore and a quencher. In the PCR reaction, the primers and probe hybridize in a sequence-dependent manner to the complementary DNA strand of the region of interest. Because the probe is intact, the fluorophore and quencher are in close proximity and the quencher absorbs fluorescence emitted by the fluorophore. The polymerase extends from the primers and begins DNA synthesis. When the polymerase reaches the probe, the exonuclease activity of the polymerase cleaves the hybridized probe. As a result of cleavage, the fluorophore is separated from the quencher and fluoresces. This fluorescence is detected by the real time instrument. These steps are repeated for each PCR cycle and allow detection of specific products.

In the instant application, three separate sets of primers and probes were designed. The first set of primers (SEQ ID NO: 556 and 557) flanked the unedited genomic sequence comprising SEQ ID NO: 249 and a probe (SEQ ID NO: 558) which binds to the unedited genomic DNA in between the primers. The second set of primers (SEQ ID NO: 559 and 560) flanked the unedited genomic sequence comprising SEQ ID NO: 256, and a probe (SEQ ID NO: 561) binds the unedited between the primers. The final set of primers (SEQ ID NO: 562 and 563) flanked the desired Exon 7 deletion edit created by excision of the sequence between the cut sites of SEQ ID NO: 249 and SEQ ID NO: 256. A probe (SEQ ID NO: 564) was designed to bind the desired edit in between these primers. A commercial real-time PCR kit was then used to probe various animals for the desired edit. A variety of commercial real-time PCR kits exist including, such as, but without limitation, PRIMETIME® from IDT, TAQMAN® (Roche Molecular Systems, Inc, Pleasanton, CA) from Applied Biosystems, and various kits from Qiagen and Bio-Rad. Skilled persons will recognize that any such kit can be used with the primers and methods of the present teachings to achieve like results.

EXAMPLES

Example 1

This Example illustrates target site selection of a porcine CD163 gene knockout in pig cells.

A *Streptococcus* Cas9/gRNA RNA-directed DNA endonuclease was used to generate DNA sequence insertions, deletions, and combinations thereof, in the porcine CD163 gene (Sscrofa11.1, GenBank accession: GCA_000003025.6), whereby guide RNAs and protein combinations were delivered singly or as pairs, such that sequence changes in the CD163 gene reduce or abolish the function, stability, or expression of the CD163 messenger RNA or protein. The sequence of the CD163 gene from 120 nucleotides upstream (chr5:63300192) of the translational start site to 59 nucleotides downstream of CD163 exon 7 (chr5:63323390), was screened for the guide RNA binding sites having either an adjacent nGG or nGGnG PAM sequence required for cutting by the Cas9 proteins derived from *Streptococcus pyogenes* or *Streptococcus thermophilus* CRISPR3 (*S. thermophilus* CR3), respectively, the sequences of which are in the sequence listing filed herewith, as listed in Table 2. The DNA sequences for the target sites for editing, the locations of the target sites on the CD163 gene, and the editing activity (measured as described in Example 3) are provided in Table 3. Guide RNA molecules had the same sequence as the target, with corresponding RNA nucleotides, without the PAM sequence (nGG for *S. pyogenes* and nGGnG for *S. thermophilus*). Guide polynucleotide molecules could also consist of DNA bases or mixtures of DNA and RNA bases. The target site sequences are listed in the sequence listing filed herewith as SEQ ID NOs: 22 to 271 and 347 to 425. The target site sequences shown are conserved across pig germplasm and screened by DNA sequencing.

Example 2

This example illustrates nucleofection for the delivery of guide RNA/Cas9 endonuclease to porcine fetal fibroblasts.

To test the DNA cutting activity in living cells to produce an edited porcine CD163 allele, the CRISPR-Cas endonuclease and guide RNA targeting the sequences listed in Table 3 were nucleofected into porcine fetal fibroblast cells. Porcine fetal fibroblast (PFF) cells lines were prepared from 28-35 day-old fetuses and 3.2 µg of Cas9 protein (*S. pyogenes* or *S. thermophilus*) and 2.2 µg of in vitro transcribed single guide RNA were combined in water to a total volume of 2.23 µl, then were nucleofected into PFF cells using a Lonza electroporator. In preparation for nucleofection, PFF cells were harvested using TrypLE express (recombinant Trypsin), upon which the culture medium was removed from cells, washed 1× with HBSS or DPBS, and incubated for 3-5 minutes at 38.5° C. in the presence of TrypLE. Cells were then harvested with complete medium. Cells were pelleted via centrifugation (300×g for 5 minutes at room temperature), supernatant was discarded, then the cells were resuspended in 10 mL PBS to obtain single cell suspension counting cells using trypan blue staining.

The appropriate amount of cells was pelleted by centrifugation (300×g for 5 minutes at room temperature), the supernatant was discarded, and the cells were resuspended in nucleofection buffer P3 at a final concentration of $7.5 \times 10^6$ cells/ml. 20 µl of the cell suspension were added to each well of a nucleofection plate containing the RNP mixture using a multichannel pipette, then mixed gently to resuspend the cells. The RNP/cell mixture was transferred in the nucleofection plate, nucleofected with program CM138 (supplied by the manufacturer). 80 µl of warm Embryonic Fibroblast Medium, EFM, (Dulbecco's Modified Eagle's Medium (DMEM) containing 2.77 mM glucose, 1.99 mM L-glutamine, and 0.5 mM sodium pyruvate, supplemented with 100 µM 2-Mercaptoethanol, 1× Eagle's minimum essential medium non-essential amino acids (MEM NEAA), 100 µg/mL Penicillin-Streptomycin, and 12% Fetal Bovine Serum were added to each well after nucleofection. The suspensions were mixed gently by pipetting, then 100 µl were transferred to a 12 well plate containing 900 µl of EFM pre-incubated at 38.5° C. The plate was then incubated at 38.5° C., 5% $CO_2$ for 48 hours. Forty-eight hours post nucleofection, genomic DNA was prepared from transfected and control PFF cells, 15 µl of QUICKEXTRACT™ DNA Extraction Solution (Lucigen, Madison, WI) were added to pelleted cells then lysed by incubating for 10 mins at 37° C., for 8 mins at 65° C., for 5 mins at 95° C., then lysate was held at 4° C. until used for DNA sequencing.

Example 3

This example illustrates the editing frequency of guide RNA/Cas9 combinations directed against porcine CD163.

Nucleotide sequence changes were introduced into the porcine CD163 gene by delivering Cas9 protein complexed with guide RNAs to fetal fibroblast cells as described in Example 2.

To evaluate DNA double strand cleavage at a porcine CD163 genomic target site mediated by the guide RNA/Cas endonuclease system, a region of approximately 250 bp genomic DNA surrounding the target site was amplified by PCR and the PCR product was then examined by amplicon deep sequencing for the presence of edits. After transfection in triplicate, PFF genomic DNA was extracted as described in Example 2. The region surrounding the intended target site was PCR amplified with NEB Q5 Polymerase, adding sequences necessary for amplicon-specific barcodes and ILLUMINA® (ILLUMINA®, San Diego, CA) sequencing using tailed primers through two rounds of PCR. The resulting PCR amplifications were deep sequenced on an ILLUMINA® MISEQ® Personal Sequencer (ILLUMINA®, San Diego, CA). The resulting reads were examined for the presence of edits at the expected site of cleavage by comparison to control experiments where the Cas9 protein and guide RNA were omitted from the transfection or by comparison to the reference genome. To calculate the frequency of NHEJ edits for a target site, Cas9 protein, guide RNA combination, the total number of edited reads (amplicon sequences containing insertions or deletions when compared to the DNA sequences from control treatments or reference genome) were divided by total read number (wild-type plus edited reads) of an appropriate length containing a perfect match to the barcode and forward primer. Total read counts averaged approximately 7000 per sample and NHEJ activity is expressed as the average (n=3) edited fraction in Table 3. As shown in Table 3, from 0 to 58.2% of the reads contained edits and the average editing frequency across all combinations was approximately 16%. This example demonstrates that, in fetal fibroblast cells, the porcine CD163 gene nucleotide sequence was edited through the stimulation of double-strand breaks mediated by transfecting Cas9 protein from either *S. pyogenes* or *S. thermophilus* complexed with various guide RNAs.

Example 4

This example illustrates generation of an in-frame stop codon using DNA repair template.

DNA repair templates were used to introduce stop codons in the porcine CD163 gene when co-delivered with Cas9 protein and guide RNA. The endonuclease-guide complexes and repair templates disclosed in Table 5 were generated and used to edit CD163 genes in blastocysts. The base deletions were verified by the methods of Example 5.

Example 5

This example illustrates the molecular characterization of edited animal genomes.

A tissue sample was taken from an animal whose genome was been edited according to the examples herein. Tail, ear notch, or blood samples were suitable tissue types. The tissue sample was frozen at −20° C. within 1 hour of sampling to preserve integrity of the DNA in the tissue sample.

DNA was extracted from tissue samples after proteinase K digestion in lysis buffer. Characterization was performed on two different sequence platforms, short sequence reads using the ILLUMINA® platform and long sequence reads on an Oxford NANOPORE™ platform (Oxford NANOPORE™ Technologies, Oxford, UK).

For short sequence reads, two-step PCR was used to amplify and sequence the region of interest. The first step was a locus-specific PCR which amplified the locus of interest from the DNA sample using a combined locus-specific primer with a vendor-specific primer. The second step attached the sequencing index and adaptor sequences to the amplicon from the first step so that sequencing could occur.

The locus-specific primers for the first step PCR were chosen so that they amplified a region <300 bp such that ILLUMINA® paired-end sequencing reads could span the amplified fragment. Multiple amplicons were preferred to provide redundancy should deletions or naturally occurring point mutations prevent primers from correctly binding. Sequence data for the amplicon was generated using an ILLUMINA® sequencing platform (MISEQ®, ILLUMINA®, San Diego, CA). Sequence reads are analyzed to characterize the outcome of the editing process.

For long sequence reads, two-step PCR was used to amplify and sequence the region of interest. The first step is a locus-specific PCR which amplified the locus of interest from the DNA sample using a combined locus-specific primer with a vendor-specific adapter. The second step PCR attached the sequencing index to the amplicon from the first-step PCR so that the DNA was ready for preparing a sequencing library. The step 2 PCR products underwent a set of chemical reactions from a vendor kit to polish the ends of the DNA and ligate on the adapter containing the motor protein to allow access to the pores for DNA strand-based sequencing.

The locus specific primers for the first step PCR range were designed to amplify different regions of the CD163 gene and amplified regions differed in length. Normalized DNA is then mixed with vendor supplied loading buffer and is loaded onto the NANOPORE™ flowcell.

Long sequence reads, while having lower per base accuracy than short reads, are very useful for observing the long range context of the sequence around the target site.

Example 6

This example illustrates methods of making pigs having edited CD163 genes conferring PRRSv resistance.

Porcine oocytes were isolated, fertilized, and then the resulting zygotes are edited to generate gene edited pigs.

CD163 RNP complexes were microinjected into the cytoplasm of in vivo or in vitro fertilized porcine one-cell zygotes. These zygotes were then incubated to generate edited multicellular embryos and transferred to surrogate gilts via standard methods to birth gene edited pigs. To prepare embryo donors and surrogates, pubertal gilts from PIC™ Line 2, Line 3, Line 15, and Line 65 were subjected to estrus synchronization by treatment with 0.22% altrenogest solution (20-36 mg/animal) for 14 days. Follicular growth was induced by the administration of PMSG 36 hours following the last dose of Matrix, and ovulation was induced by the administration of hCG 82 hours after PMSG administration. To generate in vivo fertilized zygotes, females in standing heat were then artificially inseminated (AI) with boar semen from the corresponding PIC™ line. In vivo derived zygotes were recovered surgically 12-24 hours after AI by retrograde flushing the oviduct with sterile TL-HEPES medium supplemented with 0.3% BSA (w/v). Fertilized zygotes were subjected to a single 2-50 picoliter (pl) cytoplasmic injection of Cas9 protein and guide RNA complex (25-50 ng/µl and 12.5-35 ng/µl) targeting CD163 and cultured in PZM5 medium (Yoshioka, K., et al., Biol. Reprod., 2002, 60: 112-119; Suzuki, C., et al., Reprod. Fertil. Dev., 2006 18, 789-795; Yoshioka, K., J. Reprod. Dev. 2008, 54, 208-213). Injected zygotes were surgically implanted into the oviducts of estrus synchronized, unmated surrogate females by a mid-line laparotomy under general anesthesia (each surrogate received 20-60 injected embryos).

In vitro fertilized embryos for gene editing were derived from non-fertilized PIC™ oocytes. Immature oocytes from estrus synchronized PIC™ gilts were collected from medium size (3-6 mm) follicles. Oocytes with evenly dark cytoplasm and intact surrounding cumulus cells were then selected for maturation. Cumulus oocyte complexes were placed in a well containing 500 µl of maturation medium, TCM-199 (Invitrogen) with 3.05 mM glucose, 0.91 mM sodium pyruvate, 0.57 mM cysteine, 10 ng/ml EGF, 0.5 µg/ml luteinizing hormone (LH), 0.5 µg/ml FSH, 10 ng/ml gentamicin (Sigma), and 10% follicular fluid for 42-44 h at 38.5° C. and 5% $CO_2$, in humidified air. At the end of the maturation, the surrounding cumulus cells were removed from the oocytes by vortexing for 3 min in the presence of 0.1% hyaluronidase. Then, in vitro matured oocytes were placed in 100 µl droplets of IVF medium (modified Tris-buffered medium containing 113.1 mM NaCl, 3 mM KCl, 7.5 mM $CaCl_2$), 11 mM glucose, 20 mM Tris, 2 mM caffeine, 5 mM sodium pyruvate, and 2 mg/ml bovine serum albumin (BSA)) in groups of 25-30 oocytes and were fertilized according to established protocol (Abeydeera, *Biol. Reprod.*, 57:729-734, 1997) using fresh extended boar semen. One ml of extended semen was mixed with Dulbecco's Phosphate Buffered Saline (DPBS) containing 1 mg/ml BSA to a final volume of 10 ml and centrifuged at 1000×g, 25° C. for 4 minutes, and spermatozoa were washed in DPBS three times. After the final wash, spermatozoa were re-suspended in mTBM medium and added to oocytes at a final concentration of $1 \times 10^5$ spermatozoa/ml, and co-incubated for 4-5 h at 38.5° C. and 5% $CO_2$. Presumptive zygotes were microinjected 5 hours post IVF and transferred to a surrogate female after 18-42 hours (1-4 cell stage). Each surrogate receives 20-60 injected embryos. Pregnancies were confirmed by lack of return to estrus (21 days) and ultrasound at 28 days post embryo transfer.

To establish the frequency of Cas9-guide RNA targeted gene editing in porcine embryos, uninjected control zygotes and injected surplus zygotes generated by in vitro fertilization were cultivated in PZM3 or PZM5 medium at 38.5° C. for 5-7 days. Blastocysts were harvested at day 7 post cultivation and the genomic DNA isolated for next generation sequencing.

Example 7

This example illustrates the generation and characterization of gene edited pigs.

Animals from PIC™ lines 2, 3, 15, and 65 were edited by the methods described in Example 6. Successful edits were confirmed using the methods of Example 5. Fibroblast cell lines were grown from collagenase treated ear notch samples extracted from the edited animals and deposited with the American Type Culture Collection (ATCC®). The ATCC® has an address of 10801 University Boulevard, Manassas, VA 20110-2209. A representative sample of CD163 edited PIC™ Line 2 was deposited with the ATCC on Apr. 3, 2019 and assigned ATTC® Patent Deposit Number PTA-125814. A representative sample of CD163 edited PIC™ Line 3 was deposited with the ATCC on Apr. 3, 2019 and assigned ATTC® Patent Deposit Number PTA-125815. A representative sample of CD163 edited PIC™ Line 15 was deposited with the ATCC on Apr. 3, 2019 and assigned ATTC® Patent Deposit Number PTA-125816. A representative sample of CD163 edited PIC™ Line 65 was deposited with the ATCC® on Apr. 3, 2019 and assigned ATTC® Patent Deposit Number PTA-125813. Each deposit was made according to the Budapest Treaty. Representative animals from each line were confirmed to have heterozygous edits as specified in Table 16.

TABLE 16

Verified Gene Edited Animals

| Line number | CD163 Allele 1 | CD163 Allele 2 | ATCC Deposit No. |
|---|---|---|---|
| 2 | Wild type sequence | Deleted nucleotides chr5: 63301999-63302005 | PTA-125814 |
| 3 | Wild type sequence | Deleted nucleotides chr5: 63301999-63302005 | PTA-125815 |
| 15 | Wild type sequence | Deleted nucleotides chr5: 63301999-63302005 | PTA-125816 |
| 65 | Wild type sequence | Deleted nucleotides chr5: 63301999-63302005 | PTA-125813 |

Each of the animals in Table 16 presented a healthy phenotype with deleted nucleotides 63301999-63302005 (in exon 2) from chromosome 5.

Additional cell lines were grown from collagenase treated ear notch samples from unedited animals from PIC™ lines 19, 27, and 62, were deposited with the ATCC. A representative sample of PIC™ Line 19 was deposited with the ATCC® on Apr. 3, 2019 and assigned ATTC® Patent Deposit Number PTA-125811. A representative sample of PIC™ Line 27 was deposited with the ATCC on Apr. 3, 2019 and assigned ATTC® Patent Deposit Number PTA-125907. A representative sample of PIC™ Line 62 was deposited with the ATCC on Apr. 3, 2019 and assigned ATTC® Patent Deposit Number PTA-125812. Each deposit was made according to the Budapest Treaty. Using conventional cloning methods, animals are generated from the cell lines deposited as PTA-125811, PTA-125812, and PTA-125907 and edited using the methods of Example 6 in order to generate edited lines.

Single nucleotide polymorphisms (SNPs) in the vicinity of the CD163 gene were analyzed for each of the deposited PIC™ lines (2, 3, 15, 19, 27, 62, and 65) and SNP profiles of each of the lines that are capable of distinguishing each line are selected. The starting dataset for defining the line signatures was a collection of 330 whole genome sequenced animals from the 7 deposited PIC™ lines. A 6 Mb region of Chromosome 5 centered on the CD163 gene was extracted for the signatures, and variation within and between the lines was examined for each nucleotide in this region in order to identify a relatively small number of SNPs that together formed a signature for the line.

To be a candidate for inclusion in the signature of a given line, the following criteria were imposed on each chromosomal position: sequence coverage had to exist for 90% of animals in the line; the above had to be true for at least 5 of the 7 lines; and all animals with data in the target line must have had the same homozygous genotype. For each of the other lines, a genotype frequency for this genotype was calculated across all the sequenced animals for that line. A cutoff was imposed of at least 30% of the difference between the highest and lowest per-line genotype frequency of the other 6 lines (i.e., there must be a spread of genotype frequencies within the 6 lines).

A combination of metrics for discriminating power and even distribution were used to select a subset of genotypes that could define each line. Table 8 to Table 14 provide the positions on chromosome 5 for the SNPs for which the homozygous allele was fixed in each porcine line. These sets of homozygous alleles distinguish each porcine line from the other lines. The genotype listed indicates which allele is homozygous at each position, as indicated in Table 8 to Table 14.

Example 8

This example compares differing levels of PRRSv resistance of immune cells isolated from wild type and gene edited pigs.

CD163 surface expression analysis was conducted on Monocyte Derived Macrophages (MoMØs) recovered from edited and wild type animals, each with and without edits to the CD163 gene according to the methods described in the previous examples. The edits tested are presented in Table 17. Four edits comprise deletions of various sizes as shown, and the fifth comprises a 2 base pair insertion; all edits in Table 15 are in exon 2. All deletions or insertions result in a truncated CD163 polypeptide. CD163 expression was assessed by immunofluorescence labelling and FACS analysis using clone 2A 10/11, a mouse anti-pig CD163 monoclonal antibody. CD163 edited cells, MoMØs, lacked a functional epitope on the surface of the cell as evident from cell surface expression analysis.

TABLE 17

CD163 gene edits tested for protein expression

| Region Chr5 Location of guideRNAs binding site | 63301997-02016 | 63301997-02016 | 63301997-02016 | 63301997-02016 | 63301997-02016 |
|---|---|---|---|---|---|
| SEQ ID NO | 14 | 15 | 16 | 17 | 18 |
| Guide RNA spacer (DNA) SEQ ID NO | 42 | 42 | 42 | 42 | 42 |
| Guide RNA spacer (RNA) SEQ ID NO | 288 | 288 | 288 | 288 | 288 |
| Translation of Deletion | 339 | 340 | 341 | 342 | 343 |
| Base deletion or insertion coordinates | chr5: 63302012-63302013 | chr5: 63302009-63302041 | chr5: 63302012-63302013 | chr5: 63302005-63302020 | chr5: 63302011-63302020 |
| Deleted or inserted bases (#) | TC (2 bp deletion) | SEQ ID NO: 344; (33 bp deletion) | TC (2 bp insertion) | SEQ ID NO: 345; (16 bp deletion) | SEQ ID NO: 346; (10 bp deletion) |

To test the two base pair deletion edit to CD163 in homozygous edited cells for PRRSv viral infection, MoMØs were infected with PRRSv type 1 and type 2. Twenty-four (24) hours post infectivity, in a microscope field of view, cells were counted to determine the number of cells which contain replicating PRRSv. CD163 homozygous edited MoMØ cells were found to be not permissive to both PRRSv types 1 and 2.

Example 9

This example demonstrates the use of two guides for removal of exon 7 from *S. scrofa* CD163 in porcine fibroblasts.

In order to remove CD163 exon 7 DNA sequences which encode SRCR5 of the mature CD163 polypeptide, DNA sequences located in the intronic regions 450 bp upstream and 59 bp downstream of CD163 exon 7 were examined for *Streptococcus pyogenes* (NGG) and *Streptococcus thermophilus* (NGGNG) Cas9 protein and guideRNA recognition sites. 48 sites were identified within the 450 bp of intron 6 and 10 sites were identified within a 59 bp region of intron 7. The ability of these 58 sites to bind to Cas9 and guideRNAs to direct gene editing was first tested using single guides in porcine fetal fibroblasts. A subset of these single guideRNA-Cas9 proteins—the guideRNAs which generated a high frequency of edits across the spacer recognition site—were further tested as guide pairs for their ability to remove CD163 exon 7. Guides were introduced to porcine fetal fibroblasts by nucleofection as described in Example 2: each guide was prepared as an RNP and then the two sets of complexes were combined in a total volume of 2.23 µl prior to transfection. Editing frequency for guide pairs was determined as described in Example 3. The frequencies of NHEJ-mediated repairs whereby the endonuclease cut sites are brought together resulting in the deletion of CD163 exon 7 are shown in Table 18.

TABLE 18

End-to-end repair frequencies using paired guideRNAs for CD163 exon 7 deletion in porcine fetal fibroblasts

| SEQ ID NO: (5') | Cut site (5') | SEQ ID NO: (3') | Cut site (3') | Deletion size (bp) | Desired repair outcome (%) |
|---|---|---|---|---|---|
| 229 | 63322816 | 256 | 63323377 | 561 | 23.3 |
| 230 | 63322814 | 256 | 63323377 | 562 | 24.7 |
| 231 | 63322826 | 256 | 63323377 | 551 | 15.3 |
| 237 | 63322861 | 256 | 63323377 | 516 | 20.7 |
| 241 | 63322891 | 256 | 63323377 | 486 | 20.0 |
| 229 | 63322816 | 258 | 63323378 | 562 | 5.3 |
| 230 | 63322814 | 258 | 63323378 | 563 | 7.0 |
| 231 | 63322826 | 258 | 63323378 | 552 | 4.3 |
| 237 | 63322861 | 258 | 63323378 | 517 | 15.7 |
| 241 | 63322891 | 258 | 63323378 | 487 | 5.7 |
| 229 | 63322816 | 261 | 63323373 | 558 | 15.0 |
| 230 | 63322814 | 261 | 63323373 | 559 | 18.0 |
| 231 | 63322826 | 261 | 63323373 | 548 | 0.0 |
| 237 | 63322861 | 261 | 63323373 | 513 | 12.0 |
| 241 | 63322891 | 261 | 63323373 | 483 | 14.0 |
| 219 | 63322697 | 256 | 63323377 | 680 | 28.0 |
| 221 | 63322709 | 256 | 63323377 | 668 | 33.7 |
| 224 | 63322747 | 256 | 63323377 | 630 | 27.0 |
| 227 | 63322786 | 256 | 63323377 | 591 | 22.7 |
| 219 | 63322697 | 258 | 63323378 | 681 | 7.7 |
| 221 | 63322709 | 258 | 63323378 | 669 | 13.0 |
| 224 | 63322747 | 258 | 63323378 | 631 | 7.3 |
| 227 | 63322786 | 258 | 63323378 | 592 | 6.3 |
| 219 | 63322697 | 261 | 63323373 | 677 | 14.5 |
| 221 | 63322709 | 261 | 63323373 | 665 | 20.7 |
| 224 | 63322747 | 261 | 63323373 | 627 | 14.7 |
| 227 | 63322786 | 261 | 63323373 | 588 | 11.3 |
| 249 | 63322963 | 256 | 63323377 | 414 | 38.0 |
| 250 | 63322973 | 256 | 63323377 | 404 | 36.7 |

TABLE 18-continued

End-to-end repair frequencies using paired guideRNAs for CD163 exon 7 deletion in porcine fetal fibroblasts

| SEQ ID NO: (5') | Cut site (5') | SEQ ID NO: (3') | Cut site (3') | Deletion size (bp) | Desired repair outcome (%) |
|---|---|---|---|---|---|
| 249 | 63322963 | 258 | 63323378 | 415 | 20.3 |
| 250 | 63322973 | 258 | 63323378 | 405 | 14.7 |
| 249 | 63322963 | 261 | 63323373 | 411 | 17.7 |
| 250 | 63322973 | 261 | 63323373 | 401 | 11.7 |

The excision guides had a wide range of editing frequencies for the desired edit.

Example 10

This example illustrates the excision of Exon 7 in porcine blastocysts using dual guide RNAs.

A subset of guides screened in porcine fetal fibroblasts were additionally tested for their ability to remove CD163 exon 7 in porcine blastocysts. The subset of guides to be tested in porcine embryos was chosen based on a combination of their efficacy in generating exon 7 deletions in porcine fibroblasts and low number of off-target edits for each guide in the pair (see Detailed Description). Edited porcine embryos were generated as described above. Briefly, oocytes recovered from slaughterhouse ovaries were in vitro fertilized as described in Example 6. The sgRNP solution was injected into the cytoplasm of presumptive zygotes at 4-5 hours post-fertilization by using a single pulse from a FEMTOJET® 4i microinjector (Eppendorf; Hamburg, Germany) with settings at pi=200 hPa, ti=0.25 s, pc=15 hPa. Glass capillary pipettes (Sutter Instrument, Navato, CA, USA) with an outer diameter of 1.2 mm and an inner diameter of 0.94 mm were pulled to a very fine point of <0.5 µm. Microinjection was performed in TL-Hepes (ABT360, LLC) supplemented with 3 mg/ml BSA (Proliant) on the heated stage of an inverted microscope equipped with Narishige (Narishige International USA, Amityville, NY) micromanipulators. Following injections, presumptive zygotes were cultured for 7 days in PZM5 (Cosmo Bio, Co LTD, Tokyo, Japan) in an incubator environment of 5% $CO_2$, 5% $O_2$, 90% $N_2$. Editing frequency of blastocysts was determined as described in Example 3. The frequencies of end-to-end NHEJ repairs resulting in the deletion of CD163 exon 7 are shown in Table 19.

TABLE 19

End-to-end repair frequencies using paired guideRNAs for in CD163 exon 7 deletion in porcine embryos

| SEQ ID NO: (5') | Cut site (5') | SEQ ID NO: (3') | Cut site (3') | Deletion size (bp) | Desired repair outcome (%) |
|---|---|---|---|---|---|
| 229 | 63322816 | 256 | 63323377 | 561 | 38.0 |
| 230 | 63322814 | 256 | 63323377 | 562 | 21.0 |
| 231 | 63322826 | 256 | 63323377 | 551 | 24.0 |
| 241 | 63322891 | 256 | 63323377 | 486 | 29.0 |
| 229 | 63322816 | 258 | 63323378 | 562 | 7.0 |
| 231 | 63322826 | 258 | 63323378 | 552 | 12.0 |
| 241 | 63322891 | 258 | 63323378 | 487 | 20.0 |
| 219 | 63322697 | 256 | 63323377 | 680 | 35.0 |
| 221 | 63322709 | 256 | 63323377 | 668 | 36.0 |
| 224 | 63322747 | 256 | 63323377 | 630 | 24.0 |
| 227 | 63322786 | 256 | 63323377 | 591 | 0.0 |

TABLE 19-continued

End-to-end repair frequencies using paired guideRNAs for in CD163 exon 7 deletion in porcine embryos

| SEQ ID NO: (5') | Cut site (5') | SEQ ID NO: (3') | Cut site (3') | Deletion size (bp) | Desired repair outcome (%) |
|---|---|---|---|---|---|
| 227 | 63322786 | 258 | 63323378 | 592 | 0.0 |
| 221 | 63322709 | 261 | 63323373 | 665 | 15.0 |
| 249 | 63322963 | 256 | 63323377 | 414 | 44.0 |
| 250 | 63322973 | 256 | 63323377 | 404 | 14.0 |
| 249 | 63322963 | 258 | 63323378 | 415 | 7.0 |
| 249 | 63322963 | 261 | 63323373 | 411 | 53.0 |

This example demonstrates that a number of guide pairs can be used to delete CD163 exon 7, but the efficiency can vary greatly between guide pairs and cell types.

Example 11

This example demonstrates the use of two guides to introduce a premature stop codon into exon 7 of *S. scrofa* CD163.

Guides within exon 7 of CD163 were screened by bioinformatic methods for their ability to generate an in-frame stop codon when the cuts generated by those guides are ligated together during NHEJ. Bioinformatic predictions were tested in porcine fetal fibroblasts as described in Example 2: guides were complexed separately before being combined in a total volume of 2.23 µl prior to transfection. Editing frequency was determined as described in Example 3. The frequencies of end-to-end NHEJ repairs resulting in the introduction of a premature stop codon in exon 7 of CD163 are shown in Table 20.

TABLE 20

End-to-end repair frequencies for introduction of a stop codon in CD163 exon 7 deletion in porcine fetal fibroblasts

| SEQ ID NO: (5') | Cut site (5') | SEQ ID NO: (3') | Cut site (3') | Deletion size (bp) | Desired repair outcome (%) |
|---|---|---|---|---|---|
| 351 | 63323023 | 365 | 63323103 | 80 | 50.5 |
| 351 | 63323023 | 387 | 63323235 | 212 | 1.0 |
| 348 | 63323027 | 390 | 63323236 | 209 | 53.5 |
| 348 | 63323027 | 388 | 63323236 | 209 | 50.0 |
| 348 | 63323027 | 395 | 63323284 | 257 | 31.0 |
| 352 | 63323035 | 365 | 63323103 | 68 | 29.0 |
| 352 | 63323035 | 387 | 63323235 | 200 | 12.5 |
| 352 | 63323035 | 399 | 63323283 | 248 | 21.0 |
| 353 | 63323038 | 365 | 63323103 | 65 | 21.0 |
| 353 | 63323038 | 387 | 63323235 | 197 | 6.0 |
| 353 | 63323038 | 399 | 63323283 | 245 | 11.0 |
| 354 | 63323039 | 390 | 63323236 | 197 | 55.5 |
| 354 | 63323039 | 388 | 63323236 | 197 | 18.0 |
| 354 | 63323039 | 395 | 63323284 | 245 | 17.0 |
| 358 | 63323056 | 361 | 63323077 | 21 | 0.0 |
| 358 | 63323056 | 362 | 63323087 | 31 | 4.0 |
| 358 | 63323056 | 368 | 63323124 | 68 | 37.0 |
| 358 | 63323056 | 384 | 63323203 | 147 | 34.0 |
| 358 | 63323056 | 394 | 63323272 | 216 | 56.0 |
| 358 | 63323056 | 399 | 63323283 | 227 | 34.0 |
| 359 | 63323057 | 390 | 63323236 | 179 | 13.0 |
| 359 | 63323057 | 388 | 63323236 | 179 | 3.0 |
| 359 | 63323057 | 395 | 63323284 | 227 | 4.0 |
| 360 | 63323058 | 368 | 63323124 | 66 | 7.5 |
| 360 | 63323058 | 384 | 63323203 | 145 | 6.0 |
| 360 | 63323058 | 389 | 63323237 | 179 | 0.0 |
| 360 | 63323058 | 394 | 63323272 | 214 | 16.5 |
| 360 | 63323058 | 397 | 63323285 | 227 | 0.0 |
| 361 | 63323077 | 365 | 63323103 | 26 | 42.0 |
| 361 | 63323077 | 387 | 63323235 | 158 | 0.0 |
| 362 | 63323087 | 390 | 63323236 | 149 | 45.0 |
| 362 | 63323087 | 388 | 63323236 | 149 | 17.5 |
| 362 | 63323087 | 395 | 63323284 | 197 | 22.5 |
| 364 | 63323089 | 365 | 63323103 | 14 | 0.0 |
| 364 | 63323089 | 387 | 63323235 | 146 | 14.5 |
| 364 | 63323089 | 399 | 63323283 | 194 | 35.5 |
| 365 | 63323103 | 368 | 63323124 | 21 | 0.0 |
| 365 | 63323103 | 384 | 63323203 | 100 | 17.0 |
| 365 | 63323103 | 389 | 63323237 | 134 | 0.0 |
| 365 | 63323103 | 394 | 63323272 | 169 | 32.5 |
| 365 | 63323103 | 397 | 63323285 | 182 | 1.0 |
| 366 | 63323118 | 368 | 63323124 | 6 | 0.0 |
| 366 | 63323118 | 384 | 63323203 | 85 | 29.0 |
| 366 | 63323118 | 389 | 63323237 | 119 | 14.0 |
| 366 | 63323118 | 394 | 63323272 | 154 | 48.5 |
| 366 | 63323118 | 397 | 63323285 | 167 | 10.0 |
| 354 | 63323039 | 211 | 63323163 | 123 | 29.0 |

This example illustrates that guide pairs designed to introduce a stop codon have a wide variety of editing efficiencies in porcine fibroblasts.

Example 12

This example illustrates the editing efficiency of guides introducing stop codons in porcine blastocysts.

A subset of guides screened in porcine fetal fibroblasts were additionally tested for their ability to introduce a premature stop codon in exon 7 of CD163 in porcine embryos. The subset of guides to be tested in porcine embryos was chosen based on a combination of their efficacy in introducing a premature stop codon in exon 7 of CD163 in porcine fibroblasts and the lack of observed off-targets for each guide in the pair as described supra. Editing frequency was determined as described in Example 3. The frequencies of end-to-end NHEJ repairs resulting in the introduction of a premature stop codon in exon 7 of CD163 are shown in Table 21.

TABLE 21

End-to-end repair frequencies for introduction of a stop codon in CD163 exon 7 deletion in porcine blastocysts

| SEQ ID NO: (5') | Cut site (5') | SEQ ID NO: (3') | Cut site (3') | Deletion size (bp) | Desired repair outcome (%) |
|---|---|---|---|---|---|
| 351 | 63323023 | 365 | 63323103 | 80 | 39.6 |
| 348 | 63323027 | 390 | 63323236 | 209 | 31 |
| 348 | 63323027 | 388 | 63323236 | 209 | 35.4 |
| 354 | 63323039 | 390 | 63323236 | 197 | 30.4 |
| 358 | 63323056 | 394 | 63323272 | 216 | 29.2 |
| 362 | 63323087 | 390 | 63323236 | 149 | 31 |
| 366 | 63323118 | 394 | 63323272 | 154 | 33 |
| 354 | 63323039 | 211 | 63323163 | 123 | 27.4 |

This example demonstrates that guide pairs that can be used to introduce a premature stop codon into exon 7 of CD163 have a wide variety of editing efficiencies.

Example 13

This example illustrates variable repair outcomes for NHEJ repair.

A subset of guideRNAs designed to delete CD163 exon 7 were tested for their ability to delete the exon 7 coding and flanking regions in porcine blastocysts, as described in Example 9. Editing frequency of blastocysts was determined as described in Example 3. In this example, a subset of the DNA sequences observed in porcine blastocysts in vivo as the result of NHEJ-mediated repair are shown for five guideRNA pairs in Table 7. It is known that simple nucleotide deletions also occur, as well as more complex NHEJ-mediated repair DNA sequences which contain deletions, insertions, rearrangements, inversions, and any combination thereof. Without being limited by theory, these varied repair outcomes also occur as a result of endonuclease cutting of DNA using single and paired guides in porcine blastocysts. Table 7 also shows that the frequencies of the observed DNA sequence associated with each repair outcome vary between guideRNA pairs. In some, but not all, instances the frequency of DNA sequence associated with the end-to-end joining of cut sites of the paired guideRNA was the most highly represented repair outcome. For some guideRNA pairs there was a single predominant DNA repair outcome, while for other guideRNA pairs there were DNA repair outcomes that occurred with equal frequency. Most of the DNA repair outcomes shown for these five guideRNA pairs resulted in the deletion of CD163 exon 7 DNA sequences corresponding to the SRCR 5 domain. Therefore, the decision for which guideRNA pair to use for generation of edited pigs depends largely on the tolerance for multiple alleles in a population.

This example demonstrates that the NHEJ-mediated repair outcomes that result when two intronic guideRNAs are used to delete genomic DNA vary between guideRNA pairs, not only in the manner in which DNA breaks are resolved but in the frequency of these resolutions. It is advantageous to screen guideRNA pairs in fibroblasts or embryos to observe DNA repair outcomes of single or dual guideRNAs for the generation of edited animals.

Example 14

This example illustrates a real time PCR assay for identifying the presence of the spacer sequence set forth in SEQ ID NO: 249 and/or the desired Exon 7 excision edit in cells.

Two sets of primers and two probes were designed for this assay. One set of primers were designed to flank the spacer sequence set forth in SEQ ID NO: 249 in the unedited genome. The sequences of these primers are set forth in SEQ ID NOs: 556 and 557. A probe of sequence SEQ ID NO: 558 and labeled with the HEX fluorescent moiety was designed to anneal to the unedited genome between the PCR primers. The other set of primers, having sequences set forth in SEQ ID NOs: 562 and 563, were designed to flank the desired edit sequence. A probe, having a sequence set forth in SEQ ID NO: 564 and labeled with the FAM fluorescent moiety, was designed to anneal to nucleotides spanning the joining region of the edit. Real time PCR was performed using both primer sets and with genomic DNA extracted from tail and/or ear samples of pigs that had known allelic status (wild type, homozygous, or heterozygous). 5 µl of 2× PRIME-TIME® Master Mix (Integrated DNA Technologies, Coralville, IA) was mixed with 0.5 µl of each primer (10 µM), 0.5 µl of each probe (2.5 µM), and 2 µl of genomic DNA. PCR was performed with 3 minutes initial denaturing at 95° C., then 35 cycles of: 95° C. for 15 seconds, 64° C. for 30 seconds, and 72° C. for 30 seconds. A final elongation was performed at 72° C. for 2 minutes, and then the reaction was held in the cycler at 4° C. Fluorescence was measured and charted and, as expected, the homozygotes were close to the y axis (representing the FAM moiety wavelength), the heterozygotes grouped near the center of the chart, and the wild type pigs grouped close to the X axis (representing the HEX moiety wavelength). The assay was therefore successful in detecting the edit based on the spacer sequence set forth in SEQ ID NO: 249.

Example 15

This example illustrates a real time PCR assay for identifying the presence of the spacer sequence set forth in SEQ ID NO: 256 and/or the desired Exon 7 excision edit in cells.

Two sets of primers and two probes were designed for this assay. One set of primers flanked the spacer sequence set forth in SEQ ID NO: 256. The sequence of these primers is set forth in SEQ ID NOs: 559 and 560. A probe, having a sequence set forth in SEQ ID NO: 561 and labeled with the HEX fluorescent moiety, was designed to anneal to the unedited version of the spacer sequence. The other set of primers and probe are designed to target the desired edit and are described in Example 14 (SEQ ID NOs: 562-564.) Real time PCR was performed as described in Example 14, but with the instant primers and probes. Fluorescence was charted and, as expected, the homozygotes were close to the y axis (representing the FAM moiety), the heterozygotes grouped near the center of the chart, and the wild type pigs grouped close to the X axis (representing the HEX moiety). The assay was therefore successful in detecting the edit based on the spacer sequence set forth in SEQ ID NO: 256.

Example 16

This example illustrates a comparison of CD163 CRISPR-CAS gRNA activity in cells between previously published guide pairs and guide pairs of the present teachings.

Each pair of guides was tested in porcine fibroblasts as described in Example 2. Each pair was further tested in porcine blastocysts as described in Example 10. The results are shown below in Table 22.

TABLE 22

Comparative Activity in Porcine Cells

| guide pair SEQ ID NOs: | Source | % desired repair fibroblasts | % desired repair blastocysts |
|---|---|---|---|
| 272 and 273 | Burkard 2017 | 6 | 20 |
| 249 and 256 | Present Disclosure | 38 | 44 |
| 354 and 211 | Whitworth 2014 | 17 | n.d. |
| 362 and 390 | Present Disclosure | 45 | 31 |

These data illustrate that the guides of the present disclosure provide at least a two-fold improvement in the percentage of cells that have the desired edit relative to the guides that were previously disclosed in the literature. Therefore, the guides of the present disclosure are more efficient than the guides previously disclosed in the literature.

Example 17

This example illustrates CD163 edited pigs challenged with PRRSv Type I.

Pigs from PIC™ Line 2 were edited with guides as set forth in SEQ ID NOs: 249 and 256 as described in Example 6. Edits were confirmed as described in Example 5. Edited pigs were then crossbred to create pigs that were homozygous for the edit. These homozygous edited pigs were inoculated with 3 ml of PRSSv Type I (SD13-15) having $10^4$ to $10^5$ virions (4-5 log $TCID_{50}$). 1.5 ml was administered intramuscularly with a 21 gauge needle. The remaining 1.5 ml was administered intranasally. Serum samples were obtained on Day 0 (prior to inoculation on that day), Day 3, Day 5, Day 10, Day 14, and Day 21. Realtime PCR to determine the presence of virus in the serum samples using TETRACORE® EZ-PRRSV MPX 4.0 Master Mix and Enzyme with ROX (TETRACORE®, Rockville, MD) according to manufacturer directions. The real time PCR EU adjusted counts are shown in Table 23. The counts have been inverted using standard methods known in the art to make the data more intuitive-higher numbers indicate more virus detected.

TABLE 23

Realtime PCR EU Adjusted Counts for Type I PRRSv Challenge

| Animal | CD163 | Day 0 | Day 3 | Day 5 | Day 10 | Day 14 | Day 21 |
|---|---|---|---|---|---|---|---|
| 2 | WT | 0 | 19.8 | 22.6 | 20 | 19.6 | 18.3 |
| 4 | WT | 0 | 17 | 17.7 | 18.6 | 16.8 | 17.5 |
| 5 | WT | 0 | 18.9 | 21.5 | 17.3 | 14.2 | 13.6 |
| 6 | WT | 0 | 15.8 | 19.7 | 15.6 | 14.5 | 13.4 |
| 17 | WT | 0 | 17.1 | 17.8 | 18.5 | 18 | 15.8 |
| 18 | WT | 0 | 15.8 | 17.9 | 17 | 16.8 | 15 |
| 20 | WT | 0 | 17.2 | 20.3 | 18.8 | 17 | 12.8 |
| 3 | Edit | 0 | 0 | 0 | 0 | 0 | 0 |
| 7 | Edit | 0 | 0 | 0 | 0 | 0 | 0 |
| 14 | Edit | 0 | 0 | 0 | 0 | 0 | 0 |
| 19 | Edit | 0 | 0 | 0 | 0 | 0 | 0 |

No PRRSv was detected in the serum of the edited animals throughout the experiment.

The serum samples were also subjected to ELISA using the IDEXX PRRS X3 antibody test kit; the test was performed by an accredited Veterinary Diagnostic Laboratory. The results are shown as a Sample:Positive ratio. Ratios greater than or equal to 0.40 are considered positive. The ratios for each sample are shown in Table 24.

TABLE 24

ELISA S/P Results for Type I PRRSv Challenge

| Animal | CD163 | Day 0 | Day 3 | Day 5 | Day 10 | Day 14 | Day 21 |
|---|---|---|---|---|---|---|---|
| 2 | WT | 0.0 | 0.0 | 0.0 | 0.5 | 0.6 | 1.4 |
| 4 | WT | 0.0 | 0.0 | 0.0 | 0.1 | 0.2 | 0.8 |
| 5 | WT | 0.0 | 0.0 | 0.0 | 0.9 | 1.3 | 1.8 |
| 6 | WT | 0.0 | 0.0 | 0.0 | 1.3 | 1.3 | 1.9 |
| 17 | WT | 0.0 | 0.0 | 0.0 | 0.2 | 0.2 | 1.1 |
| 18 | WT | 0.0 | 0.0 | 0.0 | 0.3 | 0.3 | 1.4 |
| 20 | WT | 0.0 | 0.0 | 0.0 | 0.3 | 0.4 | 1.2 |
| 3 | Edit | 0.0 | 0.0 | 0.0 | 0.0 | 0.0 | 0.0 |
| 7 | Edit | 0.0 | 0.0 | 0.0 | 0.0 | 0.0 | 0.0 |
| 14 | Edit | 0.0 | 0.0 | 0.0 | 0.0 | 0.0 | 0.0 |
| 19 | Edit | 0.0 | 0.0 | 0.0 | 0.0 | 0.0 | 0.0 |

The edited pigs do not have any positive ratios. In contrast, by day 21, all of the wild type pigs have positive ratios. This further illustrates that there is no PRRSv circulating in the edited pigs' serum.

This example illustrates that pigs edited with guides of SEQ TD NOs: 249 and 256 are resistant to PRRSv Type I virus infection.

Example 18

This example illustrates CD163 edited pigs challenged with PRRSv Type II.

Pigs from PIC™ Lines 2 and 3 were edited with guides as set forth in SEQ ID NOs: 249 and 256 as described in Example 6. Edits were confirmed as described in Example 5. Edited pigs were then crossbred to create pigs that were homozygous for the edit. These homozygous edited pigs were then inoculated with 3 ml of PRRSv Type II (NVSL 97-7895) having $10^4$ to $10^5$ virions (4-5 log $TCID_{50}$). 1.5 ml was administered intramuscularly with a 21 gauge needle. The remaining 1.5 ml was administered intranasally. Serum samples were obtained on Day 0 (prior to inoculation on that day), Day 3, Day 5, Day 10, Day 14, and Day 21. Realtime PCR to determine the presence of virus in the serum samples using TETRACORE® EZ-PRRSV MPX 4.0 Master Mix and Enzyme with ROX according to manufacturer directions. The NA adjusted counts for real time PCR are shown in Table 25. The numbers were inverted to make them more intuitive—the higher the count, the more virus is present.

TABLE 25

Realtime PCR NA Adjusted Counts for Type II PRRSv Challenge

| Animal | CD163 | Day 0 | Day 3 | Day 5 | Day 10 | Day 14 | Day 21 |
|---|---|---|---|---|---|---|---|
| 21 | WT | 0.0 | 18.4 | 22.0 | 21.9 | 18.0 | 16.1 |
| 23 | WT | 0.0 | 16.4 | 22.0 | 21.8 | 20.0 | 19.7 |
| 25 | WT | N/A | 17.2 | 21.2 | 21.9 | 19.2 | 19.8 |
| 30 | WT | 0.0 | 16.2 | 17.8 | 21.4 | 21.1 | 17.6 |
| 33 | WT | 0.0 | 18.5 | N/A | 21.8 | 18.5 | 15.3 |
| 35 | WT | N/A | 17.0 | 22.9 | 21.8 | 20.5 | 20.9 |
| 36 | WT | 0.0 | 16.7 | 21.4 | 21.9 | 19.9 | 17.4 |
| 38 | WT | 0.0 | 16.0 | 18.1 | 20.2 | 20.9 | 9.4 |
| 24 | Edit | N/A | 1.9 | 0.0 | 0.0 | 0.0 | 0.0 |
| 37 | Edit | 0.0 | 0.0 | 0.0 | 0.0 | 0.0 | 0.0 |

The edited pigs have very little to no virus counts relative to the wild type pigs.

The serum samples were also subjected to ELISA using the IDEXX PRRS X3 antibody test kit; the test was performed by an accredited Veterinary Diagnostic Laboratory. The results are shown as a Sample:Positive ratio. Ratios greater than or equal to 0.40 are considered positive. The ratios for each sample are shown in Table 26.

TABLE 26

ELISA S/P Ratios for Type II PRRSv Challenge

| Animal | Edit | Day 0 | Day 3 | Day 5 | Day 10 | Day 14 | Day 21 |
|---|---|---|---|---|---|---|---|
| 21 | WT | 0.0 | 0.0 | 0.0 | 1.7 | 2.0 | 1.9 |
| 23 | WT | 0.0 | 0.0 | 0.0 | 1.2 | 1.7 | 1.9 |
| 25 | WT | N/A | 0.0 | 0.0 | 1.2 | 1.6 | 1.7 |
| 30 | WT | 0.0 | 0.0 | 0.0 | 0.4 | 0.6 | 0.6 |
| 33 | WT | 0.0 | 0.0 | N/A | 0.7 | 0.6 | 0.7 |
| 35 | WT | N/A | 0.0 | 0.0 | 1.3 | 1.3 | 1.4 |
| 36 | WT | 0.0 | 0.0 | 0.0 | 1.2 | 1.5 | 1.8 |
| 38 | WT | 0.0 | 0.0 | 0.0 | 0.5 | 0.9 | 1.0 |

TABLE 26-continued

ELISA S/P Ratios for Type II PRRSv Challenge

| Animal | Edit | Day 0 | Day 3 | Day 5 | Day 10 | Day 14 | Day 21 |
|---|---|---|---|---|---|---|---|
| 24 | Edit | N/A | 0.2 | 0.1 | 0.2 | 0.1 | 0.1 |
| 37 | Edit | 0.0 | 0.0 | 0.0 | 0.0 | 0.0 | 0.0 |

The edited pigs do not have any positive ratios; in contrast, by day 10, all of the wild type pigs have positive ratios. Taken together, these data illustrate that there is no virus circulating in the edited pigs' blood.

This example illustrates that the pigs with a CD163 gene edited with SEQ ID NOs: 249 and 256 are resistant to PRRSv Type II infection.

The contents of each of the foregoing references and applications are incorporated herein by reference in their entireties. Having described the present disclosure in detail, it will be apparent that modifications and variations are possible without departing from the scope of the teachings defined in the appended claims.

What is claimed is:

1. A gene edited pig whose genome comprises a CD163 gene comprising the nucleic acid sequence of SEQ ID NO: 453, wherein the pig exhibits reduced cellular uptake of porcine reproductive and respiratory syndrome virus (PRRSV) relative to a pig whose genome comprises a wild-type CD163 gene.

2. A cell isolated from the gene edited pig of claim 1, wherein the cell exhibits reduced cellular uptake of PRRSV relative to a cell isolated from a pig whose genome comprises a wild-type CD163 gene.

3. A cell line isolated from the gene edited pig of claim 1, wherein the cell line exhibits reduced cellular uptake of PRRSV relative to a cell line isolated from a pig whose genome comprises a wild-type CD163 gene.

4. A fibroblast isolated from the gene edited pig of claim 1, wherein the fibroblast exhibits reduced cellular uptake of PRRSV relative to a fibroblast isolated from a pig whose genome comprises a wild-type CD163 gene.

5. The gene edited pig of claim 1, wherein the CD163 gene is heterozygous for the nucleic acid sequence of SEQ ID NO: 453.

6. A cell isolated from the gene edited pig of claim 5, wherein the cell exhibits reduced cellular uptake of PRRSV relative to a cell isolated from a pig whose genome comprises a wild-type CD163 gene.

7. A cell line isolated from the gene edited pig of claim 5, wherein the cell line exhibits reduced cellular uptake of PRRSV relative to a cell line isolated from a pig whose genome comprises a wild-type CD163 gene.

8. A fibroblast isolated from the gene edited pig of claim 5, wherein the fibroblast exhibits reduced cellular uptake of PRRSV relative to a fibroblast isolated from a pig whose genome comprises a wild-type CD163 gene.

9. The gene edited pig of claim 1, wherein the CD163 gene is homozygous for the nucleic acid sequence of SEQ ID NO: 453.

10. A cell isolated from the gene edited pig of claim 9, wherein the cell exhibits reduced cellular uptake of PRRSV relative to a cell isolated from a pig whose genome comprises a wild-type CD163 gene.

11. A cell line isolated from the gene edited pig of claim 9, wherein the cell line exhibits reduced cellular uptake of PRRSV relative to a cell line isolated from a pig whose genome comprises a wild-type CD163 gene.

12. A fibroblast isolated from the gene edited pig of claim 9, wherein the fibroblast exhibits reduced cellular uptake of PRRSV relative to a fibroblast isolated from a pig whose genome comprises a wild-type CD163 gene.

13. A method of producing a gene edited pig, the method comprising:
a) introducing:
i) a Cas9 protein or a nucleic acid sequence encoding a Cas9 protein;
ii) a guide RNA (gRNA) comprising the nucleic acid sequence of SEQ ID NO: 249; and
iii) a gRNA comprising the nucleic acid sequence of SEQ ID NO: 256 into an isolated pig cell;
b) producing a gene edited pig from the isolated pig cell, wherein the gene edited pig comprises at least some cells whose genomes comprise the nucleic acid sequence of SEQ ID NO: 453 and exhibit reduced cellular uptake of porcine reproductive and respiratory syndrome virus (PRRSV) relative to pig cells whose genomes comprise a wild-type CD163 gene.

14. The method according to claim 13, further comprising breeding the gene edited pig to a wild-type pig such that a first generation progeny is obtained that exhibits reduced cellular uptake of PRRSV relative to a pig whose genome comprises a wild-type CD163 gene.

15. The method according to claim 14, further comprising breeding the first generation progeny such that a second generation progeny is obtained that exhibits reduced cellular uptake of PRRSV relative to a pig whose genome comprises a wild-type CD163 gene.

16. The method according to claim 15, wherein the second progeny is homozygous for the nucleic acid sequence of SEQ ID NO: 453.

17. A gene edited pig produced by the method of claim 13 comprising at least some cells whose genomes comprise the nucleic acid sequence of SEQ ID NO: 453 and exhibit reduced cellular uptake of PRRSV relative to pig cells whose genomes comprise a wild-type CD163 gene.

18. The method according to claim 13, wherein the producing comprises somatic cell nuclear transfer of the isolated pig cell or a cell derived therefrom.

19. The method according to claim 13, further comprising implanting a pig embryo into a surrogate mother.

\* \* \* \* \*